United States Patent
Zeng et al.

(10) Patent No.: US 7,897,619 B2
(45) Date of Patent: Mar. 1, 2011

(54) HETEROCYCLIC MODULATORS OF PKB

(75) Inventors: Qingping Zeng, Thousand Oaks, CA (US); Dawei Zhang, Thousand Oaks, CA (US); Guomin Yao, Newbury Park, CA (US); George E. Wohlhieter, Lake Balboa, CA (US); Xianghong Wang, Moorpark, CA (US); James Rider, Woodland Hills, CA (US); Andreas Reichelt, Moorpark, CA (US); Holger Monenschein, Camarillo, CA (US); Fang-Tsao Hong, Thousand Oaks, CA (US); James R. Falsey, Moorpark, CA (US); Celia Dominguez, Los Angeles, CA (US); Matthew P. Bourbeau, Woodland Hills, CA (US); John G. Allen, Newbury Park, CA (US)

(73) Assignee: Amgen Inc., Thousand Oaks, CA (US)

(*) Notice: Subject to any disclaimer, the term of this patent is extended or adjusted under 35 U.S.C. 154(b) by 407 days.

(21) Appl. No.: 12/218,754

(22) Filed: Jul. 16, 2008

(65) Prior Publication Data
US 2009/0275592 A1   Nov. 5, 2009

Related U.S. Application Data

(60) Provisional application No. 60/959,972, filed on Jul. 17, 2007.

(51) Int. Cl.
*A61K 31/47* (2006.01)
*A61K 31/416* (2006.01)
*C07D 217/02* (2006.01)
*C07D 231/56* (2006.01)

(52) U.S. Cl. ......... 514/311; 544/224; 544/235; 544/242; 544/253; 544/283; 546/112; 546/139; 546/152; 546/157; 548/360.1; 548/361.1; 548/302.7; 548/306.4; 514/248; 514/299; 514/387; 514/403

(58) Field of Classification Search ............... 544/224, 544/235, 242, 253, 283; 546/112, 139, 152, 546/157; 548/302.7, 306.4, 360.1, 361.1; 514/248, 299, 311, 387, 403
See application file for complete search history.

(56) References Cited

U.S. PATENT DOCUMENTS

| | | | |
|---|---|---|---|
| 3,452,035 A | 6/1969 | Berkelhammer et al. | |
| 5,550,138 A | 8/1996 | Sohda et al. | |
| 5,693,643 A | 12/1997 | Gilbert et al. | |
| 5,834,401 A | 11/1998 | Kawamura et al. | |
| 5,856,347 A | 1/1999 | Hashiguchi et al. | |
| 5,977,027 A | 11/1999 | Kawamura et al. | |
| 6,323,315 B1 | 11/2001 | Pettit et al. | |
| 6,420,400 B1 | 7/2002 | Zhang et al. | |
| 6,521,643 B1 | 2/2003 | Tomishima et al. | |
| 6,525,052 B2 | 2/2003 | Bekkali et al. | |
| 6,620,911 B1 | 9/2003 | Pettit et al. | |
| 6,720,427 B2 | 4/2004 | Sanner et al. | |
| 6,894,054 B2 | 5/2005 | Laborde et al. | |
| 6,962,933 B1 | 11/2005 | Ohkawa et al. | |
| 6,982,272 B2 | 1/2006 | Emmanuel et al. | |
| 7,354,944 B2 * | 4/2008 | Zeng et al. | 514/363 |
| 7,514,566 B2 * | 4/2009 | Zeng et al. | 548/198 |
| 7,700,636 B2 * | 4/2010 | Monenschein et al. | 514/363 |
| 2001/0044545 A1 | 11/2001 | Dhanca et al. | |
| 2002/0025976 A1 | 2/2002 | Chu et al. | |
| 2002/0115863 A1 | 8/2002 | Patel et al. | |
| 2002/0119962 A1 | 8/2002 | Jacobs et al. | |
| 2003/0078252 A1 | 4/2003 | Sanner et al. | |
| 2003/0216403 A1 | 11/2003 | Lively et al. | |
| 2004/0053948 A1 | 3/2004 | McDonald et al. | |
| 2004/0053973 A1 | 3/2004 | Ohkawa et al. | |
| 2004/0097555 A1 | 5/2004 | Ohkawa et al. | |
| 2004/0102360 A1 | 5/2004 | Barnett et al. | |
| 2004/0106540 A1 | 6/2004 | Barnett et al. | |
| 2004/0116439 A1 | 6/2004 | Lively et al. | |
| 2004/0122016 A1 | 6/2004 | Cao et al. | |
| 2004/0152747 A1 | 8/2004 | Chen et al. | |
| 2004/0157827 A1 | 8/2004 | Pevarello et al. | |
| 2004/0171643 A1 | 9/2004 | De Cointet et al. | |
| 2005/0004134 A1 | 1/2005 | Tsutsumi et al. | |

(Continued)

FOREIGN PATENT DOCUMENTS

| | | |
|---|---|---|
| CA | 1045136 | 12/1978 |
| DE | 3407505 A1 | 9/1985 |
| GB | 2022085 A | 12/1979 |
| JP | 64-75475 A2 | 3/1989 |
| JP | 5117280 | 5/1993 |
| JP | 8073460 | 3/1996 |

(Continued)

OTHER PUBLICATIONS

Murer, P. et al., "Combinatorial Library On-Bead Approach to Polymeric Materials with Vastly Enhanced Chiral Recognition", Chem. Commun., 23, 2559-2560 (1998Murer, P. et al., "On-Bead Combinatorial Approach to the Design of Chiral Stationary Phases for HPLC", Anal. Chem., 71, 1278-1284 (1999).
Namikawa, K. et al., "AKT/Protein Kinase B Prevents Injury-Induced Motoneuron Death and Accelerates Axonal Regeneration", J. Neurosci., 20, 2875-2886 (2000).

(Continued)

Primary Examiner — Golam M Shameem
(74) Attorney, Agent, or Firm — Bernard P. Friedrichsen

(57) ABSTRACT

The invention relates to heterocyclic compounds of Formula I and compositions thereof useful for treating diseases mediated by protein kinase B (PKB) where the variables have the definitions provided herein.

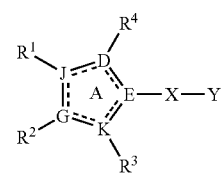

The invention also relates to the therapeutic use of such compounds and compositions thereof in treating disease states associated with abnormal cell growth, cancer, inflammation, and metabolic disorders.

41 Claims, No Drawings

U.S. PATENT DOCUMENTS

| | | |
|---|---|---|
| 2005/0038059 A1 | 2/2005 | Mueller et al. |
| 2005/0043372 A1 | 2/2005 | Chen |
| 2005/0053594 A1 | 3/2005 | Alessi et al. |
| 2005/0080113 A1 | 4/2005 | Ohkawa et al. |
| 2005/0119320 A1 | 6/2005 | Bruce et al. |
| 2005/0143384 A1 | 6/2005 | Sartori et al. |
| 2005/0148640 A1 | 7/2005 | Come et al. |
| 2005/0176789 A1 | 8/2005 | Hadida Ruah et al. |
| 2005/0182104 A1 | 8/2005 | Balter et al. |
| 2005/0192300 A1 | 9/2005 | Wang et al. |
| 2005/0222219 A1 | 10/2005 | Chen et al. |
| 2005/0256121 A1 | 11/2005 | Jefferson et al. |
| 2006/0003944 A1 | 1/2006 | Glinka et al. |
| 2006/0052426 A1 | 3/2006 | Despeyroux et al. |
| 2006/0154961 A1 | 7/2006 | Zeng et al. |
| 2006/0178388 A1 | 8/2006 | Wrobleski et al. |
| 2006/0205731 A1 | 9/2006 | Kodama et al. |
| 2006/0287317 A1 | 12/2006 | Smith et al. |
| 2006/0293365 A1 | 12/2006 | Baltzer et al. |
| 2006/0293366 A1 | 12/2006 | Baltzer et al. |
| 2007/0032487 A1 | 2/2007 | Bruce et al. |
| 2007/0173506 A1 | 7/2007 | Zeng et al. |
| 2008/0255145 A1 | 10/2008 | Monenschein et al. |
| 2008/0269243 A1 | 10/2008 | Monenschein et al. |
| 2009/0099221 A1 | 4/2009 | Vanotti et al. |
| 2009/0203690 A1 | 8/2009 | Akritopoulou-Zanze et al. |

FOREIGN PATENT DOCUMENTS

| | | |
|---|---|---|
| JP | 9221424 | 8/1997 |
| JP | 2002-53565 | 2/2002 |
| JP | 20020-53566 | 2/2002 |
| WO | WO 93/19054 | 9/1993 |
| WO | WO 96/38419 | 12/1996 |
| WO | WO 97/22360 | 6/1997 |
| WO | WO 99/31096 | 6/1999 |
| WO | WO 99/65884 | 12/1999 |
| WO | WO 00/45635 | 8/2000 |
| WO | WO 01/44178 A1 | 6/2001 |
| WO | WO 01/44179 A1 | 6/2001 |
| WO | WO 01/87877 A1 | 11/2001 |
| WO | WO 02083064 A2 | 10/2002 |
| WO | WO 03/014095 A1 | 2/2003 |
| WO | WO 03/068227 A1 | 8/2003 |
| WO | WO 03/084473 A2 | 10/2003 |
| WO | WO 03/094831 A2 | 11/2003 |
| WO | WO 2004/014864 A1 | 2/2004 |
| WO | WO 2004/041813 A1 | 5/2004 |
| WO | WO 2004/046120 A2 | 6/2004 |
| WO | WO 2004/056789 A1 | 7/2004 |
| WO | WO 2004/089937 A1 | 10/2004 |
| WO | WO 2004/096131 A2 | 11/2004 |
| WO | WO 2005/014554 A1 | 2/2005 |
| WO | WO 2005/046678 A1 | 5/2005 |
| WO | WO 2005/052147 A2 | 6/2005 |
| WO | WO 2005/068444 A2 | 7/2005 |
| WO | WO 2005/089443 A2 | 9/2005 |
| WO | WO 2005/113762 | 12/2005 |
| WO | WO 2005/116025 A2 | 12/2005 |
| WO | WO 2006/020767 A2 | 2/2006 |
| WO | WO 2006/038734 A1 | 4/2006 |
| WO | WO 2006/044860 A2 | 4/2006 |
| WO | WO 2006/045716 A1 | 5/2006 |
| WO | WO 2006/051270 A1 | 5/2006 |
| WO | WO 2007/008541 A2 | 1/2007 |
| WO | WO 2007/033780 A2 | 3/2007 |
| WO | WO 2007/066805 A1 | 6/2007 |
| WO | WO 2007/070600 A2 | 6/2007 |
| WO | WO 2007/084391 A2 | 7/2007 |
| WO | WO 2007/110344 A1 | 10/2007 |
| WO | WO 2008/036308 A2 | 3/2008 |
| WO | WO 2008/154241 A1 | 12/2008 |
| WO | WO 2009/133170 A1 | 11/2009 |

OTHER PUBLICATIONS

Nicholson, K. M. et al., "The Protein Kinase B/AKT Signalling Pathway in Human Malignancy", Cell. Signal., 14, 381-395 (2002).

Pachhaimia, V. L. et al., "Studies on Thiadiazoles: Part I: Preparation and Antimicrobial Activity of 2-(α Carbamylarylmethylamino)-5-(4'-Pyridyl)-1, 3, 4-Thiadiazoles," J. Inst. Chem.. (India), 61, 54-56 (1989). ).

Pande, K. et al., "Anti-Inflammatory and AntiProteolytic Activities of Substituted Imidazolones," Indian Drugs, 23(1), 13-17 (1985).

Park, C-M. et al., "Non-peptidic Small Molecule Inhibitors of XIAP," Bioorg. and Med. Chem. Lett., 15(3), 771-775 (2005).

Pathak, V.N. et al., "Synthesis and Biological Activities of Some New 2-(N-Arylamino)-4-(Fluoroaryl)thiazoles," J. Ind. Chem. Soc., vol. LVI, pp. 1010-1012 (1979).

Pettit, R. K. et al., "Specific Activities of Dolastatin 10 and Peptide Derivatives against *Cryptococcus neoformans*," Antimicrob. Agents and Chemo., 42, 2961-2965 (1998).

Sanchez, J. P. et al., "Quinolone Antibacterial Agents. Synthesis and Structure-Activity Relationships of a Series of Amino Acid Prodrugs of Racemic and Chiral 7-(3-Amino-1-pyrrolidinyl)quinolones. Highly Soluble Quinolone Prodrugs with In Vivo Pseudomonas Activity", J. Med. Chem., 35 (10), 1764-1773 (1992).

Senapti, R. M. et al., "Studies on Thiadiazoles," Proc. Instit. Chem. (India), 37(3), 111-113 (1965).

Shah, V. H. et al., "Studies on Acetamide Derivatives: Preparation and Antimicrobial Activity of 2-α-Arylaminoacetamido/α-Carbamoyl benzylamino/Arylcarbamoylmethylamino-5-o-Nitrophenyl/Benzoylaminomethyl-1,3,4-Thiadiazole," J. Ind. Chem. Soc., LIX, 678-690 (1982).

Singh, H. et al., "Synthesis, Characterization and Fungitoxicity of Manganese (II), Iron (II), Colbalt (II), Nickel (II), Copper (II), and Zinc (II) Complexes of N-Phenyl-5-phenyl-1,3,4-oxadiazole-2-sulphonamide and 5-Phenyl-1,3,4-oxadiazole-2-imino Sulphonamide," Ind. J. Chem., 33A, 350-353 (1994).

Suzuki, N. et al., "Synthesis and Antiallergy Activity of [1,3,4]Thiadiazolo[3,2-a]-1,2,3,-triazolo[4,5-d]pyrimidin-9(3H)-one", Chem. Pharm. Bull., 40(2), 357-363 (1992).

Tanaka, A. et al., "Antiplatelet Agents Based on Cyclooxygenase Inhibition without Ulcerogenesis. Evaluation and Synthesis of 4,5-Bis (4-methoxyphenyl)-2-substituted-thiazoles," J. Med. Chem., 37(8), 1189-1199 (1994).

Testa, J. R. et al., "AKT Plays a Central Role in Tumorigenesis," PNAS, 98, 10983-10985 (2001).

Tripathi, M, et al., "Antipyrine Congeners as Antidepressant Agents", Arzneimittel-Forschung, 43(10), 1045-1049 (1993).

Verdu, J. et al., "Cell-Autonomous Regulation of Cell and Organ Growth in *Drosophila* by Akt/PKB," Nat. Cell Biol., 1, 500-506 (1999).

Vivanco, I. et al., "The Phosphatidylinositol 3-Kinase-AKT Pathway in Human Cancer," Nat. Rev. Cancer, 2, 489-501 (2002).

Wengel, J. et al. "Analogs of the Antibiotic Puromycin as Potential Prodrugs of 3'-Amino-3'-deoxythymidine", J. Heterocyc. Chem., 29(1), 5-9 (1992).

Yadav, L. D. S. et al., "A Facile Ring Transformation of 5-Oxazolone Derivatives to New 1,3,4-Oxa(thia)diazolo[3,2-a]pyrimidin-5-ones", Ind. J. Chem., 34B, 500-503 (1995).

Yadav L. et al., "One-Pot Annulation of Pyrimidine Ring on Azoles Under Microwave Irradiation and Solvent-Free Conditions," Synthesis, 1, 63-66 (2003).

Yang, L. et al., "Akt/Protein Kinase B Signaling Inhibitor-2, a Selective Small Molecule Inhibitor of Akt Signaling with Antitumor Activity in Cancer Cells Overexpressing Akt," Cancer Res., 64, 4394-4399 (2004).

Yuan, Z. Q. et al., "Frequent Activation of AKT2 and Induction of Apoptosis by Inhibition of Phosphoinositide-3-OH Kinase/ Akt Pathway in Human Ovarian Cancer," Oncogene, 19, 2324-2330 (2000).

International Search Report from co-pending PCT Application No. PCT/US2008/008723 (WO 2009/011880 A3) mailed on Feb. 16, 2009.

Mishra L., et al., "Synthesis and Fungicidal Activity of Some 5-Membered Heterocyclic Derivatives Containing Benzimidazoles," Biosci. Biotech. and Biochem. 57(6), pp. 989-991 (1993).

Zhuravel, I. O. et al., "Synthesis of Substituted 3-(5-Amino-[1,3,4]thiadiazol-2-yl)-2H-pyrano [2,3-c]pyridin-2-ones," J. Heterocyc. Chem. 41(4), pp. 517-524 (2004).

Aoyama, T. et al., "One Pot Synthesis using Supported Reagents System KSCN/SiO$_2$-RNH$_3$OAc/Al$_2$O$_3$:synthesis of 2-aminothiazoles and N-Allylthioureas," Tetrahedron, 62(14), 3201-3213 (2006).

Arevalo, M. J. et al., "Expeditious Formation of 1,2,4-Triazine Derivatives via a Thioisomunchnone Cycloaddition Reaction," Tet. Lett., 40, 8675-8678 (1999).

Bellacosa, A. et al., "Molecular Alterations of the AKT2 Oncogene in Ovarian and Breast Carcinomas," Int. J. Cancer (Pred. Oncol.), 64, 280-285 (1995).

Besson, A. et al., "PTEN/MMAC1/TEP1 in Signal Transduction and Tumorigenesis," Eur. J. Biochem., 263, 605-611 (1999).

Beyer, H. et al., "Folgeprodukte der Thiazolyl-(2)-cyanamide," Chem. Ber., 99(9), 2937-2943 (1966). This is in German. English language abstract is attached.

Blume-Jensen, P. et al., "OncogenicKinase Signalling," Nature, 411, 355-365 (2001).

Brazil, D. P. et al., "Ten Years of Protein Kinase B Signalling: a hard Akt to follow," Trends Biochem Sci., 11, 657-664 (2001).

Brodbeck, D. et al., "A Human Protein Kinase Bγ with Regulatory Phosphorylation Sites in the Activation Loop and in the C-terminal Hydrophobic Domain," J. Biol. Chem., 274, 9133-9136 (1999).

Cheng, J. Q. et al., "AKT2, a Putative Oncogene Encoding a Member of a Subfamily of Protein-Serine/Threonine Kinases, is Amplified in Human Ovarian Carcinomas", PNAS, 89, 9267-9271 (1992).

Cheng, J. Q. et al.,"Amplification of AKT2 in Human Pancreatic Cancer Cells and Inhibition of AKT2 Expression and Tumorigenicity by Antisense RNA", PNAS, 93, 3636-3641 (1996).

Czech, M. P. et al., "Signaling Mechanisms that Regulate Glucose Transport," J. Biol. Chem., 274, 1865-1868 (1999).

Datta, S. R. et al., "Cellular Survival: a Play in Three Akts," Genes Dev., 13, 2905-2927 (1999).

Duan, C. et al., "Phosphatidylinositol 3-Kinase Is Required for Insulin-Like Growth Factor-I—Induced Vascular Smooth Muscle Cell Proliferation and Migration," Circ. Res., 86, 15-23 (2000).

Fathalla et al., "Synthesis of Some New 1,8-Naphthyridine Derivatives of Expected Biological Activity", Egypt. J. Chem., 46(1), 135-152 (2003).

Fennel, B. J. et al., "Effects of the Antimitotic Natural Product Dolastatin 10, and Related Peptides, on the Human Malarial Parasite *Plasmodium falciparum*", J. Antimicrob. Chemo., 51(4), 833-841 (2003).

Ghattas, A.G. et al., "Synthesis of Some New Heterocyclic 1,3,4-Oxadiazoles with Antibacterial Activity," Fac. Sci., Assuit University, 37(6), 410-412 (1982).

Ghodousi, A. et al., "Pyrrolobenzimidazoles Linked to Heterocycles and Peptides. Design of DNA Base Pair Specific Phosphate Hydrolyzing Agents and Novel Cytotoxic Agents", J. Med. Chem., 47(1), 90-100 (2004).

Gommaa, A. M. et al., " Synthesis of Some New Substituted Aminoacylthiazoles and Dipeptide Derivatives", Asian J. Chem., 4(3), 527-533 (1992).

Grehn, Leif, "A Method for Nitration of Thiazoles," J. Heterocyc. Chem., 14, 917-919 (1977).

Hackbarth, C. J. et al., "N-Alkyl Urea Hydroxamic Acids as a New Class of Peptide Deformylase Inhibitors with Antibacterial Activity," Antimicrob. Agents and Chemo., 46(9), 2752-2764 (2002).

Hassan, H. M. et al., "Synthesis and Antimicrobial Activity of Some New N-Aminoacyl Derivatives of 2-Amino-4-phenylthiazole", Acta Pharm., 47, 159-166 (1997).

Hemmings,, B. A. "Akt Signaling: Linking Membrane Events to Life and Death Decisions," Science, 275, 628-630 (1997).

Hill, M. M. et al., "Identification of a Plasma Membrane Raft-Associated PKB Ser473 Kinase Activity that Is Distinct from ILK and PDK1," Current Biol., 12, 1251-1255 (2002).

Hiremath, S. P. et al., "Synthesis of 2-Phenyl(indol-3-yl)Isothiocyanates, 1-Substituted-3-(Substituted-2'-Phenylindol-3'-yl) Thiosemicarbazides and their Reacations," Ind. J. Heterocyc. Chem., 2, 119-124 (1992).

Hiremath, S. P. et al., "Synthesis of Substituted indolylthiadiazolines and indolylisoxazolines," Ind. J. Chem., 30B, 744-748 (1991).

Hresko, R. C. et al., "Phosphionositide-dependent Kinase-2 is a Distinct Protein Kinase Enriched in a Novel Cytoskeletal Fraction Associated with Adipocyte Plasma Membranes," J. Biol. Chem., 278, 21615-21622 (2003).

Jeske, J. et al., "Preliminary Evaluation of Analgesic Effect of Amino Acid 4-Aminoantipyrine Derivatives", Pol. Med. Sci. Hist. Bull., 17(6) 475-480 (1974).

Jeske, J. et al., "Some Pharmacological Effects of Amino Acid 4-Aminoantipyrine Derivatives", Pol. Med. Sc. Hist. Bull., 17(6) 481-485 (1974).

Jeske, J. et al., "The Effect of Amino Acid Substituents in 4-Antipyrineamide on the LD50 Value", Pol. Med. Sci. Hist. Bull., 17(4) 323-325 (1974).

Jeske, J. et al., "Evaluation of Spasmolytic Action of Amino Acid 4-Aminoantipyrine Derivatives", Pol. Med. Sci. Hist. Bull., 17(6) 487-490 (1974).

Khwaja, A. "AKT Is More Than Just a Bad Kinase", Nature, 401, 33-34 (1999).

Kidwai, M. et al., "Microwave Induced Synthesis and Antibacterial Activity of Cephalosporin Derivatives Using Solid Support," Bioorg. Chem., 29, 380-386 (2001).

Kidwai, M. et al., "Solid Supported Reaction of Substituted 2-Oxazoline with Amines under Microwave Irradiation," J. Chin. Chem. Soc., 50, 1075-1078 (2003).

Kodomari, M. et al., "One-Pot Synthesis of 2-Aminothiazoles using Supported Reagents," Tet. Lett., 43(9), 1717-1720 (2002).

Komori, T. et al., "Structure Activity Relationships of Synthetic Antibiotic Analogs of Chryscandin", J. of Antibiotics, 38(9), 1182-1203 (1985).

Kulik, G. et al., "Antiapoptotic Signalling by the Insulin-Like Growth Factor I Receptor, Phosphatidylinositol 3-Kinase, and Akt," Mol. and Cell. Biol., 17, 1595-1606 (1997).

Kulkarni, R.A. et al., "O,O-Dialkyl-S-(4-substituted-phenyl-5-phenylacetamido-thiazol-2-yl)phosphorothiaotes and O,O-Dialkyl-s-(4-substituted-phenyl-5-phenylthiazol-2-yl)phosphorothioate," J. Ind. Chem. Soc., 65(6), 432-434 (1988).

Kureishi, Y. et al., "The HMG-CoA Reductase Inhibitor Simvastatin Activates the Protein Kinase Akt and Promotes Angiogenesis in Normocholesterolemic Animals," Nat. Med., 6, 1004-1010 (2000).

Kwapiszewski, W. et al., "4-Antipyrinylamides of Amino Acids. II. 4-Antipyrinylamides of DL-Leucine, Phenylalanine, Tyrosine, Glutamic Acid, and ε-Aminocaproic Acid", Acta Poloniae Pharmaceutica, 34(1), 45-50 (1977). This is in Polish, but an English Language Abstract is provided.

Kwapiszewski, W. et al., "Preparation of the Aminoacyl Derivatives of 4-Aminoantipyrine. IV. Derivatives of D-Amino Acids", Acta Poloniae Pharmaceutica, 41(1), 21-24 (1984). This is in Polish, but an English Language Abstract is provided.

Lawlor, M. A. et al., "PKB/Akt: a Key Mediator of Cell Proliferation, Survival and Insulin Responses?" J. Cell Sci., 114, 2903-2910 (2001).

Li , D-M. et al., "TEP1, Encoded by a Candidate Tumor Suppressor Locus, Is a Novel Protein Tyrosine Phosphatase Regulated by Transforming Growth Factor β[1]," Cancer Res., 57, 2124-2129 (1997).

Lin, H-K et al., "Akt Suppresses Androgen-Induced Apoptosis by Phosphorylating and Inhibiting Androgen Receptor," PNAS, 98, 7200-7205 (2001).

Luo, Z. et al., "Acute Modulation of Endothelial Akt/PKB Activity Alters Nitric Oxide-Dependent Vasomotor Activity in vivo," J. Clin. Invest., 106, 493-499 (2000).

Mankad, P. R. et al., "Analgesic & Muscle Tension Relaxing Agents: Part I—Synthesis of Some New 2-β-Hydroxyphenethylaminothiazoles," Ind. J. Chem., 1 (10), 441-442 (1963).

Masakazu, B. et al., "Novel Antiallergic and Antiinflammatory Agents. Part I: Synthesis and Pharmacology of Glycolic Amide Derivatives," Bioorg. and Med. Chem., 6, 1069-1076 (1998).

Mazzone, G. et al., "Synthesis and Local Anesthetic Activity of Alkylaminoacyl Derivatives of 2-Amino-1,3,4-Thiadiazole", Il Farmaco, 48(9), 1207-1224 (1993).

Miao, W. et al., "Intracoronary, Adenovirus-mediated Akt Gene Transfer in Heart Limits Infarct Size Following Ischemia-reperfusion Injury in Vivo," J. Mol. Cell. Cardiol., 32, 2397-2402 (2000).

Misterek, K, et al., "Effects of Pyrazolone-5 Derivatives on Amphetamine-Induced Hyperthermia and Behavioral Changes in Rats", Pol. J. Pharmacology Pharmacy, 28(6), 593-599 (1976).

U.S. Appl. No. 12/218,523, filed Jul. 15, 2008, Zeng et al.

U.S. Appl. No. 12/378,195, filed Feb. 11, 2009, Zeng et al.

Hanada, Masahito, et al., "Structure, Regulation and Function of PKB/AKT—A Major Therapeutic Target," Biochim. et Biophys. Acta 1697, pp. 3-16 (2004).

Supplementary European Search Report for EP 05812533 dated Oct. 16, 2009.

* cited by examiner

HETEROCYCLIC MODULATORS OF PKB

CROSS REFERENCES TO RELATED APPLICATIONS

This application claims the benefit of U.S. Provisional Application No. 60/959,972, filed on Jul. 17, 2007, which is hereby incorporated by reference in its entirety and for all purposes as if fully set forth herein.

FIELD OF THE INVENTION

The invention relates to heterocyclic compounds useful for treating diseases mediated by protein kinase B (PKB). The invention also relates to the therapeutic use of such compounds and compositions thereof in treating disease states associated with abnormal cell growth, cancer, inflammation, and metabolic disorders.

BACKGROUND OF THE INVENTION

Protein kinases represent a large family of proteins which play a central role in the regulation of a wide variety of cellular processes, maintaining control over cellular function. A partial list of such kinases includes abl, bcr-abl, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, GSK3α, GSK3β, Hck, IGF-1R, INS-R, Jak, KDR, Lck, Lyn, MEK, MK2, MSK1, p38, PDGFR, PIK, PKB, PKA, PIM1, PIM2, PRAK, PRK2, PKC, PYK2, P70S6, ROCK2, ros, tie, tie2, TRK, Yes, and Zap70. Inhibition of such kinases has become an important therapeutic approach.

AKT (also known as protein kinase B (PKB) or RAC-PK), including three isoforms AKT1/PKBα/RAC-PKα, AKT2/PKBα/RAC-PKβ, AKT3/PKBγ/RAC-PKγ, has been identified as a serine/threonine protein kinase. Testa et al., *Proc. Natl. Acad. Sci.*, 2001, 98, 10983-10985; Brazil et al., *Trends Biochem Sci.*, 2001, 11, 657-64; Lawlor et al., *J. Cell Sci.*, 2001, 114, 2903-2910; Cheng, *Proc. Natl. Acad. Sci. USA*, 1992, 89, 9267-9271; Brodbeck, et al., *J. Biol. Chem.* 1999, 274, 9133-9136. PKB mediates many effects of IGF-1 and other growth factors on tumor growth and inhibition of apoptosis. Nicholson, et al., *Cell. Signal.*, 2002, 14, 381-395. PKB plays an important role in cell proliferation, apoptosis and response to insulin. For these reasons, modulation of PKBs is of interest in the treatment of tumorigenesis, abnormal cell proliferation, and diabetes.

The molecular structure of the PKBs comprises a regulatory site near the carboxy terminus of the polypeptide, a catalytic domain with an activation loop having a threonine, and an amino-terminal pleckstrin homology domain. The pleckstrin homology domain permits anchorage of the enzyme to the cell membrane through interaction with phospholipids, which triggers the activation of the PKBs. The role of the pleckstrin homology domain requires phosphorylation of phosphatidylinositol at the D-3 position via phosphatidylinositol 3-kinase PI3K, an SH2 domain protein that associates with activated receptor tyrosine kinases, particularly IGF-1R. In particular, phosphoinositol-3-kinase, when activated by receptor tyrosine kinase, catalyzes the synthesis of phosphoinositol-3,4-diphosphate and phosphatidylinositol 3,4,5-triphosphate. The pleckstrin homology domain binds 3-phosphoinositides, which are synthesized by PI3K upon stimulation by growth factors such as platelet derived growth factor (PDGF), nerve growth factor (NGF) and insulin-like growth factor (IGF-1). Kulik et al., *Mol. Cell. Biol.*, 1997, 17, 1595-1606; Hemmings, *Science*, 1997, 275, 628-630; Datta, et al. *Genes Dev.*, 1999, 13, 2905-2927. Lipid binding to the pleckstrin homology domain promotes translocation of PKB to the plasma membrane. Further activation of PKB occurs by phosphorylation by another protein kinase, PDK1 at Thr308, Thr309, and Thr305 for the PKB isoforms α, β and γ, respectively. A third step of activation is catalyzed by a kinase that phosphorylates Ser473, Ser474 or Ser472 in the C-terminal tails of PKBα, β, and γ respectively. The Ser473 kinase activity has been identified to be associated with plasma membrane and is not due to PKB and PDK1 kinase activity. Hill et al., *Current Biology*, 2002, 12, 1251-1255; Hresko et al., *J. Biol. Chem.*, 2003, 278, 21615-21622. The process produces the fully activated form of PKB.

Activation of PKB can also occur by inhibiting the D-3 phosphoinositide specific phosphatase, PTEN, which is a membrane-associated FYVE finger phosphatase commonly inactivated in many cancers due to genetic alteration, including prostate cancer. Besson, et al., *Eur. J. Biochem.*, 1999, 263, 605-611; Li, et al., *Cancer Res.*, 1997, 57, 2124-2129.

The catalytic domain of PKB is responsible for the phosphorylation of serine or threonine in the target protein.

Once activated, PKB mediates several cellular functions including proliferation, cell growth, and promotion of survival. Intracoronary, adenovirus-mediated akt gene transfer in heart limits infarct size following ischemia-reperfusion injury in vivo. Miao et al., *J. Mol. Cell. Cardiol.*, 2000, 32, 2397-2402. The antiapoptotic function of PKB is reported to be mediated by its ability to phosphorylate apoptosis regulatory molecules including BAD, caspase 9, IKK-, and the forkhead transcriptional factor FKHRL1. Datta et al., at 2905. PKB signaling is also implicated in the physiological regulation of organ size (Verdu, et al., *Nat. Cell Biol.*, 1999, 1, 500-506), glucose homeostasis (Czech, et al., *J. Biol. Chem.*, 1999, 274, 1865-1868), vasomotor tone (Luo, et al. *J. Clin. Invest.* 1999, 106, 493-499), and angiogenesis (Kureishi, et al., *Nat. Med.*, 2000, 6, 1004-1010).

Manifestations of altered PKB regulation appear in both injury and disease, the most important role being in cancer. PKB kinase activity is constitutively activated in tumors with PTEN mutation, PI 3-kinase mutation and overexpression, and receptor tyrosine kinase overexpression. PKB is also a mediator of normal cell functions in response to growth factor signaling. Expression of the PKB gene was found to be amplified in 15% of human ovarian carcinoma cases. Cheng, et al., *Proc. Natl. Acad. Sci. U.S.A.*, 1992, 89, 9267-9271. PKB has also been found to be over expressed in 12% of pancreatic cancers. Cheng, et al., *Proc. Natl. Acad. Sci. U.S.A.*, 1996, 93, 3636-3641. In particular, PKBβ is over-expressed in 12% of ovarian carcinomas and in 50% of undifferentiated tumors, suggesting that PKB may be associated with tumor aggressiveness. Bellacosa, et al., *Int. J. Cancer*, 1995, 64, 280-285. PKB is also a mediator of normal cell functions. Khwaja, *Nature*, 1999, 401, 33-34; Yuan, et al., *Oncogene*, 2000, 19, 2324-2330; Namikawa, et al., *J Neurosci.*, 2000, 20, 2875-2886.

Elucidation of the role of PKB in the increase of growth and inhibition of apoptosis is complicated by the many protein substrates of PKB, including BAD, Forkhead (FOXO family), GSK3, Tuberin (TSC2), p27 Kip1, p21Cip1/WAF1, Raf, Caspase-9, and Mdm2. Lin, et al., *Proc. Natl. Acad. Sci. U.S.A.*, 2001, 98, 7200-7205; Blume-Jensen, et al., *Nature* 2001, 411, 355-365; Vivanco, et al., *Nat. Rev. Cancer*, 2002, 2, 489-501.

The various PKBs vary in their abundance in different mammalian cell types. For example, PKBβ is especially abundant in highly insulin-responsive tissues, including brown fat; PKBα is widely expressed in most of the tissues; and PKBγ is more abundant in brain and testes.

Modulation of PKB by small molecules can be achieved by identifying compounds that bind to and activate or inhibit one or more PKBs. Cao et al. in *United States Publication No.* 2004/0122016, published Jun. 24, 2004, disclose certain thiophene derivatives and thiophene analogs as inhibitors of protein kinases. In particular, the disclosure addresses compositions effective as inhibitors of Rho-associated coiled-coil forming protein serine/threonine kinase (ROCK), extracellular signal regulated kinase (ERK), glycogen synthase kinase (GSK), and members of the AGC sub-family of protein kinases. Id. at 4. The AGC sub-family of kinases includes protein kinase A (PKA), PDK, $p70^{S6K}$-1, $p70^{S6K}$-2, and PKB. Id.

Triciribine has been reported to inhibit cell growth in PKBβ overexpressing cells, transformed cells, and was effective at a concentration of 50 nM. Yang et al., *Cancer Res.*, 2004, 64, 4394-4399.

In other work, U.S. Pat. No. 5,232,921, issued Aug. 3, 1993, discloses thiazole derivatives that are active on the cholinergic system. The patent does not address modulation of PKB.

U.S. Patent Publication No. US 2005/0004134, published Jan. 6, 2005, discloses certain thiazole derivatives, a method of obtaining them, and pharmaceutical compositions containing them. The derivatives are described as adenosine antagonists useful in the prevention and/or treatment of cardiac and circulatory disorders, degenerative disorders of the central nervous system, respiratory disorders, and many diseases for which diuretic treatment is suitable.

Derivatives of thiazole were synthesized and used in treating conditions alleviated by antagonism of a 5-HT2b receptor in International Publication No. WO 03/068227. Thiazolyl substituted aminopyrimidines were also made and tested as fungicides in U.S. Patent Publication No. US 2005/0038059, published February, 2005. Derivatives of thiazole were also synthesized by Sanner et al. and indicated to have activity inhibiting cdk5, cdk2, and GSK-3. U.S. Patent Publication No. US 2003/0078252, published Apr. 24, 2003.

Thiadiazole compounds useful for treating diseases mediated by PKB are disclosed in WO 2006/044860, published on Apr. 27, 2006, and in U.S. Patent Publication No. U.S. Patent Application Publication No. 2006/0154961, published on Jul. 13, 2006 both of which are hereby incorporated by reference in their entireties and for all purposes as if specifically set forth herein. Thiazole compounds useful treating disease mediated by PKB are disclosed in U.S. Patent Application Publication No. 2007/0173506, published on Jul. 26, 2007, which is hereby incorporated by reference in its entirety and for all purposes as if specifically set forth herein. Various heterocycle compounds are disclosed in WO 2008/036308, published on Mar. 27, 2008, which are reportedly useful in inhibiting the PKB pathway.

A need exists for new compounds that can be used to modulate PKB and can be used to treat various disease conditions associated with PKB.

SUMMARY OF THE INVENTION

This invention encompasses novel compounds useful for treating diseases or conditions mediated by PKB. The invention also encompasses the therapeutic use of such compounds and compositions thereof in the treatment of disease states associated with abnormal cell growth, such as cancer, or metabolic disease states, such as diabetes, or inflammation.

The invention further provides pharmaceutical compositions that include the compounds of the invention and the use of the compounds in the preparation of medicaments for treating various conditions and disease states.

In one aspect the invention comprises a compound of Formula I

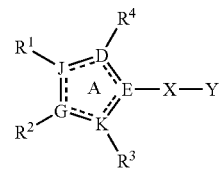

wherein:
Y is selected from

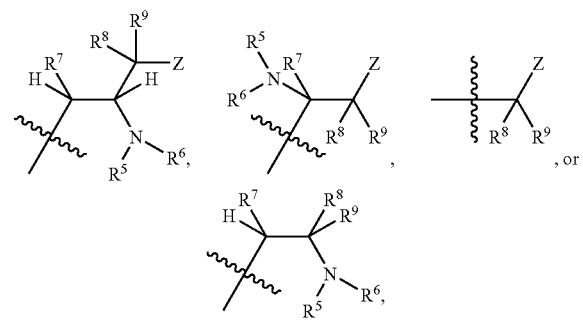

and the wavy line indicates the point of attachment to X, wherein:
D is selected from N, C, O, or S;
E is selected from N or C;
K is selected from N, C, O, or S;
G is selected from N or C:
J is selected from N, C, O, or S;
  and further wherein:
  at least one of D, E, K, G, and J is other than C;
  K is not S when D is N, E is C, G is C, and J is C;
  K is not S when D is N, J is N, E is C, and G is C;
  0 or 1 of D, K, and J is selected from O or S;
  at least two of E, D, K, G, and J are C;
  a dashed line indicates that a second bond between the ring atoms is optionally present; and
  ring A includes two double bonds;
X is —N($R^{10}$)— or —$CR^{10a}R^{10b}$—;
$R^1$ is absent if J is O, or S; or
$R^1$ is selected from —H, $C_1$-$C_6$ alkyl, —($C_1$-$C_6$ alkyl)-O—$R^{11}$, —($C_1$-$C_6$ haloalkyl)-O—$R^{11}$, —($C_2$-$C_6$ alkenyl)-O—$R^{11}$, —($C_1$-$C_6$ alkyl)N($R^{10}$)$_2$, —($C_1$-$C_6$ alkyl)aryl, —$CHR^{12}$—N(H)—$R^{11}$, —$CHR^{12}$—O—$R^{11}$, $C_2$-$C_6$ alkynyl, ($C_2$-$C_6$ alkynyl)-O—$R^{11}$, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl)-N($R^{10}$)S(O)$_2$—$R^{11}$, aryl, heteroaryl, cycloalkyl if J is N; or $R^1$ is absent if J is N and either of the bonds between J and G or J and D is a double bond; or
$R^1$ is selected from —H, halo, —$OR^{11}$, $C_1$-$C_6$ alkyl, —($C_1$-$C_6$ alkyl)-O—$R^{11}$, —($C_1$-$C_6$ haloalkyl)-O—$R^{11}$, —($C_2$-$C_6$ alkenyl)-O—$R^{11}$, —($C_1$-$C_6$ alkyl)N($R^{10}$)$_2$, —($C_1$-$C_6$ alkyl)aryl, —C(O)$R^{11}$, —C(O)O—$R^{11}$, —C(O)N($R^{10}$)$_2$, —$CHR^{12}$—N (H)—$R^{11}$, —$CHR^{12}$—O—$R^{11}$, $C_2$-$C_6$ alkynyl, ($C_2$-$C_6$ alkynyl)-O—$R^{11}$,     —C≡N,     —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl)-N($R^{10}$)S(O)$_2$—$R^{11}$, aryl, heteroaryl, cycloalkyl, or heterocyclyl if J is C;

$R^2$ is a carbocyclic ring system or is a heterocyclic ring system;

$R^3$ is absent if K is S or O; or $R^3$ is selected from —H, $C_1$-$C_6$ alkyl, —($C_1$-$C_6$ alkyl)aryl, or aryl if K is N; or is absent if K is N and either of the bonds between K and E or K and G is a double bond; or $R^3$ is selected from —H, $C_1$-$C_6$ alkyl, —($C_1$-$C_6$ alkyl)aryl, or aryl if K is C;

$R^4$ is absent if D is S or O; or $R^4$ is selected from —H, $C_1$-$C_6$ alkyl, —($C_1$-$C_6$ alkyl)aryl, or aryl if D is N; or is absent if D is N and either of the bonds between D and E or D and J is a double bond; or $R^4$ is selected from —H, $C_1$-$C_6$ alkyl, —($C_1$-$C_6$ alkyl)aryl, or aryl if D is C;

$R^5$ is —H, $C_1$-$C_8$ alkyl, —C(O)($CR^{13}R^{14}$)$_t$N($R^{10}$)$_2$, —C(O)($CR^{13}R^{14}$)$_t$, —C(O)$_2$($CR^{13}R^{14}$)$_t$, —($CR^{13}R^{14}$)$_t$(aryl), —($CR^{13}R^{14}$)$_t$(heteroaryl), —($CR^{13}R^{14}$)$_t$(cycloalkyl), or —($CR^{13}R^{14}$)$_t$(heterocyclyl);

$R^6$ and $R^{10}$, in each instance, are independently selected from —H, $C_1$-$C_8$ alkyl, —($C_1$-$C_6$ alkyl)aryl, or —C(O)($C_1$-$C_6$ alkyl);

$R^7$ is —H, —$OR^{11}$, —O—($C_1$-$C_6$ alkyl)-O—$R^{11}$, $C_1$-$C_6$ alkyl, $C_1$-$C_6$ alkenyl, —($C_1$-$C_6$ alkyl)-O—$R^{11}$, or —($C_1$-$C_6$ alkyl)-O—C(O)—$R^{11}$;

$R^8$ is —H, or $C_1$-$C_6$ alkyl;

$R^9$ is —H, —$OR^{11}$, —O—($C_1$-$C_6$ alkyl)-O—$R^{11}$, $C_1$-$C_6$ alkyl, $C_1$-$C_6$ alkenyl, —($C_1$-$C_6$ alkyl)-O—$R^{11}$, or —($C_1$-$C_6$ alkyl)-O—C(O)—$R^{11}$;

$R^{10a}$ and $R^{10b}$ are independently selected from —H, $C_1$-$C_8$ alkyl, —($C_1$-$C_6$ alkyl)aryl, $NR^5R^6$, or —C(O)($C_1$-$C_6$ alkyl);

$R^{11}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)-O—($C_1$-$C_6$ alkyl), cycloalkyl, or heterocyclyl;

$R^{12}$, $R^{13}$, and $R^{14}$, in each instance, are independently selected from —H, $C_1$-$C_6$ alkyl, or aryl;

Z is aryl or heteroaryl; and each t is independently selected from 0, 1, 2, or 3;

and further wherein:

each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—($C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;

or a pharmaceutically acceptable salt, hydrate, stereoisomer, or mixture thereof.

In some embodiments, the compound of Formula I has the Formula I'

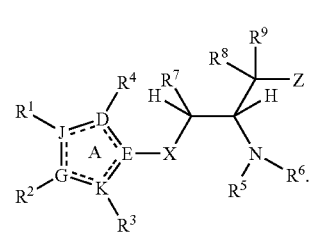

In some embodiments, X is —N($R^{10}$)—. In some such embodiments, $R^{10}$ is H. In other embodiments, $R^{10}$ is a $C_1$-$C_4$ alkyl group such as a methyl, ethyl, propyl, or butyl group. In some such embodiments, the compound of Formula I has the Formula I'.

In other embodiments, X is —$R^{10a}R^{10b}$—. In some such embodiments, at least one of $rR^{10a}$ or $R^{10b}$ is H. In some such embodiments, both $R^{10a}$ and $R^{10b}$ are H. In some such embodiments, the compound of Formula I has the Formula I'.

In other embodiments, Y has the formula

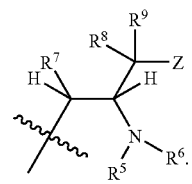

In other embodiments, Y has the formula

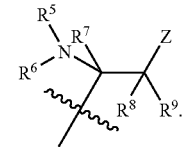

In other embodiments, Y has the formula

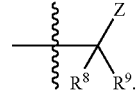

In other embodiments, Y has the formula

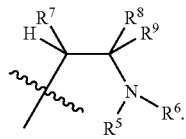

In some embodiments of any of those described above, two of E, D, K, G, and J are C and the other three of E, D, K, G, and J are not C. In other embodiments, three of E, D, K, G, and J are C and the other two of E, D, K, G, and J are not C. In still other embodiments, four of E, D, K, G, and J are C and the other one of E, D, K, G, and J is not C.

In other embodiments, the compound of Formula I has a formula selected from any of the following:

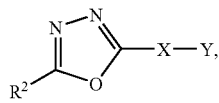 IA'

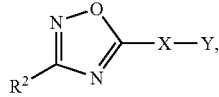 IB'

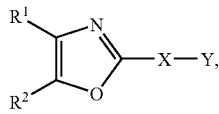 IC'

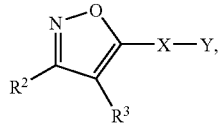 ID'

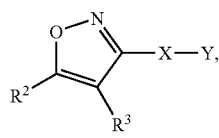 IE'

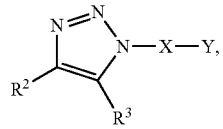 IF'

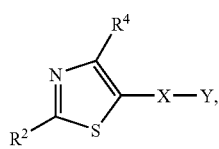 IG'

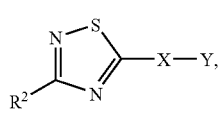 IH'

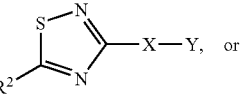 IJ'

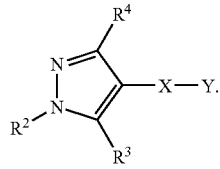 IK'

In some embodiments such embodiments, the compound of Formula I has the Formula IA'. In other embodiments, the compound of Formula I has the Formula IB'. In other embodiments, the compound of Formula I has the Formula IC'. In other embodiments, the compound of Formula I has the Formula ID'. In other embodiments, the compound of Formula I has the Formula IE'. In other embodiments, the compound of Formula I has the Formula IF'. In other embodiments, the compound of Formula I has the Formula IG'. In other embodiments, the compound of Formula I has the Formula IH'. In other embodiments, the compound of Formula I has the Formula IJ'. In other embodiments, the compound of Formula I has the Formula IK'. In still other embodiments, the compound of Formula I has the Formula IA', IB', IC', ID', or IE'.

In other embodiments, the compound of Formula I has a formula selected from any of the following:

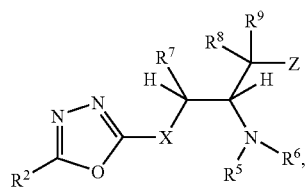 IA

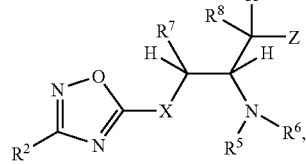 IB

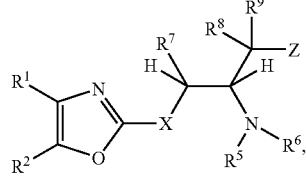 IC

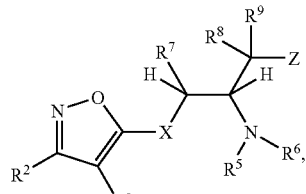 ID

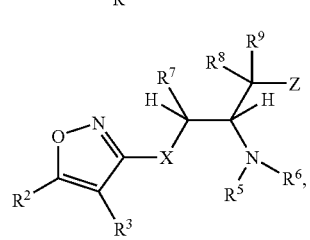 IE

-continued

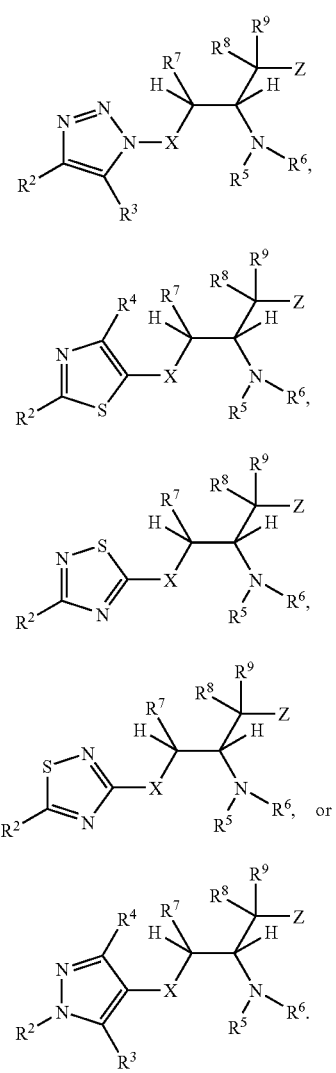

In some embodiments such embodiments, the compound of Formula I has the Formula IA. In other embodiments, the compound of Formula I has the Formula IB. In other embodiments, the compound of Formula I has the Formula IC. In other embodiments, the compound of Formula I has the Formula ID. In other embodiments, the compound of Formula I has the Formula IE. In other embodiments, the compound of Formula I has the Formula IF. In other embodiments, the compound of Formula I has the Formula IG. In other embodiments, the compound of Formula I has the Formula IH. In other embodiments, the compound of Formula I has the Formula IJ. In other embodiments, the compound of Formula I has the Formula IK. In still other embodiments, the compound of Formula I has the Formula IA, IB, IC, ID, or IE.

In other embodiments, the compound of Formula I has a formula selected from any one of the following:

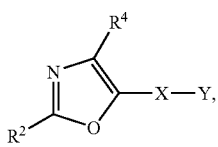

-continued

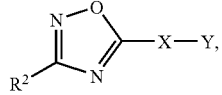

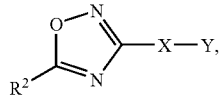

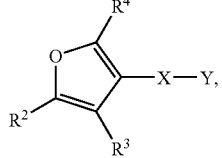

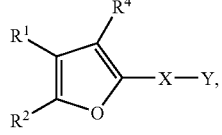

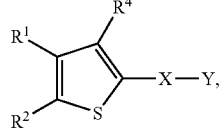

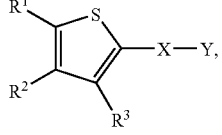

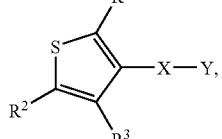

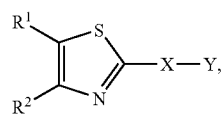

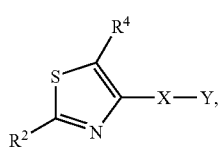

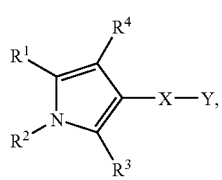

-continued
IIM'
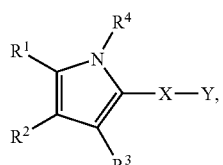
IIN'
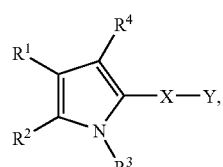
IIO'
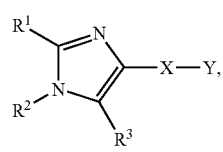
IIP'
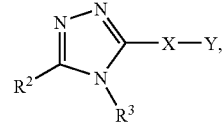
IIQ'
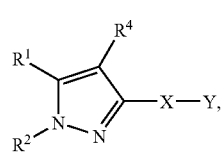
IIR'
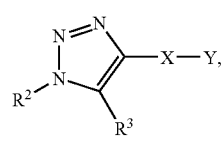
IIS'
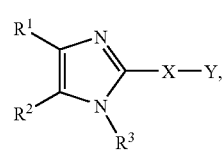
IIT'
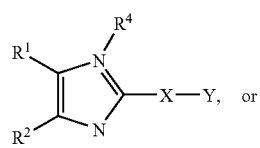, or
IIU'
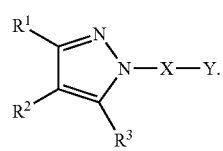.
In other embodiments, the compound of Formula I has a formula selected from any one of the following:
IIA
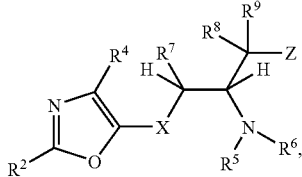
IIB
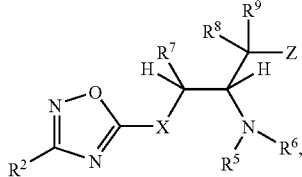
IIC
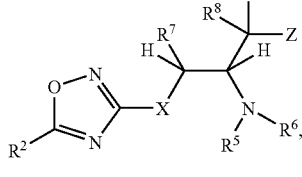
IID
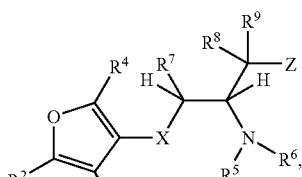
IIE
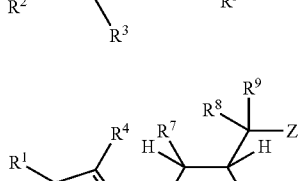
IIF
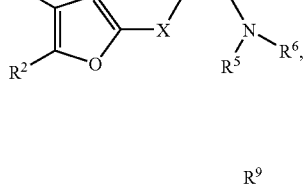
IIG
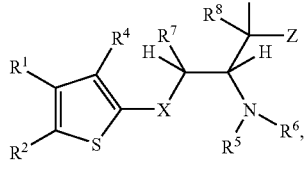
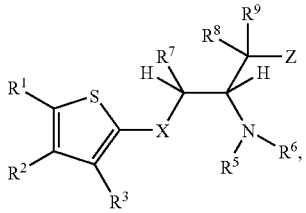

IIH 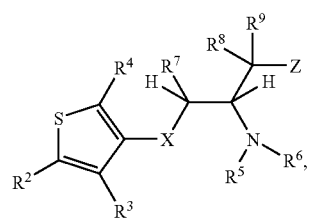
IIJ 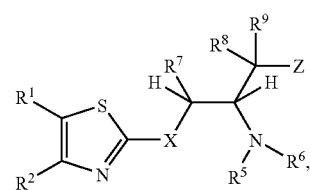
IIK 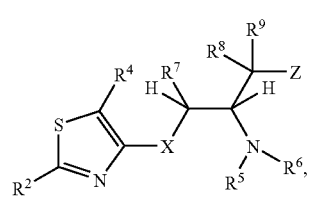
IIL 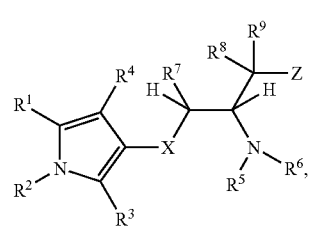
IIM 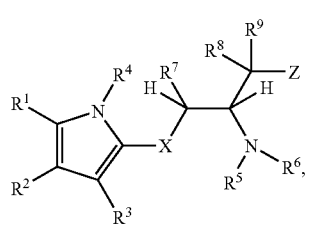
IIN 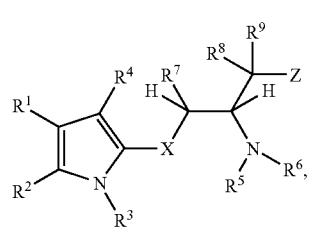
IIO 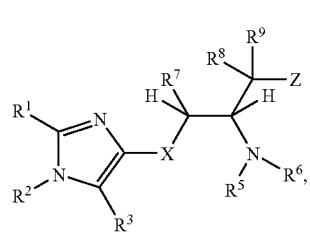
IIP 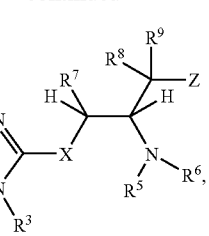
IIQ 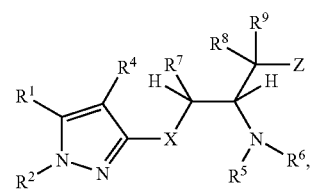
IIR 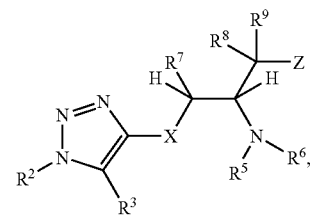
IIS 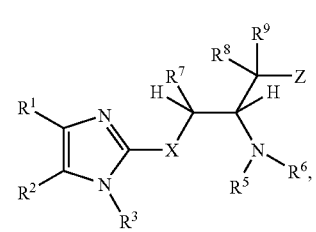
IIT 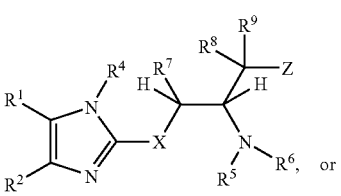
, or
IIU 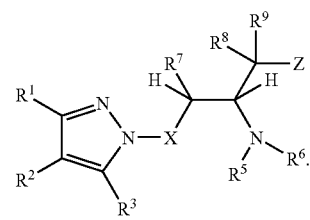
In other embodiments, the compound of Formula I has the Formula IIIA shown below:
IIIA 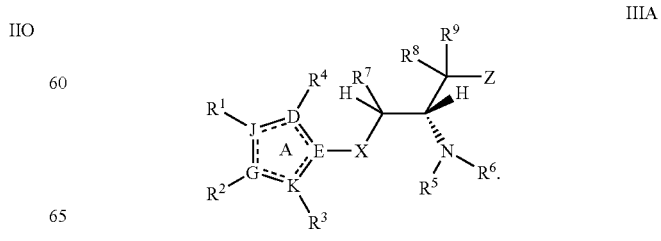

In other embodiments, the compound of Formula I has the Formula IIIB shown below:

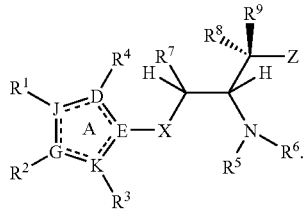

IIIB

In other embodiments, the compound of Formula I has the Formula IIIC shown below:

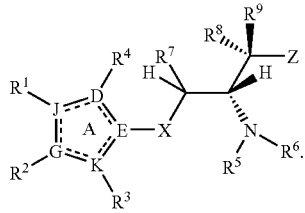

IIIC

In other embodiments, the compound of Formula I has the Formula IIID shown below:

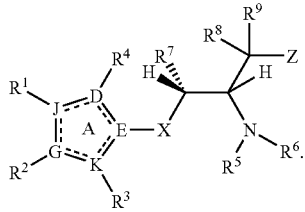

IIID

In other embodiments, the compound of Formula I has the Formula IIIE shown below:

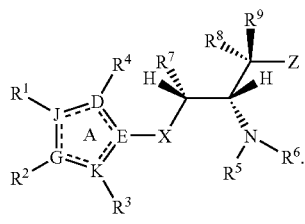

IIIE

In some embodiments of any of the embodiments described above, $R^1$ is —H.

In some embodiments of any of the embodiments described above, $R^3$ is absent or is —H. In other embodiments, $R^3$ is selected from —H, methyl, ethyl, propyl, butyl, pentyl, benzyl, —CH$_2$C(H)(CH$_3$)$_2$, or —CH$_2$CH$_2$NH$_2$.

In some embodiments of any of the embodiments described above, $R^4$ is absent or is —H. In other embodiments, $R^4$ is selected from —H, methyl, ethyl, propyl, butyl, or pentyl.

In some embodiments of any of the embodiments described above, $R^7$ is —H or C$_1$-C$_6$ alkyl. In some such embodiments, $R^7$ is —H or methyl.

In some embodiments of any of the embodiments described above, $R^8$ is —H.

In some embodiments of any of the embodiments described above, $R^9$ is —H. In other embodiments, $R^9$ is selected from $R^9$ is —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In still other embodiments, $R^9$ is selected from —H, methyl, ethyl, propyl, ethenyl, propenyl, hydroxymethyl, methoxymethyl, —CH$_2$—O—C(O)—(C$_1$-C$_6$ alkyl), 1-hydroxyethyl, or methoxymethoxy.

In some embodiments of any of the embodiments described above, Z is selected from optionally substituted phenyl, optionally substituted indolyl, optionally substituted naphthyl, optionally substituted pyridyl, or optionally substituted thiophenyl.

In some embodiments of any of the embodiments described above, Z is selected from phenyl, indolyl, naphthyl, pyridyl, or thiophenyl, each of which is optionally substituted with 1-3 substituents selected from —Cl, —F, —CF$_3$, —OH, —O—(C$_1$-C$_6$ alkyl), —O—(C$_1$-C$_6$ alkyl)-Cl, —O—(C$_1$-C$_6$ alkyl)-OH, —C$_1$-C$_6$ alkyl, —OCF$_3$, —NH(CO)—O—(C$_1$-C$_6$ alkyl)aryl, or —NH(CO)—O—(C$_1$-C$_6$ alkyl).

In some embodiments of any of the embodiments described above, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—CH$_2$-phenyl.

In some embodiments of any of those described above that are consistent therewith, $R^{10}$ is H.

In some embodiments of any of those described above, $R^5$ and $R^6$ are each H.

In some embodiments, $R^7$ is —H or C$_1$-C$_6$ alkyl, $R^8$ is —H, and $R^9$ is —H, —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In some such embodiments, $R^9$ is —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In some such embodiments, $R^5$, $R^6$, and $R^{10}$ are all H.

In some embodiments, $R^9$ is —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In some such embodiments, $R^5$, $R^6$, and $R^{10}$ are all H.

In other embodiments, $R^5$, $R^6$, and $R^{10}$ are all H.

In some embodiments of any of those described above, the carbocyclic ring system or the heterocyclic ring system of $R^2$ comprises at least one aromatic ring. In some embodiments, $R^2$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl. In some embodiments, of any of those described above, $R^2$ is selected from one of the following groups which may optionally be substituted and where the wavy line indicates the point of attachment to the ring A:

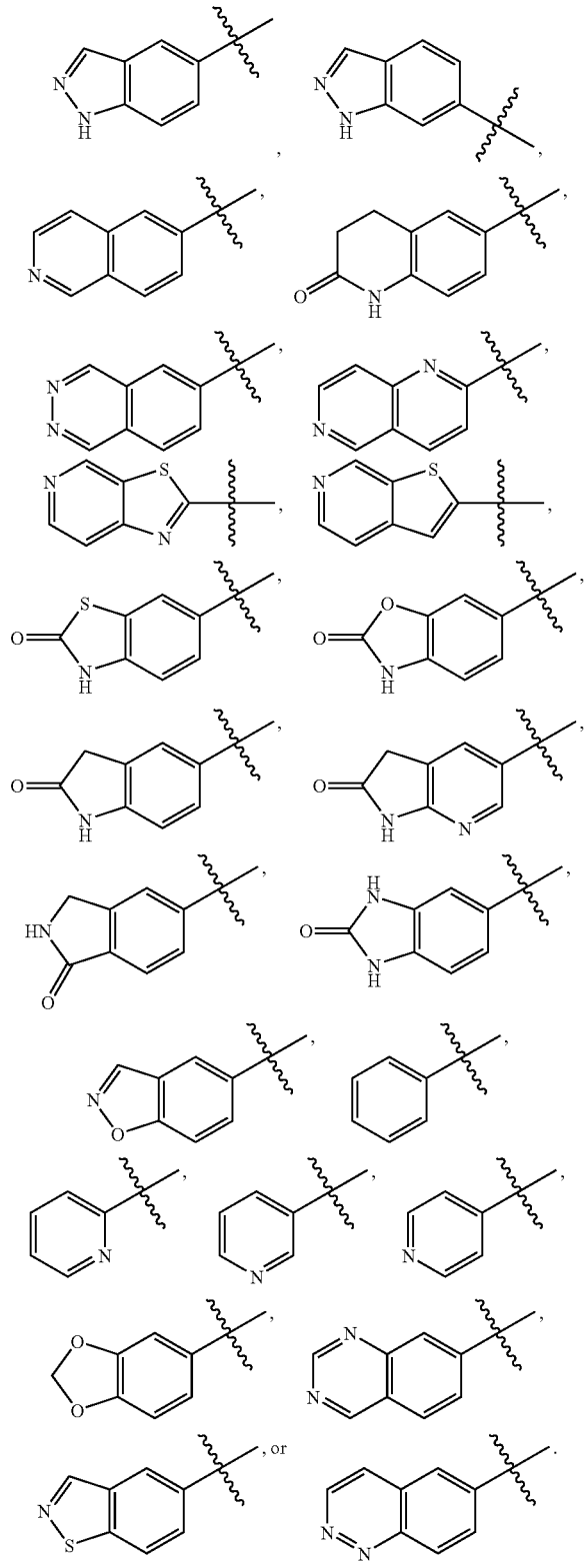

In other embodiments consistent with any of those described above, $R^2$ is selected from one of the following groups, where the wavy line indicates the point of attachment to the ring A:

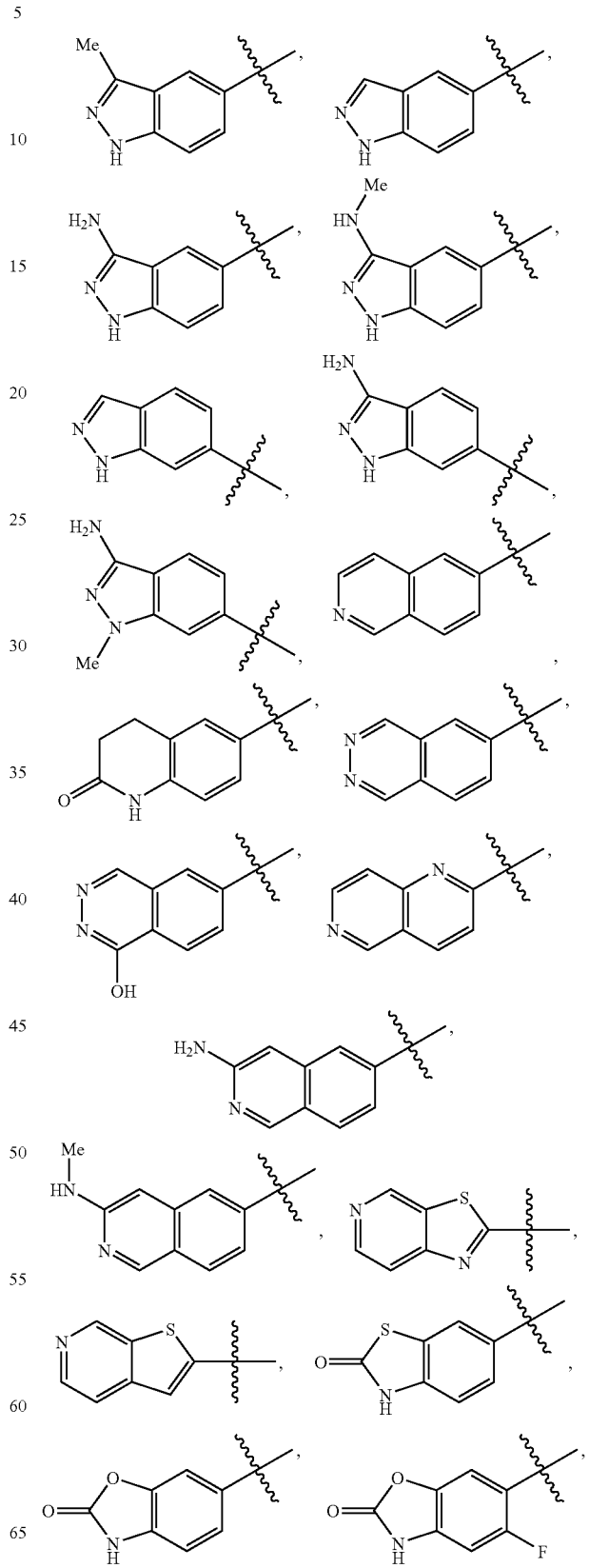

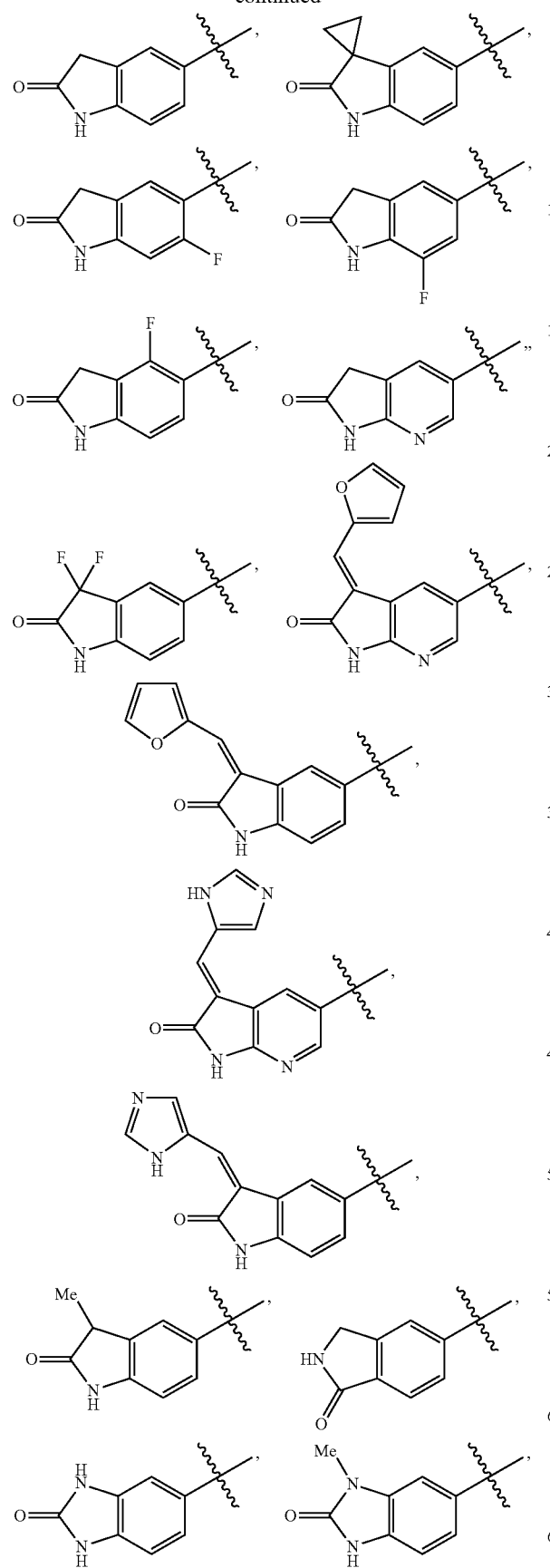

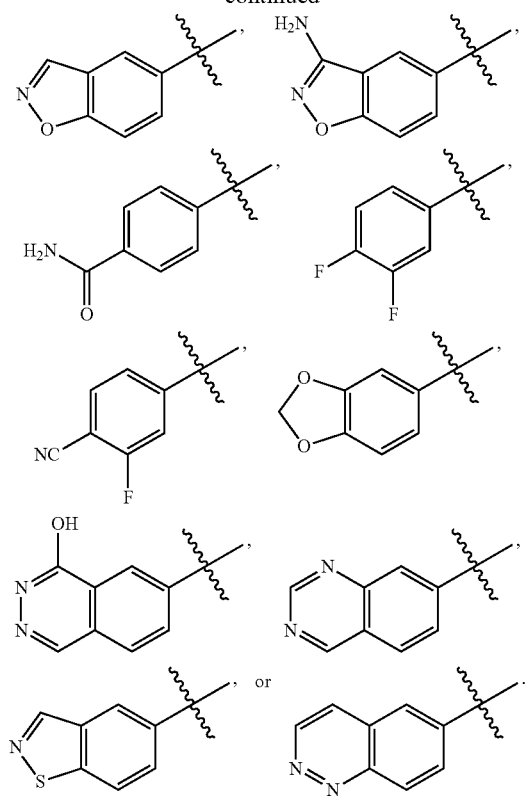

In some embodiments consistent with any of those described above. In other embodiments, $R^1$ is selected from —H, —C≡N, —Br, —Cl, —OH, —$CF_3$, —$CH_3$, —$CH_2CH_3$, —$CH_2CH_2OH$, —C(H)($CH_3$)$OCH_3$, —$CH_2OCH_2CF_3$, —$CH_2$N(H)$CH_3$, —$CH_2$N($CH_3$)$_2$, —$CF_2CH_2OH$, cyclopropyl, furanyl, tetrahydrofuranyl, phenyl, 2,3-difluorophenyl, 3,4-difluorophenyl, 4-fluorophenyl, 3-fluorophenyl, 2-fluorophenyl, pyridyl, oxazolyl, hydroxymethyl, methoxymethyl, ethoxymethyl, —C(O)OMe, —C(O)N(H)$CH_2CH_2OH$, —C(O)N(H)$CH_3$, —C(O)$NH_2$, —C(O)N($CH_3$)$_2$, or a group selected from one of the following groups where the wavy line indicates the point of attachment to the ring A:

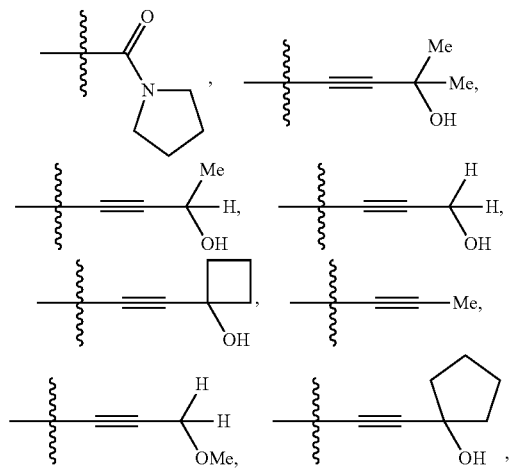

-continued

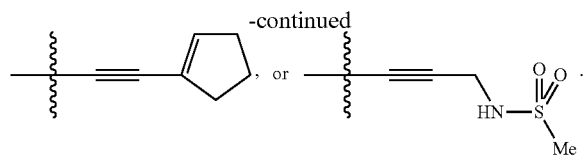

In another aspect, the invention comprises a pharmaceutically acceptable salt, hydrate, or solvate of a compound of any of the formulae or embodiments described above. In one embodiment, the pharmaceutically acceptable salts are selected from ammonium trifluoroacetate and ammonium chloride.

In another aspect, the invention comprises a pharmaceutical composition comprising a pharmaceutically-acceptable carrier and a compound of any of the formulae or embodiments described above and/or a salt of any of the compounds of any of the embodiments. In some embodiments, the invention also provides the use of a compound of any of the embodiments in the manufacture of a medicament for carrying out any of the methods of any of the embodiments of the invention. Such compositions and medicaments may further include one or more additional therapeutic agent. Therefore, in some embodiments, the composition or medicament includes at least one additional therapeutic agent.

In another aspect, the invention comprises a method for treating a kinase-mediated disorder in a mammal comprising administering to the mammal a therapeutically effective amount of a compound of any of the formulae or embodiments described above or a pharmaceutical composition of the invention. In some embodiments, the invention provides the use of a compound of any of the formulae or embodiments described above or a pharmaceutical composition of the invention for treating a kinase-mediated disorder in a mammal. The disorder can be one that is mediated by kinases including IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some embodiments, the disorder is mediated by PKB, and in some embodiments is mediated by PKBα. In some embodiments, the method comprises selective inhibition of PKB. In some such embodiments, the method comprises selective inhibition of PKBα.

In another embodiment, the invention encompasses any of the compounds of any of the embodiments that have selective kinase activity—i.e., they possess significant activity against one specific kinase while possessing less or minimal activity against a different kinase. In some embodiments, the compounds have selective PKB inhibition activity. In some such embodiments, the compounds have selective PKBα inhibition activity. In other embodiments, the invention provides the use of a compound of Formula I or Formula II or a pharmaceutical composition of the invention for selectively inhibiting a kinase activity. In some embodiments, PKB is selectively inhibited. In some such embodiments, PKBα is selectively inhibited.

In one embodiment, the invention provides a method of treating a proliferation-related disorder in a mammal in need thereof. Such methods include administering to the mammal a therapeutically effective amount of a compound of any of the embodiments described herein or a pharmaceutical composition comprising the compound. Another embodiment of the invention comprises treating abnormal cell growth by administering a therapeutically effective amount of a compound of the invention or a pharmaceutical composition of the invention to a subject in need thereof. In some embodiments, the invention provides the use of a compound of any of the embodiments or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

In another embodiment, the invention comprises a method of administering a therapeutically effective amount of a compound of any of the embodiments to a mammal for treating disease states or conditions selected from diabetes, inflammation, and metabolic disorders. In other embodiments, the invention provides the use of a compound of any of the embodiments or a pharmaceutical composition of the invention for treating a disease state or a condition selected from diabetes, inflammation, and metabolic disorders.

In another embodiment, the invention encompasses a method for treating or preventing cancer in a patient in need thereof, comprising administering to the patient a therapeutically or prophylactically effective amount of a compound of any of the embodiments and a pharmaceutically acceptable excipient, carrier, or vehicle. In other embodiments, the invention provides the use of a compound of any of the embodiments or a pharmaceutical composition of the invention for treating or preventing cancer in a patient such as in a human cancer patient. In some embodiments, the cancer is a tumor.

In another aspect, the invention encompasses a method for treating or preventing cancer in a patient in need thereof, comprising administering to the patient a therapeutically or prophylactically effective amount of a compound of any of the embodiments and at least one additional therapeutic agent.

Further objects, features, and advantages of the invention will be apparent from the following detailed description.

DETAILED DESCRIPTION OF THE INVENTION

1.1 Definitions

Where the following terms are used in this specification, they are used as defined below:

The terms "comprising" and "including" are used herein in their open, non-limiting sense. For example, a composition comprising A and B may also include other components such as C, D, and E.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include, but are not limited to, -methyl, -ethyl, -n-propyl, -n-butyl, -n-pentyl, -n-hexyl, -n-heptyl, -n-octyl, -n-nonyl and -n-decyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimetheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. An alkyl group may be designated as having a certain number of carbon atoms. For example, an alkyl group having from 1 to 8 carbon atoms may be designated as a $C_1$-$C_8$ alkyl group whereas an alkyl group having from 1 to 6 carbon atoms may be designated as a $C_1$-$C_6$ alkyl group. When such terms are used in conjunction with others such as in the term "—($C_1$-$C_6$ alkyl)aryl", the "-" symbol indicates the point of attachment to the rest of the molecule, and the term indicates that one of the hydrogens of the alkyl group is replaced by a bond to an aryl group. For example, a —($C_1$-$C_2$ alkyl)aryl includes such groups as —$CH_2$Ph, —$CH_2CH_2$Ph, and —CH(Ph)$CH_3$.

When so designated, an alkyl group can be interrupted by one or more heteroatoms such as N, O, S, or Si atoms. Insertion of a heteroatom in the alkyl group forms a heteroalkyl group. In some embodiments, the heteroatom is a N, O, or S atom. The term "heteroalkyl," by itself or in combination with another term, means, unless otherwise stated, a stable straight or branched chain radical, or combination thereof, that includes carbon atoms and from one to three heteroatoms selected from the group consisting of O, N, and S. The nitrogen and sulfur atoms may optionally be oxidized, and the nitrogen heteroatom may optionally be quaternized. The heteroatom(s) O, N, and S may be placed at any position in the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, and —$CH_2$—$CH_2$—S(O)$_2$—$CH_3$. Up to two heteroatoms may be consecutive or adjacent to one another, such as, for example, in —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2$OH (one carbon atom and one heteroatom replacing a carbon atom) and —$CH_2$SH.

To further illustrate the definition of a heteroalkyl group, where the heteroatom is oxygen, a heteroalkyl group is an oxyalkyl group. For instance, ($C_2$-$C_5$)oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2$OH, and the like.

As used herein, unless otherwise specified, the term "alkenyl" means an unsaturated straight chain or branched non-cyclic hydrocarbon having from 2 to 20 carbon atoms and at least one carbon-carbon double bond. Preferably, an alkenyl has 2 to 10 carbon atoms and most preferably has 2 to 4 carbon atoms. Exemplary straight chain alkenyls include, but are not limited to, -but-3-ene, -hex-4-ene, and -oct-1-ene. Exemplary branched chain alkenyls include, but are not limited to, -2-methyl-but-2-ene, -1-methyl-hex-4-ene, and -4-ethyl-oct-1-ene. An alkenyl group can be substituted or unsubstituted. An alkenyl group may be designated as having a certain number of carbon atoms. For example, an alkenyl group having from 2 to 8 carbon atoms may be designated as a $C_2$-$C_8$ alkenyl group whereas an alkenyl group having from 2 to 6 carbon atoms may be designated as a $C_2$-$C_6$ alkenyl group.

As used herein, and unless otherwise specified, the term "alkynyl" means an alkyl group in which one or more carbon-carbon single bonds is replaced with an equivalent number of carbon-carbon triple bonds. An alkynyl group must comprise at least two carbon atoms, and can be substituted or unsubstituted. An alkynyl group may be designated as having a certain number of carbon atoms. For example, an alkynyl group having from 2 to 8 carbon atoms may be designated as a $C_2$-$C_8$ alkynyl group whereas an alkynyl group having from 2 to 6 carbon atoms may be designated as a $C_2$-$C_6$ alkynyl group.

As used herein, the term "halo" means a halogen atom such as a fluorine, chlorine, bromine, or iodine atom (—F, —Cl, —Br, or —I).

As used herein, unless otherwise specified, the term "haloalkyl" means an alkyl group in which one or more hydrogens has been replaced by a halogen atom. A halogen atom is a fluorine, chlorine, bromine, or iodine atom. The number of halogen atoms in a haloalkyl group may range from one to (2m'+1), where m' is the total number of carbon atoms in the alkyl group. For example, the term "halo($C_1$-$C_4$) alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, an alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

As used herein, the term "cyano" means a —C≡N group.
As used herein, the term "nitro" means a —$NO_2$ group.
As used herein, the term "oxo" means a =O group.
As used herein, the terms "hydroxy" and "hydroxyl" mean an —OH group.

As used herein, unless otherwise specified, the term "hydroxyalkyl" means an alkyl group in which one or more hydrogens has been replaced with a hydroxyl group.

The term "alkoxy" means a structure of the formula —O-alkyl where alkyl has the meaning set forth above.

The term "haloalkoxy" means an alkoxy group in which one or more hydrogen is replaced by a halogen atom.

The term "hydroxyalkoxy" means an alkoxy group in which one or more hydrogen is replaced by a hydroxy group.

The term "amino" means an —NH$_2$ group.

The terms "alkylamino" and "dialkylamino" mean a structure of the formula —NH-alkyl and —N(alkyl)alkyl, respectively, wherein the alkyl is as defined above. The alkyl groups in dialkylamino groups may be the same or different.

As used herein, the terms "carbocyclic ring system" and "carbocyclic" mean a ring system in which all the ring members are carbon atoms. Carbocyclic ring systems typically include from 3 to 14 ring atoms. Carbocyclic ring systems may be aromatic or may be non-aromatic. Carbocyclic ring systems include cycloalkyl rings and may also include fused ring systems. Examples of fused ring carbocyclic ring systems include, but are not limited to, decalin, norbornane, tetrahydronaphthalene, naphthalene, indene, and adamantane. The ring atoms in a carbocyclic ring system may be substituted or unsubstituted.

As used herein, the terms "heterocyclic ring system", "heterocyclic" and "heterocyclyl" means a carbocyclic ring system in which at least one ring atom is a heteroatom such as a N, O, or S. In some embodiments, the heterocyclic ring system includes from 1 to 4 heteroatoms. In some embodiments, the heteroatom is selected from N, O, or S. Heterocyclic ring systems may include one ring or may include fused ring systems. By way of nonlimiting example, heterocyclic ring systems may include two six membered rings that are fused to one another or may include one five membered ring and one six membered ring that are fused to one another. Heterocyclic ring systems may be aromatic or may be non-aromatic and may be unsaturated, partially unsaturated, or saturated. The ring atoms in a heterocyclic ring system may be substituted or unsubstituted.

As used herein, unless otherwise specified the term "aryl" means a carbocyclic ring or ring system containing from 6 to 14 ring atoms wherein at least one ring is aromatic. The ring atoms of a carbocyclic aryl group are all carbon atoms. Aryl groups include mono-, bi-, and tricyclic groups as well as benzo-fused carbocyclic moieties such as, but not limited to, 5,6,7,8-tetrahydronaphthyl and the like. In some embodiments, the aryl group is a monocyclic ring or is a bicyclic ring. Representative aryl groups include, but are not limited to, phenyl, tolyl, anthracenyl, fluorenyl, indenyl, azulenyl, phenanthrenyl and naphthyl. An aryl group can be unsubstituted or substituted.

The term "heteroaryl" means an aryl group in which one or more, but not all, of the ring carbon atoms in any ring, whether aromatic or not, is replaced by a hetero atom. For example pyridine is a heteroaryl group as is a compound in which benzene is fused to a nonaromatic ring that includes at least one heteroatom. Exemplary heteroatoms are N, O, S, and Si. In some embodiments, the heteroatoms are N, O, or S. A heteroaryl group can be unsubstituted or substituted. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, S-thiazolyl, 2-furanyl, 3-furanyl, dibenzofuryl, 2-thienyl (2-thiophenyl), 3-thienyl (3-thiophenyl), 2-pyridyl, 3-pyridyl, 4-pyridyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl. Non-limiting examples of other heteroaryl groups include pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl. The nonaromatic rings in aryl and heteroaryl groups that include nonaromatic rings may be substituted with various groups as described herein including the oxo (=O) group for example in groups such as, but not limited to, the benzo[d]thiazol-2(3H)-onyl group.

The term "cycloalkyl" means an unsaturated or saturated hydrocarbon that forms at least one ring, having from 3 to 20 ring carbon atoms, and in some embodiments, from 3 to 10 ring, from 3 to 8, or from 3 to 6 carbon atoms. The rings in a cycloalkyl group are not aromatic. A cycloalkyl group can be unsubstituted or substituted.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "PKB" refers to protein kinase B, also known as AKT.

The term "treating" refers to:

(i) preventing a disease, disorder, or condition from occurring in a mammal that may be predisposed to the disease, disorder and/or condition, but may not yet have been diagnosed as having it;

(ii) inhibiting the disease, disorder, or condition, i.e., arresting its development; and (iii) relieving the disease, disorder, or condition, i.e., causing regression of the disease, disorder, and/or condition, or one or more of its symptoms.

The term "preventing" refers to the ability of a compound or composition of the invention to prevent a disease identified herein in mammals diagnosed as having the disease or who are at risk of developing such disease. The term also encompasses preventing further progression of the disease in mammals that are already suffering from or have symptoms of the disease.

The term "mammal" refers to non-human animals or humans.

As used herein, the term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of a cancer, the term "patient" or "subject" preferably means a monkey or a human, most preferably a human. In a specific embodiment, the patient or subject is afflicted by a cancer.

As used herein, a "therapeutically effective amount" refers to an amount of a compound of the invention, or prodrug thereof, sufficient to provide a benefit in the treatment or prevention of a condition or disease such as cancer, to delay or minimize symptoms associated with the condition or disease, or to cure or ameliorate the disease or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

As used herein, a "prophylactically effective amount" refers to an amount of a compound of the invention or other active ingredient sufficient to result in the prevention of a condition or disease such as cancer, or recurrence or metastasis of cancer. A prophylactically effective amount may refer to an amount sufficient to prevent initial disease or the recurrence or spread of the disease. The term preferably encompasses a non-toxic amount that improves overall prophylaxis or enhances the prophylactic efficacy of or synergies with another prophylactic or therapeutic agent.

As used herein, "in combination" refers to the use of more than one prophylactic and/or therapeutic agents simultaneously or sequentially. The agents may be selected and administered in such a manner that their respective effects are additive or synergistic.

As used herein, the term "pharmaceutically acceptable salts" refers to salts prepared from pharmaceutically acceptable non-toxic acids or bases including inorganic and organic acids and bases. If the Formula I or Formula II compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the Formula I or Formula II compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The neutral forms of the compounds may be regenerated from the salt by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. The term "prodrug" is intended to mean any chemical entity that, after administration, is converted to a different therapeutically effective chemical entity. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

The compounds of this invention may contain one or more asymmetric centers and thus occur as racemates and racemic mixtures, scalemic mixtures, single enantiomers, individual diastereomers, and diastereomeric mixtures. All such isomeric forms of these compounds are expressly included in the present invention.

As used herein and unless otherwise indicated, the term "optically pure" or "stereomerically pure" means a composition that comprises one stereoisomer of a compound and is substantially free of other stereoisomers of that compound. For example, a stereomerically pure compound having one chiral center will be substantially free of the opposite enantiomer of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al. (1997) *Tetrahedron* 33:2725; Eliel, E. L., *Stereochemistry of Carbon Compounds* (McGraw-Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

The compounds of the invention may exhibit the phenomenon of tautomerism. While the structural formulas set forth herein cannot expressly depict all possible tautomeric forms, it is to be understood that these structures are intended to represent all tautomeric forms of the depicted compound and are not to be limited merely to the specific compound form depicted by the formula drawings.

Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention.

1.2 Compounds

The compounds described herein are useful for treating diseases or conditions mediated by various kinases such as PKB. The invention encompasses the therapeutic use of such compounds and compositions thereof in the treatment of disease states associated with abnormal cell growth, such as cancer, or metabolic disease states, such as diabetes, or inflammation. The invention further provides pharmaceutical compositions that include the compounds of the invention and the use of the compounds in the preparation of medicaments or pharmaceutical formulations or compositions for treating various conditions and disease states.

In one aspect the invention comprises a compound of Formula I

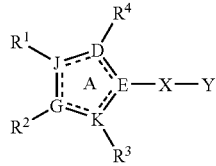

I wherein:
Y is selected from

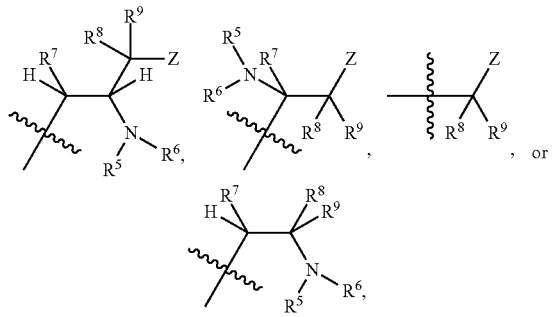

and the wavy line indicates the point of attachment to X, wherein:
D is selected from N, C, O, or S;
E is selected from N or C;
K is selected from N, C, O, or S;
G is selected from N or C;
J is selected from N, C, O, or S;
and further wherein:
   at least one of D, E, K, G, and J is other than C;
   K is not S when D is N, E is C, G is C, and J is C;
   K is not S when D is N, J is N, E is C, and G is C;
   0 or 1 of D, K, and J is selected from O or S;
   at least two of E, D, K, G, and J are C;
   a dashed line indicates that a second bond between the ring atoms is optionally present; and
   ring A includes two double bonds;
X is —N($R^{10}$)— or —C$R^{10a}R^{10b}$—;
$R^1$ is absent if J is O, or S; or
$R^1$ is selected from —H, $C_1$-$C_6$ alkyl, —($C_1$-$C_6$ alkyl)-O—$R^{11}$, —($C_1$-$C_6$ haloalkyl)-O—$R^{11}$, —($C_2$-$C_6$ alkenyl)-O—$R^{11}$, —($C_1$-$C_6$ alkyl)N($R^{10}$)$_2$, —($C_1$-$C_6$ alkyl)aryl, —CH$R^{12}$—N(H)—$R^{11}$, —CH$R^{12}$—O—$R^{11}$, $C_2$-$C_6$ alkynyl, ($C_2$-$C_6$ alkynyl)-O—$R^{11}$, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl)-N($R^{10}$)S(O)$_2$—$R^{11}$, aryl, heteroaryl, cycloalkyl if J is N; or $R^1$ is absent if J is N and either of the bonds between J and G or J and D is a double bond; or
$R^1$ is selected from —H, halo, —O$R^{11}$, $C_1$-$C_6$ alkyl, —($C_1$-$C_6$ alkyl)-O—$R^{11}$, —($C_1$-$C_6$ haloalkyl)-O—$R^{11}$, —($C_2$-$C_6$ alkenyl)-O—$R^{11}$, —($C_1$-$C_6$ alkyl)N($R^{10}$)$_2$, —($C_1$-$C_6$ alkyl)aryl, —C(O)$R^{11}$, —C(O)O—$R^{11}$, —C(O)N($R^{10}$)$_2$, —CH$R^{12}$—N(H)—$R^{11}$, —CH$R^{12}$—O—$R^{11}$, $C_2$-$C_6$ alkynyl, ($C_2$-$C_6$ alkynyl)-O—$R^{11}$, —C≡N, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl)-N($R^{10}$)S(O)$_2$—$R^{11}$, aryl, heteroaryl, cycloalkyl, or heterocyclyl if J is C;
$R^2$ is a carbocyclic ring system or is a heterocyclic ring system;
$R^3$ is absent if K is S or O; or
$R^3$ is selected from —H, $C_1$-$C_6$ alkyl, —($C_1$-$C_6$ alkyl)aryl, or aryl if K is N; or is absent if K is N and either of the bonds between K and E or K and G is a double bond; or
$R^3$ is selected from —H, $C_1$-$C_6$ alkyl, —($C_1$-$C_6$ alkyl)aryl, or aryl if K is C;
$R^4$ is absent if D is S or O; or
$R^4$ is selected from —H, $C_1$-$C_6$ alkyl, —($C_1$-$C_6$ alkyl)aryl, or aryl if D is N; or is absent if D is N and either of the bonds between D and E or D and J is a double bond; or
$R^4$ is selected from —H, $C_1$-$C_6$ alkyl, —($C_1$-$C_6$ alkyl)aryl, or aryl if D is C;
$R^5$ is —H, $C_1$-$C_8$ alkyl, —C(O)(C$R^{13}R^{14}$)$_t$N($R^{10}$)$_2$, —C(O)(C$R^{13}R^{14}$)$_t$, —C(O)$_2$(C$R^{13}R^{14}$)$_t$, —(C$R^{13}R^{14}$)$_t$(aryl), —(C$R^{13}R^{14}$)$_t$(heteroaryl), —(C$R^{13}R^{14}$)$_t$(cycloalkyl), or —(C$R^{13}R^{14}$)$_t$(heterocyclyl);
$R^6$ and $R^{10}$, in each instance, are independently selected from —H, $C_1$-$C_8$ alkyl, —($C_1$-$C_6$ alkyl)aryl, or —C(O)($C_1$-$C_6$ alkyl);
$R^7$ is —H, —O$R^{11}$, —O—($C_1$-$C_6$ alkyl)-O—$R^{11}$, $C_1$-$C_6$ alkyl, $C_1$-$C_6$ alkenyl, —($C_1$-$C_6$ alkyl)-O—$R^{11}$, or —($C_1$-$C_6$ alkyl)-O—C(O)—$R^{11}$;
$R^8$ is —H, or $C_1$-$C_6$ alkyl;
$R^9$ is —H, —O$R^{11}$, —O—($C_1$-$C_6$ alkyl)-O—$R^{11}$, $C_1$-$C_6$ alkyl, $C_1$-$C_6$ alkenyl, —($C_1$-$C_6$ alkyl)-O—$R^{11}$, or —($C_1$-$C_6$ alkyl)-O—C(O)—$R^{11}$;
$R^{10a}$ and $R^{10b}$ are independently selected from —H, $C_1$-$C_8$ alkyl, —($C_1$-$C_6$ alkyl)aryl, N$R^5R^6$, or —C(O)($C_1$-$C_6$ alkyl);
$R^{11}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)-O—($C_1$-$C_6$ alkyl), cycloalkyl, or heterocyclyl;
$R^{12}$, $R^{13}$, and $R^{14}$, in each instance, are independently selected from —H, $C_1$-$C_6$ alkyl, or aryl;

Z is aryl or heteroaryl; and
each t is independently selected from 0, 1, 2, or 3;
and further wherein:
each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—($C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or
—O-aryl;
or a pharmaceutically acceptable salt, hydrate, stereoisomer, or mixture thereof.

In some embodiments, the compound of Formula I has the Formula I'

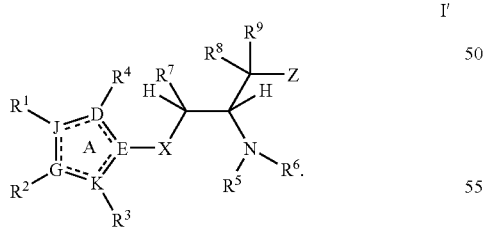

In some embodiments, X is —N($R^{10}$)—. In some such embodiments, $R^{10}$ is H. In other embodiments, $R^{10}$ is a $C_1$-$C_4$ alkyl group such as a methyl, ethyl, propyl, or butyl group. In some such embodiments, the compound of Formula I has the Formula I'.

In other embodiments, X is —$CR^{10a}R^{10b}$—. In some such embodiments, at least one of r$R^{10a}$ or $R^{10b}$ is H. In some such embodiments, both $R^{10a}$ and $R^{10b}$ are H. In some such embodiments, the compound of Formula I has the Formula I'.

In other embodiments, Y has the formula

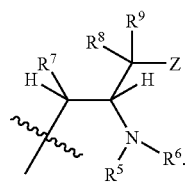

In other embodiments, Y has the formula

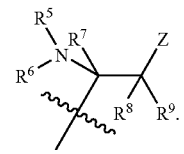

In other embodiments, Y has the formula

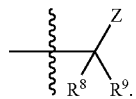

In other embodiments, Y has the formula

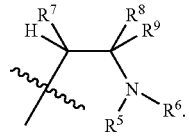

In some embodiments of any of those described above, two of E, D, K, G, and J are C and the other three of E, D, K, G, and J are not C. In other embodiments, three of E, D, K, G, and J are C and the other two of E, D, K, G, and J are not C. In still other embodiments, four of E, D, K, G, and J are C and the other one of E, D, K, G, and J is not C.

In other embodiments, the compound of Formula I has a formula selected from any of the following:

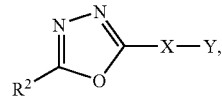

IA'

IB'

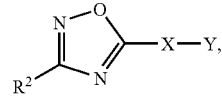

IC'

-continued

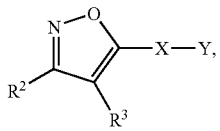
ID'

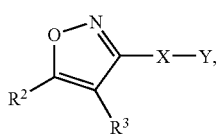
IE'

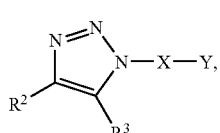
IF'

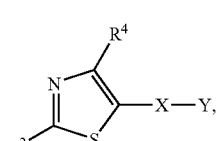
IG'

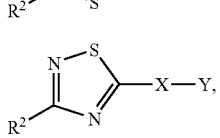
IH'

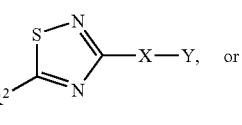
IJ', or

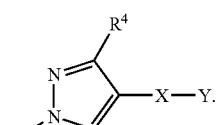
IK'

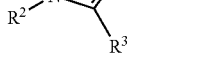

In some embodiments such embodiments, the compound of Formula I has the Formula IA'. In other embodiments, the compound of Formula I has the Formula IB'. In other embodiments, the compound of Formula I has the Formula IC'. In other embodiments, the compound of Formula I has the Formula ID'. In other embodiments, the compound of Formula I has the Formula IE'. In other embodiments, the compound of Formula I has the Formula IF'. In other embodiments, the compound of Formula I has the Formula IG'. In other embodiments, the compound of Formula I has the Formula IH'. In other embodiments, the compound of Formula I has the Formula IJ'. In other embodiments, the compound of Formula I has the Formula IK'. In still other embodiments, the compound of Formula I has the Formula IA', IB', IC', ID', or IE'.

In other embodiments, the compound of Formula I has a formula selected from any of the following:

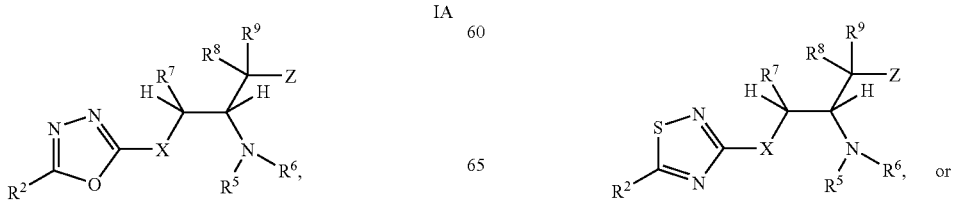
IA

-continued

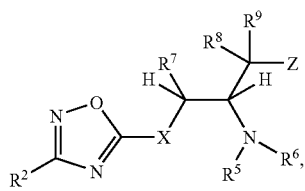
IB

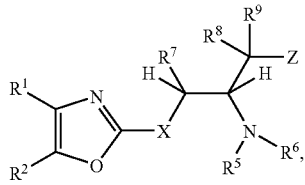
IC

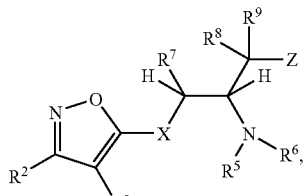
ID

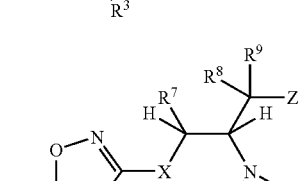
IE

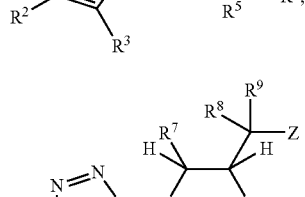
IF

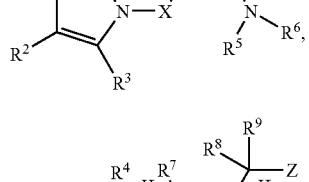
IG

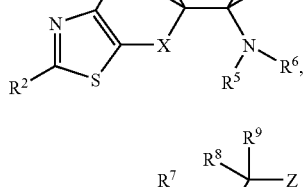
IH

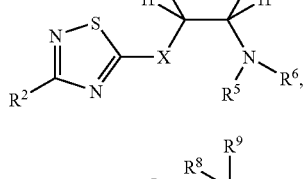
IJ

In some embodiments such embodiments, the compound of Formula I has the Formula IA. In other embodiments, the compound of Formula I has the Formula IB. In other embodiments, the compound of Formula I has the Formula IC. In other embodiments, the compound of Formula I has the Formula ID. In other embodiments, the compound of Formula I has the Formula IE. In other embodiments, the compound of Formula I has the Formula IF. In other embodiments, the compound of Formula I has the Formula IG. In other embodiments, the compound of Formula I has the Formula IH. In other embodiments, the compound of Formula I has the Formula IJ. In other embodiments, the compound of Formula I has the Formula IK. In still other embodiments, the compound of Formula I has the Formula IA, IB, IC, ID, or IE.

In other embodiments, the compound of Formula I has a formula selected from any one of the following:

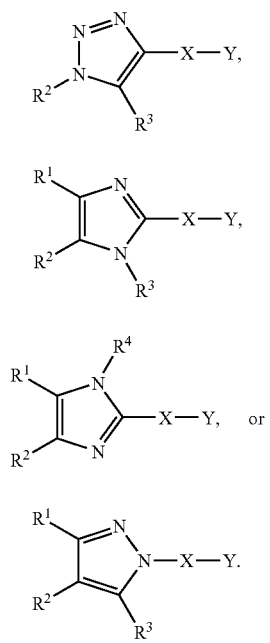
In other embodiments, the compound of Formula I has a formula selected from any one of the following:
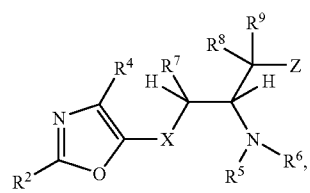
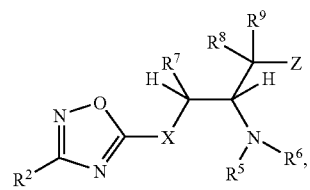
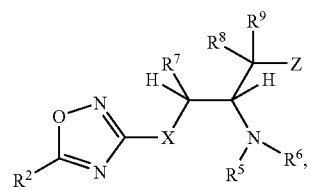
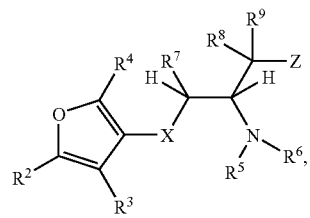
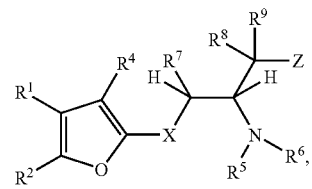
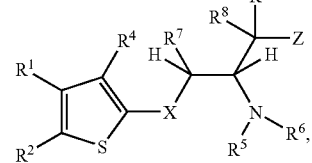
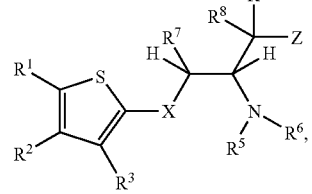
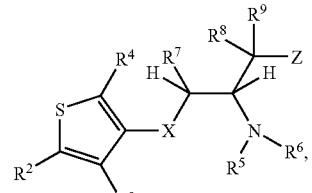
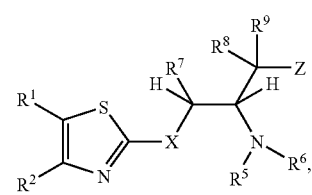
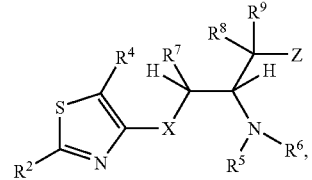
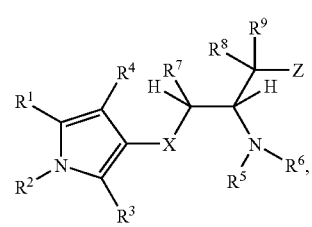

-continued
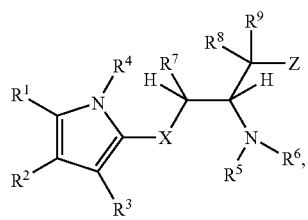
IIM
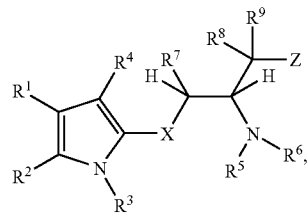
IIN
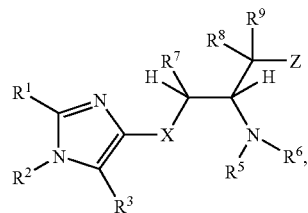
IIO
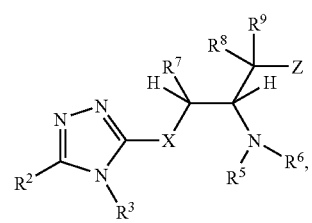
IIP
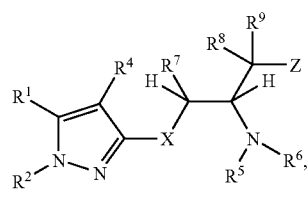
IIQ
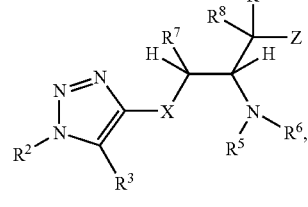
IIR
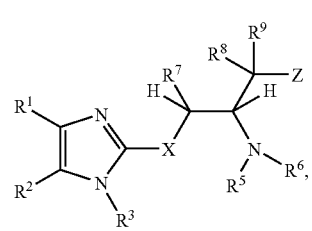
IIS
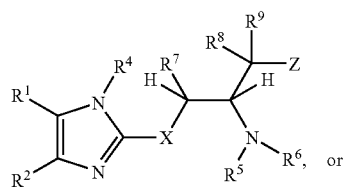
IIT
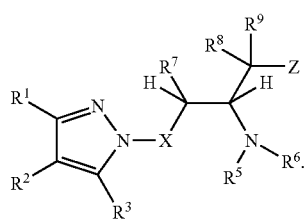
IIU
In other embodiments, the compound of Formula I has the Formula IIIA shown below:
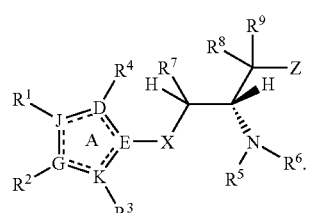
IIIA
In other embodiments, the compound of Formula I has the Formula IIIB shown below:
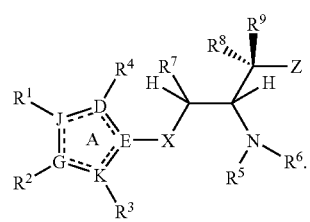
IIIB
In other embodiments, the compound of Formula I has the Formula IIIC shown below:
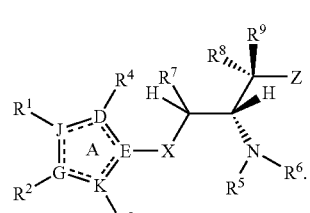
IIIC In other embodiments, the compound of Formula I has the Formula IIID shown below:

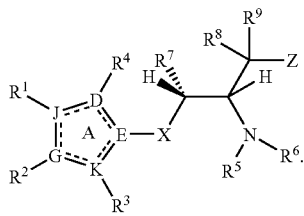

IIID

In other embodiments, the compound of Formula I has the Formula IIIE shown below:

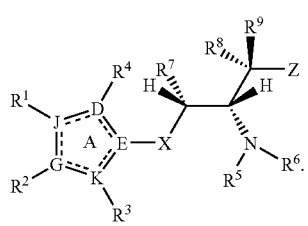

IIIE

In some embodiments of any of the embodiments described above, $R^1$ is —H.

In some embodiments of any of the embodiments described above, $R^3$ is absent or is —H. In other embodiments, $R^3$ is selected from —H, methyl, ethyl, propyl, butyl, pentyl, benzyl, —CH$_2$C(H)(CH$_3$)$_2$, or —CH$_2$CH$_2$NH$_2$.

In some embodiments of any of the embodiments described above, $R^4$ is absent or is —H. In other embodiments, $R^4$ is selected from —H, methyl, ethyl, propyl, butyl, or pentyl.

In some embodiments of any of the embodiments described above, $R^7$ is —H or $C_1$-$C_6$ alkyl. In some such embodiments, $R^7$ is —H or methyl.

In some embodiments of any of the embodiments described above, $R^8$ is —H.

In some embodiments of any of the embodiments described above, $R^9$ is —H. In other embodiments, $R^9$ is selected from $R^9$ is —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In still other embodiments, R$^9$ is selected from —H, methyl, ethyl, propyl, ethenyl, propenyl, hydroxymethyl, methoxymethyl, —CH$_2$—O—C(O)—(C$_1$-C$_6$ alkyl), 1-hydroxyethyl, or methoxymethoxy.

In some embodiments of any of the embodiments described above, Z is selected from optionally substituted phenyl, optionally substituted indolyl, optionally substituted naphthyl, optionally substituted pyridyl, or optionally substituted thiophenyl.

In some embodiments of any of the embodiments described above, Z is selected from phenyl, indolyl, naphthyl, pyridyl, or thiophenyl, each of which is optionally substituted with 1-3 substituents selected from —Cl, —F, —CF$_3$, —OH, —O—(C$_1$-C$_6$ alkyl), —O—(C$_1$-C$_6$ alkyl)-Cl, —O—(C$_1$-C$_6$ alkyl)-OH, —C$_1$-C$_6$ alkyl, —OCF$_3$, —NH(CO)—O—(C$_1$-C$_6$ alkyl)aryl, or —NH(CO)—O—(C$_1$-C$_6$ alkyl).

In some embodiments of any of the embodiments described above, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—CH$_2$-phenyl.

In some embodiments of any of those described above that are consistent therewith, $R^{10}$ is H.

In some embodiments of any of those described above, $R^5$ and $R^6$ are each H.

In some embodiments, $R^7$ is —H or C$_1$-C$_6$ alkyl, $R^8$ is —H, and $R^9$ is —H, —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In some such embodiments, $R^9$ is —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In some such embodiments, $R^5$, $R^6$, and $R^{10}$ are all H.

In some embodiments, $R^9$ is —OR$^{11}$, —O—(C$_1$-C$_6$ alkyl)-O—R$^{11}$, C$_1$-C$_6$ alkyl, C$_1$-C$_6$ alkenyl, —(C$_1$-C$_6$ alkyl)-O—R$^{11}$, or —(C$_1$-C$_6$ alkyl)-O—C(O)—R$^{11}$. In some such embodiments, $R^5$, $R^6$, and $R^{10}$ are all H.

In other embodiments, $R^5$, $R^6$, and $R^{10}$ are all H.

In some embodiments of any of those described above, the carbocyclic ring system or the heterocyclic ring system of $R^2$ comprises at least one aromatic ring. In such embodiments, the aromatic ring may be carbocyclic, or the aromatic ring may include one or more heteroatoms such as, but not limited to, in pyridine or pyrimidine rings. In some embodiments, the at least one aromatic ring in the carbocyclic ring system or the heterocyclic ring system of $R^2$ is a phenyl ring or is a pyridyl ring. In some embodiments, the carbocyclic ring system or the heterocyclic ring system of $R^2$ includes an aromatic ring, and the aromatic ring is bonded to the A ring shown in the structure of Formula I. In some embodiments, the carbocyclic ring system or the heterocyclic ring system of $R^2$ is a fused ring system comprising at least two rings. In some such embodiments, $R^2$ is a heterocyclic ring system comprising two six membered rings or one six membered ring and one 5 membered ring. In some embodiments, $R^2$ is a carbocyclic or heterocyclic ring system that includes two rings. In some such embodiments, $R^2$ is a bicyclic system in which both rings are aromatic. In other such embodiments, $R^2$ is a bicyclic system in which one of the rings is aromatic and the other ring is not aromatic.

In some embodiments, $R^2$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.

In some embodiments, of any of those described above, $R^2$ is selected from one of the following groups which may optionally be substituted and where the wavy line indicates the point of attachment to the ring A:

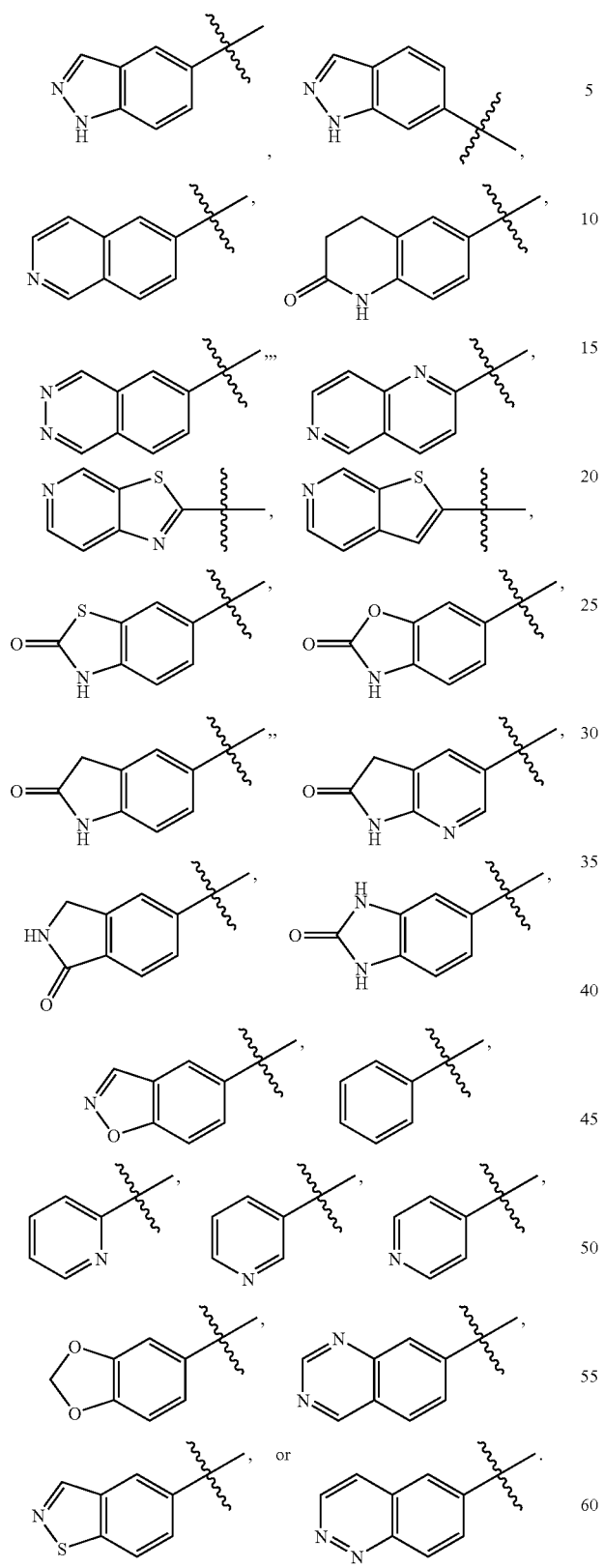
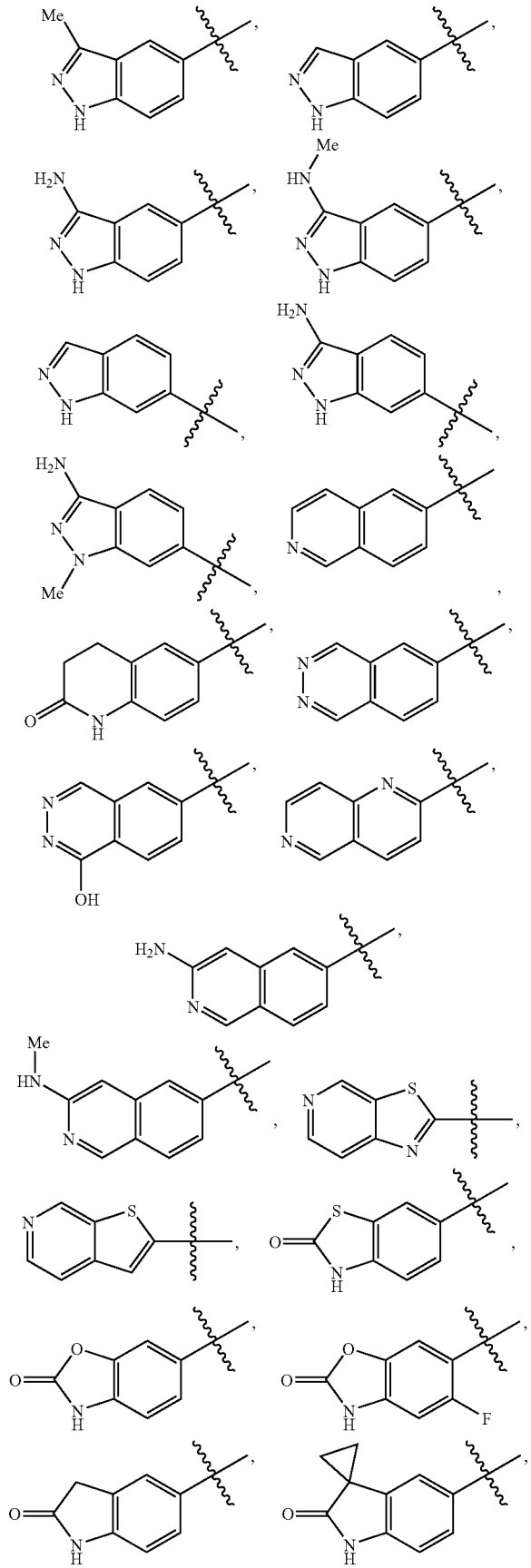
In other embodiments consistent with any of those described above, R² is selected from one of the following groups, where the wavy line indicates the point of attachment to the ring A:

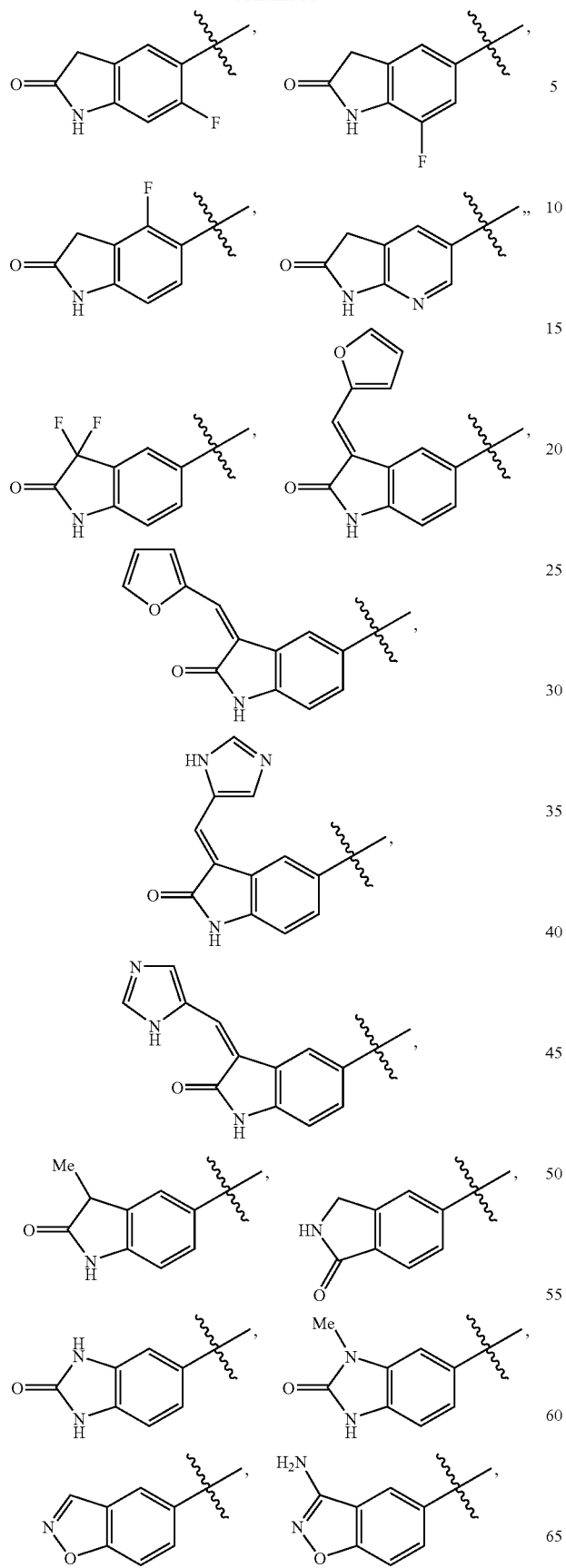

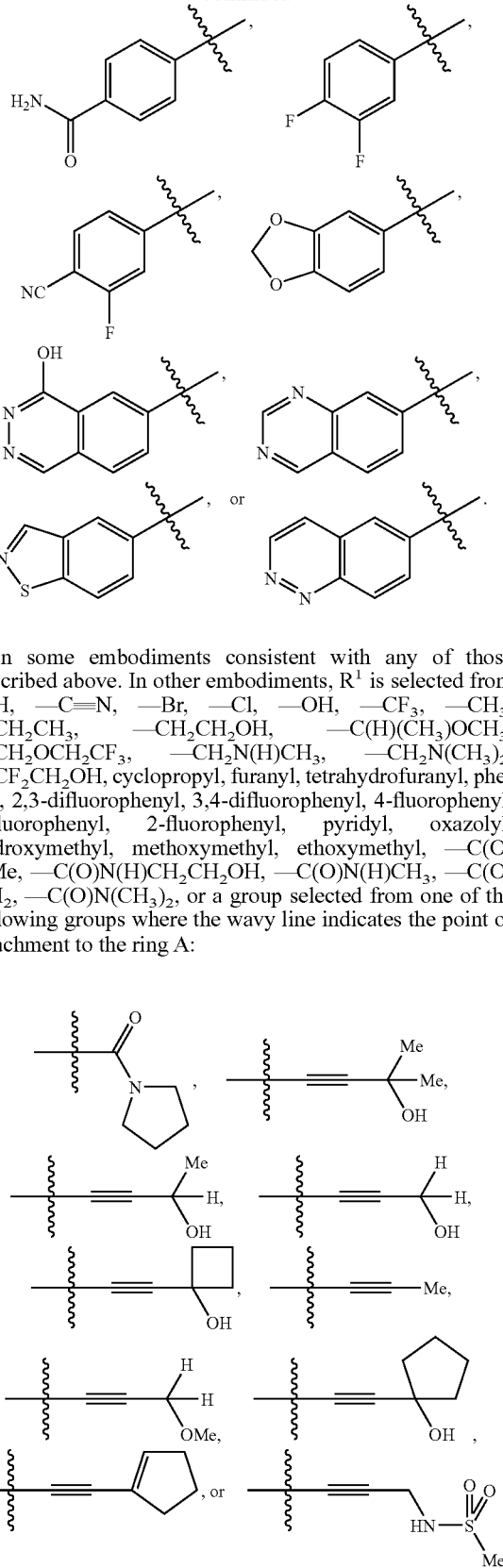

In some embodiments consistent with any of those described above. In other embodiments, $R^1$ is selected from —H, —C≡N, —Br, —Cl, —OH, —$CF_3$, —$CH_3$, —$CH_2CH_3$, —$CH_2CH_2OH$, —C(H)($CH_3$)$OCH_3$, —$CH_2OCH_2CF_3$, —$CH_2N(H)CH_3$, —$CH_2N(CH_3)_2$, —$CF_2CH_2OH$, cyclopropyl, furanyl, tetrahydrofuranyl, phenyl, 2,3-difluorophenyl, 3,4-difluorophenyl, 4-fluorophenyl, 3-fluorophenyl, 2-fluorophenyl, pyridyl, oxazolyl, hydroxymethyl, methoxymethyl, ethoxymethyl, —C(O)OMe, —C(O)N(H)$CH_2CH_2OH$, —C(O)N(H)$CH_3$, —C(O)$NH_2$, —C(O)N($CH_3$)$_2$, or a group selected from one of the following groups where the wavy line indicates the point of attachment to the ring A:

In another aspect, the invention comprises a pharmaceutically acceptable salt, hydrate, or solvate of a compound of any of the formulae or embodiments described above. In one embodiment, the pharmaceutically acceptable salts are selected from ammonium trifluoroacetate and ammonium chloride.

In one embodiment, the invention comprises one or more compound selected from any one or all of the exemplary compounds described in the examples or in Table 1 individually or as a member of a group, or a pharmaceutically acceptable salt, hydrate, or stereoisomer thereof. In some embodiments, any of the groups of the exemplary compounds that corresponds to any of the variables of the embodiments is selected.

In another aspect, the invention comprises a pharmaceutically acceptable salt, hydrate, or solvate of a compound of any of the embodiments described herein. In one embodiment, the pharmaceutically acceptable salt is selected from a chloride or trifluoroacetate salt. In some such embodiments, the salt is an ammonium trifluoroacetate, ammonium chloride, or hydrochloride salt.

1.3 Pharmaceutical Compositions and Dosage Forms

Compounds of any of the embodiments thereof, or a pharmaceutically acceptable salt, hydrate, or stereoisomer thereof may be used to prepare pharmaceutical compositions and single unit dosage forms. Therefore, in some embodiments, the invention provides a pharmaceutical composition that includes a compound of any of the embodiments, or a pharmaceutically acceptable salt, hydrate, or stereoisomer thereof. Pharmaceutical compositions and individual dosage forms of the invention may be suitable for oral, mucosal (including sublingual, buccal, rectal, nasal, or vaginal), parenteral (including subcutaneous, intramuscular, bolus injection, intra-arterial, or intravenous), transdermal, or topical administration. Pharmaceutical compositions and dosage forms of the invention typically also comprise one or more pharmaceutically acceptable carrier, excipient, or diluent. Sterile dosage forms are also contemplated.

The term "composition" as used herein is intended to encompass a product comprising the specified ingredients (and in the specified amounts, if indicated), as well as any product which results, directly or indirectly, from combination of the specified ingredients. The term "pharmaceutically acceptable" carrier, excipient, or diluent means that the carrier, excipient, or diluent is compatible with the other ingredients of the formulation and is not deleterious to the recipient thereof. Composition formulation may improve one or more pharmacokinetic properties (e.g., oral bioavailability, membrane permeability) of a compound of the invention (herein referred to as the active ingredient).

The pharmaceutical compositions of the invention may conveniently be presented in unit dosage form and may be prepared by any of the methods well known in the art. All methods include the step of bringing the active ingredient such as a compound of any of the embodiments into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect in the subject.

In some embodiments, pharmaceutical compositions include a compound of the invention, or a pharmaceutically acceptable salt, hydrate or stereoisomer thereof, and at least one additional therapeutic agent. Examples of additional therapeutic agents include, but are not limited to, those listed above. Such compositions may include one or more pharmaceutically acceptable carrier, excipient, or diluent.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 20th ed., Mack Publishing, Easton Pa. 2000. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

Like the amounts and types of excipients, the amounts and specific types of active ingredients in a dosage form may differ depending on factors such as, but not limited to, the route by which it is to be administered to patients. However, typical dosage forms of the invention comprise a compound of the invention, or a pharmaceutically acceptable salt, hydrate, or stereoisomer thereof in an amount of from 0.1 mg to 1500 mg per unit to provide doses of about 0.01 to 200 mg/kg per day.

The invention further provides the use of a compound of any of the embodiments thereof, or a pharmaceutically acceptable salt, hydrate, or stereoisomer thereof, in the preparation of a pharmaceutical composition or medicament. In some embodiments, the composition or medicament may be used to treat a disease mediated by a kinase such as PKB. In some embodiments, the disease is mediated by PKBα. In some embodiments, the disease is cancer and in some such embodiments, the cancer is a solid tumor.

1.4 Methods of Treatment and Prevention of Disease States

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some such embodiments, the disorder is mediated by PKB. In some such embodiments, the administration of the compound or pharmaceutical composition produces selective inhibition of PKB, and in some cases PKBα, in the subject after administration. In some embodiments, the disorder is cancer. The present invention thus provides methods for treating or preventing PKB-mediated disease states, such as cancer. In some embodiments, the cancer is a tumor such as a solid tumor.

The compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor.

The magnitude of a prophylactic or therapeutic dose of a Formula I or Formula II compound of the invention or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I or Formula II may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methyla-nilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering A G, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering A G, Germany); ZK Angio, (Schering A G, Germany); ZK 229561, (Novartis, Switzerland, and Schering A G, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

2. Working Examples

The compounds of Formula I and Formula II were prepared according to the following synthetic Schemes and individual examples detailed herein. The compounds were named using Chemdraw Ultra, v.8.07. These Schemes and examples are provided for the purpose of illustration only and are not intended to limit the scope of the invention.

Unless otherwise noted, all materials were obtained from commercial suppliers and were used without further purification. Anhydrous solvents such as DMF, THF, DCM, and toluene were obtained from the Aldrich Chemical Company. All reactions involving air- or moisture-sensitive compounds were performed under a nitrogen atmosphere. Flash chromatography was performed using Aldrich Chemical Company silica gel (200-400 mesh, 60A) or Biotage pre-packed column. Thin-layer chromatography (TLC) was performed with Analtech gel TLC plates (250 mµ.). Preparative TLC was performed with Analtech silica gel plates (1000-2000.mu.). Preparative HPLC was conducted on a Varian, Shimadzu, Beckman, or Waters HPLC system with 0.1% TFA/$H_2O$ and 0.1% TFA/$CH_3CN$ as mobile phase. The flow rate was at 20 mL/minute and the gradient method was used. $^1H$ NMR spectra were obtained with super conducting FT NMR spectrometers operating at 400 MHz or a Varian 300 MHz instrument. Chemical shifts are expressed in ppm downfield from the tetramethylsilane internal standard. All compounds showed NMR spectra consistent with their assigned structures. Mass spectra (MS) were obtained using a Perkin Elmer-SCIEX API 165 electrospray mass spectrometer (positive and/or negative) or an HP 1100 MSD LC-MS with electrospray ionization and quadrupole detection. All parts are by weight and temperatures are in degrees centigrade unless otherwise indicated.

The following abbreviations are used: AcOH (acetic acid), ATP (adenosine triphosphate), Boc (tert-butyloxycarbonyl), $Boc_2O$ (Boc anhydride), $Br_2$ (bromine), t-BuOH (tert-butanol), $CH_3CN$ or ACN (acetonitrile), MeI (iodomethane or methyl iodide), $CCl_4$ (carbon tetrachloride), $CHCl_3$ (chloroform), $CDCl_3$ (deuterated chloroform), CDI (1,1'carbonyldiimidazole), $CD_3OD$ ($d_4$-methanol), $CO_2$ (carbon dioxide), $Cs_2CO_3$ (cesium carbonate), CuI (copper iodide), DIAD (diisopropyl azodicarboxylate), DEA (diisopropylethylamine), DCM (dichloromethane), dppf (1,1-diphenylphosphinoferrocene), DMAP (4-(dimethylamino)pyridine), DMF (dimethylformamide), DMSO (dimethylsulfoxide), EDC 1-(3-dimethylaminopropyl)-3 (ethylcarbodiimide hydrochloride), EtOAc (ethyl acetate), EtOH (ethanol), $Et_2O$ (diethyl ether), Fe (iron), g (gram), h (hour), HATU (O-(7-azabenzotriazol-1-yl)-N,N,N',N'-tetramethyluronium hexafluorophosphate) $H_2$ (hydrogen), $H_2O$ (water), HCl (hydrochloric acid), $H_2SO_4$ (sulfuric acid), HOBt (1-hydroxybenzotriazole), $K_2CO_3$ (potassium carbonate), KOAc (potassium acetate), KOH (potassium hydroxide), LAH (lithium aluminum hydride), LCMS (liquid chromatography mass spectrometry), LiCl (lithium chloride), MeOH (methanol), $MgSO_4$ (magnesium sulfate), mg (milligram), min (minute), mL (milliliter), NBS (N-bromosuccinimide), NMP (N-methylpyrrolidone), $Na_2SO_4$ (sodium sulfate), $NaHCO_3$ (sodium bicarbonate), $Na_2CO_3$ (sodium carbonate), NaCl (sodium chloride), NaH (sodium hydride), NaHMDS (sodium hexamethylsilazane), NaOH (sodium hydroxide), $NaBH_4$ (sodium borohydride), $NH_4Cl$ (ammonium chloride), Pd/C (palladium on carbon), $PdCl_2(PPh_3)_2$ (palladium chloride bis(triphenylphosphine)), $Pd_2(dba)_3$ (palladium dibenzylideneacetone), $PdCl_2(dppf)$ (1,1'-bis(diphenylphosphino)ferrocene, palladium chloride), $Pd(PPh_3)_4$ (palladium tetrakis triphenylphosphine), $Pd(OH)_2$ (palladium hydroxide), $Pd(OAc)_2$ (palladium acetate), PMB (para methoxybenzyl), $PPh_3$ (triphenylphosphine), RT (room temperature), $SiO_2$ (silica), $SOCl_2$ (thionyl chloride), TEA (triethylamine), TFA (trifluoroacetic acid), THF (tetrahydrofuran), and Zn (zinc).

A number of examples are disclosed in US 2007/0173506 that demonstrate the synthesis of different side chains of Y and different $R^1$ and $R^2$ groups in the compounds of the invention and how these groups are incorporated into certain thiazole compounds may be used with the heterocyclic cores of the present invention.

EXAMPLES

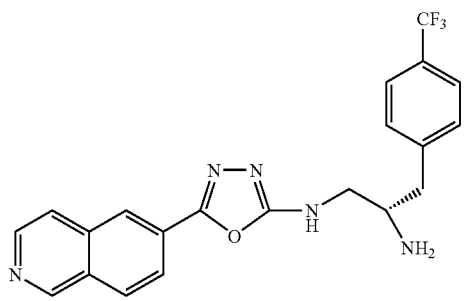

Example 1

N-((S)-2-amino-3-(4-(trifluoromethyl)phenyl)propyl)-5-(isoquinolin-6-yl)-1,3,4-oxadiazol-2-amine: This compound was synthesized as shown in Scheme 1.

Scheme 1

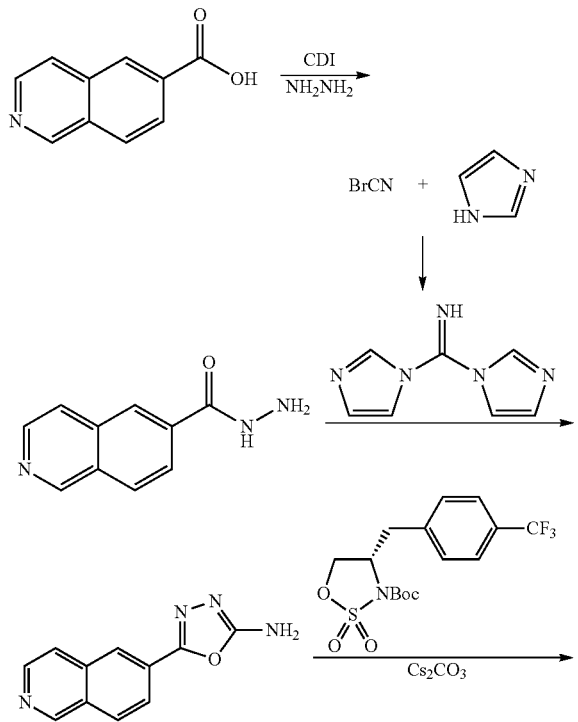

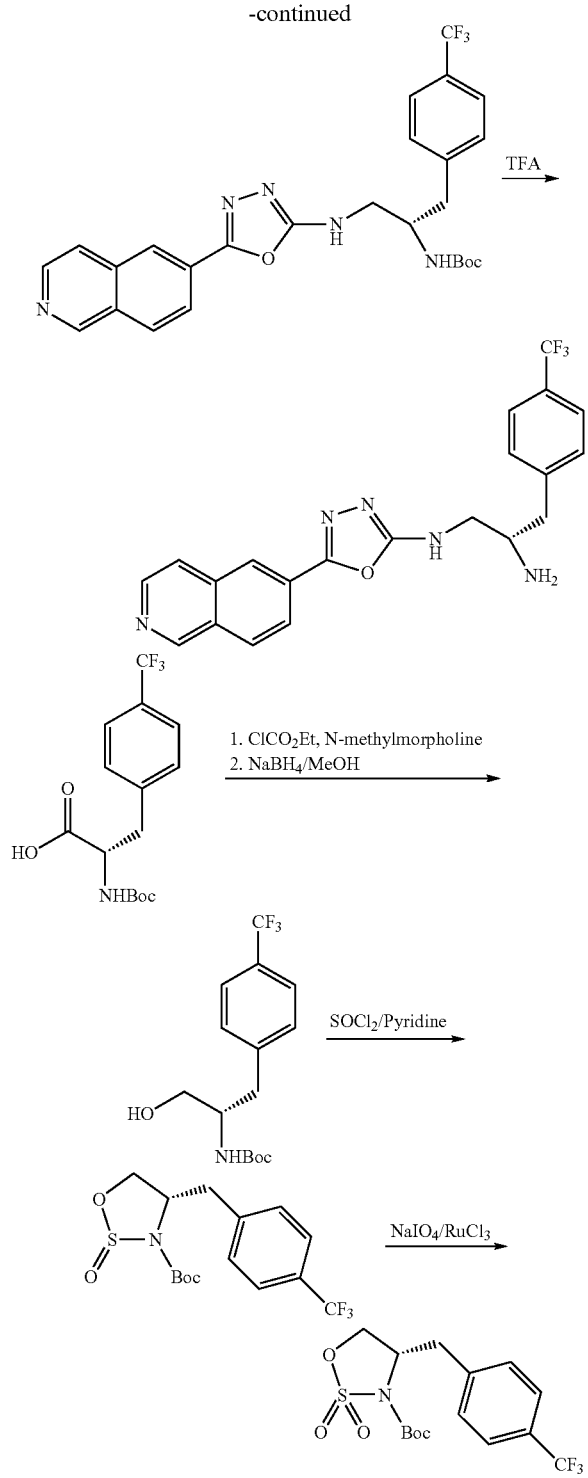

white solid was obtained as the desired product. LCMS (API-ES) m/z (%): 188.0 (100%, M$^+$+H).

5-(Isoquinolin-6-yl)-1,3,4-oxadiazol-2-amine: A 3 M DCM solution of bromoformonitrile (0.2 mL, 0.6 mmol) (commercially available from Aldrich) was mixed with imidazole (0.157 g, 2.3 mmol) (commercially available from Aldrich) in 10 mL DCM. The mixture was heated and maintained to reflux for 30 minutes in a round bottom flask. After the DCM was removed under a reduced pressure, isoquinoline-6-carbohydrazide (0.1 g, 0.53 mmol) suspended in 50 mL THF was added into the flask. The mixture was heated and maintained at reflux for 3 hours. After removing the THF, the remaining residue was mixed with 10 mL water and filtered. After washing with water and air drying, a white solid was obtained as the desired product (0.107 g, 96%) LCMS (API-ES) m/z (%): 213.0 (100%, M$^+$+H).

(S)-tert-Butyl 1-hydroxy-3-(4-(trifluoromethyl)phenyl)propan-2-ylcarbamate: In a 1 L round bottom flask, (S)-2-(tert-butoxycarbonyl)-3-(4-(trifluoromethyl)phenyl)propanoic acid purchased from Peptech (CAS No. 114873-07-3) (30.00 g, 90.1 mmol) was dissolved in 300 mL THF and cooled to −10° C. in an acetone-dry ice bath. 4-Methylmorpholine (9.54 g, 94.6 mmol) (commercially available from Aldrich) was added in one portion. To this mixture was added ethyl chloroformate (19.56 g, 180.2 mmol) drop wise. After the addition, the reaction mixture was stirred for 45 minutes at −10° C. To this mixture was then added NaBH$_4$ in one portion. The reaction flask was cooled to 0° C. by switching to an ice-water bath. MeOH (100 mL) was added slowly using a dropping funnel over one hour. After the addition, the mixture was stirred for an additional three hours from 0° C. to room temperature. The reaction mixture was cooled to 0° C. again and quenched with careful addition of 30 mL 1N HCl. After quenching, the cold bath was removed and the reaction mixture was allowed to warm to room temperature. The reaction mixture was filtered. The solid obtained was washed with EtOAc until the filtrate was not UV active. After the solvent was evaporated under reduced pressure, the crude product was re-dissolved in EtOAc. The organic layer was washed with saturated ammonium chloride solution and saturated sodium bicarbonate and then dried over sodium sulfate. After removing the solvent, the crude product was subjected to a silica gel column chromatography separation using DCM as the eluant. The product was isolated as a white solid (15 g, yield 63%). LCMS (API-ES) m/z (%): 264.0 (100%, M-55).

tert-Butyl-(S)-4-(4-trifluoromethylbenzyl)-1,2,3-oxathiazolidine-3-carboxylate-2-oxide: A 1000 mL round bottom flask was charged with thionyl chloride (22.40 g, 188 mmol) in 200 mL DCM and cooled to between −40° C. and −50° C. with stirring. (S)-tert-Butyl 1-hydroxy-3-(4-(trifluoromethyl)phenyl)propan-2-ylcarbamate (24.00 g, 75.23 mmol) in 200 mL DCM was dropped into the flask while keeping the bath temperature between −40 to −50° C. Pyridine (30.00 g, 375 mmol) was then added dropwise. After the addition, the cold bath was removed, and the resulting mixture was stirred for an additional 3 hours. The DCM solution was washed with distilled water three times and once with brine. After removing the solvent, the residue was subjected to a silica gel column chromatography separation to yield a white solid as the mixture of the two diastereomers (23.3 g, yield 85%). The mixture was used directly in the next step.

(S)-tert-Butyl 4-(4-(trifluoromethyl)benzyl)-1,2,3-oxathiazolidine-3-carboxylate-2,2-dioxide: tert-Butyl-(S)-4-(4-trifluoromethylbenzyl)-1,2,3-oxathiazolidine-3-carboxylate-2-oxide (4.6 g, 12.6 mmol) was dissolved in 60 mL ACN in a 500 mL round bottom flask. Sodium periodate (10.7 g, 50.44 mmol) was dissolved in 20 mL water and added to the Isoquinoline-6-carbohydrazide: Isoquinoline-6-carboxylic acid (1.2 g, 6.94 mmol) purchased from Gateway Chemical Technology, Inc. was mixed with CDI (1.68 g, 10.4 mmol) in DMF (20 Ml) in a round bottom flask. After the mixture was stirred for 30 minutes at 20° C., anhydrous hydrazine (2 mL) was added and the resulting mixture was stirred at 20° C. for one hour. After removing the solvent at a reduced pressure, the remaining residue was mixed with 20 mL water. After filtration, washing with water and air drying, an off- ACN solution. Ruthenium(III) chloride (13.0 mg, 0.063 mmol) was then added to the flask followed by 10 mL EtOAc. The final solvent ratio was $CH_3CN$:water:EtOAc=30:10:5. The flask was cooled in an ice-water bath and the mixture was stirred rigorously for 18 hours from 0° C. to room temperature. The reaction mixture was filtered through filter paper and the solid obtained was washed with DCM until its solution was not UV active. The filtrate was evaporated under reduced pressure and the remaining residue was re-dissolved in DCM. The DCM solution was washed three times with brine and then dried over sodium sulfate. After removing the solvent, a white solid powder was obtained as the pure product (4.51 g, yield 94%). $^1$H NMR (400 MHz, $CDCl_3$) δ ppm 1.53 (s, 9H) 3.03 (dd, J=13.50, 9.19 Hz, 1H) 3.40 (dd, J=13.50, 4.70 Hz, 1H) 4.29 (d, J=8.61 Hz, 1H) 4.51 (ddd, J=14.28, 9.19, 5.28 Hz, 2H) 7.37 (d, J=7.82 Hz, 2H) 7.62 (d, J=8.02 Hz, 2H).

tert-Butyl(S)-1-(5-(isoquinolin-6-yl)-1,3,4-oxadiazol-2-ylamino)-3-(4-(trifluoromethyl)phenyl)propan-2-ylcarbamate: 5-(Isoquinolin-6-yl)-1,3,4-oxadiazol-2-amine (0.083 g, 0.39 mmol) was mixed with (S)-tert-Butyl 4-(4-(trifluoromethyl)benzyl)-1,2,3-oxathiazolidine-3-carboxylate-2,2-dioxide (0.15 g, 0.39 mmol) and $Cs_2CO_3$ (0.381 g, 1.17 mmol) in 2 mL DMF. The mixture was stirred at room temperature for 3 hours, then at 60° C. for 1 hour. After removing the DMF at a reduced pressure, the remaining residue was treated with 1N HCl for 30 minutes. It was then partitioned between EtOAc and saturated aqueous ammonium chloride. The EtOAc solution was washed twice with saturated aqueous ammonium chloride and dried over sodium sulfate. After removing the EtOAc, the remaining residue was subjected to a silica gel column using 70% EtOAc in hexane as the eluant. A white solid was obtained as the desired product (0.040 g, 20%). LCMS (API-ES) m/z (%): 514.0 (100%, M$^+$+H).

N-((S)-2-Amino-3-(4-(trifluoromethyl)phenyl)propyl)-5-(isoquinolin-6-yl)-1,3,4-oxadiazol-2-amine: tert-Butyl(S)-1-(5-(isoquinolin-6-yl)-1,3,4-oxadiazol-2-ylamino)-3-(4-(trifluoromethyl)phenyl)propan-2-ylcarbamate (0.04 g, 0.078 mmol) was treated with 2 mL TFA in 2 mL DCM for 30 minutes. After removing the solvent, the remaining residue was made basic with 2M ammonia in MeOH and loaded on a preparative TLC plate. The TLC plate was developed with 5% 2M ammonia in MeOH in DCM. A white solid was obtained as the desired product (20 mg, 63%). LCMS (API-ES) m/z (%): 414.0 (100%, M$^+$+H); $^1$H NMR (400 MHz, $CD_3OD$) δ ppm 2.72 (dd, J=13.60, 7.53 Hz, 1H) 2.94 (dd, J=13.50, 5.28 Hz, 1H) 3.30-3.37 (m, 2H) 3.39-3.45 (m, 1H) 7.43 (d, J=8.02 Hz, 2H) 7.56 (d, J=8.22 Hz, 2H) 7.87 (d, J=5.87 Hz, 1H) 8.10-8.15 (m, 1H) 8.16-8.20 (m, 1H) 8.34 (s, 1H) 8.47 (d, J=5.87 Hz, 1H) 9.24 (s, 1H).

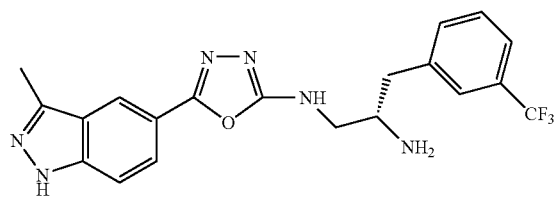

Example 2

N-((S)-2-amino-3-(3-(trifluoromethyl)phenyl)propyl)-5-(3-methyl-1H-indazol-5-yl)-1,3,4-oxadiazol-2-amine: LCMS (API-ES) m/z (%): 417.2 (100%, M$^+$+H); $^1$H NMR (300 MHz, $CD_3OD$) δ ppm 2.61 (s, 3H) 2.71 (dd, J=13.56, 8.85 Hz, 1H) 2.94 (dd, J=13.56, 4.90 Hz, 1H) 3.49 (s, 1H) 3.69-3.79 (m, 1H) 4.20-4.29 (m, 1H) 4.32-4.41 (m, 1H) 4.99 (b, 2H) 7.39-7.53 (m, 5H) 7.96 (dd, J=8.85, 1.51 Hz, 1H) 8.20 (s, 1H). This compound was synthesized in a similar manner as that described for Example 1 in Scheme 1 using 3-methyl-1H-indazole-5-carboxylic acid as the starting material instead of isoquinoline-6-carboxylic acid. 3-Methyl-1H-indazole-5-carboxylic acid was prepared as shown in Scheme 2. To introduce the side chain, (S)-tert-Butyl 4-(3-(trifluoromethyl)benzyl)-1,2,3-oxathiazolidine-3-carboxylate-2,2-dioxide was used which was prepared in a similar manner as that described for (S)-tert-Butyl 4-(4-(trifluoromethyl)benzyl)-1,2,3-oxathiazolidine-3-carboxylate-2,2-dioxide in Scheme 1, using (S)-2-(tert-butoxycarbonyl)-3-(3-(trifluoromethyl)phenyl)propanoic acid commercially available from 3B Scientific Corporation Product List (Order Number 3B3-015703) instead of (S)-2-(tert-butoxycarbonyl)-3-(4-(trifluoromethyl)phenyl)propanoic acid.

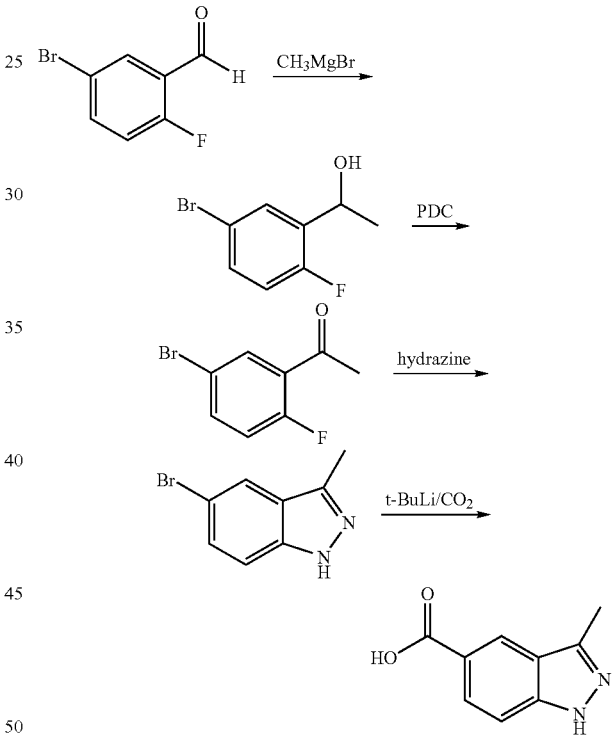

Scheme 2

5-Bromo-2-fluoro-phenyl-methanol: 5-Bromo-2-fluorobenzaldehyde (commercially available from Aldrich) (150.0 g, 739 mmol) was charged into a 2 liter round bottom flask. The reaction mixture in the flask was immersed in an ice-water bath. Methylmagnesium bromide (270 mL, 812 mmol) was added dropwise via an addition funnel. The reaction mixture was stirred for one hour following completion of the addition. After the reaction was completed, the mixture was slowly poured into 500 mL ice water and 250 mL saturated ammonium chloride. The resulting aqueous solution was extracted with ether (800 mL×2) in a separation funnel. The combined ether layer was washed with brine and dried over sodium sulfate. Removal of the solvent gave the product (150 g, yield=93%). The product was used directly in the next step without further purification.

1-(5-Bromo-2-fluoro-phenyl)-ethanone: 5-Bromo-2-fluoro-phenyl-methanol (50.0 g, 228 mmol) along with 300 mL DCM was charged into 2 liter round bottom flask. Crushed pyridinium dichromate (171.0 g, 456 mmol) and powdered molecular sieves (10 g) were both added into the flask. The heterogeneous reaction mixture was stirred for 16 hours at 20° C. The resulting reaction mixture was filtered through Celite and washed with ether (500 mL×3). The combined filtrate was concentrated under reduced pressure. The crude product was eluted through a short silica gel pad (3 inch in length) with 10% EtOAc in hexane. The resulting product (42.0 g, yield=84%) was used in the following step.

5-Bromo-3-methyl-1H-indazole: 1-(5-Bromo-2-fluoro-phenyl)-ethanone (66.0 g, 304 mmol) and 350 mL anhydrous hydrazine were charged into a 1 Liter round bottom flask. The resulting reaction mixture was refluxed at 117° C. for 5 hours. After this period, the reaction mixture was allowed to cool to room temperature, and the excess hydrazine was evaporated under reduced pressure to yield a white solid. 400 mL water was poured into the resulting solid and the water was then filtered off. The solid was washed with 400 mL water twice. To remove the trace amount of hydrazine, the white solid was taken up in 600 mL EtOAc and washed with 300 mL water twice and saturated brine solution. The EtOAc layer was then dried over sodium sulfate. Removal of the solvent gave the desired product as a white amorphous solid (60.0 g, yield=94%). The product was used directly in the next step without further purification.

3-Methyl-1H-indazole-5-carboxylic acid: A three necked round bottom flask equipped with an internal thermometer and an overhead stir motor was charged with 600 mL of THF and chilled to −78° C. t-BuLi (1.7 M in THF, 200 mL, 0.340 mol) was added to the flask, and the mixture was stirred for 15 minutes. 5-Bromo-3-methyl-1H-indazole (22.4 g, 0.106 mol) in 200 mL THF was then added dropwise via an addition funnel. The rate of addition was closely monitored to make sure that the internal temperature remained below −70° C. The resulting orange solution was stirred for 30 minutes, at which point $CO_2$ was bubbled through the mixture. A white precipitate was observed. After 20 minutes, the ice bath was removed and the temperature was allowed to warm to room temperature. The resulting mixture was stirred for an additional 30 minutes. Water was then added to the mixture (40 mL initially followed by a further 200 mL). The biphasic mixture was partially concentrated under reduced pressure, removing about 75% of the original organic portion. The biphasic solution was then transferred to an addition funnel, and the organic phase was extracted with 100 mL of 2M NaOH. The combined aqueous extracts were washed with ether and then acidified to pH=2.0 with concentrated HCl. A precipitate began to form, and the mixture was cooled to 0° C. to complete the precipitation. The resulting solid was filtered, washed with 1M HCl, and dried under reduced pressure at 160° C. over phosphorus pentoxide, affording 3-methyl-1H-indazole-5-carboxylic acid (18.1 g, 96% yield) as a pink/beige solid. LCMS (API-ES) m/z (%): 177.0 (100%, $M^++H$); $^1$H NMR (400 MHz, $CD_3OD$) δ ppm 2.61 (s, 3H) 3.33 (b, 2H), 7.52 (d, J=6.0 Hz, 1H), 8.05 (d, J=6.0 Hz, 1H), 8.50 (s, 1H).

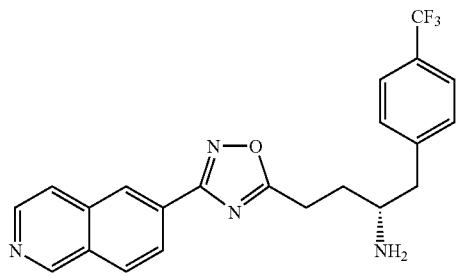

Example 3

(2R)-4-(3-(Isoquinolin-6-yl)-1,2,4-oxadiazol-5-yl)-1-(4-(trifluoromethyl)phenyl)butan-2-amine: This compound was synthesized as shown in Scheme 3.

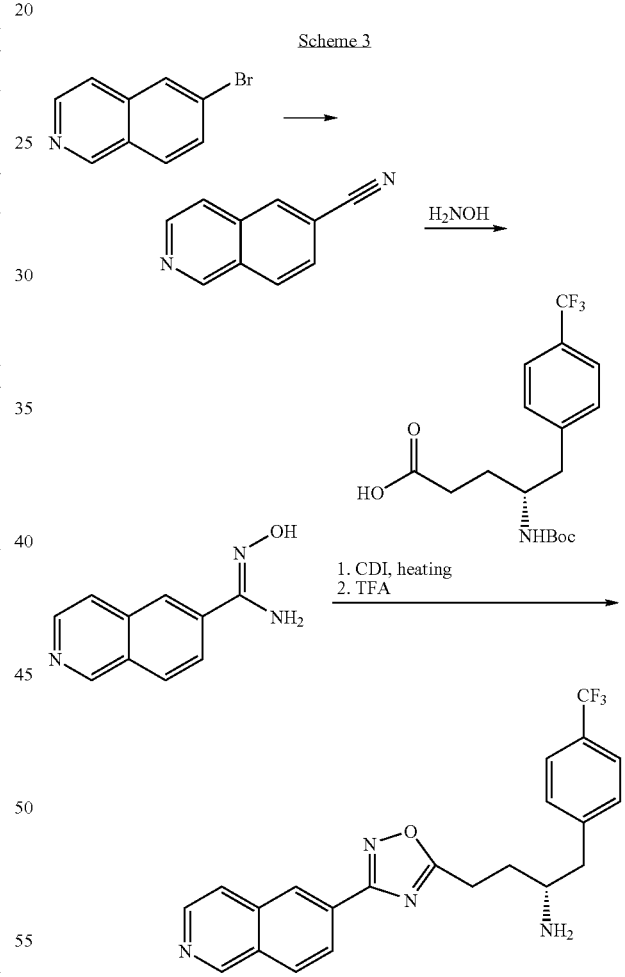

Isoquinoline-6-carbonitrile: 6-Bromoisoquinoline (0.876 g, 4.18 mmol) purchased from Gateway Chemical Technology, Inc. was mixed with CuCN (1.12 g, 12.54 mmol) in 5 mL NMP in a microwave heating tube. The tube was heated under microwave to 150° C. for 1 hour and 170° C. for one hour. The reaction mixture was partitioned between EtOAc and saturated aqueous $NaHCO_3$. After removing the solvent, the remaining residue was passed through a silica gel plug using 5% 2M ammonia in MeOH in DCM as the eluant. The crude product (100 mg) was used directly in the next step.

N'-Hydroxyisoquinoline-6-carboxamidine: Isoquinoline-6-carbonitrile was treated with $H_2NOH\_HCl$ (0.12 g) in 10 mL MeOH in the presence of $Na_2CO_3$ (0.4 g) at room temperature for 12 hours and at 50° C. for 3 hours. The reaction mixture was filtered through a pad of celite. After removing the solvent, the remaining residue was subjected to a short silica gel plug chromatography using 5% 2M ammonia MeOH solution in DCM to yield the pure product (0.067 g). LCMS (API-ES) m/z (%): 188.0 (100%, $M^++H$).

tert-Butyl(R)-4-(3-(isoquinolin-6-yl)-1,2,4-oxadiazol-5-yl)-1-(4-(trifluoromethyl)phenyl)butan-2-ylcarbamate: (R)-4-(tert-Butoxycarbonyl)-5-(4-(trifluoromethyl)phenyl)pentanoic acid (36 mg, 0.1 mmol) (prepared according to the procedure set forth by Smrcina, M. et al. Facile stereoselective synthesis of .gamma.-substituted .gamma.-amino acids from the corresponding .alpha.-amino acids *Tetrahedron* (1997), 53(38), 12867-12874 which is hereby incorporated by reference in its entirety and for all purposes as if specifically set forth herein) and CDI (20 mg, 0.12 mmol) were mixed in a round bottom flask with 5 mL DMF. The mixture was sonicated to a suspension for 5 minutes. N-hydroxyisoquinoline-6-carboxamidine (20 mg, 0.11 mmol) dissolved in 5 mL DMF was added into the flask and the resulting mixture was sonicated for 5 minutes. The suspension was heated in a 100° C. oil bath for 3 hours. After removing the solvent, the remaining residue was partitioned between EtOAc and aqueous saturated ammonium chloride, washed with brine, and dried over sodium sulfate. After removing the EtOAc, the remaining residue was subjected to a silica gel column separation using 15% EtOAc in hexane to yield the desired product as a white solid (16 mg, 31%). LCMS (API-ES) m/z (%): 513.0 (100%, $M^++H$).

(2R)-4-(3-(Isoquinolin-6-yl)-1,2,4-oxadiazol-5-yl)-1-(4-(trifluoromethyl)phenyl)butan-2-amine: tert-Butyl(R)-4-(3-(isoquinolin-6-yl)-1,2,4-oxadiazol-5-yl)-1-(4-(trifluoromethyl)phenyl)butan-2-ylcarbamate (0.016 g, 0.03 mmol) was treated with TFA (1 mL, 13 mmol) in 1 mL DCM for 1 hour. After removing the solvent and making the remaining residue basic with 2M ammonia in MeOH, the residue was subjected to a silica gel plug using 3% 2M ammonia in MeOH in DCM as the eluant to yield an off-white solid as the desired product. LCMS (API-ES) m/z (%): 413.0 (100%, $M^++H$); $^1H$ NMR (400 MHz, $CD_3OD$) δ ppm 2.07-2.18 (m, 1H) 2.22 (s, 1H) 2.95-3.03 (m, 1H) 3.05-3.13 (m, 1H) 3.17-3.28 (m, 2H) 3.48-3.58 (m, 1H) 7.52 (d, J=7.53 Hz, 2H) 7.68 (d, J=8.03 Hz, 2H) 7.95 (d, J=5.52 Hz, 1H) 8.23-8.31 (m, 2H) 8.54 (d, J=6.02 Hz, 1H) 8.64 (s, 1H) 9.33 (s, 1H).

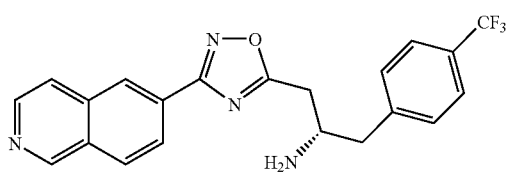

Example 4

(2S)-1-(3-(Isoquinolin-6-yl)-1,2,4-oxadiazol-5-yl)-3-(4-(trifluoromethyl)phenyl)propan-2-amine: This compound was prepared in a similar manner as Example 3 using (S)-3-(tert-butoxycarbonyl)-4-(4-(trifluoromethyl)phenyl)butanoic acid, commercially available from 3B Scientific Corporation Product List (Order Number 3B3-013816), instead of (R)-4-(tert-butoxycarbonyl)-5-(4-(trifluoromethyl)phenyl)pentanoic acid. LCMS (API-ES) m/z (%): 399.1 (100%, $M^++H$); $^1H$ NMR (400 MHz, $CDCl_3$) δ ppm 2.84 (dd, J=13.50, 8.02 Hz, 1H) 2.97-3.06 (m, 2H) 3.13-3.21 (m, 1H) 3.71-3.78 (m, 1H) 7.40 (d, J=7.82 Hz, 2H) 7.60 (t, J=8.12 Hz, 2H) 7.76 (d, J=5.67 Hz, 1H) 8.09 (d, J=8.61 Hz, 1H) 8.28 (dd, J=8.41, 1.56 Hz, 1H) 8.58-8.63 (m, 2H) 9.32 (s, 1H).

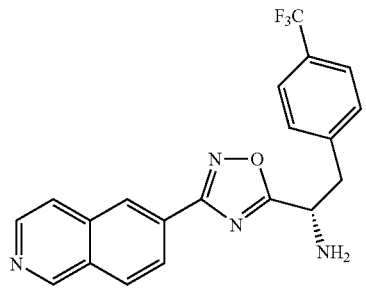

Example 5

(1S)-1-(3-(Isoquinolin-6-yl)-1,2,4-oxadiazol-5-yl)-2-(4-(trifluoromethyl)phenyl)ethanamine: This compound was prepared in a similar manner as Example, using (S)-2-(tert-butoxycarbonyl)-3-(4-(trifluoromethyl)phenyl)propanoic acid purchased from Peptech (CAS No. 114873-07-3) instead of (R)-4-(tert-butoxycarbonyl)-5-(4-(trifluoromethyl)phenyl)pentanoic acid. LCMS (API-ES) m/z (%): 385.1 (100%, $M^++H$); $^1H$ NMR (400 MHz, $CDCl_3$) δ ppm 3.24 (dd, J=13.69, 8.02 Hz, 1H) 3.43 (dd, J=13.69, 5.67 Hz, 1H) 4.59 (dd, J=8.02, 5.67 Hz, 1H) 7.37 (d, J=7.83 Hz, 2H) 7.58 (t, J=8.80 Hz, 2H) 7.76 (d, J=5.67 Hz, 1H) 8.10 (d, J=8.61 Hz, 1H) 8.28 (dd, J=8.61, 1.57 Hz, 1H) 8.59-8.64 (m, 2H) 9.33 (s, 1H).

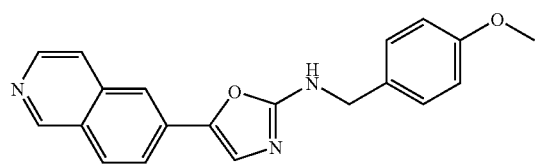

Example 6

N-(4-Methoxybenzyl)-5-(isoquinolin-6-yl)oxazol-2-amine: This compound was prepared as shown in Scheme 4.

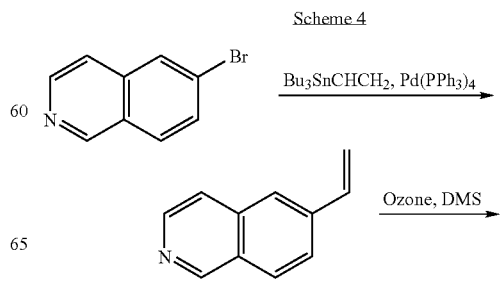

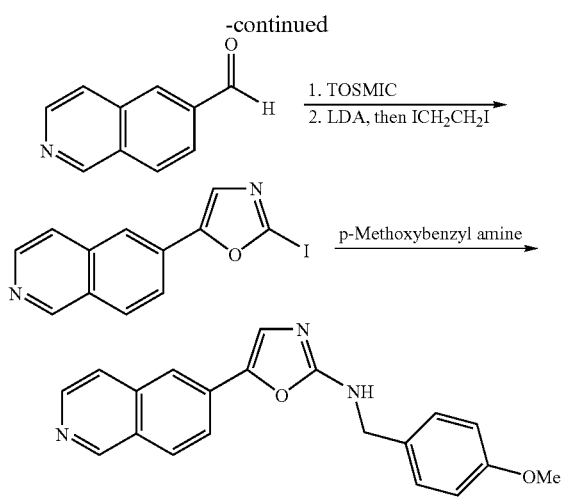

6-Vinylisoquinoline: In a 250 mL round bottom flask, 6-bromoisoquinoline (5 g, 24 mmol) (commercially available from Kalexsyn Product List Order Number 2003-005) was dissolved in dioxane (50 ml). Vinyltributylstannane (9 mL, 29 mmol) was added and the solution was degassed with nitrogen for 10 minutes. Tetrakis(triphenylphosphine)palladium (3 g, 2 mmol) was added in one portion. The reaction mixture was stirred for 3 hours at 100° C. The reaction mixture was adsorbed onto silica gel, and purified by flash chromatography (5-30%, EtOAc in hexane) to provide the product (3.0 g, 80%). LCMS (API-ES) m/z (%): 156 (M+H$^+$).

Isoquinoline-6-carbaldehyde: To a 150 mL round-bottomed flask was added 6-vinylisoquinoline (2.47 g, 16 mmol) and MeOH (35 mL)/DCM (35 mL). The resulting solution was cooled to −78° C. The reaction was ozonized until a blue color persisted, then nitrogen gas was bubbled through the solution for 15 minutes to purge the ozone. The reaction was then treated with solid sodium bicarbonate. (1.5 g) and dimethyl sulfide (3.2 mL, 0.2 mL/mmol of SM) and the mixture was warmed to room temperature and stirred overnight. The reaction mixture was diluted with water (100 mL) and extracted with DCM (3×75 mL). The combined organic layers were dried over Na$_2$SO$_4$, filtered, and the residue product isoquinoline-6-carbaldehyde (2.35 g, 94% yield) was used without further manipulation. LCMS (API-ES) m/z (%): 158.1 (100%, M$^+$+H).

6-(Oxazol-5-yl)isoquinoline: To a 150 mL round-bottomed flask was added p-toluenesulfonylmethyl isocyanide (3.50 g, 18.0 mmol) and MeOH, followed by sodium methoxide (11.0 mL, 50.9 mmol) and a MeOH solution of isoquinoline-6-carbaldehyde (2.35 g, 15.0 mmol). The solution was stirred at reflux for about 1 hour and followed by LCMS. Water was added (50 mL) and the MeOH was removed in vacuo. The suspension was cooled to 0° C., and the resulting precipitate was filtered and dried in a vacuum oven overnight to give 6-(oxazol-5-yl)isoquinoline (2.50 g, 85% yield) as a tan powder. LCMS (API-ES) m/z (%): (100%, M$^+$+H).

6-(2-Iodooxazol-5-yl)isoquinoline: To a 150 mL round-bottomed flask was added 6-(oxazol-5-yl)isoquinoline (0.50 g, 2.55 mmol) and THF (20 mL), and the resulting reaction mixture was stirred at −78° C. The solution was then treated dropwise via syringe with lithium bis(trimethylsilyl)amide (1.0 M solution in THF (3.06 mL, 3.06 mmol)), and the reaction was stirred for 1 hour at −78° C. A THF solution of 1,2-diiodoethane (0.826 g, 2.93 mmol) was then added dropwise, and the reaction was allowed to warm to room temperature for 1 hour. The reaction was then poured into a 1:1 mixture of ether and saturated sodium thiosulfate. Approximately 100 mg was purified on a Varian HPLC, 5-70% ACN in water, 60 minutes run, to give 68 mg of pure compound. LCMS (API-ES) m/z (%): 323 (100%, M$^+$+H); $^1$H NMR (400 MHz, CDCl$_3$) δ ppm 9.19 (s, 1H) 8.51 (d, J=5.67 Hz, 1H) 8.01 (s, 1H) 7.96 (d, J=8.61 Hz, 1H) 7.73 (dd, J=8.61, 1.57 Hz, 1H) 7.63 (d, J=5.67 Hz, 1H) 7.42 (s, 1H).

N-(4-Methoxybenzyl)-5-(isoquinolin-6-yl)oxazol-2-amine: A glass microwave reaction vessel was charged with 6-(2-iodooxazol-5-yl)isoquinoline (0.10 g, 310 μmol), (4-methoxyphenyl)methanamine (0.28 mL, 217 μmol) and NMP (2.00 mL). The reaction mixture was stirred and heated in a Smith Synthesizer® microwave reactor (Personal Chemistry, Inc., Upssala, Sweden) at 165° C. for 10 minutes. The residual product was adsorbed onto a plug of silica gel and chromatographed through two stacked Redi-Sep® prepacked silica gel column (12 g), eluting with a gradient of 1% to 10% of 2 M NH3.MeOH in DCM to provide N-(4-methoxybenzyl)-5-(isoquinolin-6-yl)oxazol-2-amine (98 mg, 95% yield). LCMS (API-ES) m/z (%): 332.1 (100%, M$^+$+H); $^1$H NMR (400 MHz, MeOH-d$_4$) δ ppm 9.12 (s, 1H) 8.38 (d, J=5.87 Hz, 1H) 8.04 (d, J=8.80 Hz, 1H) 7.94 (s, 1H) 7.84 (dd, J=8.61, 1.56 Hz, 1H) 7.76 (d, J=5.87 Hz, 1H) 7.42 (s, 1H) 7.33 (d, J=8.80 Hz, 2H) 6.90 (d, J=8.61 Hz, 2H) 4.47 (s, 2H) 3.77 (s, 3H).

The following compounds were made in a manner analogous to Scheme 4, starting from the appropriate 5-aryl-2-iodooxazole.

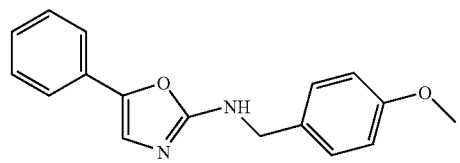

Example 7

N-(4-Methoxybenzyl)-5-phenyloxazol-2-amine: This compound was prepared according to Scheme 4 using benzaldehyde commercially available from Aldrich instead of isoquinoline-6-carbaldehyde. LCMS (API-ES) m/z (%): 281.1 (100%, M$^+$+H); $^1$H NMR (400 MHz, CDCl$_3$) δ ppm 7.47 (d, J=7.83 Hz, 2H) 7.29-7.38 (m, 4H) 7.21 (t, J=7.34 Hz, 1H) 7.04 (s, 1H) 6.89 (d, J=8.41 Hz, 2H) 5.30 (s, 1H) 4.88 (s, 1H) 4.51 (d, J=5.87 Hz, 2H) 3.81 (s, 3H).

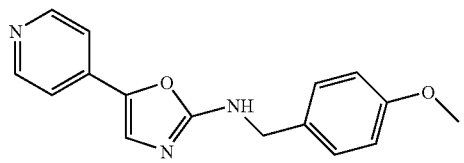

Example 8

N-(4-Methoxybenzyl)-5-(pyridin-4-yl)oxazol-2-amine: This compound was prepared according to Scheme 4 using isonicotinaldehyde commercially available from Aldrich instead of isoquinoline-6-carbaldehyde. LCMS (API-ES) m/z (%): 282.1 (100%, M$^+$+H); $^1$H NMR (400 MHz, CDCl$_3$)

δ ppm 8.53 (d, J=6.06 Hz, 2H) 7.23-7.36 (m, 5H) 6.90 (d, J=8.61 Hz, 2H) 5.22-5.32 (m, 1H) 4.53 (d, J=5.87 Hz, 2H) 3.81 (s, 3H).

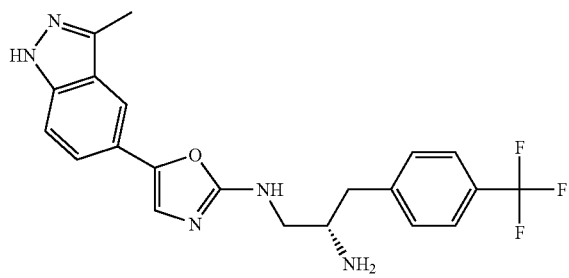

Example 9

N-((S)-2-Amino-3-(4-(trifluoromethyl)phenyl)propyl)-5-(3-methyl-1H-indazol-5-yl)oxazol-2-amine: This compound was prepared as shown in Scheme 5.

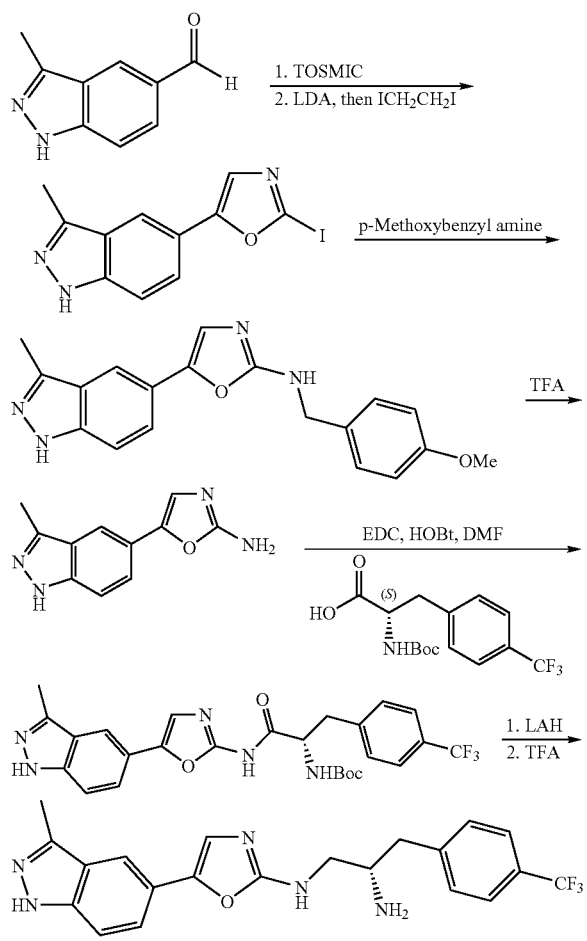

3-Methyl-5-(oxazol-5-yl)-1H-indazole: To a 150 mL round-bottom flask was added p-toluenesulfonylmethyl isocyanide (1.46 g, 7.5 mmol) and MeOH, followed by sodium methoxide (4.60 mL, 21.2 mmol) and a MeOH solution of 3-methyl-1H-indazole-5-carbaldehyde (1.00 g, 6.24 mmol) (prepared as described in WO 2007/124288). The solution was stirred at reflux for about 1 hour and followed by LCMS. Water was added (50 mL) and the MeOH was removed in vacuo. The suspension was cooled to 0° C. and the resulting precipitate was filtered and dried in the vacuum oven overnight to give 3-methyl-5-(oxazol-5-yl)-1H-indazole (1.01 g, 81% yield) as a tan powder. LCMS (API-ES) m/z (%): 200 (100%, M$^+$+H).

5-(2-Iodooxazol-5-yl)-3-methyl-1H-indazole: To a 150 mL round-bottomed flask was added 3-methyl-5-(oxazol-5-yl)-1H-indazole (0.90 g, 4.52 mmol), and THF (20 mL). The resulting reaction mixture was stirred at −78° C. The solution was then treated dropwise via syringe with lithium bis(trimethylsilyl)amide (1.0 M solution in THF (13.6 mL, 13.6 mmol)), and the reaction was stirred for 1 hour at −78° C. A THF solution of 1,2-diiodoethane (5.20 mmol) was then added dropwise and the reaction was allowed to warm to room temperature for 1 hour. The reaction was then poured into a 1:1 mixture of ether and saturated sodium thiosulfate. The crude product was adsorbed onto a plug of silica gel and chromatographed through a Redi-Sep® pre-packed silica gel column (40 g), eluting with a gradient of 10 to 50% EtOAc in Hexanes to give the desired product as a tan powder (1.01 g, 69% yield). LCMS (API-ES) m/z (%): 325 (100%, M$^+$+H).

N-(4-Methoxybenzyl)-5-(3-methyl-1H-indazol-5-yl)oxazol-2-amine: A glass microwave reaction vessel was charged with 5-(2-iodooxazol-5-yl)-3-methyl-1H-indazole (0.40 g, 123 μmol), (4-methoxyphenyl)methanamine (1.13 mL, 8620 μmol) and NMP (2.0 mL). The reaction mixture was stirred and heated in a Smith Synthesizer® microwave reactor (Personal Chemistry, Inc., Upssala, Sweden) at 165° C. for 10 minutes. The crude product was adsorbed onto a plug of silica gel and chromatographed through two stacked Redi-Sep® pre-packed silica gel column (12 g), eluting with a gradient of 1% to 10% 2 M NH3.MeOH in DCM, to give N-(4-methoxybenzyl)-5-(3-methyl-1H-indazol-5-yl)oxazol-2-amine (422 mg, 98% yield). LCMS (API-ES) m/z (%): 355 (100%, M$^+$+H); $^1$H NMR (400 MHz, MeOH-d4) 7.76 (s, 1H) 7.52 (s, 1H) 7.48-7.57 (m, 1H) 7.38-7.46 (m, 1H) 7.26-7.34 (m, 2H) 6.96-7.02 (m, 1H) 6.80-6.91 (m, 2H) 4.42 (s, 2H) 3.75 (d, J=6.06 Hz, 3H) 3.30 (s, 3H).

5-(3-Methyl-1H-indazol-5-yl)oxazol-2-amine: A glass microwave reaction vessel was charged with N-(4-methoxybenzyl)-5-(3-methyl-1H-indazol-5-yl)oxazol-2-amine (196 mg, 587 μmol) and TFA (2.00 mL). The reaction mixture was stirred and heated in a Smith Synthesizer® microwave reactor (Personal Chemistry, Inc., Upssala, Sweden) at 150° C. for 6 minutes. Toluene was added and the solvents were removed in vacuo to give the desired product. The residual material was treated with 2.0 M NH$_3$ in MeOH and 1 N NaOH and the resulting precipitate was filtered to give a yellow solid which was used without further purification.

tert-Butyl(S)-1-(5-(3-methyl-1H-indazol-5-yl)oxazol-2-ylamino)-1-oxo-3-(4-(trifluoromethyl)phenyl)propan-2-yl-carbamate: This intermediate was prepared by EDC-HOBt coupling of 5-(3-methyl-1H-indazol-5-yl)oxazol-2-amine with (S)-2-(tert-butoxycarbonylamino)-3-(4-(trifluoromethyl)phenyl)propanoic acid (purchased from Peptech (CAS No. 114873-07-3)) using a standard procedure such as described in Bioorg. Med. Chem. 14(2), 418-425; 2006) which is hereby incorporated by reference in its entirety as if specifically set forth herein.

N-((S)-2-Amino-3-(4-(trifluoromethyl)phenyl)propyl)-5-(3-methyl-1H-indazol-5-yl)oxazol-2-amine: The compound was synthesized by reducing tert-butyl(S)-1-(5-(3-methyl-1H-indazol-5-yl)oxazol-2-ylamino)-1-oxo-3-(4-(trifluoromethyl)phenyl)propan-2-ylcarbamate with LAH followed with a TFA treatment. LCMS (API-ES) m/z (%): 416 (100%, M++H); $^1$H NMR (400 MHz, MeOH-d4) δ ppm 6.31 (s, 1H) 6.12 (d, J=8.02 Hz, 2H) 5.91-6.03 (m, 4H) 5.75 (s, 1H) 2.27 (dd, J=7.14, 4.40 Hz, 1H) 2.07-2.15 (m, 1H) 1.97-2.07 (m, 1H) 1.56-1.64 (m, 1H) 1.54 (d, J=6.85 Hz, 1H).

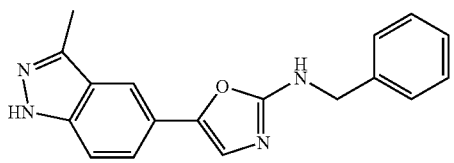

Example 10

N-Benzyl-5-(3-methyl-1H-indazol-5-yl)oxazol-2-amine: The title compound was prepared from 5-(2-iodooxazol-5-yl)-3-methyl-1H-indazole, Scheme 5. A glass microwave reaction vessel was charged with 5-(2-iodooxazol-5-yl)-3-methyl-1H-indazole (0.050 g, 154 μmol), benzyl amine (0.120 mL, 1100 μmol) and NMP (1.0 mL). The reaction mixture was stirred and heated in a Smith Synthesizer® microwave reactor (Personal Chemistry, Inc., Upssala, Sweden) at 165° C. for 10 minutes. The obtained product was adsorbed onto a plug of silica gel and chromatographed through a Redi-Sep® pre-packed silica gel column (12 g), eluting with a gradient of 1% to 10% 2 M $NH_3$.MeOH in DCM, to give the title compound (14 mg, 30% yield) LCMS (API-ES) m/z (%): 305 (100%, M++H); $^1$H NMR (400 MHz, DMSO-d6) δ ppm 7.69 (s, 1H) 7.48 (dd, J=8.72, 1.40 Hz, 1H) 7.42 (d, J=8.72 Hz, 1H) 7.38 (m, 2H) 7.31 (m, 2H) 7.22 (m, 1H) 7.14 (s 1H) 4.44 (s, 2H).

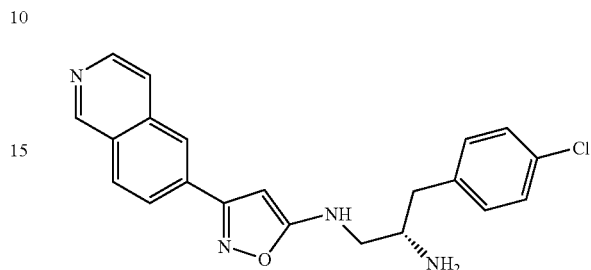

Example 11

N-((S)-2-Amino-3-(4-chlorophenyl)propyl)-3-(isoquinolin-6-yl)isoxazol-5-amine: This compound was synthesized as shown in Scheme 6.

Scheme 6

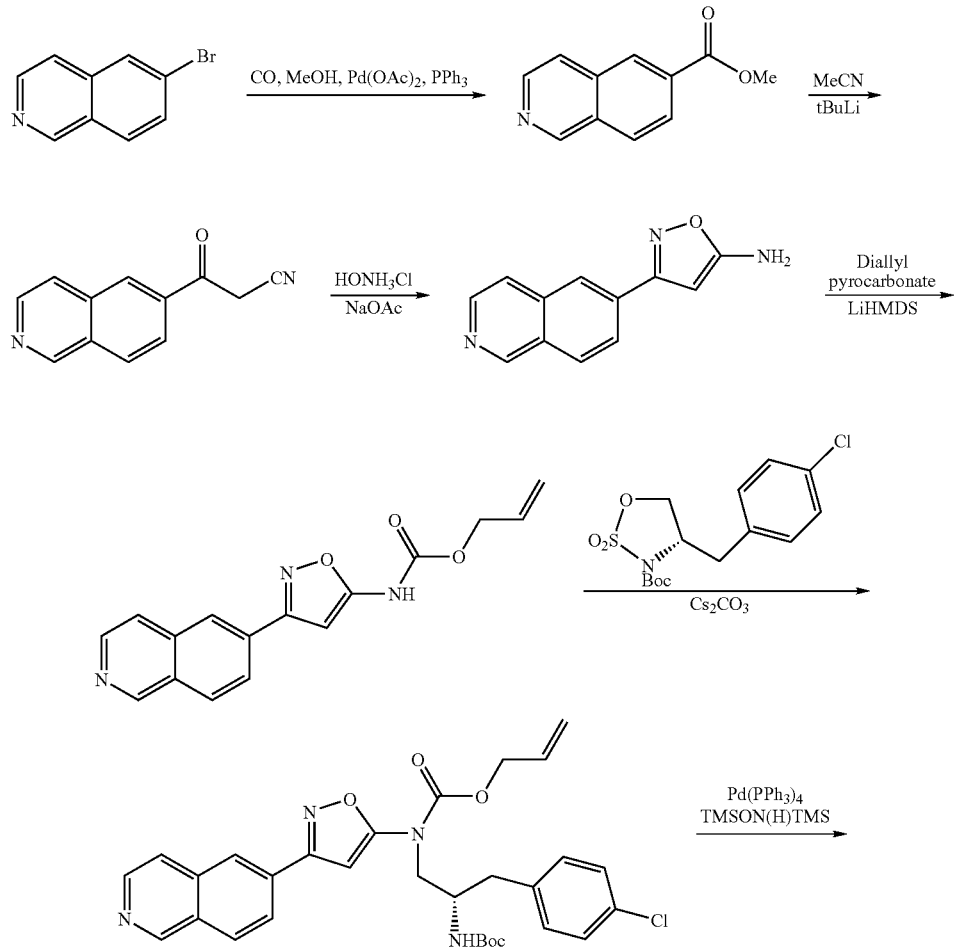

-continued

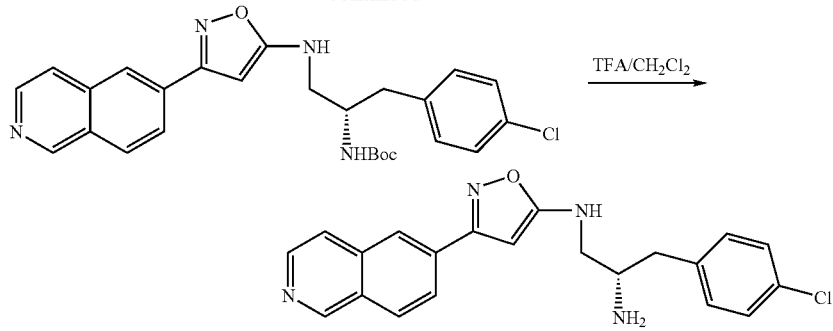

TFA/CH$_2$Cl$_2$

Methyl isoquinoline-6-carboxylate: To a solution of 6-bromoisoquinoline (10 g, 48 mmol), purchased from Gateway Chemical Technology, Inc., in 200 mL of 1:1 DMF:MeOH was added sodium acetate (5.0 g, 61 mmol), triphenylphosphine (3.8 g, 14 mmol), and palladium(II) acetate (2.8 g, 12 mmol). The vessel was charged with 300 kPa of carbon monoxide. The vessel was then purged. This charging purging sequence was repeated three times, then the vessel was charged with 300 kPa of CO and heated to 100° C. After 15 hours, the reaction was judged to be complete by LC/MS. The reaction was filtered through Celite (eluting with EtAOc) and the resulting mixture was concentrated under reduced pressure. The residue was taken up in 250 mL of EtOAc and washed three times with water and once with brine. The mixture was then dried over MgSO$_4$, filtered, and concentrated under reduced pressure. Flash chromatography on silica gel (10% to 35% EtOAc/hexanes) afforded methyl isoquinoline-6-carboxylate as a white powder (7.0 g, 78% yield): LCMS (API ES) m/z 188 [M+1$^+$].

3-(Isoquinolin-6-yl)-3-oxopropanenitrile: To a solution of ACN (1.8 g, 43 mmol) in 90 mL of THF at −78° C. was added tert-butyllithium (25 mL, 1.7 M in heptane). After 20 minutes, methyl isoquinoline-6-carboxylate (2.0 g, 11 mmol) was added slowly in 10 mL of THF. After 1 hour, the reaction was quenched with 100 mL of aqueous NH$_4$Cl and warmed to room temperature. The biphasic mixture was extracted twice with 100 mL of EtOAc, and the combined organic extracts were washed with 100 mL of brine and dried over MgSO$_4$. Filtration and concentration under reduced pressure afforded 3-(isoquinolin-6-yl)-3-oxopropanenitrile (2.1 g, 100% yield crude). The product thus obtained was used in the next step without any further purification.

3-(Isoquinolin-6-yl)isoxazol-5-amine: To a solution of 3-(isoquinolin-6-yl)-3-oxopropanenitrile (2.1 g, 11 mmol) in 60 mL of EtOH was added sodium acetate (5.3 g, 64 mmol) and hydroxylamine hydrochloride (3.7 g, 54 mmol) in 60 mL of water. The mixture was heated to reflux. After 3 hours, the reaction mixture was cooled to room temperature and diluted with 300 mL of EtOAc. The mixture was transferred to a separatory funnel and washed three times with 50 mL of water and once with 50 mL of brine. The remaining liquid was dried over MgSO$_4$, filtered, and concentrated under reduced pressure. The residue was purified by flash chromatography on silica gel (1 to 5% MeOH/CH$_2$Cl$_2$), affording 3-(isoquinolin-6-yl)isoxazol-5-amine (0.96 g, 42% yield) as a white solid. $^1$H NMR (400 MHz, DMSO-d$_6$) δ ppm 9.35 (s, 1H), 8.56 (d, J=6.5 Hz, 1H), 8.36 (s, 1H), 8.19 (d, J=8.6 Hz, 1H), 8.04 (dd, J=1.4 Hz, 8.5 Hz, 1H), 7.91 (d, J=5.9 Hz, 1H), 6.92 (s, 2H), 5.60 (s, 1H).

Allyl 3-(isoquinolin-6-yl)isoxazol-5-ylcarbamate: To a solution of 3-(isoquinolin-6-yl)isoxazol-5-amine (0.30 g, 1.4 mmol) in 14 mL of dry DMF at 0° C. was added LiHMDS (1.7 mL, 1.0 M in THF) dropwise via syringe. The mixture was stirred for 1 hour. Diallyl pyrocarbonate (0.53 g, 2.8 mmol) was added. After 1 hour, the reaction was quenched with 15 mL of aq. NH$_4$Cl. The mixture was then diluted with 15 mL of water and transferred to a separatory funnel. The mixture was partitioned and the aqueous portion was extracted three times with 10 mL of DCM. The combined organic extracts were dried over MgSO$_4$ and filtered. The solvent was removed by rotary evaporation under high vacuum (to remove the residual DMF). The residue was purified by flash chromatography on silica gel (0% to 10% MeOH/DCM), affording allyl 3-(isoquinolin-6-yl)isoxazol-5-ylcarbamate (0.25 g, 60% yield). $^1$H NMR (400 MHz, DMSO-d$_6$) δ ppm 11.68 (s, 1H), 9.38 (s, 1H), 8.58 (d, J=5.7 Hz, 1H), 8.55 (s, 1H), 8.24 (d, J=8.6 Hz, 1H), 8.14 (dd, J=1.4 Hz, 8.6 Hz, 1H), 7.94 (d, J=5.9 Hz, 1H), 6.76 (s, 1H), 6.05-5.95 (m, 1H0, 5.40 (d, J=15.6, 1H), 5.29 (dd, J=1.4 Hz, 10.6 Hz, 1H), 4.72 (d, J=5.7 Hz, 2H).

2-Propen-1-yl((2S)-2-((tert-butoxycarbonyl)amino)-3-(4-chlorophenyl)propyl)(3-(6-isoquinolinyl)-5-isoxazolyl)carbamate: To a solution of allyl 3-(isoquinolin-6-yl)isoxazol-5-ylcarbamate (0.055 g, 0.19 mmol) in 3 mL of DMF was added cesium carbonate (0.12 g, 0.37 mmol). The mixture was heated to 50° C. (S)-tert-Butyl 4-(4-chlorobenzyl)-1,2,3-oxathiazolidine-3-carboxylate 2,2-dioxide (0.097 g, 0.28 mmol) was added slowly in 0.75 mL of THF. After 30 minutes, the reaction was cooled to room temperature and diluted with 10 mL of EtOAc. 10 mL of 10% HCl was then carefully added. After 30 minutes, the reaction was diluted with 15 mL of 5% aq. NaOH. The biphasic mixture was partitioned and the aqueous portion was extracted twice with 20 mL of EtOAc. The combined organic extracts were washed with twice with 10 mL of water and 15 mL of brine and then dried over MgSO$_4$. Filtration and concentration under reduced pressure, followed by flash chromatography on silica gel (20% to 50% EtOAc/hexanes) afforded the desired adduct (0.095 g, 91% yield) as a yellow solid. (S)-tert-Butyl 4-(4-chlorobenzyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-3-(4-chlorophenyl)-2-(tert-butoxycarbonylamino)propanoic acid commercially available from 3B Scientific Corporation Product List (Order Number 3B3-011434) instead of (S)-2-(tert-butoxycarbonylamino)-3-(4-(trifluoromethyl)phenyl) propanoic acid.

N-((S)-2-Amino-3-(4-chlorophenyl)propyl)-3-(isoquinolin-6-yl)isoxazol-5-amine: To a solution of 2-propen-1-yl ((2S)-2-((tert-butoxycarbonyl)amino)-3-(4-chlorophenyl) propyl)(3-(6-isoquinolinyl)-5-isoxazolyl)carbamate (0.095 g, 0.17 mmol) in 2.5 mL of DCM was added N,O-bis(trimethylsilyl)hydroxylamine (0.11 mL, 0.51 mmol) and tetrakis (triphenylphosphine) palladium(0) (0.0058 g, 0.0051 mmol). The mixture was stirred for 15 minutes. The reaction was quenched with 5 mL of aqueous NH₄Cl and the biphasic mixture was stirred for 2 hours. The mixture was then partitioned and the aqueous portion was extracted twice with 5 mL of DCM. The combined organic extracts were dried over $MgSO_4$. Filtration and concentration under reduced pressure afforded a residue that was taken up in 3 mL of DCM and 0.5 mL of TFA was then added. After 30 minutes, the reaction was diluted with 20 mL of DCM and transferred to a separatory funnel. 10 mL of 5% aqueous NaOH was added, and the biphasic mixture was shaken vigorously and partitioned. The aqueous portion was extracted twice with 15 mL of DCM, and the combined organic extracts were dried over $MgSO_4$. Filtration and concentration under reduced pressure, followed by flash chromatography on silica gel (2.5 to 7.5% MeOH/$CH_2Cl_2$) afforded N-((S)-2-amino-3-(4-chlorophenyl)propyl)-3-(isoquinolin-6-yl)isoxazol-5-amine (0.025 g, 39% yield) as a yellow powder. LCMS (API-ES) m/z: 379 (M+1); ¹H NMR (400 MHz, $CD_3OD$) δ ppm 9.29 (s, 1H), 8.51 (d, J=5.7 Hz, 1H), 8.29 (s, 1H), 8.20 (d, J=8.4 Hz, 1H), 8.07 (d, J=8.6 Hz, 1H), 7.92 (d, J=5.7 Hz, 1H), 7.37 (d, J=8.2 Hz, 2H), 7.30 (d, J=8.2 Hz, 2H), 5.60 (s, 1H), 3.45-3.20 (m, 3H), 2.92 (dd, J=5.7 Hz, 13.9 Hz, 1H), 2.72 (dd, J=7.1 Hz, 13.5 Hz, 1H).

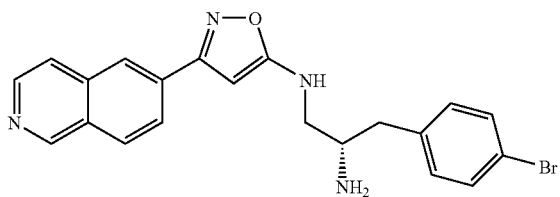

Example 12

N-((S)-2-Amino-3-(4-bromophenyl)propyl)-3-(isoquinolin-6-yl)isoxazol-5-amine: This compound was synthesized in an analogous manner to Example 11 using (S)-tert-butyl 4-(4-bromobenzyl)-1,2,3-oxathiazolidine-3-carboxylate 2,2-dioxide instead of (S)-tert-butyl 4-(4-chlorobenzyl)-1,2,3-oxathiazolidine-3-carboxylate 2,2-dioxide. (S)-tert-Butyl 4-(4-bromobenzyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-3-(4-bromophenyl)-2-(tert-butoxycarbonylamino)propanoic acid commercially available from 3B Scientific Corporation Product List (Order Number 3B3-012656) instead of (S)-2-(tert-butoxycarbonylamino)-3-(4-(trifluoromethyl)phenyl) propanoic acid. LCMS (API-ES) m/z: 423, 425 (M+1); ¹H NMR (400 MHz, $CD_3OD$) δ ppm 9.26 (s, 1H), 8.48 (d, J=5.8 Hz, 1H), 8.26 (s, 1H), 8.17 (d, J=8.4 Hz, 1H), 8.04 (dd, J=1.2 Hz, 8.6 Hz, 1H), 7.90 (d, J=5.7 Hz, 1H), 7.47 (d, J=8.2 Hz, 2H), 7.20 (d, J=8.3 Hz, 2H), 5.56 (s, 1H), 3.34-3.14 (m, 3H), 2.84 (dd, J=5.5 Hz, 13.5 Hz, 1H), 2.64 (dd, J=7.2 Hz, 13.7 Hz, 1H).

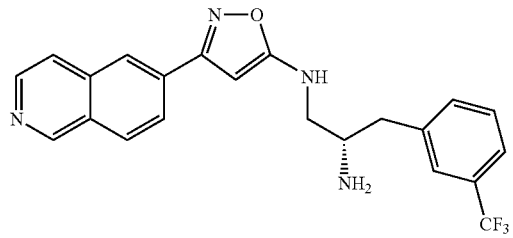

Example 13

N-((S)-2-Amino-3-(3-(trifluoromethyl)phenyl)propyl)-3-(isoquinolin-6-yl)isoxazol-5-amine: This compound was synthesized in an analogous manner to Example 11 using (S)-tert-butyl 4-(3-(trifluoromethyl)benzyl)-1,2,3-oxathiazolidine-3-carboxylate 2,2-dioxide instead of (S)-tert-butyl 4-(4-chlorobenzyl)-1,2,3-oxathiazolidine-3-carboxylate 2,2-dioxide. (S)-tert-Butyl 4-(3-(trifluoromethyl)benzyl)-1,2,3-oxathiazolidine-3-carboxylate-2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(3-(trifluoromethyl)phenyl)propanoic acid commercially available from 3B Scientific Corporation Product List (Order Number 3B3-015703) instead of (S)-2-(tert-butoxycarbonylamino)-3-(4-(trifluoromethyl)phenyl)propanoic acid. LCMS (API-ES) m/z: 413 (M+1); ¹H NMR (400 MHz, $CD_3OD$) δ ppm 9.26 (s, 1H), 8.48 (d, J=5.8 Hz, 1H), 8.27 (s, 1H), 8.17 (d, J=8.6 Hz, 1H), 8.05 (d, J=7.3 Hz, 1H), 7.88 (d, J=5.9 Hz, 1H), 7.60-7.45 (m, 4H), 5.60 (s, 1H), 3.34-3.15 (m, 3H), 2.98 (dd, J=5.5 Hz, 13.7 Hz, 1H), 2.76 (dd, J=7.6 Hz, 13.7 Hz, 1H).

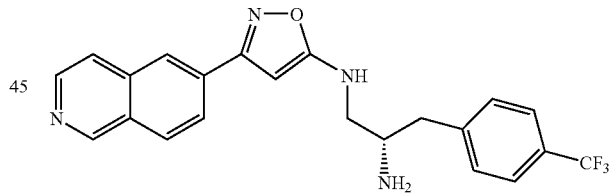

Example 14

N-((S)-2-Amino-3-(4-(trifluoromethyl)phenyl)propyl)-3-(isoquinolin-6-yl)isoxazol-5-amine: This compound was synthesized in an analogous manner to Example 11 using (S)-tert-Butyl 4-(4-(trifluoromethyl)benzyl)-1,2,3-oxathiazolidine-3-carboxylate-2,2-dioxide, as prepared in Scheme 1, instead of (S)-tert-butyl 4-(4-chlorobenzyl)-1,2,3-oxathiazolidine-3-carboxylate 2,2-dioxide. LCMS (API ES) m/z: 413 (M+1); ¹H NMR (400 MHz, $CD_3OD$) δ ppm 9.27 (s, 1H), 8.48, (d, J=6.7 Hz, 1H), 8.27 (s, 1H), 8.18 (d, J=8.6 Hz, 1H), 8.05 (dd, J=1.2 Hz, 8.6 Hz, 1H), 7.89 (d, J=5.9 Hz, 1H), 7.65 (d, J=8.0 Hz, 2H), 7.49 (d, J=8.0 Hz, 2H), 5.64 (s, 1H), 3.45-4.26 (m, 3H), 3.03 (dd, J=5.9 Hz, 13.5 Hz, 1H), 2.85 (dd, J=7.4 Hz, 13.7 Hz, 1H).

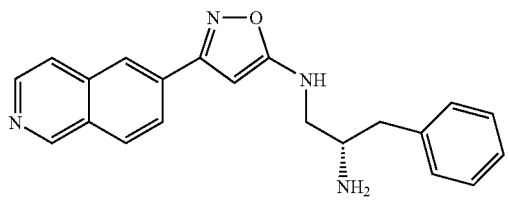

Example 15

N-((S)-2-Amino-3-phenylpropyl)-3-(isoquinolin-6-yl)isoxazol-5-amine: This compound was synthesized in an analogous manner to Example 11 using (S)-tert-butyl 4-benzyl-1,2,3-oxathiazolidine-3-carboxylate 2,2-dioxide instead of (S)-tert-butyl 4-(4-chlorobenzyl)-1,2,3-oxathiazolidine-3-carboxylate 2,2-dioxide. (S)-tert-Butyl 4-benzyl-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(phenyl)propanoic acid commercially available from Acros Organics (Order Number 27564) instead of (S)-2-(tert-butoxycarbonylamino)-3-(4-(trifluoromethyl)phenyl)propanoic acid. LCMS (API-ES) m/z: 345 (M+1); $^1$H NMR (400 MHz, CD$_3$OD) δ ppm 9.27 (s, 1H), 8.48 (d, J=5.9 Hz, 1H), 8.26 (s, 1H), 8.18 (d, J=8.6 Hz, 1H), 8.04 (dd, J=1.4 Hz, 8.6 Hz, 1H), 7.90 (d, J=5.9 Hz, 1H), 7.37-7.25 (m, 5H), 5.58 (s, 1H), 3.40-3.20 (m, 3H), 2.92 (dd, J=6.0 Hz, 13.7 Hz, 1H), 2.76 (dd, J=6.8 Hz, 13.7 Hz, 1H).

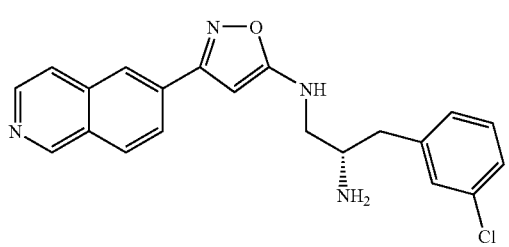

Example 16

N-((S)-2-Amino-3-(3-chlorophenyl)propyl)-3-(isoquinolin-6-yl)isoxazol-5-amine: This compound was synthesized in an analogous manner to Example 11 using (S)-tert-butyl 4-(3-chlorobenzyl)-1,2,3-oxathiazolidine-3-carboxylate 2,2-dioxide instead of (S)-tert-butyl 4-(4-chlorobenzyl)-1,2,3-oxathiazolidine-3-carboxylate 2,2-dioxide. (S)-tert-Butyl 4-(3-chlorobenzyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(3-chlorophenyl)propanoic acid commercially available from 3B Scientific Corporation Product List (Order Number 3B3-015702) instead of (S)-2-(tert-butoxycarbonylamino)-3-(4-(trifluoromethyl)phenyl)propanoic acid. MS m/z: 379, 381 (M+1); $^1$H NMR (400 MHz, CD$_3$OD) δ ppm 9.25 (s, 1H), 8.46 (d, J=5.9 Hz, 1H), 8.25 (s, 1H), 8.16 (d, J=8.7 Hz, 1H), 8.04 (dd, J=1.2 Hz, 8.4 Hz, 1H), 7.88 (d, J=5.9 Hz. 1H), 7.33-7.21 (m, 4H), 5.57 (s, 1H), 3.30-3.16 (m, 3H), 2.86 (dd, J=5.5 Hz, 13.3 Hz, 1H), 2.66 (dd, J=7.2 Hz, 13.3 Hz, 1H).

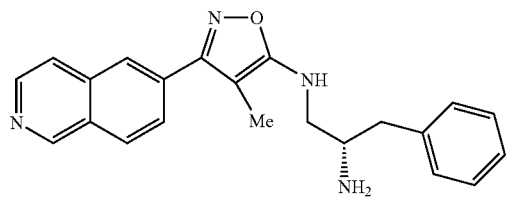

Example 17

N-((S)-2-Amino-3-phenylpropyl)-3-(isoquinolin-6-yl)-4-methylisoxazol-5-amine: This compound was synthesized in an analogous manner to Example 15, using propionitrile instead of acetonitrile. LCMS (API ES) m/z: 359 (M+1); $^1$H NMR (400 MHz, CD$_3$OD) δ ppm 9.30 (s, 1H), 8.49 (d, J=5.8 Hz, 1H), 8.22 (d, J=8.5 Hz, 1H), 8.16 (s, 1H), 7.91 (dd, J=1.5 Hz, 13.3 Hz, 1H), 7.91 (s, 1H), 7.33-7.22 (m, 5H), 3.47-3.26 (m, 3H), 2.88 (dd, J=5.3 Hz, 13.3 Hz, 1H), 2.68 (dd, J=6.9 Hz, 13.9 Hz, 1H), 2.00 (s, 3H).

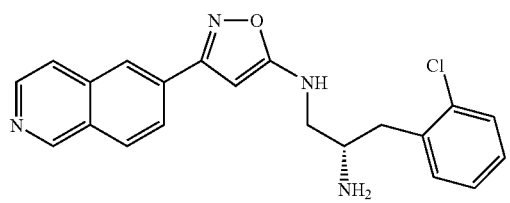

Example 18

N-((S)-2-Amino-3-(2-chlorophenyl)propyl)-3-(isoquinolin-6-yl)isoxazol-5-amine: This compound was synthesized in an analogous manner to Example 11 using (S)-tert-butyl 4-(2-chlorobenzyl)-1,2,3-oxathiazolidine-3-carboxylate 2,2-dioxide instead of (S)-tert-butyl 4-(4-chlorobenzyl)-1,2,3-oxathiazolidine-3-carboxylate 2,2-dioxide. (S)-tert-Butyl 4-(2-chlorobenzyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(2-chlorophenyl)propanoic acid commercially available from 3B Scientific Corporation Product List (Order Number 3B3-070094) instead of (S)-2-(tert-butoxycarbonylamino)-3-(4-(trifluoromethyl)phenyl)propanoic acid. MS m/z: 379, 381 (M+1); $^1$H NMR (400 MHz, CD$_3$OD) δ ppm 9.25 (s, 1H), 8.47 (d, J=5.9 Hz, 1H), 8.25 (s, 1H), 8.16 (d, J=8.6 Hz, 1H), 8.03 (dd, J=1.2 Hz, 8.6 Hz, 1H), 7.88 (d, J=5.8 Hz, 1H), 7.42-7.23 (m, 4H), 5.55 (s, 1H), 3.40-3.20 (m, 3H), 3.07 (dd, J=6.1 Hz, 13.5 Hz, 1H), 2.80 (dd, J=7.7 Hz, 13.5 Hz, 1H).

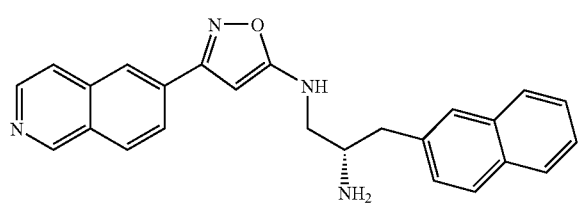

Example 19

N-((S)-2-Amino-3-(naphthalen-2-yl)propyl)-3-(isoquinolin-6-yl)isoxazol-5-amine: This compound was synthesized in an analogous manner to Example 11 using (S)-tert-butyl 4-(2-naphthalenylmethyl)-1,2,3-oxathiazolidine-3-carboxylate 2,2-dioxide instead of (S)-tert-butyl 4-(4-chlorobenzyl)-1,2,3-oxathiazolidine-3-carboxylate 2,2-dioxide. (S)-tert-Butyl 4-(2-naphthalenylmethyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(naphthalen-2-yl)propanoic acid commercially available from 3B Scientific Corporation Product List (Order Number 3B3-056882) instead of (S)-2-(tert-butoxycarbonylamino)-3-(4-(trifluoromethyl)phenyl)propanoic acid. MS m/z: 395 (M+1); $^1$H NMR (400 MHz, CD$_3$OD) δ ppm 9.25 (s, 1H), 8.47 (d, J=5.9 Hz, 1H), 8.18 (s, 1H), 8.14 (d, J=7.4 Hz, 1H), 7.97 (d, J=8.7 Hz, 1H), 7.85-7.80 (m, 4H), 7.73 (s, 1H), 7.50-7.40 (m, 3H), 5.46 (s, 1H), 3.37-3.20 (m, 3H), 3.03 (dd, J=5.8 Hz, 13.5 Hz, 1H), 2.86 (dd, J=6.8 Hz, 13.3 Hz, 1H).

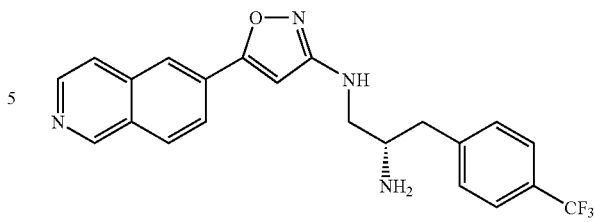

Example 20

N-((S)-2-Amino-3-(4-(trifluoromethyl)phenyl)propyl)-5-(isoquinolin-6-yl)isoxazol-3-amine: This compound was synthesized as shown in Scheme 7.

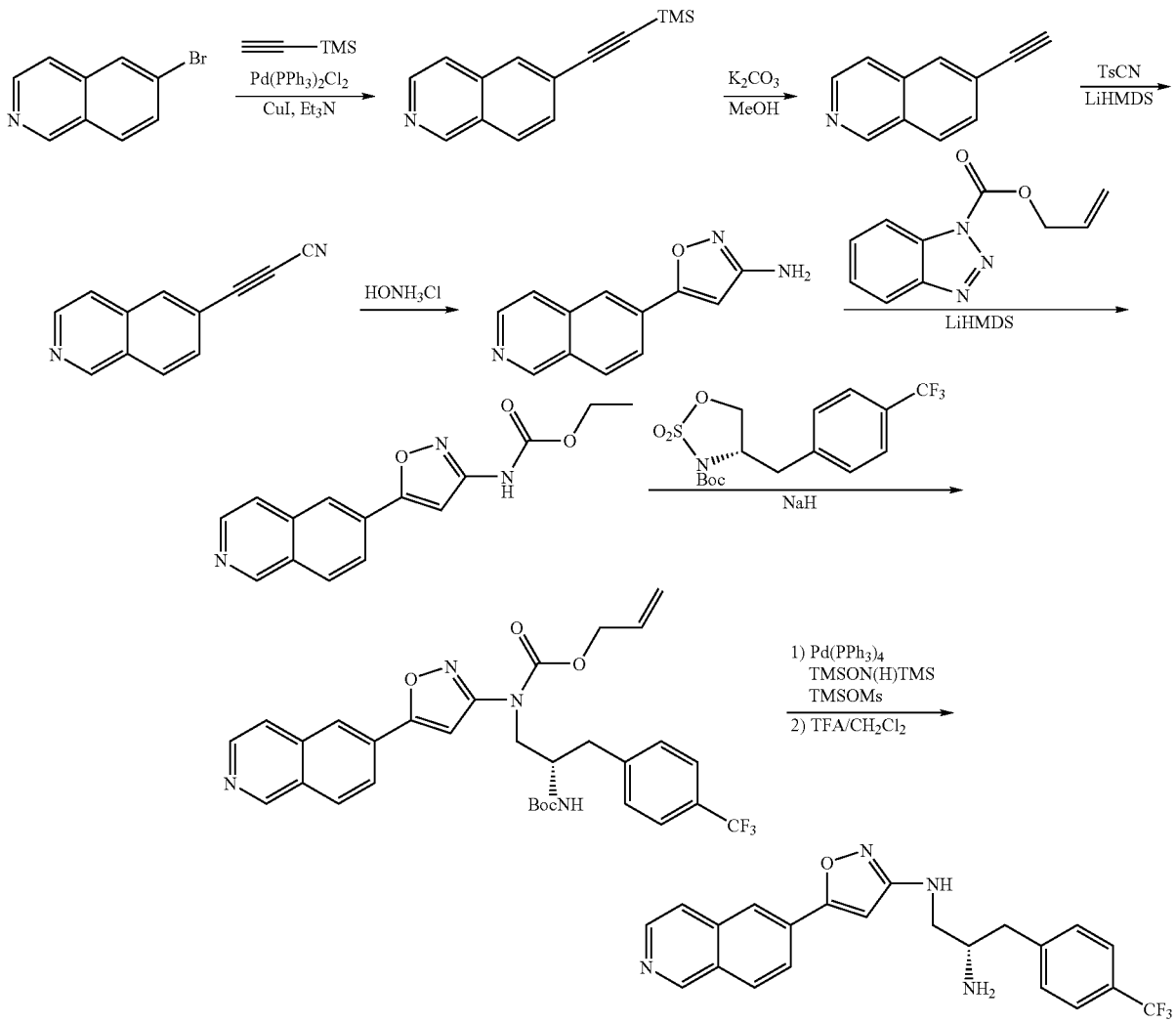

6-(2-(Trimethylsilyl)ethynyl)isoquinoline: To a solution of 6-bromoisoquinoline (2.0 g, 9.6 mmol) (commercially available from Gateway Chemical Technology, Inc.) in 45 mL of Et₃N was added PdCl₂(PPh₃)₂ (0.34 g, 0.48 mmol) and copper(I) iodide (0.27 g, 1.4 mmol). The mixture was degassed by bubbling nitrogen through the mixture for 1 minute. Ethynyltrimethylsilane (2.7 mL, 19 mmol) was added. The mixture was heated to 50° C. After 1 hour, the solvent was removed by rotary evaporation and the residue was purified by flash chromatography on silica gel (5% to 30% EtOAc/hexanes), affording 6-(2-(trimethylsilyl)ethynyl)isoquinoline (2.2 g, 100% yield).

6-Ethynylisoquinoline: To a solution of 6-(2-(trimethylsilyl)ethynyl)isoquinoline (2.2 g, 9.8 mmol) in 45 mL of MeOH was added potassium carbonate (2.7 g, 20 mmol). After 1 hour, the reaction mixture was diluted with 100 mL of EtOAc and 50 mL of water. The mixture was partitioned and the aqueous portion was extracted three times with 50 mL of EtOAc. The combined organic layers were washed with 100 mL of brine and dried over MgSO₄. Filtration and concentration under reduced pressure, followed by flash chromatography on silica gel (5% to 30% EtOAc/hexanes) afforded 6-ethynylisoquinoline (1.3 g, 87% yield) as a white solid. $^1$H NMR (400 MHz, CDCl₃) δ ppm 9.25 (s, 1H), 8.56 (d, J=5.7 Hz, 1H), 7.99 (s, 1H), 7.93 (d, J=8.4 Hz, 1H), 7.65 (dd, J=1.2 Hz, 8.6 Hz, 1H), 7.62 (d, J=5.8 Hz, 1H), 3.26 (s, 1H).

3-(Isoquinolin-6-yl)propiolonitrile: To a solution of 6-ethynylisoquinoline (0.10 g, 0.65 mmol) in 6.5 mL of THF at −78° C. was added LiHMDS, (0.78 mL, 1.0 M in THF). After 5 minutes, the mixture was warmed to 0° C. The mixture was stirred for 30 minutes and then chilled to −78° C. Tosyl cyanide (0.18 g, 0.98 mmol) was added. After 5 minutes, the reaction was warmed to 0° C. and stirred for 1 hour. The reaction was quenched with 10 mL of aq. NH₄Cl. The biphasic mixture was extracted twice with 10 mL of EtOAc and the combined organic extracts were washed with 15 mL of brine and dried over MgSO₄. Filtration and concentration under reduced pressure, followed by flash chromatography on silica gel (5% to 20% EtOAc/hexanes) afforded 3-(isoquinolin-6-yl)propiolonitrile (0.065 g, 0.36 mmol, 56% yield) as a white solid.

5-(Isoquinolin-6-yl)isoxazol-3-amine: 3-(Isoquinolin-6-yl)propiolonitrile (0.060 g, 0.34 mmol) was suspended in 3.0 mL of EtOH. Hydroxylamine hydrochloride (0.070 g, 1.0 mmol) was added to the mixture in 1.5 mL of 10% aq. NaOH. The solution turned a clear, light yellow color immediately. After 3 hours, the reaction mixture was diluted with 20 mL of EtOAc and transferred to a separatory funnel. The mixture was washed with 3 mL of water and 5 mL of brine. The organic extracts were dried over MgSO₄, filtered, and concentrated under reduced pressure, affording 5-(isoquinolin-6-yl)isoxazol-3-amine (0.070 g, 98% yield) as a yellow solid. MS m/z: 212 (M+1); $^1$H NMR (400 MHz, DMSO-d₆) δ ppm 9.36 (s, 1H), 8.56 (d, J=5.7 Hz, 1H), 8.40 (s, 1H), 8.23 (d, J=8.6 Hz, 1H), 8.05 (d, J=8.4 Hz, 1H), 7.93 (d, J=5.9 Hz, 1H), 6.57 (s, 1H).

Allyl 5-(isoquinolin-6-yl)isoxazol-3-ylcarbamate: To a solution of 5-(isoquinolin-6-yl)isoxazol-3-amine (0.10 g, 0.47 mmol) in 4 mL of DMF at 0° C. was added LiHMDS (0.57 mL, 1.0 M in THF). The mixture was stirred for 20 minutes. Allyl 1H-benzo[d][1,2,3]triazole-1-carboxylate (0.14 g, 0.71 mmol) (prepared as described by Katritzky, A. et al. J. Phys. Org. Chem. 1993, 6(10), 567-73 which is hereby incorporated by reference for all purposes as if specifically set forth herein) was added to the mixture. The mixture was stirred for 20 minutes. The reaction was quenched with 5 mL of aqueous NH₄Cl. The mixture was extracted three times with 10 mL of EtOAc, and the combined organic extracts were washed with 20 mL of brine and dried over MgSO₄. Filtration and concentration under reduced pressure, followed by flash chromatography on silica gel (20% to 50% EtOAc/hexanes) afforded allyl 5-(isoquinolin-6-yl)isoxazol-3-ylcarbamate (0.075 g, 0.25 mmol, 54% yield) as a white solid. $^1$H NMR (400 MHz, DMSO-d₆) δ ppm 10.92 (s, 1H), 9.39 (s, 1H), 8.59 (d, J=5.7 Hz, 1H), 8.57 (s, 1H), 8.27 (d, J=8.6 Hz, 1H), 8.16 (d, J=8.6 Hz, 1H), 7.96 (d, J=7.8 Hz, 1H), 7.45 (s, 1H), 6.03-5.95 (m, 1H), 5.39 (dd, J=1.4 Hz, 17.1 Hz, 1H), 5.27 (d, J=10.5 Hz, 1H), 4.68 (d, J=5.5 Hz, 2H).

2-Propen-1-yl (5-(6-isoquinolinyl)-3-isoxazolyl)((2S)-2-methyl-3-(4-(trifluoromethyl)phenyl)propyl)carbamate: To a solution of allyl 5-(isoquinolin-6-yl)isoxazol-3-ylcarbamate (0.030 g, 0.10 mmol) in 1 mL of DMF was added sodium hydride (0.0049 g, 0.20 mmol). After 15 minutes, (S)-tert-butyl 4-(4-(trifluoromethyl)benzyl)-1,2,3-oxathiazolidine-3-carboxylate-2,2-dioxide (0.077 g, 0.20 mmol) (prepared as shown in Scheme 1) was added. The mixture was stirred for 30 minutes. The solvent was removed under reduced pressure and the residue was taken up in 5 mL of EtOAc. 5 mL of 10% aq. HCl was then added and the mixture was stirred for 1 hour. A precipitate formed during this period. 10 mL of 5% aqueous NaOH was then added to solubilize the precipitate and the biphasic mixture was partitioned in a separatory funnel. The aqueous portion was extracted three times with 5 mL of EtOAc. The combined organic extracts were washed with 5 mL of brine and dried over MgSO₄. Filtration and concentration under reduced pressure, followed by flash chromatography on silica gel (10% to 50% EtOAc/hexanes) afforded the desired adduct (0.031 g, 51% yield) as a white solid.

tert-Butyl(S)-1-(5-(isoquinolin-6-yl)isoxazol-3-ylamino)-3-(4-(trifluoromethyl)phenyl)propan-2-ylcarbamate: To a solution of the previous product (0.031 g, 0.052 mmol) in 5 mL of DCM was added TMSN(H)OTMS (0.028 g, 0.16 mmol), trimethylsilyl methanesulfonate (0.026 g, 0.16 mmol), and Pd(PPh₃)₄ (0.0030 g, 0.0026 mmol). After 2 hours, an additional 0.006 g of Pd(PPh₃)₄ was added. The mixture was stirred for 12 hours. The reaction was quenched with 5 mL of 10% aq. HCl. After 15 minutes, a precipitate had formed. The reaction was diluted with 5 mL of DCM and 10 mL of 5% aqueous NaOH to solubilize the precipitate. The mixture was partitioned, and the aqueous portion was extracted three times with 10 mL of DCM. The combined organic layers were dried over MgSO₄. Filtration and concentration under reduced pressure afforded tert-butyl(S)-1-(5-(isoquinolin-6-yl)isoxazol-3-ylamino)-3-(4-(trifluoromethyl)phenyl)propan-2-ylcarbamate (0.027 g, 100% yield). The product was carried on to the next reaction without any further purification.

N-((S)-2-Amino-3-(4-(trifluoromethyl)phenyl)propyl)-5-(isoquinolin-6-yl)isoxazol-3-amine: To a solution of tert-butyl(S)-1-(5-(isoquinolin-6-yl)isoxazol-3-ylamino)-3-(4-(trifluoromethyl)phenyl)propan-2-ylcarbamate (0.027 g, 0.053 mmol) in 5 mL of DCM was added TFA (0.50 mL, 6.5 mmol). The mixture was stirred for 30 minutes and diluted with 20 mL of EtOAc. The mixture was washed twice with 10 mL of 10% aqueous Na₂CO₃ and dried over MgSO₄. Filtration and concentration under reduced pressure, followed by flash chromatography on silica gel (5% to 10% MeOH/DCM) afforded N-((S)-2-amino-3-(4-(trifluoromethyl)phenyl)propyl)-5-(isoquinolin-6-yl)isoxazol-3-amine (0.013 g, 60% yield) as a clear oil. MS m/z: 413 (M+1); $^1$H NMR (400 MHz, CD₃OD) δ ppm 9.26 (s, 1H), 8.48 (d, J=5.8 Hz, 1H), 8.34 (s, 1H), 8.19 (d, J=8.6 Hz, 1H), 8.01 (dd, J=1.3 Hz, 8.6 Hz, 1H), 7.90 (d, J=5.9 Hz, 1H), 7.62 (d, J=8.2 Hz, 2H), 7.47 (d, J=8.0 Hz, 2H), 6.52 (s, 1H), 3.45-3.25 (m, 2H), 3.34 (s, 2H), 3.18 (dd, J=7.4 Hz, 13.5 Hz, 1H), 3.00 (dd, J=5.5 Hz, 13.5 Hz, 1H), 2.75 (dd, J=7.9 Hz, 13.5 Hz, 1H), 2.22 (dt, 1.8 Hz, 6.7 Hz, 1H).

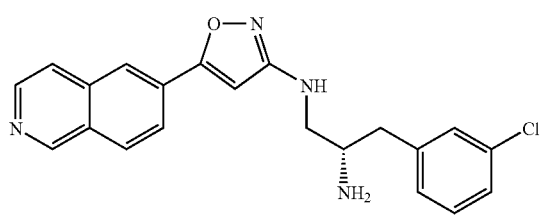

Example 21

N-((S)-2-Amino-3-(3-chlorophenyl)propyl)-5-(isoquinolin-6-yl)isoxazol-3-amine: This compound was synthesized in an analogous manner to Example 20 using (S)-tert-butyl 4-(3-chlorobenzyl)-1,2,3-oxathiazolidine-3-carboxylate 2,2-dioxide instead of (S)-tert-butyl 4-(4-(trifluoromethyl)benzyl)-1,2,3-oxathiazolidine-3-carboxylate-2,2-dioxide. (S)-tert-Butyl 4-(3-chlorobenzyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(3-chlorophenyl)propanoic acid commercially available from 3B Scientific Corporation Product List (Order Number 3B3-015702) instead of (S)-2-(tert-butoxycarbonylamino)-3-(4-(trifluoromethyl)phenyl)propanoic acid. MS m/z: 379 (M+1); $^1$H NMR (400 MHz, CD$_3$OD) δ ppm 9.65 (s, 1H), 8.61 (s, 1H), 8.59 (d, J=6.4 Hz, 1H), 8.49 (d, J=8.6 Hz, 1H), 8.38 (d, J=4.5 Hz, 1H), 8.28 (d, J=8.6 Hz, 1H), 7.39-7.27 (m, 4H), 6.72 (s, 1H), 3.85-3.79 (m, 1H), 3.54 (dd, J=4.5 Hz, 14.5 Hz, 1H), 3.42 (dd, J=7.6 Hz, 14.5 Hz, 1H), 3.06 (dd, J=7.2 Hz, 14.1 Hz, 1H), 2.98 (dd, J=7.0 Hz, 14.3 Hz, 1H).

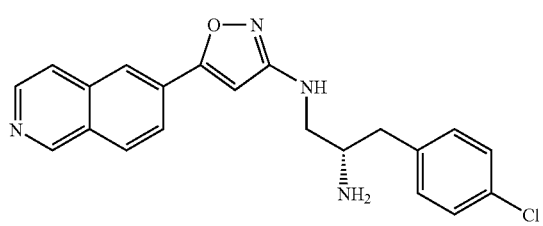

Example 22

N-((S)-2-Amino-3-(4-chlorophenyl)propyl)-5-(isoquinolin-6-yl)isoxazol-3-amine: This compound was synthesized in an analogous manner to Example 20 using (S)-tert-butyl 4-(4-chlorobenzyl)-1,2,3-oxathiazolidine-3-carboxylate 2,2-dioxide instead of (S)-tert-butyl 4-(4-(trifluoromethyl)benzyl)-1,2,3-oxathiazolidine-3-carboxylate-2,2-dioxide. (S)-tert-Butyl 4-(4-chlorobenzyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(4-chlorophenyl)propanoic acid commercially available from 3B Scientific Corporation Product List (Order Number 3B3-011434) instead of (S)-2-(tert-butoxycarbonylamino)-3-(4-(trifluoromethyl)phenyl)propanoic acid. MS m/z: 379 (M+1); $^1$H NMR (400 MHz, CD$_3$OD) δ ppm 9.27 (s, 1H), 8.49 (d, J=5.9 Hz, 1H), 8.35 (s, 1H), 8.21 (d, J=8.6 Hz, 1H), 8.02 (d, J=8.6 Hz, 1H), 7.92 (d, J=5.8 Hz, 1H), 7.34-7.22 (m, 4H), 6.53 (s, 1H), 3.56-3.45 (m, 1H), 3.38 (dd, J=4.5 Hz, 13.7 Hz, 1H), 3.24 (dd, J=7.4 Hz, 13.7 Hz, 1H), 2.96 (dd, J=7.6 Hz, 13.9 Hz, 1H), 2.76 (dd, J=7.7 Hz, 13.9 Hz, 1H).

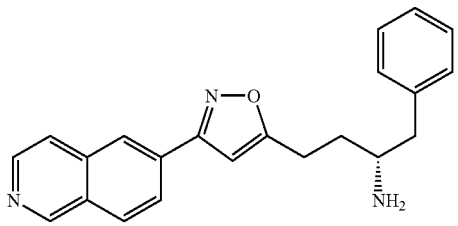

Example 23

(2R)-4-(3-(isoquinolin-6-yl)isoxazol-5-yl)-1-phenylbutan-2-amine: This compound was synthesized as shown in Scheme 8 and Scheme 9.

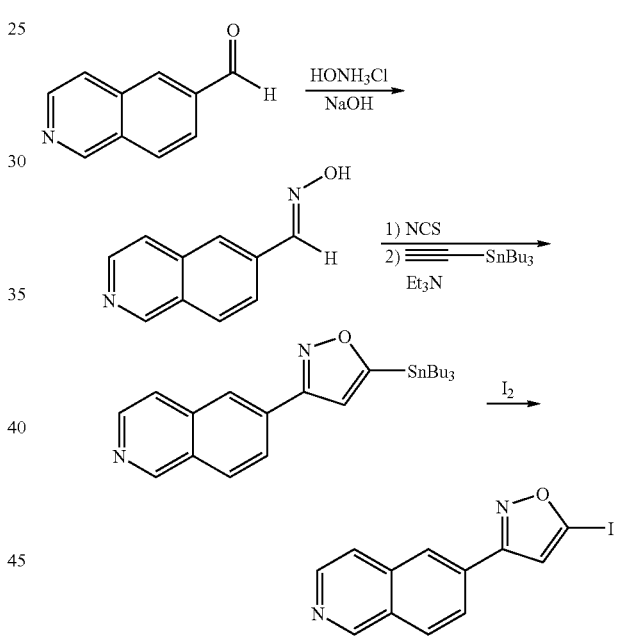

(E)-Isoquinoline-6-carbaldehyde oxime: To a solution of isoquinoline-6-carbaldehyde (2.48 g, 15.8 mmol) (prepared as shown in Example 6) in 160 mL of 1:2 EtOH:H$_2$O was added hydroxylamine hydrochloride (1.21 g, 17.4 mmol). The mixture was cooled to 0° C., and 50 wt % NaOH in H$_2$O (3.2 mL, 0.2 mL per mmol of aldehyde) was added dropwise. The mixture was then stirred at 0° C. for 2 hours, at which time the pH was adjusted to about 6 with 10% aqueous HCl. The resulting biphasic mixture was then transferred to a separatory funnel and extracted five times with 150 mL of DCM. The combined organic layers were dried over MgSO$_4$. Concentration under reduced pressure afforded (E)-isoquinoline-6-carbaldehyde oxime (2.14 g, 78.8% yield) as a white solid. $^1$H NMR (400 MHz, CD$_3$OD) δ ppm 9.20 (s, 1H), 8.44 (d, J=5.9 Hz, 1H), 8.28 (s, 1H), 8.06 (s, 2H), 7.99 (s, 1H), 7.83 (s, 5.9 Hz, 1H).

6-(5-(Tributylstannyl)isoxazol-3-yl)isoquinoline: To a solution of (E)-isoquinoline-6-carbaldehyde oxime (2.14 g, 12.4 mmol) in 60 mL of DMF at 0° C. was added 1-chloropyrrolidine-2,5-dione (1.66 g, 12.4 mmol) (commercially available from Aldrich). The mixture was stirred for 10 minutes and then heated to 5° C. After 2½ hours, the DMF was removed by rotary evaporation. The residue was dissolved in 100 mL of THF and chilled to 0° C. To this mixture was added tributyl(ethynyl)stannane (4.50 g, 14.3 mmol) (commercially available from Aldrich). TEA (3.81 mL, 27.3 mmol) was then added dropwise. The mixture was gradually warmed to room temperature over 12 hours. The reaction was quenched with 50 mL of aqueous NH$_4$Cl and diluted with 50 mL of water. The mixture was partitioned in a separatory funnel. The aqueous portion was extracted twice with 100 mL of EtOAc, and the combined organic layers were washed with 100 mL of brine and dried over MgSO$_4$. Filtration and concentration under reduced pressure, followed by flash chromatography on silica gel (5% to 30% EtOAc/hexanes), afforded 6-(5-(tributylstannyl)isoxazol-3-yl)isoquinoline (1.87 g, 31.0% yield) as a yellow oil. $^1$H NMR (400 MHz, CDCl$_3$) δ ppm 9.29 (s, 1H), 8.58 (d, J=5.8 Hz, 1H), 8.26 (s, 1H), 8.14 (dd, J=1.3 Hz, 8.5 Hz, 1H), 8.05 (d, J=8.5 Hz, 1H), 7.72 (d, J=5.7 Hz, 1H), 6.83 (s, 1H), 1.65-1.57 (m, 6H), 1.38 (q, 7.3 Hz, 6H), 1.23 (t, J=8.2 Hz, 6H), 0.92 (t, 7.2 Hz, 9H).

6-(5-Iodoisoxazol-3-yl)isoquinoline: To a solution of 6-(5-(tributylstannyl)isoxazol-3-yl)isoquinoline (1.00 g, 2.1 mmol) in 20 mL of THF in a sealable tube was added iodine (0.52 g, 2.1 mmol). The tube was sealed and heated to 80° C. by immersion in an oil bath. After 12 hours, the mixture was concentrated under reduced pressure and the residue was purified by flash chromatography on silica gel (0 to 2.5% MeOH/DCM), affording 6-(5-iodoisoxazol-3-yl)isoquinoline (0.60 g, 90% yield) as a grey powder. $^1$H NMR (400 MHz, DMSO-d$_6$) δ ppm 9.40 (s, 1H), 8.59 (d, J=5.6 Hz, 1H), 8.52 (s, 1H), 8.27 (d, J=8.6 Hz, 1H), 8.12 (dd, J=1.6 Hz, 8.6 Hz, 1H), 7.92 (d, J=5.7 Hz, 1H).

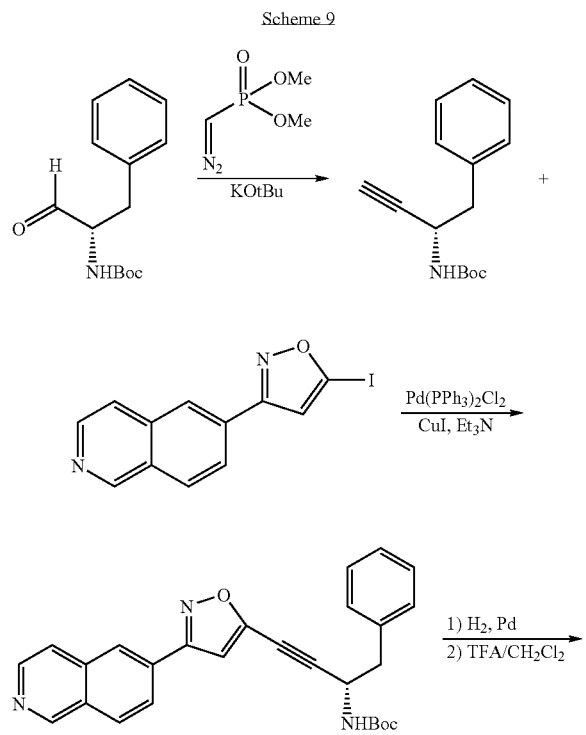

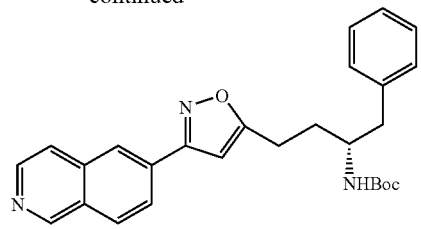

(S)-tert-Butyl 1-phenylbut-3-yn-2-ylcarbamate: To a solution of dimethyl diazomethylphosphonate (0.60 g, 4.0 mmol) (prepared as described by Brown, D. et al., J. Org. Chem. 1996, 61(7), 2540-1 which is hereby incorporated by reference in its entirety and for all purposes as if specifically set forth herein) in 20 mL of THF at −78° C. was added potassium tert-butoxide (4.0 mL, 4.0 mmol). The mixture was stirred for 15 minutes and (S)-(−)-2-(tert-butoxycarbonylamino)-3-phenylpropanal (0.50 g, 2.0 mmol) (commercially available from 3B Scientific Corporation Product List (Order Number 3B3-015684)), was added in 2 mL of THF. The mixture was stirred for 10 minutes and then warmed to −35° C. and stirred for 1 hour. The reaction was then quenched with 10 mL of aqueous NH$_4$Cl and stirred for 15 minutes. The biphasic mixture was diluted with 10 mL of water and partitioned in a separatory funnel. The aqueous portion was then extracted three times with 10 mL of EtOAc. The combined organic layers were washed with 25 mL of brine and dried over MgSO$_4$. Filtration and concentration under reduced pressure, followed by flash chromatography on silica gel (2.5% to 20% EtOAc/hexanes) afforded (S)-tert-butyl 1-phenylbut-3-yn-2-ylcarbamate (0.18 g, 37% yield). $^1$H NMR (400 MHz, CDCl$_3$) δ ppm 7.40-7.23 (m, 5H), 4.81-4.75 (m, 1H), 4.40-4.29 (m, 2H), 3.16 (dd, J=5.3 Hz, 14.2 Hz, 1H), 3.03 (dd, J=9.2 Hz, 5.1 Hz, 1H), 1.42 (s, 9H).

tert-Butyl(S)-4-(3-(isoquinolin-6-yl)isoxazol-5-yl)-1-phenylbut-3-yn-2-ylcarbamate: To a solution of (S)-tert-butyl 1-phenylbut-3-yn-2-ylcarbamate (0.16 g, 0.65 mmol) in 6 mL of Et$_3$N in a sealable tube were added 6-(5-iodoisoxazol-3-yl)isoquinoline (0.18 g, 0.54 mmol), bis(triphenylphosphine) palladium(II) dichloride (0.019 g, 0.027 mmol), and copper (I) iodide (0.016 g, 0.082 mmol). The tube was sealed and heated to 65° C. for 12 hours. The solvent was removed under reduced pressure and the residue was purified by flash chromatography on silica gel, affording tert-butyl(S)-4-(3-(isoquinolin-6-yl)isoxazol-5-yl)-1-phenylbut-3-yn-2-ylcarbamate (0.12 g, 50% yield) as a yellow solid. $^1$H NMR (400 MHz, CDCl$_3$) δ ppm 9.30 (s, 1H), 8.63-8.57 (m, 1H), 8.20-8.17 (m, 1H), 8.09-8.03 (m, 2H), 7.73-7.69 (m, 1H), 7.39-7.27 (m, 5H), 6.81 (s, 1H), 5.05-4.94 (m, 1H), 4.86-4.74 (m, 1H), 3.17-3.03 (m, 2H), 1.46 (s, 9H).

tert-Butyl(R)-4-(3-(isoquinolin-6-yl)isoxazol-5-yl)-1-phenylbutan-2-ylcarbamate: To a solution of tert-butyl(S)-4-(3-(isoquinolin-6-yl)isoxazol-5-yl)-1-phenylbut-3-yn-2-ylcarbamate (0.089 g, 0.20 mmol) in 10 mL of MeOH was added 10% palladium on carbon (0.089 g). Hydrogen was bubbled through the reaction mixture for 5 minutes. The reaction was kept under a balloon atmosphere of hydrogen for 2 hours. The reaction mixture was then filtered through Celite and concentrated under reduced pressure. The obtained tert-butyl(R)-4-(3-(isoquinolin-6-yl)isoxazol-5-yl)-1-phenylbutan-2-ylcarbamate was used without any purification.

(2R)-4-(3-(Isoquinolin-6-yl)isoxazol-5-yl)-1-phenylbutan-2-amine: To a solution of tert-butyl(R)-4-(3-(isoquinolin-6-yl)isoxazol-5-yl)-1-phenylbutan-2-ylcarbamate (0.089 g, 0.20 mmol) in 5 mL of DCM was added 1 mL of TFA. After 30 minutes, the solvent was removed by rotary evaporation. The residue was taken up in 2 N NH₃/MeOH to free base the amine. Concentration under reduced pressure, followed by flash chromatography on silica gel (5% to 10% MeOH/DCM) afforded (2R)-4-(3-(isoquinolin-6-yl)isoxazol-5-yl)-1-phenylbutan-2-amine (0.015 g, 22% yield) as a brown solid. MS m/z: 344 (M+1); ¹H NMR (400 MHz, CD₃OD) δ ppm 9.46 (s, 1H), 8.58-8.55 (m, 1H), 8.48 (s, 1H), 8.35-8.25 (m, 2H), 8.12 (d, J=6.2 Hz, 1H), 7.40-7.27 (m, 5H), 6.79 (s, 1H), 3.61-3.50 (m, 2H), 3.19-2.94 (m, 3H), 2.16-2.03 (m, 2H).

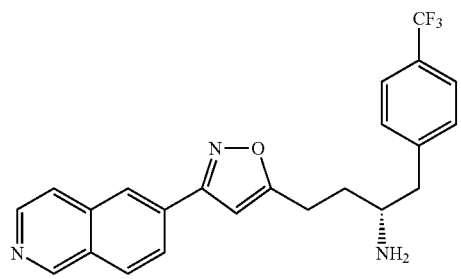

Example 24

(2R)-4-(3-(Isoquinolin-6-yl)isoxazol-5-yl)-1-(4-(trifluoromethyl)phenyl)butan-2-amine: This compound was synthesized in an analogous manner to Example 23 using (S)-tert-butyl 1-oxo-3-(4-(trifluoromethyl)phenyl)propan-2-ylcarbamate (prepared as described by Lescop, C. et al., Bioorg. Med. Chem. Lett. 2005, 15(23), 5176-5181 which is hereby incorporated by reference in its entirety as if specifically set forth herein) instead of (S)-(−)-2-(tert-butoxycarbonylamino)-3-phenylpropanal. MS m/z: 412 (M+1); ¹H NMR (400 MHz, CD₃OD) δ ppm 9.27 (s, 1H), 8.47 (d, J=5.9 Hz, 1H), 8.36 (s, 1H), 8.20 (d, J=8.6 Hz, 1H), 8.14 (dd, J=1.4 Hz, 8.6 Hz, 1H), 7.90 (d, J=5.9 Hz, 1H), 7.61 (d, J=8.0 Hz, 2H), 7.43 (d, J=8.0 Hz, 2H), 6.76 (s, 1H), 3.17-2.90 (m, 4H), 2.76 (dd, J=7.7 Hz, 13.3 Hz, 1H), 2.00-1.90 (m, 1H), 1.86-1.77 (m, 1H).

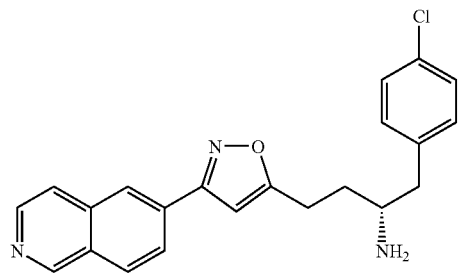

Example 25

(2R)-1-(4-Chlorophenyl)-4-(3-(isoquinolin-6-yl)isoxazol-5-yl)butan-2-amine: This compound was synthesized in an analogous manner to Example 23 using (S)-tert-butyl 1-oxo-3-(4-chlorophenyl)propan-2-ylcarbamate (prepared as described by Lescop, C. et al., Bioorg. Med. Chem. Lett. 2005, 15(23), 5176-5181 which is hereby incorporated by reference in its entirety as if specifically set forth herein) instead of (S)-(−)-2-(tert-butoxycarbonylamino)-3-phenylpropanal. MS m/z: 378 (M+1); ¹H NMR (400 MHz, CD₃OD) δ ppm 9.26 (s, 1H), 8.50 (d, J=4.7 Hz, 1H), 8.36 (s, 1H), 8.20 (d, J=8.6 Hz, 1H), 8.14 (dd, J=1.3 Hz, 8.6 Hz, 1H), 7.91 (d, J=4.6 Hz, 1H), 7.36 (d, J=8.4 Hz, 2H), 7.28 (d, J=8.4 Hz, 2H), 6.76 (s, 1H), 3.40 (broad s, 1H), 3.11-2.94 (m, 3H), 2.88 (dd, J=6.8 Hz, 13.7 Hz, 1H), 2.12-1.95 (m, 2H).

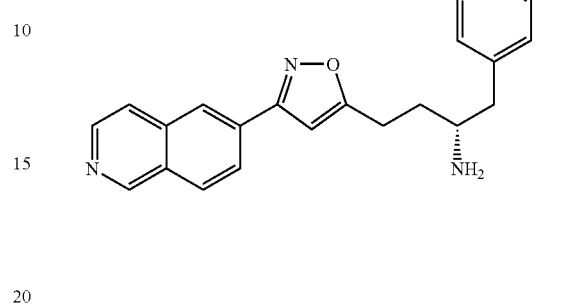

Example 26

(2R)-1-(3-chlorophenyl)-4-(3-(isoquinolin-6-yl)isoxazol-5-yl)butan-2-amine: This compound was synthesized in an analogous manner to Example 23 using (S)-tert-butyl 1-oxo-3-(3-chlorophenyl)propan-2-ylcarbamate (Lescop, C. et al., Bioorg. Med. Chem. Lett. 2005, 15(23), 5176-5181 which is hereby incorporated by reference in its entirety as if specifically set forth herein) instead of (S)-(−)-2-(tert-butoxycarbonylamino)-3-phenylpropanal. MS m/z: 378 (M+1); ¹H NMR (400 MHz, CD₃OD) δ ppm 9.23 (s, 1H), 8.46 (d, J=5.7 Hz, 1H), 8.30 (s, 1H), 8.14 (d, J=8.6 Hz, 1H), 8.10 (d, J=8.6 Hz, 1H), 7.86 (d, J=5.7 Hz, 1H), 7.30-7.14 (m, 4H), 6.70 (s, 1H), 3.14-2.89 (m, 3H), 2.82 (dd, J=6.3 Hz, 13.7 Hz, 1H), 2.67 (dd, J=7.6 Hz, 13.5 Hz, 1H), 1.99-1.89 (m, 1H), 1.84-1.75 (m, 1H).

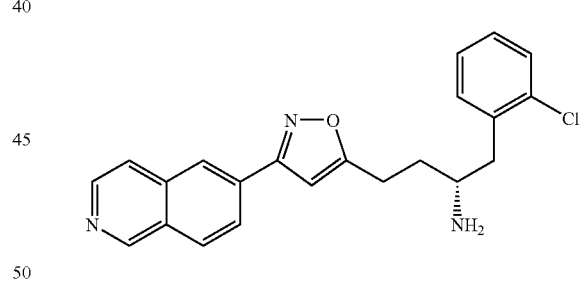

Example 27

(2R)-1-(2-chlorophenyl)-4-(3-(isoquinolin-6-yl)isoxazol-5-yl)butan-2-amine: This compound was synthesized in an analogous manner to Example 23 using (S)-tert-butyl 1-oxo-3-(2-chloromethyl)phenyl)propan-2-ylcarbamate (prepared as described by Lescop, C. et al., Bioorg. Med. Chem. Lett. 2005, 15(23), 5176-5181 which is hereby incorporated by reference herein in its entirety as if specifically set forth herein) instead of (S)-(−)-2-(tert-butoxycarbonylamino)-3-phenylpropanal. MS m/z: 378 (M+1); ¹H NMR (400 MHz, CD₃OD) δ ppm 9.43 (s, 1H), 8.65 (s, 1H), 8.50 (s, 1H), 8.35 (d, J=8.6 Hz, 1H), 8.28 (dd, J=1.4 Hz, 8.5 Hz, 1H), 8.06 (d, J=4.5 Hz, 1H), 7.58-7.41 (m, 4H), 6.92 (s, 1H), 3.61 (broad s, 1H), 3.34-3.10 (m, 4H), 2.24-2.15 (m, 2H).

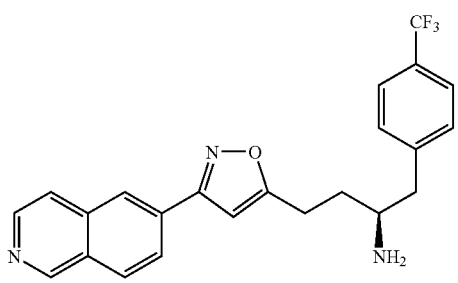

Example 28

(2S)-4-(3-(Isoquinolin-6-yl)isoxazol-5-yl)-1-(4-(trifluoromethyl)phenyl)butan-2-amine: This compound was synthesized in an analogous manner to Example 23 using (R)-tert-butyl 1-oxo-3-(4-(trifluoromethyl)phenyl)propan-2-ylcarbamate (prepared as described by Lescop, C. et al., Bioorg. Med. Chem. Lett. 2005, 15(23), 5176-5181 which is hereby incorporated by reference herein in its entirety and for all purposes as if specifically set forth herein) instead of (S)-(−)-2-(tert-butoxycarbonylamino)-3-phenylpropanal. MS m/z: 412 (M+1); $^1$H NMR (400 MHz, CD$_3$OD) δ ppm 9.27 (s, 1H), 8.47 (d, J=5.9 Hz, 1H), 8.36 (s, 1H), 8.20 (d, J=8.6 Hz, 1H), 8.14 (dd, J=1.4 Hz, 8.6 Hz, 1H), 7.90 (d, J=5.9 Hz, 1H), 7.61 (d, J=8.0 Hz, 2H), 7.43 (d, J=8.0 Hz, 2H), 6.76 (s, 1H), 3.17-2.90 (m, 4H), 2.76 (dd, J=7.7 Hz, 13.3 Hz, 1H), 2.00-1.90 (m, 1H), 1.86-1.77 (m, 1H).

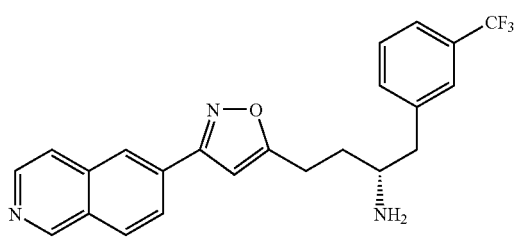

Example 29

(2R)-4-(3-(Isoquinolin-6-yl)isoxazol-5-yl)-1-(3-(trifluoromethyl)phenyl)butan-2-amine: This compound was synthesized in an analogous manner to Example 23 using (S)-tert-butyl 1-oxo-3-(3-(trifluoromethyl)phenyl)propan-2-ylcarbamate (prepared as described by Lescop, C. et al., Bioorg. Med. Chem. Lett. 2005, 15(23), 5176-5181 which is hereby incorporated by reference herein in its entirety and for all purposes as if specifically set forth herein) instead of (S)-(−)-2-(tert-butoxycarbonylamino)-3-phenylpropanal. MS m/z: 412 (M+1); $^1$H NMR (400 MHz, CD$_3$OD) δ ppm 9.23 (s, 1H), 8.46 (d, J=5.9 Hz, 1H), 8.30 (s, 1H), 8.15 (d, J=8.6 Hz, 1H), 8.10 (dd, J=0.8 Hz, 9.0 Hz, 1H), 7.86 (d, J=5.9 HZ, 1H), 7.59-7.42 (m, 4H), 6.72 (s, 1H), 3.13-2.87 (m, 4H), 2.75 (dd, J=7.6 Hz, 13.3 Hz, 1H), 1.98-1.88 (m, 1H), 1.84-1.74 (m, 1H).

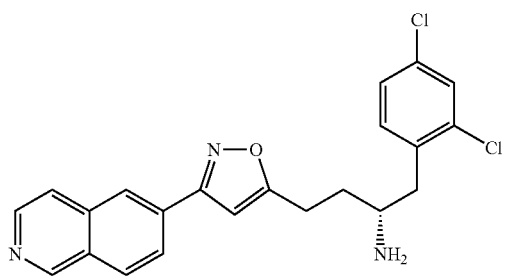

Example 30

(2R)-1-(2,4-Dichlorophenyl)-4-(3-(isoquinolin-6-yl)isoxazol-5-yl)butan-2-amine: This compound was synthesized in an analogous manner to Example 23 using (S)-tert-butyl 1-oxo-3-(2,4-dichlorophenyl)propan-2-ylcarbamate (prepared as described by Lescop, C. et al., Bioorg. Med. Chem. Lett. 2005, 15(23), 5176-5181 which is hereby incorporated by reference herein in its entirety and for all purposes as if specifically set forth herein) instead of (S)-(−)-2-(tert-butoxycarbonylamino)-3-phenylpropanal. MS m/z: 412 (M+1); $^1$H NMR (400 MHz, CD$_3$OD) δ ppm 9.24 (s, 1H), 8.46 (d, J=5.8 Hz, 1H), 8.33 (s, 1H), 8.17 (d, J=8.6 Hz, 1H), 8.11 (dd, J=1.4 Hz, 8.6 Hz, 1H), 7.88 (d, J=5.9 Hz, 1H), 7.40 (d, J=1.8 Hz, 1H), 7.30-7.23 (m, 3H), 6.71 (s, 1H), 3.15-2.71 (m, 5H), 2.00-1.75 (m, 2H).

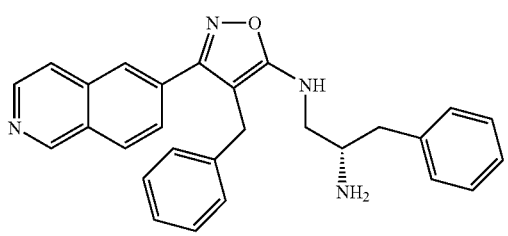

Example 31

N-((S)-2-amino-3-phenylpropyl)-4-benzyl-3-(isoquinolin-6-yl)isoxazol-5-amine: This compound was synthesized in an analogous manner to N-((S)-2-amino-3-(4-chlorophenyl)propyl)-3-(isoquinolin-6-yl)isoxazol-5-amine starting with commercial available 3-phenylpropionitrile (commercially available from Acros Organics Order Number 17399) instead of acetonitrile. MS m/z: 435 (M+1); $^1$H NMR (400 MHz, CD$_3$OD) δ ppm 9.43 (br s, 1H), 8.50 (br s, 1H), 8.23 (d, J=8.6, 1H), 8.06 (s, 1H), 7.89 (d, J=9.0, 1H), 7.87 (d, J=9.8, 1H), 7.15-7.42 (m, 10H), 3.89 (s, 2H), 3.70 (m, 1H), 3.57-3.62 (m, 2H), 3.02 (d, J=7.04 Hz, 2H).

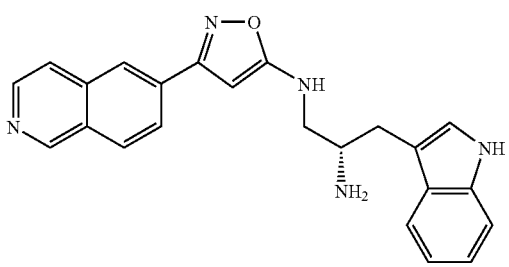

Example 32

N-((S)-2-amino-3-(1H-indol-3-yl)propyl)-3-(isoquinolin-6-yl)isoxazol-5-amine: This compound was synthesized as shown in Scheme 10.

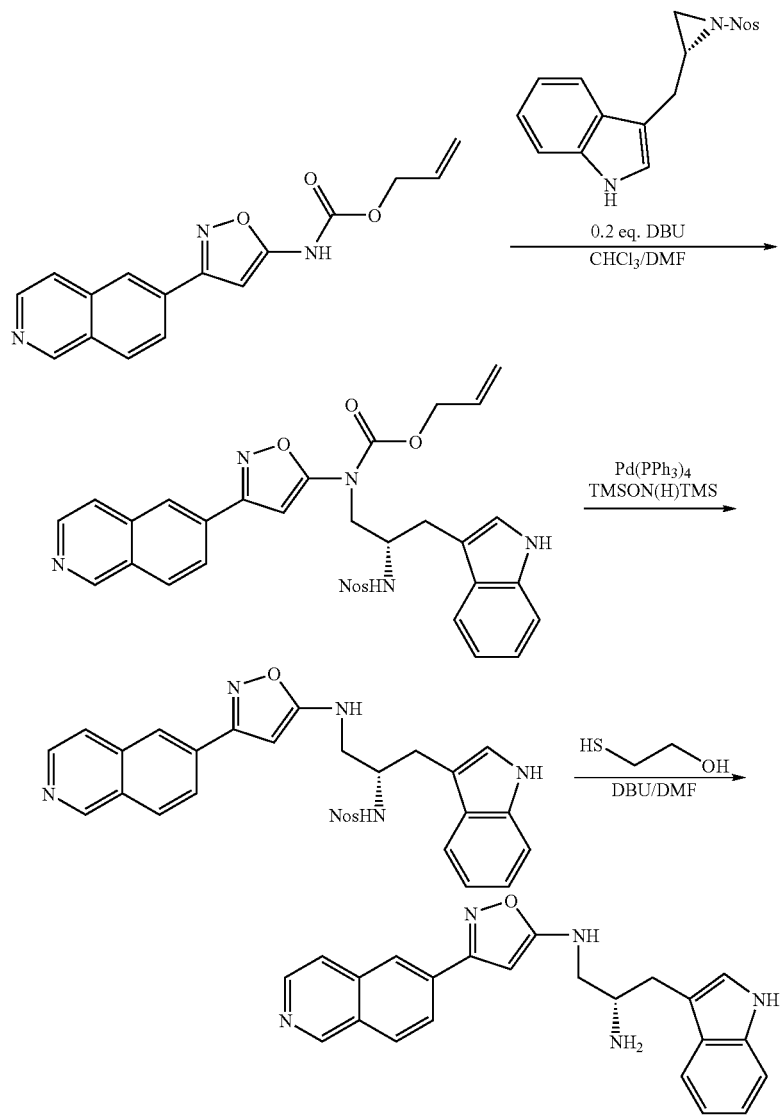

Scheme 10

Allyl(S)-3-(1H-indol-3-yl)-2-(4-nitrophenylsulfonamido)propyl(3-(isoquinolin-6-yl)isoxazol-5-yl)carbamate: To a 25 mL of round-bottom flask was added allyl 3-(isoquinolin-6-yl)isoxazol-5-ylcarbamate (68 mg, 230 μmol) (prepared as shown for Example 11), 1,8-diazabicyclo(5.4.0)-7-undecene (6.8 μl, 46 μmol) and 2 mL of DMF at room temperature. (S)-3-((1-(4-Nitrophenylsulfonyl)aziridin-2-yl)methyl)-1H-indole (98 mg, 276 μmol) (prepared as described in US Patent Publication No. US 2007/0173506 which is hereby incorporated by reference in its entirety and for all purposes as if specifically set forth herein) in 1 mL of DMF was added to the reaction mixture dropwise. After 3 hours, 10 mL of water was added, and then the reaction mixture was extracted twice with 20 mL of EtOAc. The extracts were combined, concentrated under reduced pressure, and purified by flash chromatography on silica gel (65% EtOAc/hexane) to give allyl(S)-3-(1H-indol-3-yl)-2-(4-nitrophenylsulfonamido)propyl(3-(isoquinolin-6-yl)isoxazol-5-yl)carbamate (130 mg, 86% yield). MS m/z: 653 (M+1).

N-((S)-3-(1H-Indol-3-yl)-1-(3-(isoquinolin-6-yl)isoxazol-5-ylamino)propan-2-yl)-4-nitrobenzenesulfonamide: To a solution of allyl(S)-3-(1H-indol-3-yl)-2-(4-nitrophenylsulfonamido)propyl(3-(isoquinolin-6-yl)isoxazol-5-yl)carbamate (100 mg, 153 μmol) in 2.5 mL of DCM was added Pd(PPh$_3$)$_4$ (5.3 mg, 4.6 μmol) and N,O-bis(trimethylsilyl)hydroxylamine (27 mg, 153 μmol). The mixture was stirred for 15 minutes and was then quenched with 2.5 mL saturated aqueous NH$_4$Cl and the biphasic mixture was stirred for 2 hours. The mixture was then partitioned and the aqueous portion was extracted twice with DCM. The combined organic layers were dried over MgSO$_4$, filtered, and concentrated under reduced pressure. The residue was purified by preparative LC to give N-((S)-3-(1H-indol-3-yl)-1-(3-(isoquinolin-6-yl)isoxazol-5-ylamino)propan-2-yl)-4-nitrobenzenesulfonamide (75 mg, 86% yield). MS m/z: 569 (M+1).

N-((S)-2-Amino-3-(1H-indol-3-yl)propyl)-3-(isoquinolin-6-yl)isoxazol-5-amine: To 25 mL of round-bottom flask was added N-((S)-3-(1H-indol-3-yl)-1-(3-(isoquinolin-6-yl)isoxazol-5-ylamino)propan-2-yl)-4-nitrobenzenesulfonamide (75 mg, 132 μmol), 2,3,4,6,7,8,9,10-octahydropyrimido[1,2-a]azepine (20 mg, 132 μmol) (commercially available from Aldrich), 2-mercaptoethanol (10 mg, 132 μmol) and 2 mL of DMF. After 2 hours, the reaction mixture was directly purified by preparative LC to give N-((S)-2-amino-3-(1H-indol-3-yl)propyl)-3-(isoquinolin-6-yl)isoxazol-5-amine (38 mg, 75% yield). MS m/z: 384 (M+1); $^1$H NMR (400 MHz, CD$_3$OD) δ ppm 9.69 (s, 1H), 8.61 (d, J=6.26 Hz, 1H), 8.48 (d, J=8.61 Hz, 1H), 8.37-8.42 (m, 2H), 8.18 (dd, J=8.71, 1.27 Hz, 1H), 7.63 (d, J=7.82 Hz, 1H), 7.46 (d, J=8.22 Hz, 1H), 7.29 (s, 1H), 7.20 (t, J=7.53 Hz, 1H), 7.08 (t, J=7.43 Hz, 1H), 3.81-3.83 (m, 1H), 3.60-3.63 (m, 1H), 3.46-3.54 (m, 1H), 3.20 (d, J=7.24 Hz, 2H),

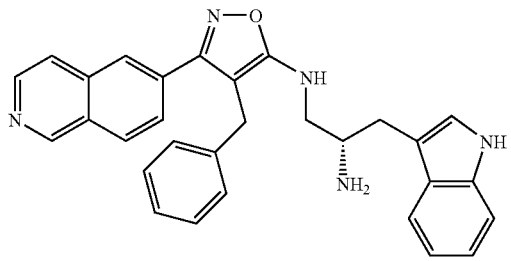

Example 33

N-((S)-2-Amino-3-(1H-indol-3-yl)propyl)-4-benzyl-3-(isoquinolin-6-yl)isoxazol-5-amine: This compound was synthesized in an analogous manner to Example 32 but using 3-phenylpropionitrile (commercially available from Acros Organics Order Number 17399) instead of acetonitrile in the preparation of allyl 4-benzyl-3-(isoquinolin-6-yl)isoxazol-5-ylcarbamate according to Scheme 6 instead of allyl 3-(isoquinolin-6-yl)isoxazol-5-ylcarbamate. MS m/z: 474 (M+1); $^1$H NMR (400 MHz, CD$_3$OD) δ ppm 9.24 (s, 1H), 8.44 (d, J=5.87 Hz, 1H), 8.11 (d, J=8.61 Hz, 1H), 7.93 (s, 1H), 7.75 (dd, J=8.61, 1.37 Hz, 1H), 7.70 (d, J=5.87 Hz, 1H), 7.55 (d, J=7.82 Hz, 1H), 7.39 (d, J=8.02 Hz, 1H), 7.04-7.24 (m, 8H), 3.82 (m, 3H), 3.60-3.73 (m, 2H), 3.21-3.25 (m, 1H), 3.13 (m, 1H).

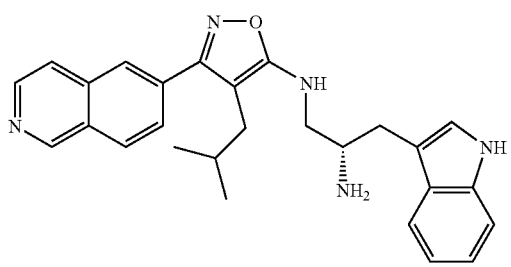

Example 34

N-((S)-2-Amino-3-(1H-indol-3-yl)propyl)-4-isobutyl-3-(isoquinolin-6-yl)isoxazol-5-amine: This compound was synthesized in an analogous manner to Example 32 but using 4-methylpentanenitrile (commercially available from TCI America Organic Chemicals Order Number M0458) instead of acetonitrile in the preparation of allyl 4-isobutyl-3-(isoquinolin-6-yl)isoxazol-5-ylcarbamate according to Scheme 6 instead of allyl 3-(isoquinolin-6-yl)isoxazol-5-ylcarbamate. MS m/z: 440 (M+1); $^1$H NMR (400 MHz, CD$_3$OD) δ ppm 9.73 (s, 1H), 8.61 (d, J=6.65 Hz, 1H), 8.53-8.57 (m, 1H), 8.43 (s, 2H), 8.15 (dd, J=8.61, 1.56 Hz, 1H), 0.57 (d, J=7.43 Hz, 1H), 7.40 (d, J=8.22 Hz, 1H), 7.25 (s, 1H), 7.15 (t, J=7.43 Hz, 1H), 7.06 (t, J=7.24 Hz, 1H), 3.78-3.83 (m, 1H), 3.63-3.68 (m, 2H), 3.22-3.28 (m, 1H), 3.10-3.16 (m, 1H), 2.37 (d, J=7.43 Hz, 2H), 1.58 (dt, J=13.60, 6.70 Hz, 1H), 0.76 (d, J=6.65 Hz, 6H).

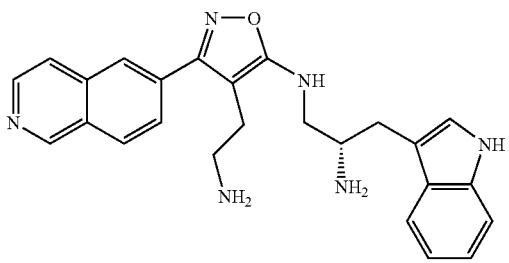

Example 35

N-((S)-2-Amino-3-(1H-indol-3-yl)propyl)-4-(2-aminoethyl)-3-(isoquinolin-6-yl)isoxazol-5-amine: This compound was prepared according to Scheme 11.

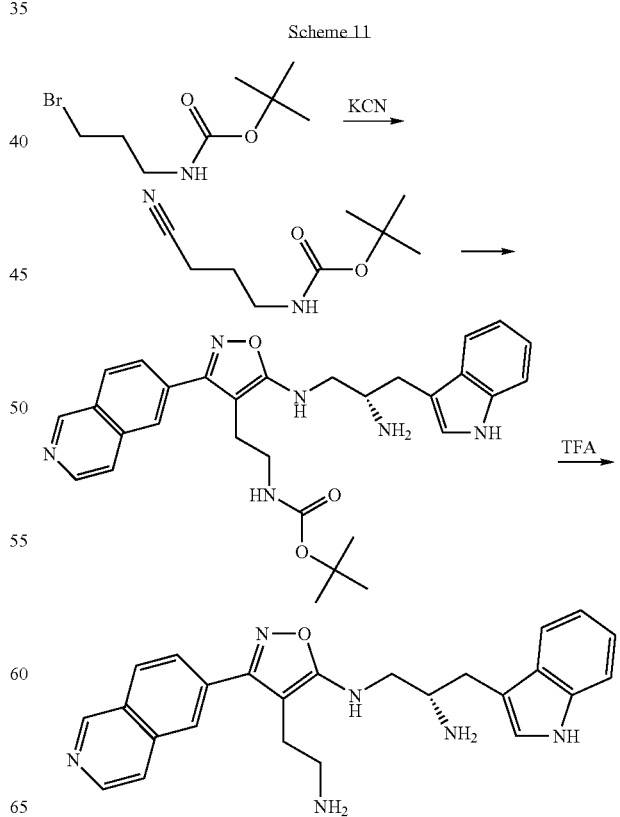

Scheme 11 tert-Butyl 3-cyanopropylcarbamate: To a 250 mL of round-bottom flask was added tert-butyl 3-bromopropylcarbamate (4.0 g, 17 mmol) (commercially available from 3B Scientific Corporation Product List Order Number 3B3-073730), potassium cyanide (1.5 mL, 20 mmol) and 100 mL of DMSO. The reaction mixture was heated at 90° C. for 16 hours. The mixture was then diluted with 100 mL of water, and extracted with 100 mL of EtOAc twice. The extracts were combined, concentrated, and purified by flash chromatography on silica gel (40% EtOAc/hexane) to give tert-butyl 3-cyanopropylcarbamate (1.7 g, 55% yield). MS m/z: 185 (M+1); $^1$H NMR (400 MHz, CDCl$_3$) δ ppm 4.70 (br s, 1H), 3.25 (q, J=6.65 Hz, 2H), 2.40 (t, J=7.24 Hz, 2H), 1.84-1.91 (m, 2H), 1.45 (s, 9H).

tert-Butyl 2-(5-((S)-2-amino-3-(1H-indol-3-yl)propylamino)-3-(isoquinolin-6-yl)isoxazol-4-yl)ethylcarbamate: This compound was synthesized in an analogous manner to Example 32 but using tert-butyl 3-cyanopropylcarbamate instead of acetonitrile in the preparation of 2-propen-1-yl (4-(2-((tert-butoxycarbonyl)amino)ethyl)-3-(6-isoquinolinyl)-5-isoxazolyl)carbamate according to Scheme 6 instead of allyl 3-(isoquinolin-6-yl)isoxazol-5-ylcarbamate. MS m/z: 527 (M+1); $^1$H NMR (400 MHz, CD$_3$OD) δ ppm 9.75 (s, 1H), 8.63 (d, J=6.26 Hz, 1H), 8.51-8.57 (m, 3H), 8.20 (d, J=8.61 Hz, 1H), 7.61 (d, J=8.02 Hz, 1H), 7.40 (d, J=8.22 Hz, 1H), 7.26-7.29 (m, 1H), 7.15 (t, J=7.53 Hz, 1H), 7.08 (t, J=7.43 Hz, 1H), 3.73-3.86 (m, 3H), 3.13-3.24 (m, 4H), 2.62 (t, J=6.94 Hz, 2H), 1.33 (s, 9H).

N-((S)-2-Amino-3-(1H-indol-3-yl)propyl)-4-(2-aminoethyl)-3-(isoquinolin-6-yl)isoxazol-5-amine: To a 25 mL of round-bottom flask was added tert-butyl 2-(5-((S)-2-amino-3-(1H-indol-3-yl)propylamino)-3-(isoquinolin-6-yl)isoxazol-4-yl)ethylcarbamate (11 mg, 21 µmol). 2 mL of 50% TFA/DCM was added to the reaction mixture dropwise. After 10 minutes, LC-MS showed that the BOC group had been removed. The reaction mixture was concentrated under reduced pressure and purified by preparative LC to give N-((S)-2-amino-3-(1H-indol-3-yl)propyl)-4-(2-aminoethyl)-3-(isoquinolin-6-yl)isoxazol-5-amine (7 mg, 79% yield). MS m/z: 427 (M+1); $^1$H NMR (400 MHz, CD$_3$OD) δ ppm 9.79 (s, 1H), 8.56-8.66 (m, 2H), 8.52 (s, 1H), 8.45 (s, 1H), 8.18 (d, J=8.22 Hz, 1H), 7.60 (d, J=7.83 Hz, 1H), 7.39 (d, J=8.02 Hz, 1H), 7.26 (s, 1H), 7.14 (t, J=7.53 Hz, 1H), 7.06 (t, J=7.43 Hz, 1H), 3.75-3.79 (m, 2H), 3.62-3.71 (m, 1H), 3.20 (td, J=14.48, 7.04 Hz, 2H), 2.99 (s, 2H), 2.88 (d, J=6.46 Hz, 2H).

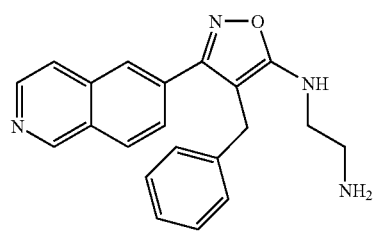

Example 36

N-(2-Aminoethyl)-4-benzyl-3-(isoquinolin-6-yl)isoxazol-5-amine: This compound was synthesized according to the following two steps.

1-(4-Nitrophenylsulfonyl)aziridine: To a 25 mL round-bottom flask was added aziridine (10 mg, 234 µmol), sodium bicarbonate (20 mg, 234 µmol), 4-nitrobenzene-1-sulfonyl chloride (45 mg, 234 µmol) and 2 mL chloroform. After 10 minutes, LC-MS showed the desired product was formed. The reaction mixture was concentrated under reduced pressure to give the crude product of the title compound, that was used directly for the next step. MS m/z: 229 (M+1).

N-(2-Aminoethyl)-4-benzyl-3-(isoquinolin-6-yl)isoxazol-5-amine: This compound was synthesized in an analogous manner to Example 33 but using 1-(4-nitrophenylsulfonyl)aziridine instead of (S)-3-((1-(4-nitrophenylsulfonyl)aziridin-2-yl)methyl)-1H-indole. MS m/z: 345 (M+1); $^1$H NMR (400 MHz, CD$_3$OD) δ ppm 9.62 (s, 1H), 8.55 (d, J=6.46 Hz, 1H), 8.39 (d, J=8.61 Hz, 1H), 8.24-8.28 (m, 1H), 8.21 (s, 1H), 8.18 (d, J=6.46 Hz, 1H), 7.99-8.03 (m, 2H), 7.11-7.24 (m, 3H), 3.91 (s, 2H), 3.71 (t, J=6.26 Hz, 2H), 3.23 (t, J=6.26 Hz, 2H).

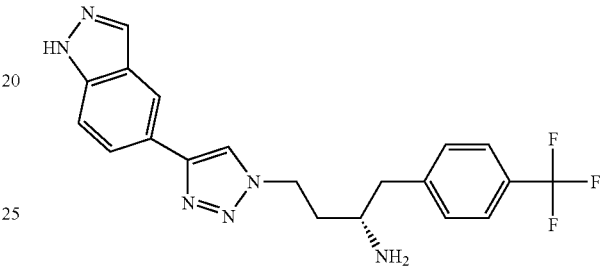

Example 37

(2S)-4-(4-(1H-Indazol-5-yl)-1H-1,2,3-triazol-1-yl)-1-(4-(trifluoromethyl)phenyl)butan-2-amine: As shown in Scheme 12, Example 37 was synthesized starting with commercially available (S)-3-amino-4-(4-(trifluoromethyl)phenyl)butanoic acid hydrochloride [PepTech Corporation, 20 Mall Road, Suite 460, Burlington, Mass. 01803, USA] and 5-bromo-1H-indazole [Fisher Scientific, 2000 Park Lane Drive, Pittsburgh, Pa. 15275, USA]. The 2 step synthesis of 5-ethynyl-1H-indazole was performed in a similar manner as the 5-ethynyl-3-methyl-1H-indazole required for Example 38, using 5-bromo-1H-indazole instead of 5-bromo-3-methyl-1H-indazole.

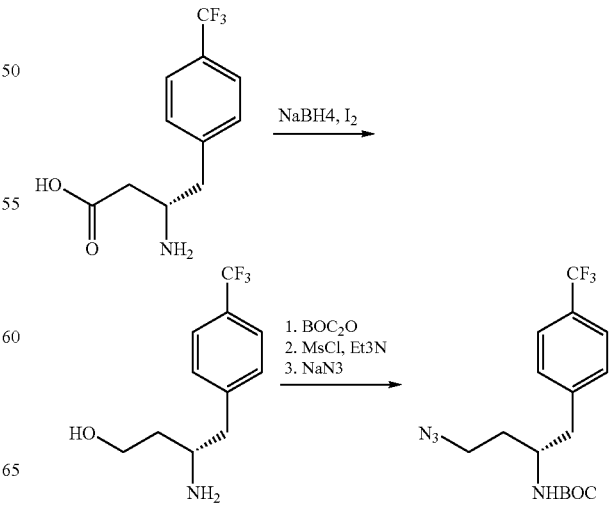

Scheme 12

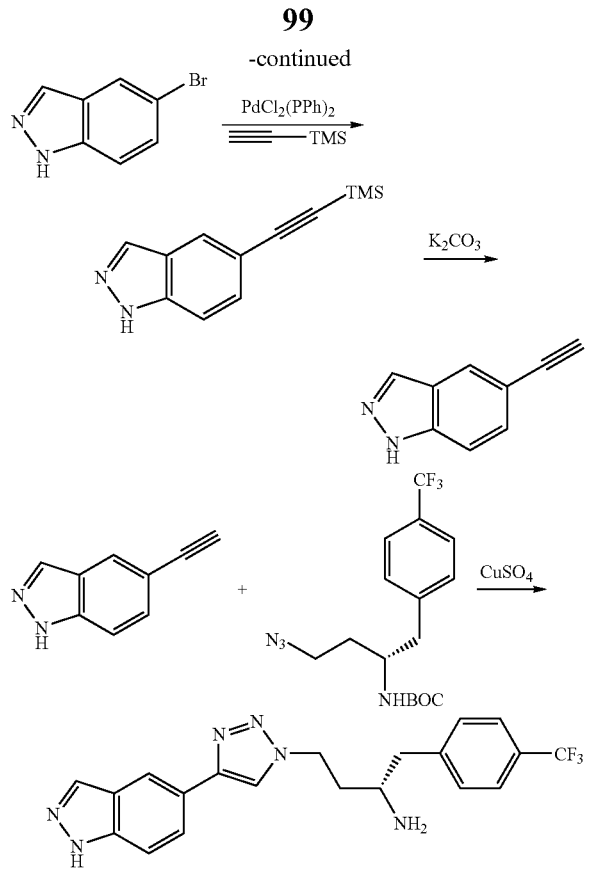

(S)-3-Amino-4-(4-(trifluoromethyl)phenyl)butan-1-ol: (S)-3-Amino-4-(4-(trifluoromethyl)phenyl)butanoic acid hydrochloride (950 mg, 3.84 mmol) and NaBH$_4$ (362 mg, 9.6 mmol) were dissolved in 20 mL THF and cooled to 0° C. A solution of I$_2$ (974 mg, 3.84 mmol) in 5 mL THF was added at 0° C. over a period of 20 minutes. The cooling bath was removed and the reaction was heated at reflux over night. The reaction was cooled to room temperature and carefully hydrolyzed with MeOH until gas evolution ceased. The clear solution was evaporated in vacuo, 20 mL KOH (20%, aqueous) was added, and the reaction was stirred for 3 hours. The reaction was extracted with DCM (3×100 mL), dried over MgSO$_4$ and evaporated. The title compound was obtained as a white solid and used without further purification in the next reaction. LCMS (API-ES) m/z (%): 234.0 (100%, M$^+$+H).

(S)-tert-Butyl 4-hydroxy-1-(4-(trifluoromethyl)phenyl) butan-2-ylcarbamate: (S)-3-Amino-4-(4-(trifluoromethyl) phenyl)butan-1-ol was dissolved in 5 mL THF and 4 mL K$_2$CO$_3$ (1M, aq.) and BOC$_2$O were added. The reaction was stirred over night and acidified (about pH 2). The reaction was extracted with EtOAc (3×100 mL), dried over MgSO4 and evaporated. The title compound was obtained as a white solid and used without further purification. LCMS (API-ES) m/z (%): 333.1 (100%, M$^+$+H).

(S)-3-(tert-Butoxycarbonylamino)-4-(4-(trifluoromethyl) phenyl)butyl methanesulfonate: (S)-tert-Butyl 4-hydroxy-1-(4-(trifluoromethyl)phenyl)butan-2-ylcarbamate was dissolved in 60 mL DCM and cooled to 0° C. MsCl (773 mL, 10 mmol) and Et$_3$N (1.67 mL, 12 mmol) were added and the reaction was stirred for 1.5 hours at 0° C. NaCl (saturated, aqueous) was added, and the mixture was extracted with DCM (3×100 mL), dried over MgSO4 and evaporated. The title compound was obtained as an off-white solid and used without further purification in the next step. LCMS (API-ES) m/z (%): 411.1 (100%, M$^+$+H).

(S)-tert-Butyl 4-azido-1-(4-(trifluoromethyl)phenyl)butan-2-ylcarbamate: (S)-3-(tert-Butoxycarbonylamino)-4-(4-(trifluoromethyl)phenyl)butyl methanesulfonate from the previous reaction was dissolved in 25 mL DMF and NaN$_3$ (1.3 g, 20 mmol) was added. The mixture was heated to 70° C. for 4 hours and cooled back to room temperature. Water and EtOAc were added and the phases were separated. The aqueous phase was extracted with EtOAc (3×100 mL) and the combined organic layers were dried over MgSO4 and evaporated. Glass column chromatography (10% EtOAc in hexanes) provided the title compound as white solid. LCMS (API-ES) m/z (%): 259.0 (100%, M$^+$+H).

(2S)-4-(4-(1H-Indazol-5-yl)-1H-1,2,3-triazol-1-yl)-1-(4-(trifluoromethyl)phenyl)butan-2-amine: 5-Ethynyl-1H-indazole (50 mg, 0.35 mmol) and (S)-tert-butyl 4-azido-1-(4-(trifluoromethyl)phenyl)butan-2-ylcarbamate (143 mg, 0.35 mmol) were dissolved in 2 mL tBuOH/H$_2$O (1/1) and CuSO$_4$.5H$_2$O (1.8 mg, 0.007 mmol) and sodium ascorbate (14 mg, 0.07 mmol) were added. The reaction was stirred for 3 days at room temperature and 10 mL DCM was added and the phases were separated. The aqueous phase was extracted with 50 mL DCM (3×50 mL) and the combined organic phases were dried over MgSO$_4$ and evaporated. The BOC protected intermediate was purified on preparative TLC (6% MeOH in DCM) and treated with 4 mL 30% TFA in DCM for 2 hours. Toluene (30 mL) was added and the mixture was evaporated. The residue was redissolved in 2 mL MeOH, 3 drops of NaOH (5 M, aqueous) was added, and the solution was applied onto a preparative TLC plate for purification (10% MeOH in DCM). 4 mg of the title compound was obtained (0.01 mmol) as a colorless film. LCMS (API-ES) m/z (%): 401.0 (100%, M$^+$+H); $^1$H NMR (300 MHz, CD$_3$OD) δ ppm 8.25-8.30 (m, 1H), 8.17-8.22 (m, 1H), 8.06-8.11 (m, 1H), 7.85 (dd, J=8.76, 1.60 Hz, 1H), 7.54-7.64 (m, 3H), 7.39 (d, J=8.10 Hz, 2H), 4.61 (t, J=7.35 Hz, 2H), 2.98-3.11 (m, 1H), 2.85-2.97 (m, 1H), 2.72-2.83 (m, 1H), 2.06-2.22 (m, 1H), 1.87-2.05 (m, 1H).

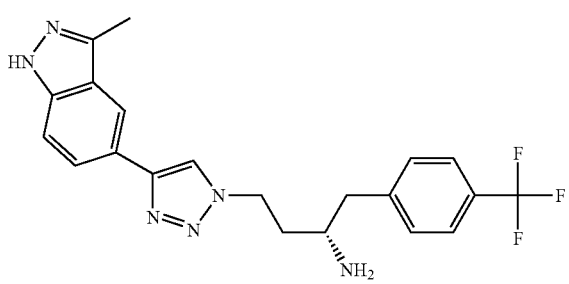

Example 38

(2S)-4-(4-(3-Methyl-1H-indazol-5-yl)-1H-1,2,3-triazol-1-yl)-1-(4-(trifluoromethyl)phenyl)butan-2-amine: Example 38 was synthesized in a similar manner as Example 37 as shown in Scheme 12 utilizing (S)-3-amino-4-(4-(trifluoromethyl)phenyl)butanoic acid hydrochloride and commercially available 5-bromo-3-methyl-1H-indazole [J & W PharmLab, LLC, 1300 W Steel Road, #1 Morrisville, Pa. 19067-3620, USA] instead of 5-bromo-1H-indazole.

3-Methyl-5-(2-(trimethylsilyl)ethynyl)-1H-indazole: 5-Bromo-3-methyl-1H-indazole (1.72 g, 8.2 mmol), PdCl$_2$(PPh)$_2$ (1.14 g, 1.64 mmol), CuI (155 mg, 0.82 mmol) and ethynyltrimethylsilane (3.5 mL, 24.6 mmol) were dissolved in 180 mL Et₃N and refluxed over night. The mixture was cooled to room temperature, filtered and evaporated. The residue was taken up in MeOH (100 mL), filtered again and evaporated. The product thus obtained was purified on glass column chromatography (20% EtOAc in hexane). The title compound was obtained as a dark solid. LCMS (API-ES) m/z (%): 229.0 (100%, M⁺+H).

5-Ethynyl-3-methyl-1H-indazole: 3-Methyl-5-(2-(trimethylsilyl)ethynyl)-1H-indazole (820 mg, 3.55 mmol) was dissolved in 20 mL THF and K₂CO₃ (4.9 g, 35.5 mmol) and 200 mL MeOH were added. The mixture was stirred for 1 hour at room temperature, filtered and evaporated. The mixture was purified via glass column chromatography (35% EtOAc in hexane) and the title compound (500 mg, 3.2 mmol) was obtained as a light yellow solid. LCMS (API-ES) m/z (%): 157.0 (100%, M⁺+H).

(2S)-4-(4-(3-Methyl-1H-indazol-5-yl)-1H-1,2,3-triazol-1-yl)-1-(4-(trifluoromethyl)phenyl)butan-2-amine: Utilizing similar cyclization conditions as described under Example 37, the title compound was obtained as a colorless film (4 mg, 0.01 mmol) LCMS (API-ES) m/z (%): 415.0 (100%, M⁺+H); ¹H NMR (300 MHz, CD₃OD) δ ppm 8.24-8.30 (m, 1H), 8.11-8.17 (m, 1H), 7.83 (dd, J=8.67, 1.51 Hz, 1H), 7.46-7.61 (m, 3H), 7.39 (d, J=8.10 Hz, 2H), 4.52-4.66 (m, 2H), 2.96-3.08 (m, 1H), 2.84-2.96 (m, 1H), 2.68-2.82 (m, 1H), 2.59 (s, 3H), 2.06-2.22 (m, 1H), 1.87-2.03 (m, 1H).

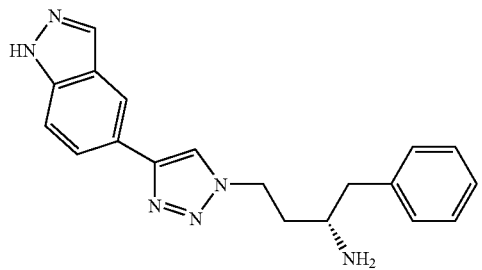

Example 39

(2S)-4-(4-(1H-Indazol-5-yl)-1H-1,2,3-triazol-1-yl)-1-phenylbutan-2-amine: Example 39 was synthesized in a similar fashion as Example 37 as shown in Scheme 12 starting with commercially available (S)-3-(tert-butoxycarbonyl)-4-phenylbutanoic acid (commercially available from PepTech Corporation) instead of (S)-3-amino-4-(4-(trifluoromethyl) phenyl)butanoic acid hydrochloride, and 5-bromo-1H-indazole. The synthesis of the required (S)-tert-butyl 4-azido-1-phenylbutan-2-ylcarbamate was performed in a similar manner as described for the (S)-tert-butyl 4-azido-1-(4-(trifluoromethyl)phenyl)butan-2-ylcarbamate (Examples 37 and 38) including one additional BOC deprotection step.

(S)-3-Amino-4-phenylbutanoic acid: (S)-3-(tert-Butoxycarbonyl)-4-phenylbutanoic acid (1 g, 3.58 mmol) was dissolved in 20 mL DCM and 6 mL TFA was added at room temperature. The mixture was stirred for 2 hours and the mixture was azeotroped 3 times with 25 mL toluene (each). The product thus obtained was used without further purification in the next step. LCMS (API-ES) m/z (%): 179.1 (100%, M⁺+H).

(2S)-4-(4-(1H-Indazol-5-yl)-1H-1,2,3-triazol-1-yl)-1-phenylbutan-2-amine: Utilizing similar cyclization conditions as described under Example 37, the title compound was obtained as white solid (60 mg, 0.188 mmol) LCMS (API-ES) m/z (%): 333.2 (100%, M⁺+H); ¹H NMR (300 MHz, CD₃OD) δ ppm 8.20 (s, 2H), 8.11 (s, 1H), 7.83 (d, J=8.77 Hz, 1H), 7.62 (d, J=8.77 Hz, 1H), 7.18-7.38 (m, 5H), 4.62 (t, J=6.87 Hz, 2H), 3.46-3.60 (m, 1H), 2.92-3.12 (m, 2H), 2.31 (ddd, J=6.72, 6.72, 6.72 Hz, 2H).

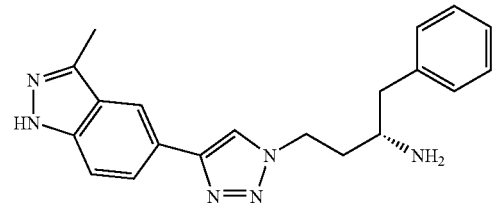

Example 40

(2S)-4-(4-(3-Methyl-1H-indazol-5-yl)-1H-1,2,3-triazol-1-yl)-1-phenylbutan-2-amine: Example 40 was synthesized in a similar fashion as Example 37 as shown in Scheme 12 starting with commercially available (S)-3-(tert-butoxycarbonyl)-4-phenylbutanoic acid instead of (S)-3-amino-4-(4-(trifluoromethyl)phenyl)butanoic acid hydrochloride and 5-bromo-3-methyl-1H-indazole. Utilizing similar cyclization conditions as described under Example 37, the title compound was obtained as a white solid (55 mg, 0.143 mmol) LCMS (API-ES) m/z (%): 347.0 (100%, M⁺+H); ¹H NMR (400 MHz, CD₃OD) δ ppm 8.70 (s, 1H), 8.51 (s, 1H), 8.22 (d, J=9.00 Hz, 1H), 7.84 (d, J=9.00 Hz, 1H), 7.21-7.39 (m, 5H), 4.74 (dd, J=7.04 Hz, 2H), 3.52-3.68 (m, 1H), 3.07 (d, J=7.04 Hz, 2H), 2.87 (s, 3H), 2.40 (ddd, J=6.78, 6.78, 6.78 Hz, 2H).

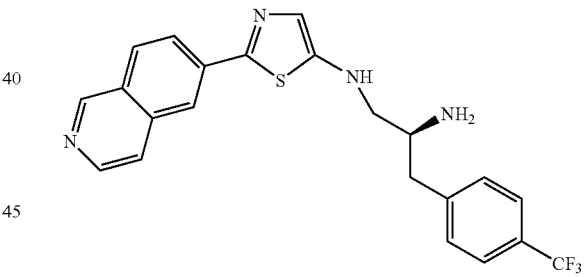

Example 41

N-((S)-2-Amino-3-(4-(trifluoromethyl)phenyl)propyl)-2-(isoquinolin-6-yl)thiazol-5-amine trifluoroacetate: HRMS Theoretical (M+H) 429.13553, found 429.13603. As shown in Scheme 13, Example 41 was synthesized starting with commercially available ethyl 2-bromothiazole-5-carboxylate hydrochloride (Aldrich).

Scheme 13

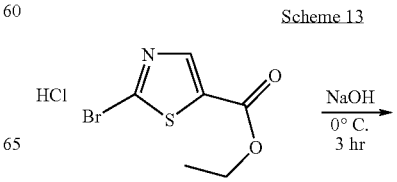

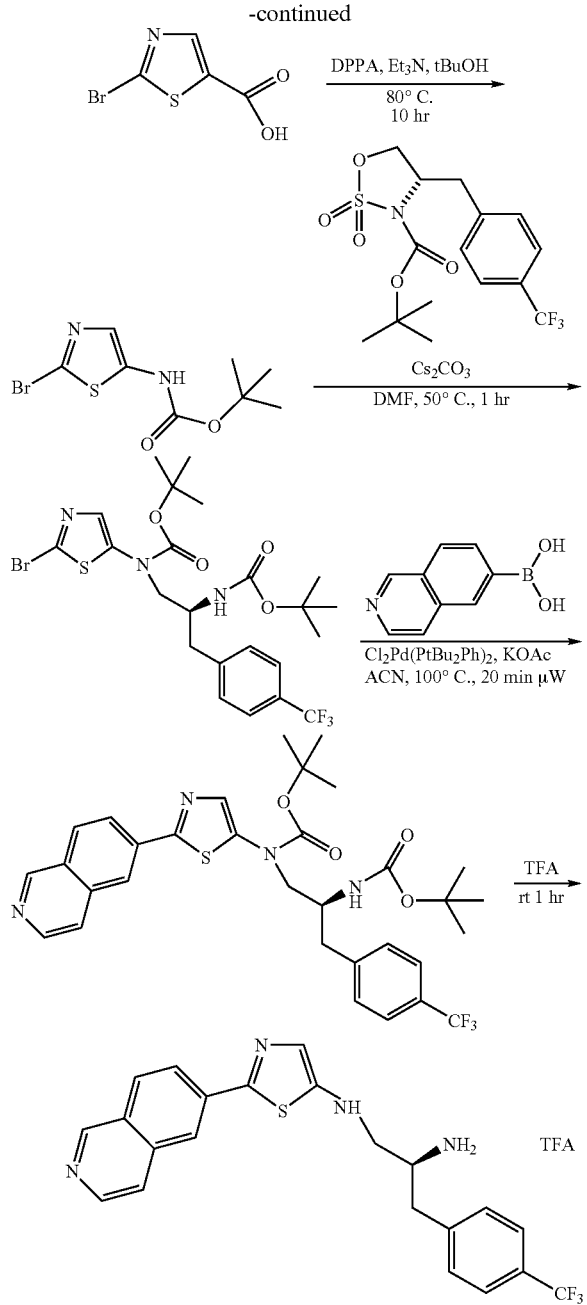

(1.53 mL, 11.0 mmol) were added and the solid quickly dissolved. Diphenylphosphoryl azide (2.61 mL, 12.1 mmol) was added, the flask was closed under a rubber septum, and the sealed flask was heated to 80° C. After 10 hours, the mixture was partitioned between brine (100 mL) and EtOAc (100 mL), and the organic layer was dried over sodium sulfate. The organic layer was evaporated onto a plug of silica gel and purified by chromatography through a Redi-Sep® prepacked silica gel column (120 g), eluting with a gradient of 0% to 80% EtOAc in hexane, to provide the product (2.02 g, 66% yield) as an off-white crystalline solid. LCMS (API-ES) m/z (%): 279 (100%, M−H).

1,1-Dimethylethyl (2-bromo-1,3-thiazol-5-yl)((2S)-2-((((1,1-dimethylethyl)oxy)carbonyl)amino)-3-(4-(trifluoromethyl)phenyl)propyl)-carbamate: To a 250 mL round-bottomed flask was added tert-butyl 2-bromothiazol-5-ylcarbamate (0.75 g, 2.69 mmol), DMF (26.9 mL, 2.69 mmol), and cesium carbonate (1.75 g, 5.37 mmol). The mixture was warmed to 50° C. and 1,1-dimethylethyl 4-((4-(trifluoromethyl)phenyl)methyl)-1,2,3-oxathiazolidine-3-carboxylate 2,2-dioxide (1.13 g, 2.96 mmol, Scheme 1) was added slowly in 10 mL DMF. After 1 hour, the mixture was cooled, diluted with ether (100 mL) and washed with brine (3×50 mL). The organic layer was dried over sodium sulfate, evaporated onto a plug of silica gel and purified by chromatography through a Redi-Sep® pre-packed silica gel column (40 g), eluting with a gradient of 20% to 100% EtOAc in hexane, to provide the product (1.42 g, 91% yield) as a white amorphous solid. LCMS (API-ES) m/z (%): 582 (100%, M+H).

1,1-Dimethylethyl((2S)-2-((((1,1-dimethylethyl)oxy)carbonyl)-amino)-3-(4-(trifluoromethyl)phenyl)propyl)(2-(6-isoquinolinyl)-1,3-thiazol-5-yl)carbamate: A 25 mL glass microwave reaction vessel was charged with isoquinolin-6-ylboronic acid (0.10 g, 0.40 mmol) (prepared as described in US Patent Publication No. US 2007/0173506 which is hereby incorporated by reference in its entirety and for all purposes as if specifically set forth herein), 1,1-dimethylethyl (2-bromo-1,3-thiazol-5-yl)((2S)-2-((((1,1-dimethylethyl) oxy)carbonyl)amino)-3-(4-(trifluoromethyl)phenyl)propyl) carbamate (0.200 g, 0.34 mmol), potassium acetate (0.17 g, 1.7 mmol), bis(ditbutylphenylphosphine)palladiumdichloride (0.019 g, 0.031 mmol), and degassed ACN (3.4 mL, 0.34 mmol) and water (1.500 mL). The reaction mixture was stirred and heated in a Discover® model microwave reactor (CEM, Matthews, N.C.) at 100° C. for 20 minutes. The mixture was diluted with EtOAc (30 mL) and extracted with brine (20 mL). The organic layer was dried over sodium sulfate, evaporated onto a plug of silica gel and purified by chromatography through a Redi-Sep® pre-packed silica gel column (40 g), eluting with a gradient of 0% to 100% EtOAc in hexane, to provide the product (8.9 mg, 4.1% yield) as a yellow oil. LCMS (API-ES) m/z (%): 629 (100%, M+H).

N-((S)-2-Amino-3-(4-(trifluoromethyl)phenyl)propyl)-2-(isoquinolin-6-yl)thiazol-5-amine trifluoroacetate: To a 250 mL round-bottomed flask containing 1,1-dimethylethyl ((2S)-2-((((1,1-dimethylethyl)oxy)carbonyl)-amino)-3-(4-(trifluoromethyl)phenyl)propyl)(2-(6-isoquinolinyl)-1,3-thiazol-5-yl)carbamate (8.9 mg, 0.014 mmol) was added TFA (1 mL). The mixture was stirred at room temperature 1 hour and evaporated. The crude product was purified by reverse-phase preparative HPLC using a Phenomenex Gemini column, 10 micron, C18, 110 Å, 150×30 mm, 0.1% TFA in $CH_3CN/H_2O$, gradient 5% to 100% over 15 minutes, to provide the product (4.9 mg, 64% yield) as a brown oil. $^1$H NMR (400 MHz, $CD_3OD$) δ ppm 3.11-3.20 (m, 2H), 3.43-3.51 (m, 2H), 3.77-3.84 (m, 1H), 7.12 (s, 1H), 7.55 (d, J=8.02 Hz, 2H), 2-Bromothiazole-5-carboxylic acid: To a 25 mL round-bottomed flask at 0° C. was added ethyl 2-bromothiazole-5-carboxylate (0.633 mL, 4.24 mmol) (commercially available from Aldrich), MeOH (4.25 mL, 4.25 mmol), and sodium hydroxide (2.5 M, 1.88 mL, 4.23 mmol). After 3 hours, 3.5 mL 1 N HCl was added and a white precipitate formed. The MeOH was evaporated by rotary evaporation. The white solid was sonicated with water (20 mL) and filtered washing with water (50 mL). The solid material was dried in a vacuum oven at 60° C. to provide the product (0.69 g, 79%) as a white crystalline solid. LCMS (API-ES) m/z (%): 208 (100%, M−H).

tert-Butyl 2-bromothiazol-5-ylcarbamate: A 250 mL round-bottom flask was charged with 2-bromothiazole-5-carboxylic acid (2.29 g, 11.0 mmol) that was crushed to a powder with a spatula. t-Butanol (12.2 mL, 11.0 mmol) and TEA 7.71 (d, J=8.22 Hz, 2H), 8.37 (d, J=6.65 Hz, 1H), 8.43 (s, 3H), 8.49 (d, J=6.65 Hz, 1H), 9.59 (s, 1H). HRMS Theoretical (M+H) 429.13553, found 429.13603.

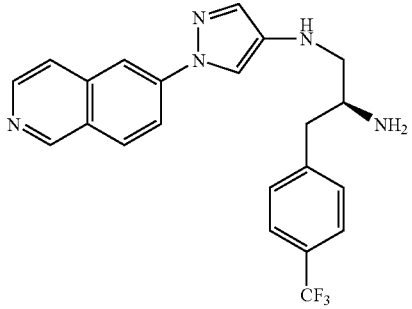

Example 42

N-((S)-2-Amino-3-(4-(trifluoromethyl)phenyl)propyl)-1-(isoquinolin-6-yl)-1H-pyrazol-4-amine: This compound was prepared analogously to Example 46 using (S)-tert-butyl 4-(4-(trifluoromethyl)benzyl)-1,2,3-oxathiazolidine-3-carboxylate-2,2-dioxide (Scheme 1) instead of (S)-tert-butyl 4-(4-chlorobenzyl)-1,2,3-oxathiazolidine-3-carboxylate-2,2-dioxide. LCMS (API-ES) m/z (%): 378.1 (100%, M⁺+H); ¹H NMR (300 MHz, CDCl₃) δ ppm 1.60 (br s, 3H), 2.72 (dd, J=13.3, 8.3 Hz, 1H), 2.89-3.00 (m, 2H), 3.17 (dd, J=12.1, 3.9 Hz, 1H), 3.33 (ddd, J=13.3, 8.0, 3.9 Hz, 1H), 7.36 (d, J=8.0 Hz, 2H), 7.47 (d, J=9.5 Hz, 2H), 7.57-7.66 (m, 3H), 7.91 (s, 1H), 7.96-8.05 (m, 2H), 8.52 (d, J=5.7 Hz, 1H), 9.21 (s, 1H).

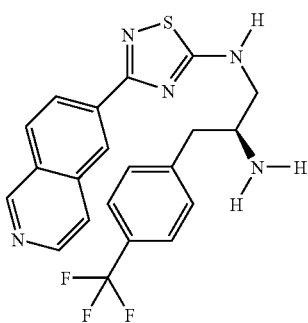

Example 43

N-((S)-2-Amino-3-(4-(trifluoromethyl)phenyl)propyl)-3-(isoquinolin-6-yl)-1,2,4-thiadiazol-5-amine: tert-Butyl-3-chloro-1,2,4-thiadiazol-5-ylcarbamate: To a stirred solution of 3,5-dichloro-1,2,4-thiadiazole (4.22 g, 27 mmol) (commercially available from 3B Scientific Corporation Product List Order Number 3B3-077966) in MeOH (20 mL) was added NH₃ in MeOH (27 mL, 2.0 M) at room temperature. The mixture was stirred at the same temperature for 4 hours. The volatile material was removed and to the white precipitate was added THF (50 mL) and Na₂CO₃ (8.7 g, 82 mmol) followed by BOC₂O (13 mL, 54 mmol). The resulting suspension was heated at 60° C. overnight, cooled, and concentrated. DCM (50 mL) was added to the residue, and the salt was filtered. The organic phase was mixed with SiO₂ and the solvent was evaporated. The residue was then purified by flash column chromatography (pure hexanes to 10% EtOAc in hexanes) to obtain the desired product as a white solid. LCMS (API-ES) m/z (%): 236.7 (100%, M⁺+H); ¹H NMR (400 MHz, CDCl₃) δ ppm 9.50 (s, 1H) 1.57 (s, 9H).

Cyclic sulfamidate opening with tert-butyl-3-chloro-1,2,4-thiadiazol-5-ylcarbamate: To a stirred suspension of tert-butyl 3-chloro-1,2,4-thiadiazol-5-ylcarbamate (180 mg, 764 μmol) and Cs₂CO₃ (498 mg, 1527 μmol) in DMF (3.00 mL, 38745 μmol) was added a solution of (S)-tert-butyl 4-(4-(trifluoromethyl)benzyl)-1,2,3-oxathiazolidine-3-carboxylate-2,2-dioxide (379 mg, 993 μmol, Scheme 1) in DMF (4 mL) slowly, and the resulting mixture was stirred at the same temperature for an additional 30 minutes. The resulting mixture was cooled, diluted with EtOAc (5 mL), and quenched with 1N HCl(aq) until slightly acidic. The mixture was vigorously stirred for 30 minutes at room temperature, and the separated aqueous layer was extracted with EtOAc (10 mL×2). The combined organic layers were washed with brine, dried over Na₂SO₄, and concentrated to give the crude residue, which was purified with flash column chromatography (ISCO Combiflash system, pure hexanes to 50% EtOAc in hexanes) to obtain the desired product as a white foam (51%, mixture of rotatomers). LCMS (API-ES) m/z (%): 537.1 (100%, M⁺+H).

N-((S)-2-Amino-3-(4-(trifluoromethyl)phenyl)propyl)-3-(isoquinolin-6-yl)-1,2,4-thiadiazol-5-amine: The title compound was prepared from the product obtained above and isoquinolin-6-ylboronic acid hydrochloride (prepared as described in US Patent Publication No. US 2007/0173506 which is hereby incorporated by reference in its entirety and for all purposes as if specifically set forth herein) using a coupling-deprotection sequence similar to that described in Example 41, and the product was isolated as a white solid (51% in two steps). LCMS (API-ES) m/z (%): 430.1 (100%, M⁺+H); 1H NMR (400 MHz, CD₃OD) δ ppm 9.26 (s, 1H) 8.66 (s, 1H) 8.47 (d, J=5.67 Hz, 1H) 8.42 (d, J=8.61 Hz, 1H) 8.14 (d, J=8.61 Hz, 1H) 7.89 (d, J=5.67 Hz, 1H) 7.64 (d, J=8.02 Hz, 2H) 7.50 (d, J=8.02 Hz, 2H) 3.38-3.68 (m, 3H) 2.98 (dd, J=13.50, 5.67 Hz, 1H) 2.78-2.88 (m, 1H).

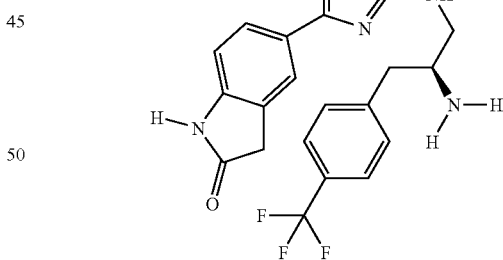

Example 44

5-(5-((S)-2-Amino-3-(4-(trifluoromethyl)phenyl)propylamino)-1,2,4-thiadiazol-3-yl)indolin-2-one: The title compound was prepared in a similar manner to that described for Example 43 using 5-(4,4,5,5-tetramethyl-1,3,2-dioxaborolan-2-yl)indolin-2-one (prepared as described in US Patent Publication No. US 2007/0173506) instead of isoquinolin-6-ylboronic acid hydrochloride. LCMS (API-ES) m/z (%): 434.1 (100%, M⁺+H); ¹H-NMR (CD₃OD, 400 MHz) δ ppm 7.89-8.26 (m, 2H) 7.65 (d, J=6.85 Hz, 2H) 7.50 (d, J=7.24 Hz, 2H) 6.95 (d, J=8.02 Hz, 1H) 3.54-3.67 (m, 2H) 3.38-3.52 (m, 3H) 2.98 (m, 1H) 2.84 (dd, J=13.80, 6.27 Hz, 1H).

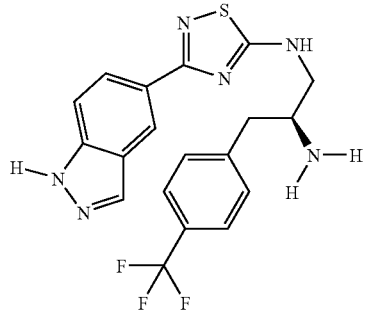

Example 45

N-((S)-2-Amino-3-(4-(trifluoromethyl)phenyl)propyl)-3-(1H-indazol-5-yl)-1,2,4-thiadiazol-5-amine: The title compound was prepared in a similar manner to that described for Example 43 using 5-bromo-1H-indazole (as prepared for Example 37) instead of isoquinolin-6-ylboronic acid. LCMS (API-ES) m/z (%): 419.1 (100%, M⁺+H); ¹H NMR (400 MHz, CD₃OD) δ ppm 8.65 (s, 1H) 8.04 (s, 1H) 7.98 (d, J=7.03 Hz, 1H) 7.75-7.81 (m, 2H) 7.52-7.61 (m, 2H) 7.32 (s, 1H) 3.35-3.57 (m, 3H) 3.04 (dd, J=13.30, 4.77 Hz, 1H) 2.79 (dd, J=13.55, 7.53 Hz, 1H).

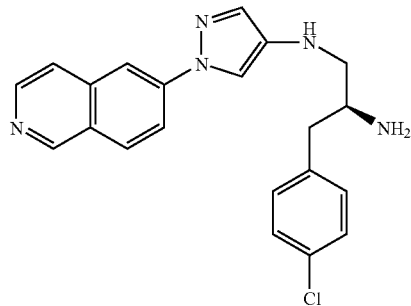

Example 46

N-((S)-2-Amino-3-(4-chlorophenyl)propyl)-1-(isoquinolin-6-yl)-1H-pyrazol-4-amine: This compound was synthesized as shown in Scheme 14 starting from 4-nitro-1H-pyrazole synthesized following the procedure of Williams, J. P. et al. as described in *J. Med. Chem.* 2005, 48, 5780-5793 which is hereby incorporated by reference in its entirety and for all purposes as if specifically set forth herein.

Scheme 14

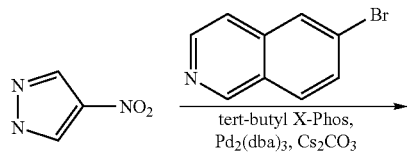

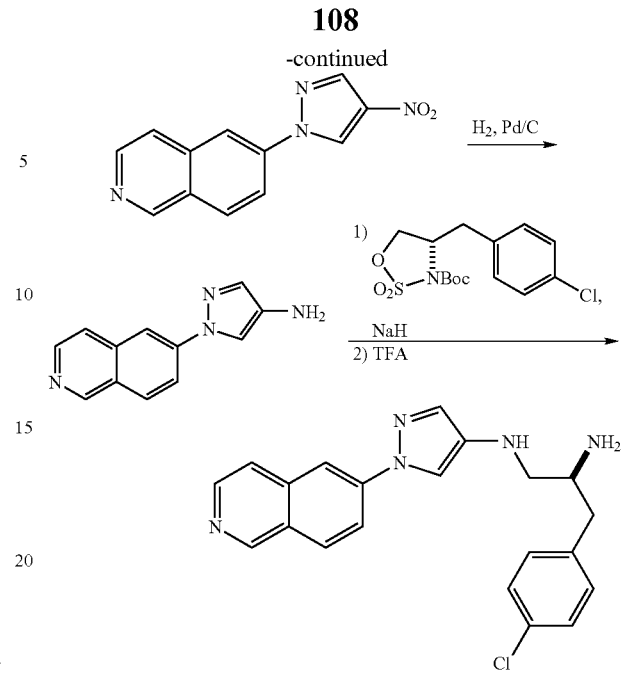

6-(4-Nitro-1H-pyrazol-1-yl)isoquinoline: A mixture of 4-nitro-1H-pyrazole (510 mg, 4.51 mmol), 6-bromoisoquinoline (375 mg, 1.80 mmol) (commercially available from Gateway Chemical Technology, Inc.), tris(dibenzylideneacetone)dipalladium (0) (165 mg, 180 μmol), 2-ditert-butylphosphino-2',4',6'-triisopropyl-1,1'-biphenyl (153 mg, 360 μmol), and cesium carbonate (1.76 g, 5.41 mmol) in dioxane (4 mL) was heated in a sealed vial at 105° C. for 6 hours. The mixture was cooled to ambient temperature and partitioned between DCM (30 mL) and H₂O (30 mL). The layers were separated, and the aqueous layer was extracted with DCM (2×20 mL) and 10% MeOH/DCM (30 mL). The combined organic layers were dried (MgSO₄) and concentrated under reduced pressure. The resulting yellow solid was dissolved in DCM, evaporated onto silica gel, and purified by flash chromatography (Biotage Si 40+M, 20% to 50% acetone/hexanes) to provide 6-(4-nitro-1H-pyrazol-1-yl)isoquinoline (374 mg, 86% yield) as a white solid. LCMS (API-ES) m/z (%): 241.1 (100%, M⁺+H); ¹H NMR (300 MHz, CDCl₃) δ ppm 7.76 (d, J=5.8 Hz, 1H), 8.01 (dd, J=8.8, 2.2 Hz, 1H), 8.14-8.23 (m, 2H), 8.36 (s, 1H), 8.65 (d, J=5.8 Hz, 1H), 8.83 (s, 1H), 9.34 (s, 1H).

1-(Isoquinolin-6-yl)-1H-pyrazol-4-amine: A mixture of 6-(4-nitro-1H-pyrazol-1-yl)isoquinoline (367 mg, 1.53 mmol) and 10 wt. % palladium on activated carbon (163 mg, 153 μmol) in THF (15 mL) was stirred under an atmosphere of hydrogen at ambient temperature for 4 hours. The mixture was filtered through a Celite pad that was washed with THF (30 mL), and the combined filtrates were concentrated under reduced pressure. The resulting yellow solid was dissolved in MeOH/DCM, evaporated onto silica gel, and purified by flash chromatography (Biotage Si 40+M, 3% to 8% MeOH/DCM) to provide 1-(isoquinolin-6-yl)-1H-pyrazol-4-amine (264 mg, 82% yield) as a yellow solid. LCMS (API-ES) m/z (%): 211.2 (100%, M⁺+H); ¹H NMR (300 MHz, CDCl₃) δ ppm 3.01 (br s, 2H), 7.48 (s, 1H), 7.62-7.69 (m, 2H), 7.93 (s, 1H), 7.96-8.06 (m, 2H), 8.52 (d, J=5.8 Hz, 1H), 9.22 (s, 1H).

N-((S)-2-Amino-3-(4-chlorophenyl)propyl)-1-(isoquinolin-6-yl)-1H-pyrazol-4-amine: A 60% dispersion of sodium hydride in mineral oil (9.6 mg, 251 μmol) was added to a mixture of 1-(isoquinolin-6-yl)-1H-pyrazol-4-amine (44 mg, 209 μmol) and (S)-tert-butyl 4-(4-chlorobenzyl)-1,2,3-oxathiazolidine-3-carboxylate-2,2-dioxide (109 mg, 314 μmol) in DMF (1 mL) at ambient temperature and the mixture was stirred at ambient temperature for 1.5 hours. H$_2$O (15 mL) was added, and the mixture was extracted with DCM (4×15 mL). The combined organic layers were dried (MgSO$_4$) and concentrated under reduced pressure. The resulting yellow solid was dissolved in DCM (3 mL), TFA (2 mL) was added, and the mixture was stirred at ambient temperature for 2 hours. Toluene (3 mL) was added, and the mixture was concentrated under reduced pressure. The resulting orange oil was dissolved in DCM, evaporated onto a silica gel plug, and purified by flash chromatography (Biotage Si 25+M, 5% to 10% 2 N NH$_3$ in MeOH/DCM) to provide N-((S)-2-amino-3-(4-chlorophenyl)propyl)-1-(isoquinolin-6-yl)-1H-pyrazol-4-amine (18 mg, 23% yield) as an off-white solid. LCMS (API-ES) m/z (%): 412.2 (100%, M$^+$+H); $^1$H NMR (300 MHz, CDCl$_3$) δ ppm 1.54 (br s, 3H), 2.62 (dd, J=13.1, 8.1 Hz, 1H), 2.79-2.94 (m, 2H), 3.15 (dd, J=11.8, 2.6 Hz, 1H), 3.25 (d, J=4.1 Hz, 1H), 7.17 (d, J=7.8 Hz, 2H), 7.31 (d, J=7.8 Hz, 2H) 7.45 (s, 2H), 7.64 (d, J=5.5 Hz, 1H), 7.89 (s, 1H), 8.00 (s, 2H), 8.51 (d, J=5.5 Hz, 1H), 9.20 (s, 1H). (S)-tert-Butyl 4-(4-chlorobenzyl)-1,2,3-oxathiazolidine-3-carboxylate 2,2-dioxide was prepared in a similar manner as that described for (S)-tert-butyl 4-(4-(trifluoromethyl)benzyl)-1,2,3-oxathiazolidine-3-carboxylate-2,2-dioxide in Scheme 1, using (S)-2-(tert-butoxycarbonylamino)-3-(4-chlorophenyl)propanoic acid (commercially available from 3B Scientific Corporation Product List (Order Number 3B3-011434)) instead of (S)-2-(tert-butoxycarbonylamino)-3-(4-(trifluoromethyl)phenyl)propanoic acid.

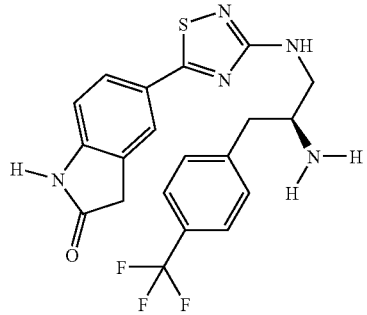

Example 47

5-(3-((S)-2-Amino-3-(4-(trifluoromethyl)phenyl)propylamino)-1,2,4-thiadiazol-5-yl)indolin-2-one 5-Chloro-1,2,4-thiadiazol-3-amine: To a stirred suspension of guanidine hydrochloride (13.0 g, 134 mmol) in DCM (200 mL) was added trichloromethanesulfenyl chloride (15 mL, 134 mmol) slowly at –10° C. The mixture was further cooled to –20° C. and a solution of NaOH (54 g, 1345 mmol) in H$_2$O (55 mL) was dropwise added in such a rate that the temperature was kept under –10° C. After the addition was complete, the overall orange mixture was stirred at –10° C. for an additional 3 hours, and slowly warmed up to room temperature overnight. The overall mixture was filtered through Celite, washed with DCM (100 mL), and then partitioned with water. The aqueous layer was extracted with DCM (100 mL), and the combined organic layers were dried over Na$_2$SO$_4$ and concentrated to give the title compound as a pale yellow solid. An analytic sample was obtained by ether-hexanes washing to afford an off-white solid. LCMS (API-ES) m/z (%): 136.7 (100%, M$^+$+H); $^1$H NMR (400 MHz, CDCl$_3$) δ ppm 4.96 (br s, 2H).

tert-Butyl 5-chloro-1,2,4-thiadiazol-3-ylcarbamate: To a stirred solution of 5-chloro-1,2,4-thiadiazol-3-amine (0.93 g, 6.9 mmol) and BOC$_2$O (2.9 mL, 12 mmol) in DMF (10 mL, 129 mmol) was added sodium hydride (60%) (0.55 g, 14 mmol) at 0° C., and the resulting mixture was stirred at room temperature for 4 hours. The reaction mixture was carefully diluted with aqueous NH$_4$Cl and water (20 mL each) and diluted with EtOAc (15 mL). The separated aqueous layer was extracted with EtOAc (15 mL×2) and the combined organic layers were washed with brine, dried over Na$_2$SO$_4$, and concentrated to give a residue which was purified with flash column chromatography (ISCO Combiflash system, pure hexanes→10% EtOAc in hexanes) to obtain the desired product (0.87 g, 54%) as an off-white solid. LCMS (API-ES) m/z (%): 180.6 (100%, (M$^+$+H)-tert-Bu); $^1$H NMR (400 MHz, CD$_3$OD) δ ppm (1.55, s, 9H).\

Cyclic sulfamidate opening with tert-butyl 5-chloro-1,2,4-thiadiazol-3-ylcarbamate: The title compound was prepared by a similar procedure to that described in Example 43, and isolated as a colorless foam (46%, mixture of rotatomers). LCMS (API-ES) m/z (%): 537.1 (100%, M$^+$+H).

5-(3-((S)-2-Amino-3-(4-(trifluoromethyl)phenyl)propylamino)-1,2,4-thiadiazol-5-yl)indolin-2-one: The title compound was prepared from the product obtained from above and 5-(4,4,5,5-tetramethyl-1,3,2-dioxaborolan-2-yl)indolin-2-one (prepared as described in US Patent Publication No. US 2007/0173506) by similar coupling-deprotection sequence as described previously in Example 41 and isolated as a white solid (9% in two steps). LCMS (API-ES) m/z (%): 434.1 (100%, M$^+$+H); $^1$H NMR (400 MHz, CD$_3$OD) δ ppm 7.82 (s, 1H) 7.81 (d, J=8.03 Hz, 1H) 7.62 (d, J=8.03 Hz, 2H) 7.48 (d, J=8.03 Hz, 2H) 7.00 (d, J=8.03 Hz, 1H) 3.53 (dd, J=12.80, 3.76 Hz, 1H) 3.35-3.45 (m, 2H) 3.33-3.37 (m, 2H) 3.00 (dd, J=13.55, 5.52 Hz, 1H) 2.77 (dd, J=13.30, 7.28 Hz, 1H).

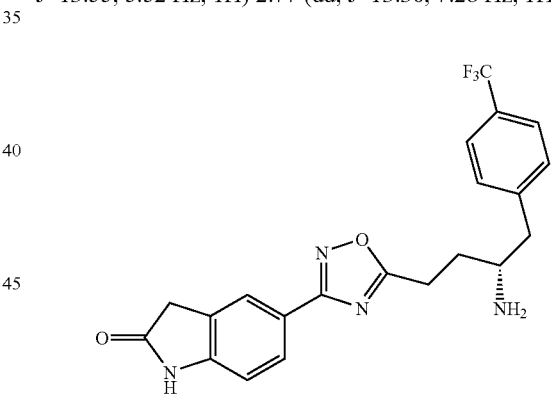

Example 48

5-(5-((R)-3-Amino-4-(4-(trifluoromethyl)phenyl)butyl)-1,2,4-oxadiazol-3-yl)indolin-2-one: This compound was synthesized as shown in Schemes 15 and 16.

Scheme 15

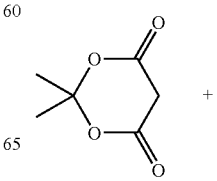

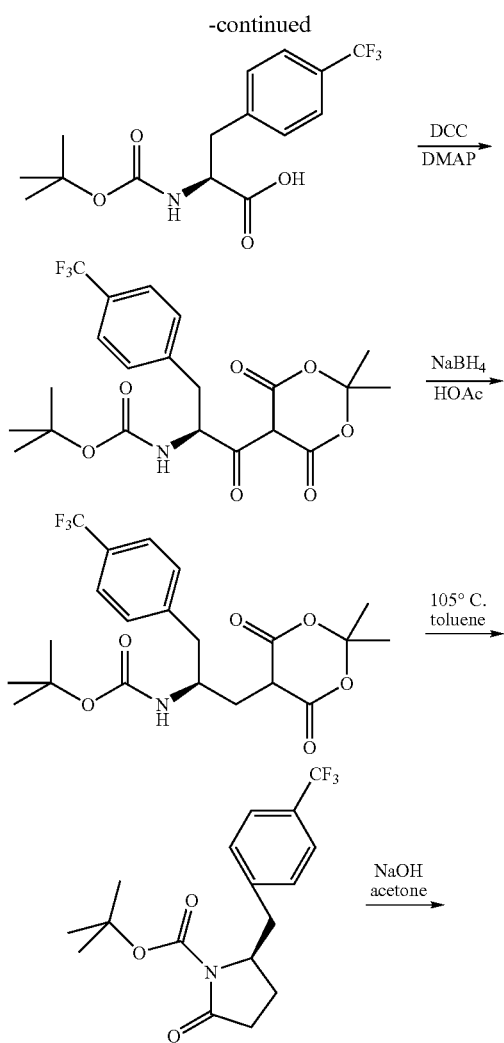

(R)-tert-Butyl 3-(2,2-dimethyl-4,6-dioxo-1,3-dioxan-5-yl)-1-(4-(trifluoromethyl)phenyl)propan-2-ylcarbamate: (S)-tert-Butyl 1-(2,2-dimethyl-4,6-dioxo-1,3-dioxan-5-yl)-1-oxo-3-(4-(trifluoromethyl)phenyl)propan-2-ylcarbamate (22.0 g, 48 mmol) in 200 mL DCM was cooled to −5° C. Acetic acid (32 g, 527 mmol) was added in one portion and sodium tetrahydroborate (4.5 g, 120 mmol) as a solid was added portion wise over about 40 minutes. The reaction mixture was stirred for another 40 minutes and the reaction mixture was stored in the freezer overnight and was then washed with brine (3×150 mL) and water (2×100 mL). The organic layer was dried over $MgSO_4$. The desired product was obtained as a white amorphous solid (21.0 g, 98%). No further purification was performed and the reaction was carried on to the next step.

(R)-tert-Butyl 2-(4-(trifluoromethyl)benzyl)-5-oxopyrrolidine-1-carboxylate: (R)-tert-Butyl 3-(2,2-dimethyl-4,6-dioxo-1,3-dioxan-5-yl)-1-(4-(trifluoromethyl)phenyl)propan-2-ylcarbamate (10.0 g, 22.5 mmol) in 100 mL toluene was heated at 105° C. for 3 hours. Hexane was added, and the mixture was sonicated. The resulting solid was filtered. The desired product was obtained as a white amorphous solid (21.0 g, yield 98%). No further purification was performed and the reaction was carried on to the next step.

(4R)-4-((tert-Butoxycarbonyl)amino)-5-(4-(trifluoromethyl)phenyl)pentanoic acid: (R)-tert-Butyl 2-(4-(trifluoromethyl)benzyl)-5-oxopyrrolidine-1-carboxylate (4.0 g, 12 mmol) was dissolved in 25 mL acetone and 40 mL of 1.0 M aqueous sodium hydroxide. The resulting mixture was stirred for 30 minutes. The acetone was removed and the mixture was acidified with 5.0 M HCl. The resulting solid was filtered and washed with water twice. The crude product was recrystallized from hexane/EtOAc solvent (10:1 ratio, total volume hexane: 100 mL). After the solution was cooled, the crystals slowly appeared and the solution was put in the freezer for 2 hours. Filtration of the solid afforded the desired compound as a white crystalline solid (3.9 g, 93%). MS (API-ES) m/z (%): 384.1 (100%, $M^+$+Na).

(S)-tert-Butyl 1-(2,2-dimethyl-4,6-dioxo-1,3-dioxan-5-yl)-1-oxo-3-(4-(trifluoromethyl)phenyl)propan-2-ylcarbamate: (S)-2-(tert-Butoxycarbonyl)-3-(4-(trifluoromethyl)phenyl)propanoic acid (16.0 g, 48 mmol) (commercially available from 3B Scientific Corporation Product List (Order Number 3B3-007199)), 2,2-dimethyl-1,3-dioxane-4,6-dione (7.6 g, 53 mmol), and N,N-dimethylpyridin-4-amine (9.1 g, 74 mmol) in 200 mL DCM were cooled to −5° C. N-((cyclohexylimino)methylene)-cyclohexanamine (11 g, 53 mmol) in 50 mL DCM was added dropwise over 40 minutes. The resulting mixture was stirred overnight at room temperature. The suspension was filtered and washed with DCM. The filtrate was washed with 5% $KHSO_4$ four times, once with brine, and dried over sodium sulfate. The desired product was obtained as a white amorphous solid (21.0 g, 95%). No further purification was performed and the reaction was carried on to the next step.

Scheme 16

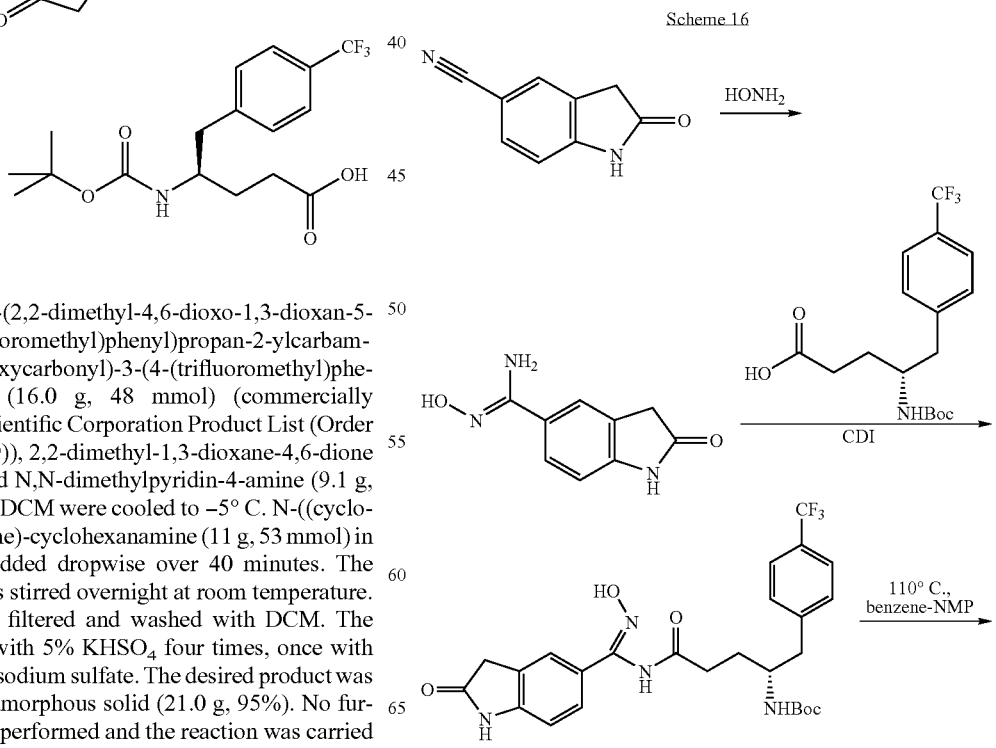

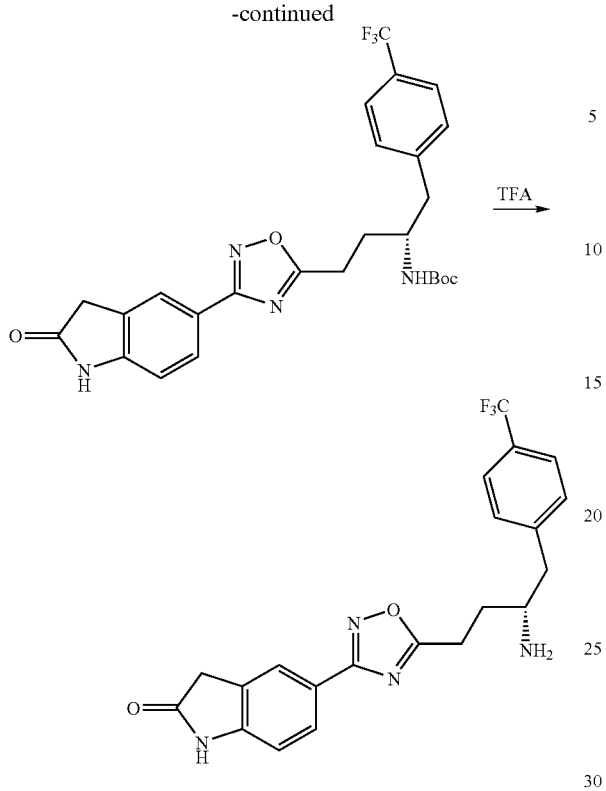

N'-Hydroxy-2-oxoindoline-5-carboxamidine: A mixture of 5-cyanooxindole (5.00 g, 32 mmol) (commercially available from the Combi-Blocks Catalog (Order Number IN-0073), hydroxylamine hydrochloride (4.4 g, 63 mmol), and sodium bicarbonate (11 g, 126 mmol) in 50 mL anhydrous MeOH was heated to 65° C. After 12 hours, the reaction was complete. The mixture was cooled and the suspension was filtered. The resulting solid was washed with 50 mL MeOH. The solid was transferred into a 500 mL round bottom flask and 200 mL distilled water was added. The resulting suspension was sonicated for 5 minutes. Filtration gave the desired compound as an off white solid (5.3 g, 88%). MS (API-ES) m/z (%): 192.0 (100%, M$^+$+H).

(R)-tert-Butyl 5-(N'-hydroxy-2-oxoindoline-5-carboxamidino)-5-oxo-1-(4-(trifluoromethyl)phenyl)pentan-2-ylcarbamate: Di(1H-imidazol-1-yl)methanone (254 mg, 1.6 mmol) and (4R)-4-((tert-butoxycarbonyl)amino)-5-(4-(trifluoromethyl)phenyl)pentanoic acid (567 mg, 1.6 mmol), as prepared in Scheme 15, were mixed in a 20 mL round bottom flask with 5 mL DMF. The mixture was heated at 50° C. for 1 hour and was then cooled to room temperature. N'-hydroxy-2-oxoindoline-5-carboxamidine (250 mg, 1.31 mmol) was added into the flask. The resulting mixture was stirred overnight. The DMF solvent was removed under reduced pressure and 50 mL EtOAc was added to the solid residue. The resulting residue was sonicated and filtered to afford the desired compound as a white solid (460 mg, 66%). MS (API-ES) m/z (%): 535.1 (100%, M$^+$+H).

tert-Butyl(R)-4-(3-(2-oxoindolin-5-yl)-1,2,4-oxadiazol-5-yl)-1-(4-(trifluoromethyl)phenyl)butan-2-ylcarbamate: (R)-tert-Butyl 5-(N'-hydroxy-2-oxoindoline-5-carboxamidino)-5-oxo-1-(4-(trifluoromethyl)phenyl)pentan-2-ylcarbamate (350 mg, 0.65 mmol) in 50 mL of benzene and 8 mL of NMP were heated at 110° C. for 5 hours. The reaction was cooled and the solvent was evaporated. 30 mL of distilled water was added to the resulting residue. A suspension formed and was recovered by filtration. The resulting solid was washed with 10 mL distilled water to afford the desired product as a white solid (221 mg, 65%). MS (API-ES) m/z (%): 517.2 (100%, M$^+$+H).

5-(5-((R)-3-Amino-4-(4-(trifluoromethyl)phenyl)butyl)-1,2,4-oxadiazol-3-yl)indolin-2-one: tert-Butyl(R)-4-(3-(2-oxoindolin-5-yl)-1,2,4-oxadiazol-5-yl)-1-(4-(trifluoromethyl)phenyl)butan-2-ylcarbamate (200 mg, 0.37 mmol) was dissolved in 5.0 mL anhydrous DCM, and 5.0 mL TFA was added. After 30 minutes stirring at room temperature, the solvent was evaporated and the residue was taken up in 100 mL EtOAc. To the resulting solution was added 50 mL of saturated aqueous sodium bicarbonate and 30 mL 5% aqueous sodium carbonate. The organic layer was washed with brine and dried over sodium sulfate to afford the product as a white solid (130 mg, 81%). MS (API-ES) m/z (%): 417.1 (100%, M$^+$+H).

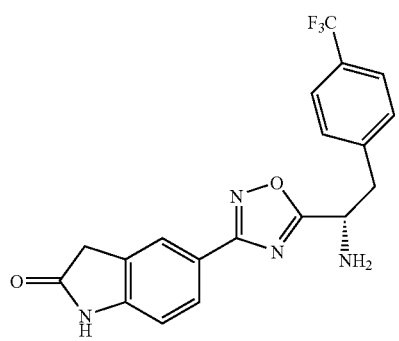

Example 49

5-(5-((S)-1-Amino-2-(4-(trifluoromethyl)phenyl)ethyl)-1,2,4-oxadiazol-3-yl)indolin-2-one: This compound was prepared in a similar manner as Example 48, using (S)-2-amino-3-(4-(trifluoromethyl)phenyl)propanoic acid instead of (4R)-4-((tert-butoxycarbonyl)amino)-5-(4-(trifluoromethyl) phenyl)pentanoic acid. LCMS (API-ES) m/z (%): 389.1 (100%, M+H$^+$). (S)-2-Amino-3-(4-(trifluoromethyl)phenyl) propanoic acid was commercially available from 3B Scientific Corporation Product List (Order Number 3B3-007199).

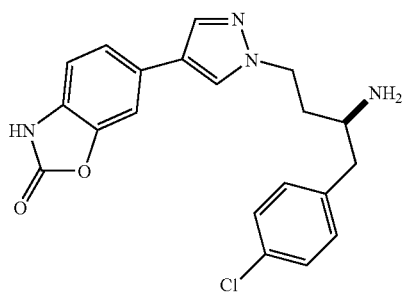

Example 50

6-(1-((S)-3-Amino-4-(4-chlorophenyl)butyl)-1H-pyrazol-4-yl)benzo[d]oxazol-2(3H)-one: This compound was synthesized as shown in Scheme 17.

Scheme 17

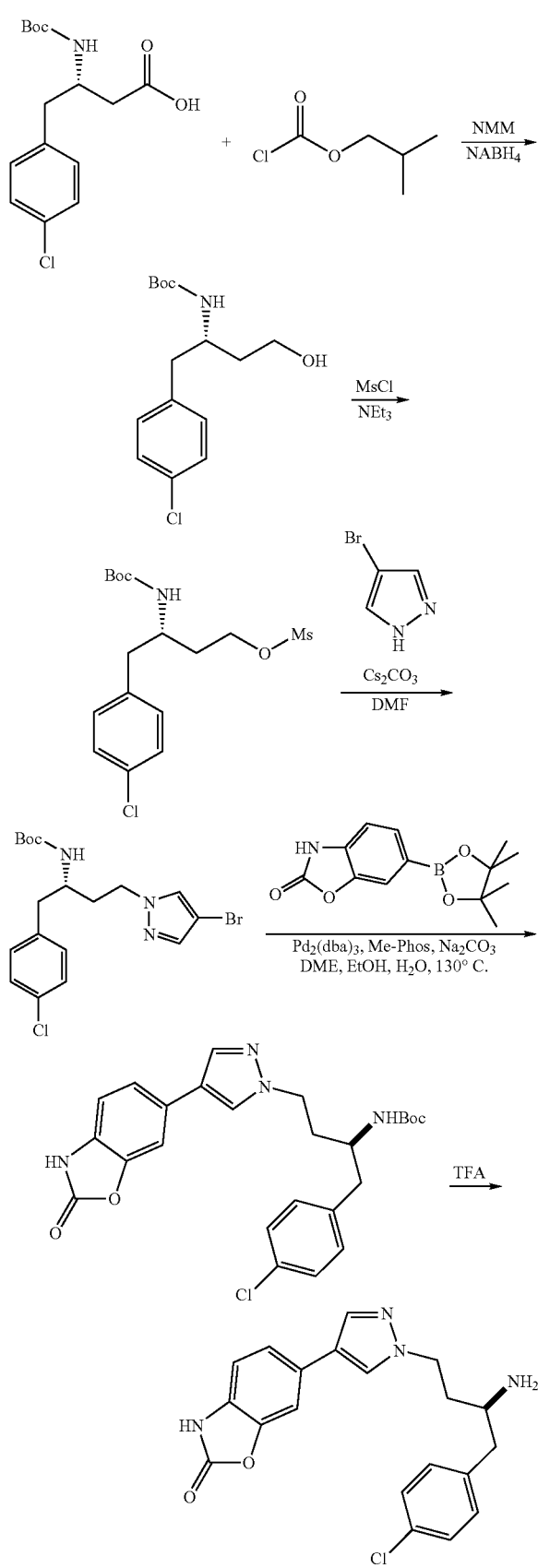

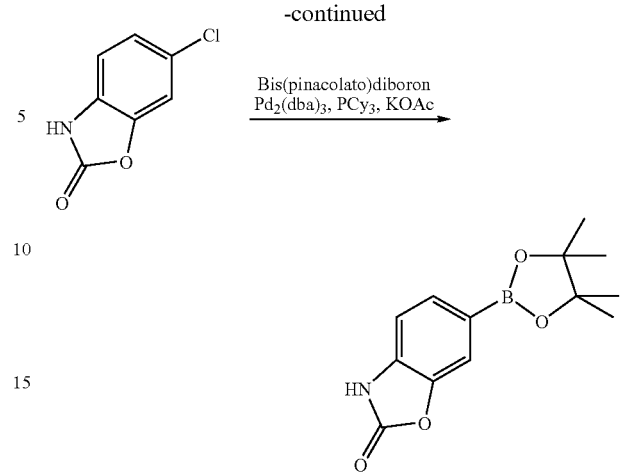

(S)-tert-Butyl 1-(4-chlorophenyl)-4-hydroxybutan-2-yl-carbamate: To a mixture of (S)-3-(tert-butoxycarbonyl)-4-(4-chlorophenyl)butanoic acid (1.00 g, 3.2 mmol) (commercially available from 3B Scientific Corporation Product List (Order Number 3B3-013689)) and N-methylmorpholine (0.35 mL, 3.2 mmol) in DME (5 mL) at −10° C. was added isobutyl chloroformate (0.42 mL, 3.2 mmol). The mixture was stirred for 5 minutes and filtered to remove the amine salt. The filtrate was then cooled to −10° C. and a solution of sodium borohydride (0.18 g, 4.8 mmol) in water (3 mL) was added. Additional water was added and the mixture was filtered to collect the product as a white solid (686 mg, 72%). LCMS (API-ES) m/z: 322 (M+Na$^+$). This procedure was adapted from a literature procedure: Rodriguez, M., Llinares, M., Doulut, S., Heitz, A., Martinez, J., Tet. Lett. 1991, 32, 923 which is hereby incorporated by reference.

(3S)-3-((tert-Butoxycarbonyl)amino)-4-(4-chlorophenyl) butyl methanesulfonate: To a mixture of (S)-tert-Butyl 1-(4-chlorophenyl)-4-hydroxybutan-2-ylcarbamate (686 mg, 2.3 mmol) and TEA (399 µl, 2.9 mmol) in DCM (10 mL) at −8° C. was added methanesulfonyl chloride (214 µl, 2.7 mmol). The resulting mixture was stirred for 2 hours. After warming to room temperature, the mixture was diluted with DCM and washed with H$_2$O (2×). The combined organic layers were dried over Na$_2$SO$_4$, filtered, and concentrated to give the product as a light yellow solid (815 mg, 94%). LCMS (API-ES) m/z: 400 (M+Na$^+$).

(S)-tert-Butyl 4-(4-bromo-1H-pyrazol-1-yl)-1-(4-chlorophenyl)butan-2-ylcarbamate: To a mixture of 4-bromopyrazole (1.26 g, 8.57 mmol) and cesium carbonate (4.66 g, 14.3 mmol) in DMF (20 mL) was added (3S)-3-((tert-butoxycarbonyl)amino)-4-(4-chlorophenyl)butyl methanesulfonate (2.70 g, 7.15 mmol). The mixture was stirred for 16 hours at room temperature. The mixture was diluted with DCM and washed with H$_2$O (2×). The combined organic layers were dried over Na$_2$SO$_4$, filtered and concentrated. The residue was purified by column chromatography (EtOAc/Hexanes, 0-25%) to give the product as an off-white solid (2.86 g, 93%). LCMS (API-ES) m/z: 428, 430 (M+H$^+$).

6-(4,4,5,5-Tetramethyl-1,3,2-dioxaborolan-2-yl)benzo[d]oxazol-2(3H)-one: Bis(pinacolato)diboron (3.6 g, 14 mmol), potassium acetate (1.7 g, 18 mmol), tricyclohexylphosphine (0.48 g, 1.7 mmol), 6-chlorobenzo[d]oxazol-2(3H)-one (2.0 g, 12 mmol) (commercially available from Acros Organics (Order Number 29726)), Pd$_2$(dba)$_3$ (0.65 g, 0.71 mmol) and 5 mL of dioxane were heated in a Smith Synthesizer® microwave reactor (Personal Chemistry, Inc., Upssala, Sweden) at 150° C. for 20 minutes. The reaction mixture was adsorbed onto silica gel. The residue was purified by chromatography on silica gel (0-40% EtOAc/hexane) to give the product as a white solid (2.0 g, 65% yield). $^1$H NMR (400 MHz, CDCl$_3$) ppm d 1.58 (s, 12H), 7.05 (d, J=7.82 Hz, 1H), 7.61-7.65 (m, 2H), 8.21 (br s, 1H).

tert-Butyl(S)-1-(4-chlorophenyl)-4-(4-(2-oxo-2,3-dihydrobenzo[d]oxazol-6-yl)-1H-pyrazol-1-yl)butan-2-ylcarbamate: A mixture of (S)-tert-butyl 4-(4-bromo-1H-pyrazol-1-yl)-1-(4-chlorophenyl)butan-2-ylcarbamate (200 mg, 0.47 mmol), 6-(4,4,5,5-tetramethyl-1,3,2-dioxaborolan-2-yl)benzo[d]oxazol-2(3H)-one (183 mg, 0.70 mmol), sodium carbonate (148 mg, 1.40 mmol), 2-(dicyclohexylphosphino)-2'-methylbiphenyl (34.0 mg, 0.09 mmol), and bis(dibenzylideneacetone)palladium(0) (42.7 mg, 0.05 mmol) in DME:EtOH:H$_2$O (7:2:3, 4 mL) was heated at 130° C. for 15 minutes in a Biotage Initiators microwave. After cooling to room temperature, the mixture was diluted with saturated aqueous NaHCO$_3$ and extracted with DCM (3×). The combined organic layers were dried over Na$_2$SO$_4$, filtered and concentrated. The material thus obtained was used without further purification.

6-(1-((S)-3-Amino-4-(4-chlorophenyl)butyl)-1H-pyrazol-4-yl)benzo[d]oxazol-2(3H)-one: tert-Butyl(S)-1-(4-chlorophenyl)-4-(4-(2-oxoindolin-5-yl)-1H-pyrazol-1-yl)butan-2-ylcarbamate was dissolved in DCM (2 mL), TFA (2 mL, 26 mmol) was added, and the mixture was stirred for 2 hours. The mixture was concentrated by vacuum distillation and partially purified with reverse-phase HPLC (Phenomenex Synergi 4m Max RP 80 A column, 150×21 mm, 20 mL/min, 10-95% CH$_3$CN/H$_2$O 0.1% TFA, 10.5 minute gradient). After concentrating the sample by vacuum distillation, the residue was dissolved in MeOH and loaded onto an Agilent AccuBOND II SCX solid phase extraction column. After washing with MeOH, the desired compound was eluted with 2M NH$_3$ in MeOH. The residue was partially purified using column chromatography (2M NH$_3$ in MeOH/DCM 0-5%). The residue was purified SFC chromatography (Princeton Chromatography Pyridine column 21×250 mm, 5 um, 65 mL/min, 40° C., outlet pressure 100 bar, 220 nm, 10-50% MeOH 2% DEA/CO$_2$, 5 minute gradient) to give a tan film (7.1 mg, 4%). HRMS (TOF) Calcd for C$_{20}$H$_{20}$ClN$_4$O$_2^+$: 383.1269, found: 383.1268.

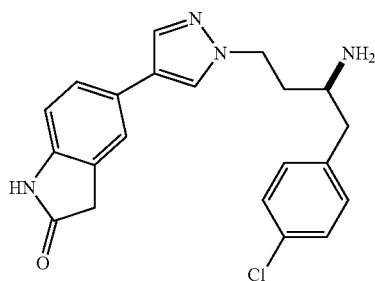

Example 51

5-(1-((S)-3-Amino-4-(4-chlorophenyl)butyl)-1H-pyrazol-4-yl)indolin-2-one: This compound was prepared in a similar manner as Example 50, using 5-bromooxindole commercially available from 3B Scientific Corporation Product List (Order Number 3B3-001953) instead of 6-chlorobenzo[d]oxazol-2(3H)-one. HRMS (TOF) Calcd for C$_{21}$H$_{22}$ClN$_4$O$^+$: 381.1477, found: 381.1477.

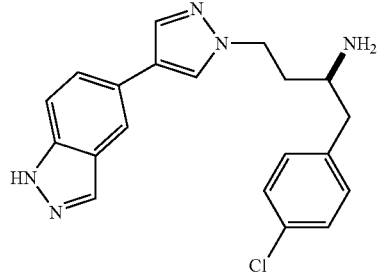

Example 52

(2S)-4-(4-(1H-Indazol-5-yl)-1H-pyrazol-1-yl)-1-(4-chlorophenyl)butan-2-amine: This compound was prepared in a manner similar to Example 50 using 5-(4,4,5,5-tetramethyl-1,3,2-dioxaborolan-2-yl)-1H-indazole, prepared in a similar manner as described in US 2007/0173506, instead of 6-(4,4,5,5-tetramethyl-1,3,2-dioxaborolan-2-yl)benzo[d]oxazol-2(3H)-one. HRMS (TOF) Calcd for C$_{20}$H$_{21}$ClN$_5^+$: 366.1480, found: 366.1477.

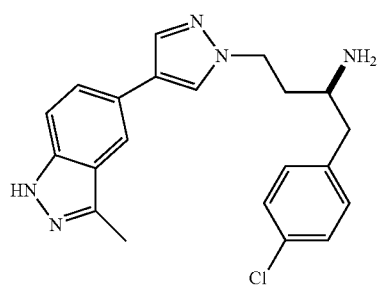

Example 53

(2S)-1-(4-Chlorophenyl)-4-(4-(3-methyl-1H-indazol-5-yl)-1H-pyrazol-1-yl)butan-2-amine: This compound was prepared in a manner similar to Example 50 using 3-methyl-5-(4,4,5,5-tetramethyl-1,3,2-dioxaborolan-2-yl)-1H-indazole (prepared as shown in US 2007/0173506), instead of 6-(4,4,5,5-tetramethyl-1,3,2-dioxaborolan-2-yl)benzo[d]oxazol-2(3H)-one. HRMS (TOF) Calcd for C$_{21}$H$_{23}$ClN$_5^+$: 380.1637, found: 380.1631.

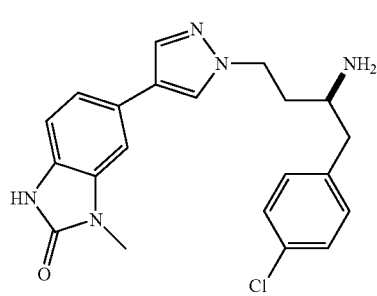

Example 54

6-(1-((S)-3-Amino-4-(4-chlorophenyl)butyl)-1H-pyrazol-4-yl)-1-methyl-1H-benzo[d]imidazol-2(3H)-one: This compound was prepared in a manner similar to Example 50 using 1-methyl-6-(4,4,5,5-tetramethyl-1,3,2-dioxaborolan-2-yl)-1H-benzo[d]imidazol-2(3H)-one instead of 6-(4,4,5,5-tetramethyl-1,3,2-dioxaborolan-2-yl)benzo[d]oxazol-2(3H)-one. HRMS (TOF) Calcd for $C_{21}H_{23}ClN_5O^+$: 396.1586, found: 396.1587. 1-methyl-6-(4,4,5,5-tetramethyl-1,3,2-dioxaborolan-2-yl)-1H-benzo[d]imidazol-2(3H)-one was prepared as shown in Scheme 18.

Scheme 18

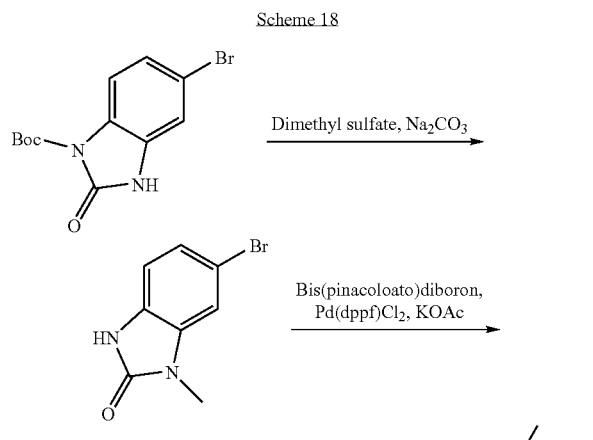

6-Bromo-1-methyl-1H-benzo[d]imidazol-2(3H)-one: tert-Butyl 5-bromo-2-oxo-2,3-dihydrobenzo[d]imidazole-1-carboxylate (12 g, 38 mmol) (Puwen Zhang, et. al., Bioorganic & Medicinal Chemistry Letters 11 (2001) 2747-2750 hereby incorporated by reference) and anhydrous disodium carbonate (3.2 mL, 77 mmol) were mixed in 200 mL THF. To this mixture was added dimethyl sulfate (15 mL, 153 mmol). The mixture was stirred at room temperature for 18 hours. The solvent was evaporated. The residue was dissolved in EtOAc and washed with brine and dried over sodium sulfate. The solvent was evaporated. The residue was taken up in MeOH (50 mL) and allowed to stand 18 hours. The solvent was evaporated, and the residue was triturated from MeOH (25 mL) to provide the product as a white solid (8.7 g, 100%). LCMS (API-ES) m/z: 227, 229 (M+H$^+$).

1-Methyl-6-(4,4,5,5-tetramethyl-1,3,2-dioxaborolan-2-yl)-1H-benzo[d]imidazol-2(3H)-one: Potassium acetate (6.4 g, 65 mmol), bis(pinacolato)diboron (6.1 g, 24 mmol), and 6-bromo-1-methyl-1H-benzo[d]imidazol-2(3H)-one (4.94 g, 22 mmol) were mixed in 20 mL DMSO, and the mixture was degassed with nitrogen bubbling for 1 minute. To this mixture was added Pd(dppf)Cl$_2$ (0.80 g, 1.1 mmol). The mixture was heated at 80° C. for 20 hours. The mixture was partitioned between 200 mL diethyl ether and 20 mL saturated ammonium chloride. The ether solution was washed with the saturated aqueous ammonium chloride (4×), dried over sodium sulfate and evaporated. The residue was crystallized from MeOH. The mother liquor was purified by chromatography on silica gel (30% EtOAc in hexane). The recovered material was combined to provide the product as a white solid (3.5 g, 59%). LCMS (API-ES) m/z: 275 (M+H$^+$).

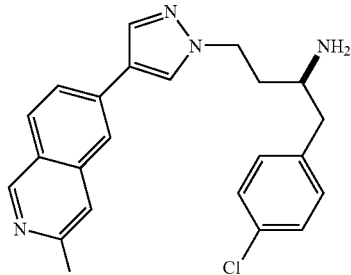

Example 55

(2S)-1-(4-Chlorophenyl)-4-(4-(3-fluoroisoquinolin-6-yl)-1H-pyrazol-1-yl)butan-2-amine: This compound was prepared in a manner similar to Example 50 using 3-fluoroisoquinolin-6-ylboronic acid instead of 6-(4,4,5,5-tetramethyl-1,3,2-dioxaborolan-2-yl)benzo[d]oxazol-2(3H)-one. HRMS (TOF) Calcd for $C_{22}H_{21}ClFN_4^+$: 395.1433, found: 395.1432. 3-Fluoroisoquinolin-6-ylboronic acid was prepared as shown in Scheme 19.

Scheme 19

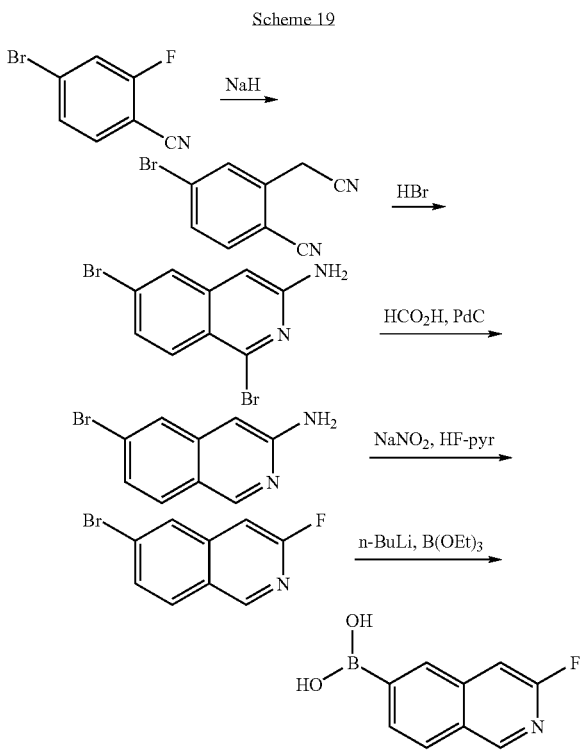

4-Bromo-2-(cyanomethyl)benzonitrile: Sodium hydride (47.2 g, 1.18 mol) was suspended in 320 mL DMSO and cooled to 0° C. in an ice-water bath. The mixture became viscous as the DMSO began to freeze. Methyl cyanoacetate (104 mL, 1.18 mol) was added slowly causing a slight temperature increase and thus a more easily stirrable solution. The mixture was stirred for 30 minutes at room temperature. 4-Bromo-2-fluorobenzonitrile (118 g, 590 mmol) (commercially available from Acros Organics (Order Number 29049)) was added via cannula as a solution in 500 mL DMSO. The mixture was heated to an internal temperature of 90° C. The mixture was cooled and allowed to stand overnight. 1.2 L of water was added to the reaction mixture. The mixture was heated to an internal temperature of 104° C. over 3 hours. 2.3 L of water was added and the mixture was heated at reflux 16 hours. The mixture was cooled to 5° C. and 700 mL of 0.2N HCl was added. The mixture was allowed to stir at 5° C. for 30 minutes. The resulting precipitate was filtered, washed with water, and dried to provide the product (102 g, 78%). LCMS (API-ES) m/z: 223, 221 (M+H$^+$).

1,6-Dibromoisoquinolin-3-amine: 4-Bromo-2-(cyanomethyl)benzonitrile (75 g, 339 mmol) was added to 2,2-dichloroacetic acid (150 mL, 339 mmol). The resulting solution was cooled to 0° C. in an ice-water bath. HBr (27.5 g, 339 mmol) was bubbled through the cold solution until a yellow precipitate crashed out of solution resulting in a yellow slurry. HBr was bubbled through the slurry for an additional 5 minutes. The solution was allowed to warm to room temperature over 1 hour. The slurry was then re-cooled to 0° C. in an ice-water bath and diethyl ether (200 mL) was added. The mixture was stirred for 20 minutes at 5° C. The product was recovered as a yellow solid by filtration (42 g, 41%). LCMS (API-ES) m/z: 303 (M+H$^+$).

6-Bromoisoquinolin-3-amine: A mixture of 1,6-dibromoisoquinolin-3-amine (13.5 g, 45 mmol), ammonium formate (10.8 g, 172 mmol) and tetrakis(triphenylphosphine)palladium (0) (3.45 g, 3.0 mmol) in 50 mL of DMF were sealed in a 350 mL screw-cap flask and heated at 50° C. for 48 hours. To the reaction was added tetrakis(triphenylphosphine)palladium (0) (950 mg) and ammonium formate (3.0 g), and the mixture was heated at 50° C. for 48 hours. The mixture was cooled to room temperature and the solid was filtered, washed with a minimal amount of DMF, washed with Et$_2$O and dried in vacuo at 50° C. to give the product as a yellow amorphous solid (10.4 g, 90%) LCMS (API-ES) m/z: 222.9, 224.9 [M+1]. $^1$H NMR (300 MHz, DMSO-d$_6$) δ ppm 8.81 (s, 1H), 7.80 (d, J=1.6 Hz, 1H), 7.73 (d, J=8.8 Hz, 1H), 7.22 (dd, J=8.6, 1.9 Hz, 1H), 6.55 (s, 1H), 6.12 (s, 2H).

6-Bromo-3-fluoroisoquinoline: To a mixture of 6-bromoisoquinolin-3-amine (0.71 g, 3.18 mmol) in pyridine hydrofluoride (10 mL, 3.18 mmol) at −78° C. was carefully added sodium nitrite (0.26 g, 3.82 mmol). The reaction mixture was stirred at −78° C. for 5 minutes. The reaction mixture was then warmed to room temperature over 40 minutes. The mixture was poured into an ice bath and the pH was adjusted to >9 with Na$_2$CO$_3$. The mixture was filtered to recover a yellow-purple solid. The solid was dissolved in EtOAc and water with stirring. The mixture was extracted with EtOAc (3×200 mL). The EtOAc was washed with brine, dried over Na$_2$SO$_4$, filtered and concentrated. The residue was taken up in DCM-MeOH and adsorbed onto silica gel. Purification by chromatography on silica gel eluting with EtOAc 0-7% in hexanes provided the product (500 mg, 70%). LCMS (API-ES) m/z: 226, 228 (M+H$^+$).

3-Fluoroisoquinolin-6-ylboronic acid: A solution of 6-bromo-3-fluoroisoquinoline (9.10 g, 40.3 mmol) and triethylborate (11.8 g, 80.5 mmol) in THF (100 mL) was cooled to −78° C. Butyllithium (1.6 M in hexanes 50.3 mL, 80.5 mmol) was added dropwise over 45 minutes. Over the course of the addition, the solution changed color from colorless to a light tan. The solution was stirred at −78° C. for 3 hours. The mixture was quenched with HCl (5 N, 120 mL) while in the cold bath at −78° C., diluted with water (100 mL), and then extracted with EtOAc (3×200 mL). The combined organic layers were dried over Na$_2$SO$_4$, filtered and evaporated. The solid residue was triturated with DCM (200 mL), and the solid was recovered by filtration to provide the title compound (6.0 g, 78%). LCMS (API-ES) m/z: 192 (M+H$^+$).

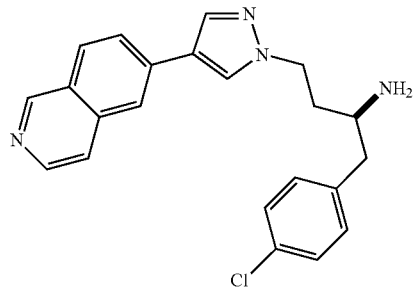

Example 56

(2S)-1-(4-Chlorophenyl)-4-(4-(isoquinolin-6-yl)-1H-pyrazol-1-yl)butan-2-amine: This compound was synthesized as shown in Scheme 20.

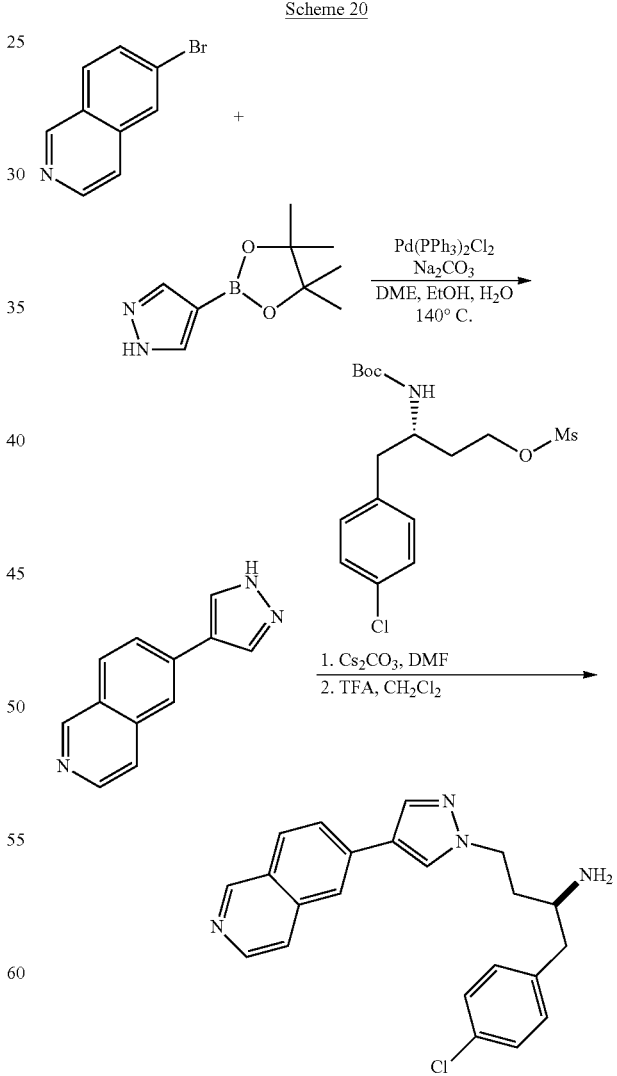

6-(1H-Pyrazol-4-yl)isoquinoline: A mixture of 6-bromoisoquinoline (500 mg, 2.40 mmol) (commercially available from Kalexsyn Product List (Order Number 2003-005)), pyrazole-4-boronic acid pinacol ester (560 mg, 2.88 mmol) (commercially available from Acros Organics (Order Number 38294)), trans-dichlorobis(triphenylphosphine)palladium(II) (118 mg, 0.17 mmol), and sodium carbonate (764 mg, 7.21 mmol) in DME:EtOH:H$_2$O=7:2:3 (4 mL) was heated at 140° C. for 10 minutes in a Biotage Initiator® microwave. After cooling to room temperature, the mixture was diluted with saturated aqueous NaHCO$_3$ and extracted with 25% i-PrOH/CHCl$_3$ (3×). The combined organic layers were dried over Na$_2$SO$_4$, filtered and adsorbed onto silica gel. The residue was purified using column chromatography (acetone/hexanes=0-50%) to provide the product as an off-white solid (177 mg, 37%). LCMS (API-ES) m/z: 196 (M+H$^+$).

tert-Butyl(S)-1-(4-chlorophenyl)-4-(4-(isoquinolin-6-yl)-1H-pyrazol-1-yl)butan-2-ylcarbamate: A mixture of 6-(1H-pyrazol-4-yl)isoquinoline (130 mg, 0.67 mmol), (S)-3-(tert-butoxycarbonylamino)-4-(4-chlorophenyl)butyl methanesulfonate (327 mg, 0.87 mmol) (prepared as shown in Scheme 15), and cesium carbonate (434 mg, 1.33 mmol) in DMF (5 mL) was stirred at room temperature for 24 hours. The mixture was diluted with saturated aqueous NaHCO$_3$ and extracted with DCM (3×). The combined organic layers were dried over Na$_2$SO$_4$, filtered and concentrated. The residue was purified using column chromatography (acetone/hexanes=0-40%) to provide the product as a tan solid (324 mg, 100%). LCMS (API-ES) m/z: 477 (M+H$^+$).

(2S)-1-(4-Chlorophenyl)-4-(4-(isoquinolin-6-yl)-1H-pyrazol-1-yl)butan-2-amine: A mixture of tert-butyl(S)-1-(4-chlorophenyl)-4-(4-(isoquinolin-6-yl)-1H-pyrazol-1-yl)butan-2-ylcarbamate (320 mg, 0.67 mmol) and TFA (5.00 mL, 64 mmol) in DCM (5 mL) was stirred at room temperature for 2 hours. After concentration by vacuum distillation, the residue was purified by reverse-phase HPLC (Phenomenex Synergi 4m Max RP 80 A column, 150×21 mm, 20 mL/min, 10-95% CH$_3$CN/H$_2$O, 0.1% TFA, 10.5 minute gradient) to give the product as an off-white solid (165 mg, 65%). HRMS (TOF) Calcd for C$_{22}$H$_{22}$ClN$_4$$^+$: 377.1535, found: 377.1531.

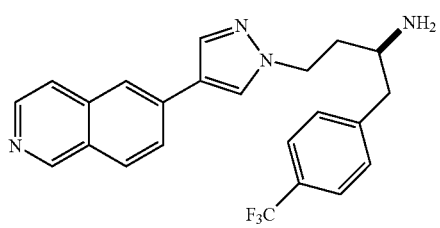

Example 57

(2S)-4-(4-(Isoquinolin-6-yl)-1H-pyrazol-1-yl)-1-(4-(trifluoromethyl)phenyl)butan-2-amine: This compound was prepared in a similar manner as Example 56, using Boc-(S)-3-amino-4-(4-trifluoromethylphenyl)butanoic acid (commercially available from 3B Scientific Corporation Product List (Order Number 3B3-013816)) instead of (S)-3-(tert-butoxycarbonyl)-4-(4-chlorophenyl)butanoic acid. HRMS (TOF) Calcd for C$_{23}$H$_{22}$F$_3$N$_4$$^+$: 411.1791, found: 411.1790.

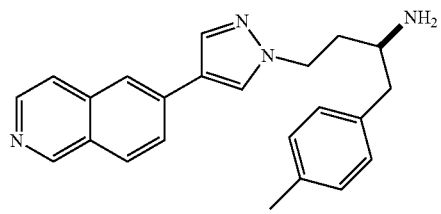

Example 58

(2S)-4-(4-(Isoquinolin-6-yl)-1H-pyrazol-1-yl)-1-p-tolylbutan-2-amine: This compound was prepared in a similar manner as Example 56 using Boc-(S)-3-amino-4-(4-methylphenyl)butanoic acid (commercially available from 3B Scientific Corporation Product List (Order Number 3B3-013780)) instead of (S)-3-(tert-butoxycarbonyl)-4-(4-chlorophenyl)butanoic acid. HRMS (TOF) Calcd for C$_{23}$H$_{25}$N$_4$$^+$: 357.2074, found: 357.2069.

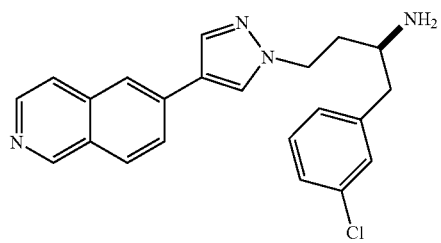

Example 59

(2S)-1-(3-Chlorophenyl)-4-(4-(isoquinolin-6-yl)-1H-pyrazol-1-yl)butan-2-amine: This compound was prepared in a similar manner as Example 56 using Boc-(S)-3-amino-4-(3-chlorophenyl)butanoic acid (commercially available from 3B Scientific Corporation Product List (3B3-013759)) instead of (S)-3-(tert-butoxycarbonyl)-4-(4-chlorophenyl) butanoic acid. HRMS (TOF) Calcd for C$_{22}$H$_{22}$ClN$_4$$^+$: 377.1527, found: 377.1523.

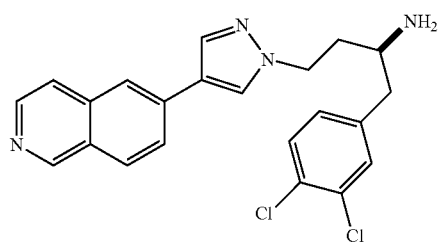

Example 60

(2S)-1-(3,4-Dichlorophenyl)-4-(4-(isoquinolin-6-yl)-1H-pyrazol-1-yl)butan-2-amine: This compound was prepared in a similar manner as Example 56 using Boc-(S)-3-amino-4-(3,4-dichlorophenyl)butanoic acid (commercially available from 3B Scientific Corporation Product List (Order Number 3B3-013796)) instead of (S)-3-(tert-butoxycarbonyl)-4-(4- chlorophenyl)butanoic acid. HRMS (TOF) Calcd for $C_{22}H_{21}Cl_2N_4^+$: 411.1138, found: 411.1132.

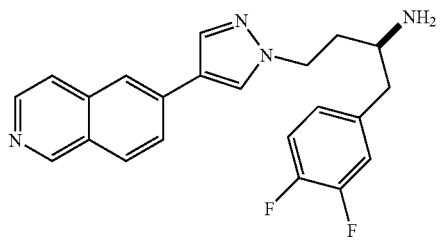

Example 61

(2S)-1-(3,4-Difluorophenyl)-4-(4-(isoquinolin-6-yl)-1H-pyrazol-1-yl)butan-2-amine: This compound was prepared in a similar manner as Example 56 using Boc-(S)-3-amino-4-(3,4-difluorophenyl)butanoic acid (commercially available from 3B Scientific Corporation Product List (Order Number 3B3-013799)) instead of (S)-3-(tert-butoxycarbonyl)-4-(4-chlorophenyl)butanoic acid. HRMS (TOF) Calcd for $C_{22}H_{21}F_2N_4^+$: 379.1729, found: 379.1724.

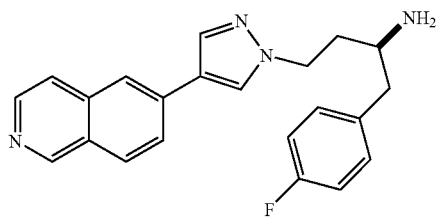

Example 62

(2S)-1-(4-Fluorophenyl)-4-(4-(isoquinolin-6-yl)-1H-pyrazol-1-yl)butan-2-amine: This compound was prepared in a similar manner as Example 56 using Boc-(S)-3-amino-4-(4-fluorophenyl)butanoic acid (commercially available from 3B Scientific Corporation Product List (Order Number 3B3-013671)) instead of (S)-3-(tert-butoxycarbonyl)-4-(4-chlorophenyl)butanoic acid. HRMS (TOF) Calcd for $C_{22}H_{22}FN_4^+$: 361.1823, found: 361.1818.

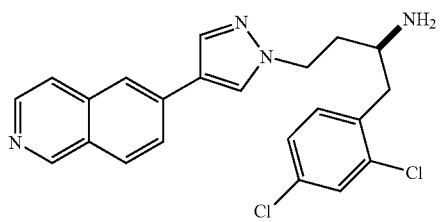

Example 63

(2S)-1-(2,4-Dichlorophenyl)-4-(4-(isoquinolin-6-yl)-1H-pyrazol-1-yl)butan-2-amine: This compound was prepared in a similar manner as Example 56 using Boc-(S)-3-amino-4-(2,4-dichlorophenyl)butanoic acid (commercially available from 3B Scientific Corporation Product List (Order Number 3B3-013793)) instead of (S)-3-(tert-butoxycarbonyl)-4-(4-chlorophenyl)butanoic acid. HRMS (TOF) Calcd for $C_{22}H_{21}Cl_2N_4^+$: 411.1138, found: 411.1134.

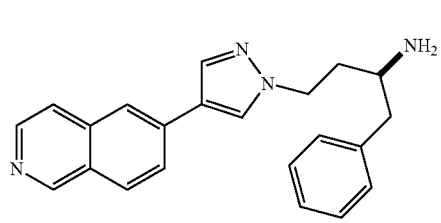

Example 64

(2S)-4-(4-(Isoquinolin-6-yl)-1H-pyrazol-1-yl)-1-phenylbutan-2-amine: This compound was prepared in a similar manner as Example 56 using (S)-3-(Boc-amino)-4-phenylbutyric acid (commercially available from 3B Scientific Corporation Product List (Order Number 3B3-034870)) instead of (S)-3-(tert-butoxycarbonyl)-4-(4-chlorophenyl)butanoic acid. HRMS (TOF) Calcd for $C_{22}H_{23}N_4^+$: 343.1917, found: 343.1920.

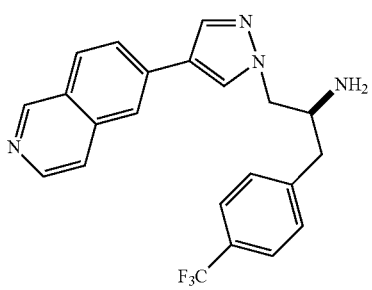

Example 65

(2S)-1-(4-(Isoquinolin-6-yl)-1H-pyrazol-1-yl)-3-(4-(trifluoromethyl)phenyl)-propan-2-amine: This compound was prepared as shown in Scheme 21.

Scheme 21

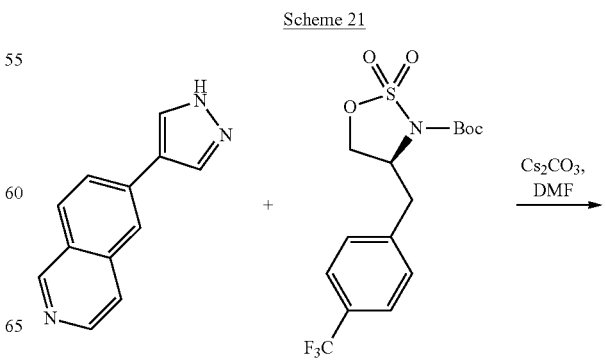

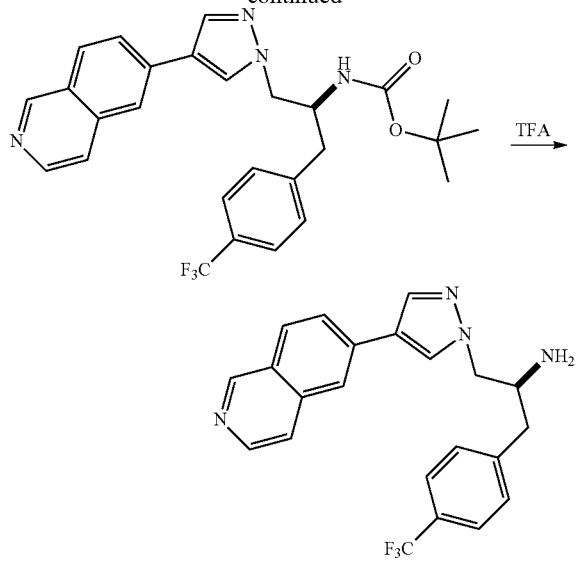

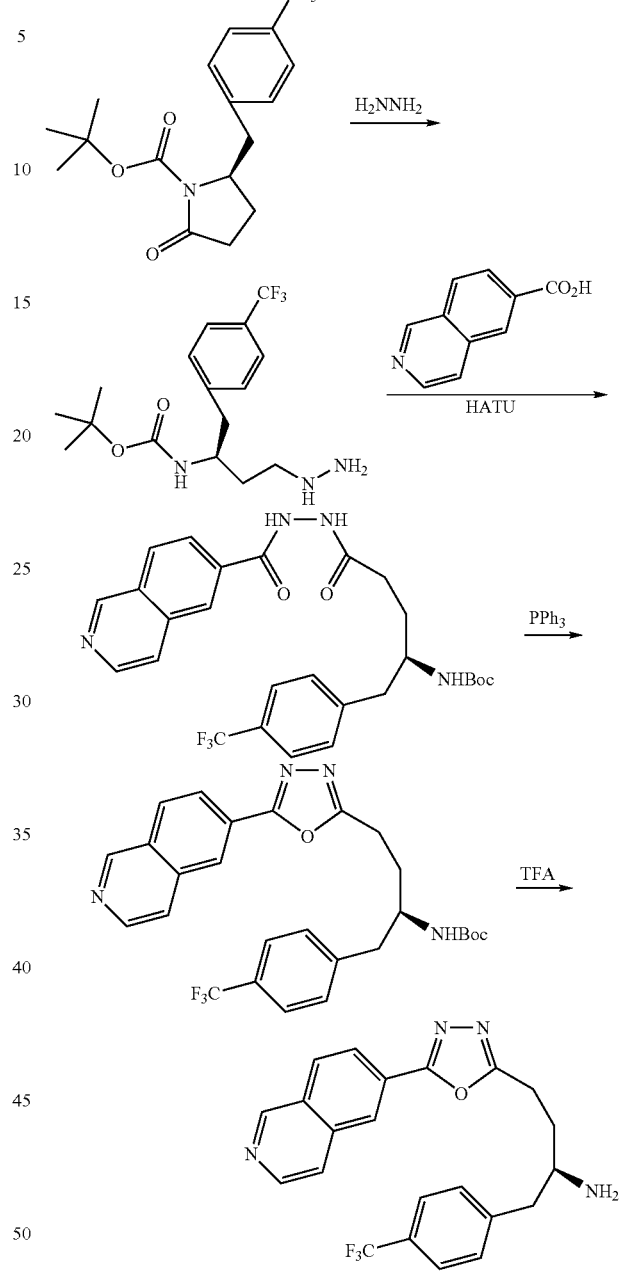

Scheme 22 tert-Butyl(S)-3-(4-(isoquinolin-6-yl)-1H-pyrazol-1-yl)-1-(4-(trifluoromethyl)-phenyl)propan-2-ylcarbamate: A mixture of 6-(1H-pyrazol-4-yl)isoquinoline (40 mg, 0.21 mmol) (prepared as shown in Scheme 20), tert-butyl (4S)-4-[4-(trifluoromethyl)benzyl]-1,2,3-oxathiazolidine-3-carboxylate 2,2-dioxide (102 mg, 0.27 mmol) (prepared as shown in Scheme 1), and cesium carbonate (134 mg, 0.41 mmol) in DMF (2 mL) was stirred at room temperature for 16 hours. The mixture was diluted with saturated aqueous NaHCO$_3$ and extracted with DCM (3×). The combined organic layers were dried over Na$_2$SO$_4$, filtered and concentrated. The residue was purified using column chromatography (acetone/hexanes=0-25%) to give the product as an off-white solid (97 mg, 95%). MS (API-ES) m/z: 497 (M+H$^+$).

(2S)-1-(4-(Isoquinolin-6-yl)-1H-pyrazol-1-yl)-3-(4-(trifluoromethyl)phenyl)-propan-2-amine: A mixture of tert-butyl(S)-3-(4-(isoquinolin-6-yl)-1H-pyrazol-1-yl)-1-(4-(trifluoromethyl)phenyl)propan-2-ylcarbamate (90 mg, 0.18 mmol) and TFA (5.00 mL, 64 mmol) in DCM (5 mL) was stirred at room temperature for 2 hours. After concentration by vacuum distillation, the residue was purified by reverse-phase HPLC (Phenomenex Synergi 4m Max RP 80 A column, 150×21 mm, 20 mL/min, 10-95% CH$_3$CN/H$_2$O, 0.1% TFA, 10.5 minute gradient) to give the product as an off-white solid (41 mg, 57%). HRMS (TOF) Calcd for C$_{22}$H$_{20}$F$_3$N$_4{}^+$: 397.1635, found: 397.1642.

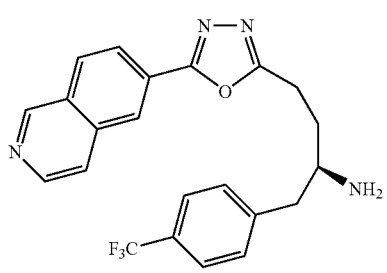

Example 66

(2R)-4-(5-(Isoquinolin-6-yl)-1,3,4-oxadiazol-2-yl)-1-(4-(trifluoromethyl)phenyl)butan-2-amine: This compound was prepared as shown in Scheme 22.

tert-Butyl((1S)-3-hydrazino-1-(4-(trifluoromethyl)benzyl)propyl)carbamate: (R)-tert-Butyl 2-(4-(trifluoromethyl)benzyl)-5-oxopyrrolidine-1-carboxylate (1.46 g, 4 mmol) (prepared as shown in Scheme 15) was treated with hydrazine (0.5 mL, 16 mmol) at 50° C. in THF for 30 minutes. The mixture was partitioned between EtOAc and saturated aqueous ammonium chloride, and dried over sodium sulfate. Evaporation provided the desired product as a white amorphous solid (1.27 g, 87%). LCMS (API-ES) m/z: 276 (M-Boc+H$^+$).

tert-Butyl((1R)-4-(2-(6-isoquinolinylcarbonyl)hydrazino)-4-oxo-1-(4-(trifluoromethyl)benzyl)butyl)carbamate: Isoquinoline-6-carboxylic acid (0.22 g, 1.3 mmol) (commercially available from AstaTech Product List (Order Number 62874)) and HATU (0.50 g, 1.3 mmol) were mixed in 10 mL DMF along with 0.21 mL DEA. The mixture was stirred at room temperature for 15 minutes. The mixture was added dropwise to a DMF solution of tert-butyl((1S)-3-hydrazino-1-(4-(trifluoromethyl)benzyl)propyl)carbamate (0.45 g, 1.2 mmol) and 0.21 mL of DEA in 10 mL DMF. The resulting mixture was stirred at room temperature for 1 hour. After the solvent was removed, the residue was dissolved in EtOAc and saturated aqueous sodium bicarbonate, and dried over sodium sulfate. The solvent was evaporated and the residue was triturated with DCM to provide the product as an off-white solid (0.45 g, 71%). LCMS (API-ES) m/z: 531 (M+H$^+$).

tert-Butyl(R)-4-(5-(isoquinolin-6-yl)-1,3,4-oxadiazol-2-yl)-1-(4-(trifluoromethyl)phenyl)butan-2-ylcarbamate: tert-Butyl((1R)-4-(2-(6-isoquinolinylcarbonyl)hydrazino)-4-oxo-1-(4-(trifluoromethyl)benzyl)butyl)carbamate (0.080 g, 0.15 mmol) and triphenylphosphine (0.070 mL, 0.30 mmol), and 0.5 mL CCl$_4$ were heated under nitrogen in 10 mL THF at 50° C. for 20 hours. 0.2 mL DIEA was added, and the reaction mixture was heated at reflux 4 hours. The reaction mixture was filtered and the solid was washed with THF. The filtrate was diluted with EtOAc and washed with saturated aqueous sodium bicarbonate (3×). The solvent was evaporated, and the residue was purified by chromatography on silica gel (60% EtOAc in hexane) to provide the product as a white solid (0.06 g, 78%). LCMS (API-ES) m/z: 513 (M+H$^+$).

(2R)-4-(5-(Isoquinolin-6-yl)-1,3,4-oxadiazol-2-yl)-1-(4-(trifluoromethyl)phenyl)butan-2-amine: tert-Butyl(R)-4-(5-(isoquinolin-6-yl)-1,3,4-oxadiazol-2-yl)-1-(4-(trifluoromethyl)phenyl)butan-2-ylcarbamate (0.060 g, 0.12 mmol) was stirred with 10 mL TFA in 10 mL DCM for 1 hour. After removing the solvent, the remaining residue was made basic with 2 M ammonia in MeOH and purified by chromatography on silica gel (4% 2M ammonia MeOH solution in DCM) to give the desired product as a white solid (0.045 g, 93%). LCMS (API-ES) m/z: 413 (M+H$^+$); $^1$H NMR (400 MHz, CD$_3$OD) δ ppm 1.87-1.97 (m, 1H), 2.17-2.27 (m, 1H), 2.63-2.79 (m, 2H), 2.91-2.98 (m, 1H), 3.12 (dd, J=13.40, 5.18 Hz, 1H), 4.18-4.25 (m, 1H), 7.50 (d, J=8.02 Hz, 2H), 7.64 (d, J=8.02 Hz, 2H), 7.92 (d, J=5.67 Hz, 1H), 8.14-8.19 (m, 1H), 8.22-8.27 (m, 1H), 8.50 (d, J=5.48 Hz, 1H), 9.30 (s, 1H), one H was obscured.

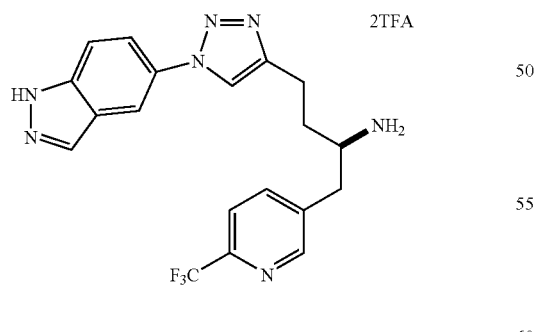

Example 67

(2R)-4-(1-(1H-Indazol-5-yl)-1H-1,2,3-triazol-4-yl)-1-(6-(trifluoromethyl)pyridin-3-yl)butan-2-amine bistrifluoroacetate. This compound was prepared as shown in Schemes 23 and 24.

Scheme 23

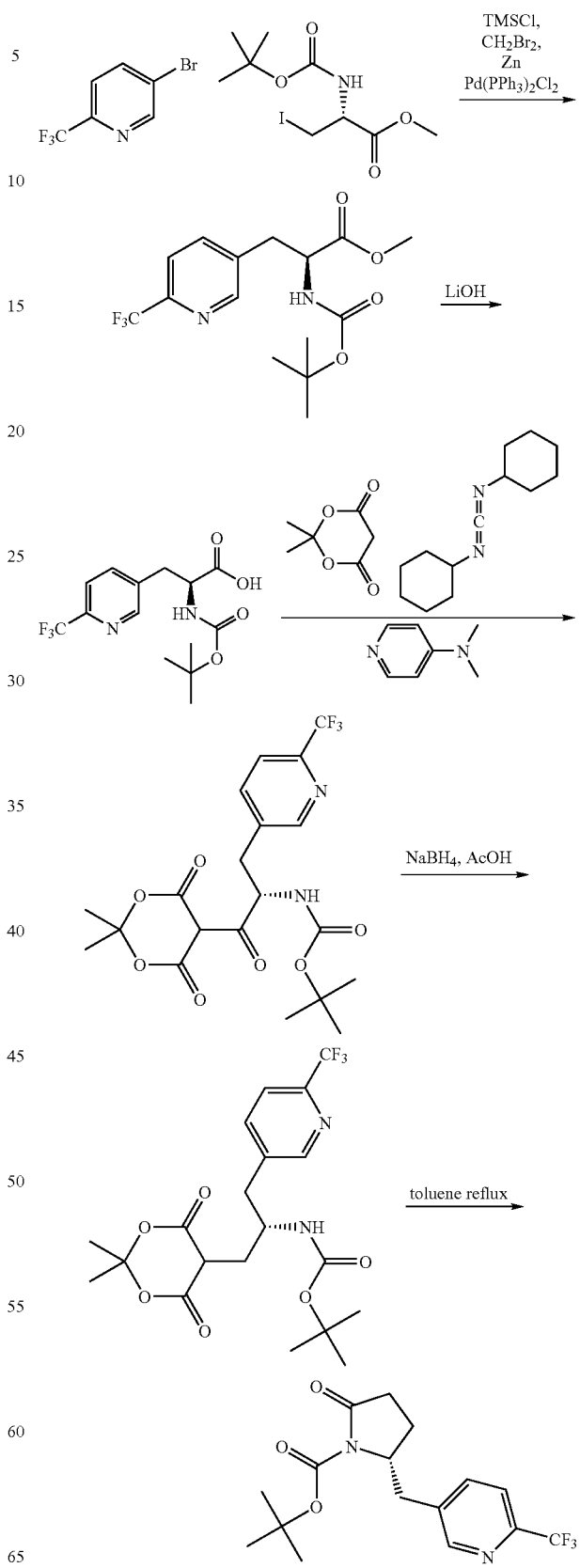

Scheme 24

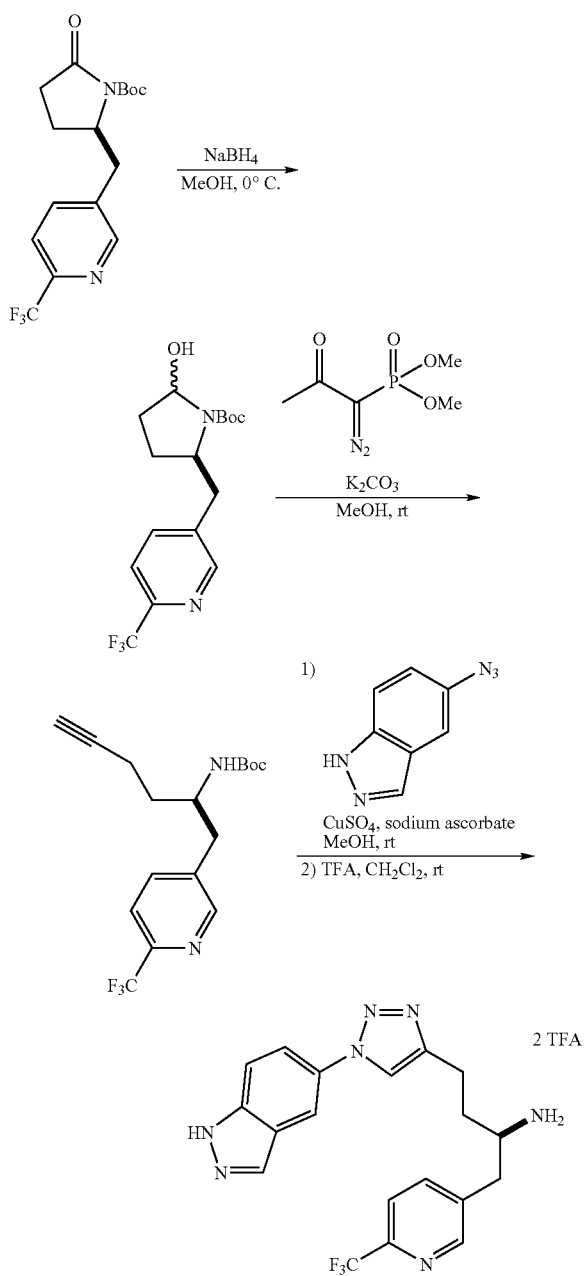

(S)-Methyl 2-(tert-butoxycarbonylamino)-3-(6-(trifluoromethyl)pyridin-3-yl)propanoate. Zinc (12 g, 186 mmol) and methylene dibromide (1.6 g, 9.3 mmol) were stirred in DMF (45 mL) at 90° C. for 30 minutes. After cooling to room temperature, trimethylsilyl chloride (0.24 mL, 1.9 mmol) was added, and the mixture was stirred at room temperature 30 minutes. Boc-3-iodo-1-alanine methyl ester (13 g, 40 mmol) (commercially available from 3B Scientific Corporation Product List (Order Number 3B3-063312)) in 15 mL DMF was added in one portion. After stirring at room temperature for 4 hours, dichlorobis(triphenyl-phosphine)palladium (ii) (1.2 g, 1.7 mmol) and 5-bromo-2-(trifluoromethyl)pyridine (7.0 g, 31.0 mmol) (commercially available from 3B Scientific Product List (Order Number 3B3-009312)) in 20 mL DMF were added. The reaction mixture was stirred at room temperature 16 hours. The reaction mixture was filtered through a pad of Celite and washed with EtOAc (3×). The solvent was evaporated. The residue was taken up in EtOAc and the organic layer was washed with saturated ammonium chloride (300 mL) and brine, dried over sodium sulfate, and evaporated. The residue was purified by chromatography on silica gel (20% EtOAc in hexane) to provide the product as a tan solid (4.0 g, 37%). LCMS (API-ES) m/z (%): 349.1 (100%, M+H$^+$).

(S)-2-(tert-Butoxycarbonylamino)-3-(6-(trifluoromethyl)pyridin-3-yl)propanoic acid. To a LiOH solution (1.0 M in 1:1:1 water:MeOH:THF, 75 mL) was added (S)-methyl 2-(tert-butoxycarbonylamino)-3-(6-(trifluoromethyl)pyridin-3-yl)propanoate (3.8 g, 10.9 mmol). The reaction was stirred at room temperature for 30 minutes. The organic solvent in the reaction mixture was evaporated. The residue was diluted with EtOAc, washed with saturated ammonium chloride (2×100 mL), and dried over sodium sulfate. The solvent was removed to provide the product as a white solid (2.4 g, 66%). LCMS (API-ES) m/z (%): 335.0 (100%, M+H$^+$).

(S)-tert-Butyl 1-(2,2-dimethyl-4,6-dioxo-1,3-dioxan-5-yl)-1-oxo-3-(6-(trifluoromethyl)pyridin-3-yl)propan-2-ylcarbamate. (S)-2-(tert-Butoxycarbonylamino)-3-(6-(trifluoromethyl)pyridin-3-yl)propanoic acid (2.4 g, 7.2 mmol), 2,2-dimethyl-1,3-dioxane-4,6-dione (1.1 g, 7.9 mmol), and N,N-dimethylpyridin-4-amine (1.4 g, 11 mmol) in 30 mL DCM were cooled in an ice-water-sodium chloride bath (−5° C.). N-((cyclohexylimino)methylene)cyclohexanamine (1.6 g, 7.9 mmol) in 50 mL DCM was added dropwise in about 40 minutes. The reaction mixture was stirred for 16 hours at room temperature. The suspension was filtered, and the solid was washed with DCM. The filtrate was washed with 5% KHSO$_4$ (4×50 mL) and once with brine, and dried over MgSO$_4$. After removing the solvent, the product was obtained as a white solid (3.0 g, 91%). LCMS (API-ES) m/z (%): 461.0 (100%, M+H$^+$).

(R)-tert-Butyl 3-(2,2-dimethyl-4,6-dioxo-1,3-dioxan-5-yl)-1-(6-(trifluoromethyl)pyridin-3-yl)propan-2-ylcarbamate. (S)-tert-Butyl 1-(2,2-dimethyl-4,6-dioxo-1,3-dioxan-5-yl)-1-oxo-3-(6-(trifluoromethyl)pyridin-3-yl)propan-2-ylcarbamate in 100 mL DCM was cooled to −5° C. Acetic acid (4.45 g, 74.1 mmol) was added in one portion. The resulting mixture was stirred for 5 minutes and sodium borohydride (0.637 g, 16.8 mmol) was added portion-wise over 40 minutes. After stirring for another 40 minutes, the reaction mixture was washed with brine (3×150 mL) and water (2×100 mL). The organic layer was dried over MgSO$_4$. After removing the solvent, the desired product compound (2.5 g, 83%) was obtained as a white solid. LCMS (API-ES) m/z (%): 447.0 (100%, M+H$^+$).

(R)-tert-Butyl 2-oxo-5-((6-(trifluoromethyl)pyridin-3-yl)methyl)pyrrolidine-1-carboxylate. (R)-tert-Butyl 3-(2,2-dimethyl-4,6-dioxo-1,3-dioxan-5-yl)-1-(6-(trifluoromethyl)pyridin-3-yl)propan-2-ylcarbamate (2.5 g, 5.6 mmol) in 100 mL toluene was heated at 105° C. for 8 hours. After removing the solvent, the residue was purified by chromatography on silica gel (20-40% EtOAc in hexane) to provide the product (1.3 g, 67%) as a white solid. LCMS (API-ES) m/z (%): 345.0 (100%, M+H$^+$).

(2R,5R)-tert-Butyl 2-hydroxy-5-((6-(trifluoromethyl)pyridin-3-yl)methyl)pyrrolidine-1-carboxylate and (2S,5R)-tert-butyl 2-hydroxy-5-((6-(trifluoromethyl)pyridin-3-yl)methyl)pyrrolidine-1-carboxylate: Sodium borohydride (153 mg, 4031 µmol) was added slowly to a solution of (R)-tert-butyl 2-oxo-5-((6-(trifluoromethyl)pyridin-3-yl)methyl)pyrrolidine-1-carboxylate (694 mg, 2016 µmol) in MeOH (5 mL) at 0° C., and the mixture was stirred at 0° C. for 1.5 hours.

Saturated aqueous NaHCO₃ (5 mL) was added, and the mixture was stirred at room temperature for 0.5 hours. H₂O (10 mL) was added, and the mixture was extracted with DCM (3×20 mL). The combined organic layers were dried (MgSO₄) and concentrated under reduced pressure. The resulting yellow solid was dissolved in MeOH/DCM, absorbed onto silica gel, and purified by flash chromatography (silica gel, 40% to 70% EtOAc/hexanes) to deliver a diastereomeric mixture of (2R,5R)-tert-butyl 2-hydroxy-5-((6-(trifluoromethyl)pyridin-3-yl)methyl)pyrrolidine-1-carboxylate and (2S,5R)-tert-butyl 2-hydroxy-5-((6-(trifluoromethyl)pyridin-3-yl)methyl)pyrrolidine-1-carboxylate (632 mg, 91%) as a white solid. LCMS (API-ES) m/z: 347.0 (M+H⁺).

(R)-tert-Butyl 1-(6-(trifluoromethyl)pyridin-3-yl)hex-5-yn-2-ylcarbamate: Dimethyl 1-diazo-2-oxopropyl phosphonate (505 mg, 2627 μmol) (commercially available from TCI America Organic Chemicals Product List (Order Number D3546)), followed by K₂CO₃ (545 mg, 3941 μmol) was added to a diastereomeric mixture of (2R,5R)-tert-butyl 2-hydroxy-5-((6-(trifluoromethyl)pyridin-3-yl)methyl)pyrrolidine-1-carboxylate and (2S,5R)-tert-butyl 2-hydroxy-5-((6-(trifluoromethyl)pyridin-3-yl)methyl)pyrrolidine-1-carboxylate (455 mg, 1314 μmol) in MeOH (1.3 mL) at room temperature. The mixture was stirred at room temperature for 4 hours, diluted with H₂O (15 mL), and extracted with DCM (3×20 mL). The combined organic layers were dried (MgSO₄) and concentrated under reduced pressure. The resulting yellow solid was dissolved in MeOH/DCM, absorbed onto silica gel, and purified by flash chromatography (silica gel, 10% to 30% EtOAc/hexanes) to deliver (R)-tert-butyl 1-(6-(trifluoromethyl)pyridin-3-yl)hex-5-yn-2-ylcarbamate (284 mg, 63%) as an off-white solid. LCMS (API-ES) m/z: 343.1 (M+H⁺).

5-Azido-1H-indazole: Neat tert-butyl nitrite (670 μL, 5633 μmol) was added to a suspension of 5-aminoindazole (500 mg, 3755 μmol) (commercially available from VWR Chemical Catalog (Order Number AAAL06705-14)) in MeCN (7 mL) at 0° C. followed by dropwise addition of trimethylsilyl azide (598 μL 4506 μmol). The mixture was stirred at 0° C. for 5 minutes room temperature for 18 hours, and at 50° C. for 24 hours. The mixture was concentrated under reduced pressure, and the resulting brown residue was absorbed onto silica gel and purified by flash chromatography (silica gel, 2% to 6% MeOH/DCM) to provide 5-azido-1H-indazole (456 mg, 76%) as a golden solid. LCMS (API-ES) m/z: 160.1 (M+H⁺).

tert-Butyl(R)-4-(1-(1H-indazol-5-yl)-1H-1,2,3-triazol-4-yl)-1-(6-(trifluoromethyl)pyridin-3-yl)butan-2-ylcarbamate: A mixture of 5-azido-1H-indazole (126 mg, 789 μmol), (R)-tert-butyl 1-(6-(trifluoromethyl)pyridin-3-yl)hex-5-yn-2-ylcarbamate (270 mg, 789 μmol), CuSO₄ (6.3 mg, 39 μmol), and sodium ascorbate (16 mg, 79 μmol) in t-BuOH/H₂O (1:1, 2 mL) was stirred at room temperature for 8 hours. The mixture was partitioned between saturated aqueous NaCO₃ (15 mL) and DCM (15 ml). The layers were separated and the aqueous layer was extracted with CH₂Cl₂ (2×15 mL). The combined organic layers were dried (MgSO₄) and concentrated under reduced pressure. The resulting yellow solid was dissolved in MeOH/DCM, absorbed onto silica gel, and purified by flash chromatography (silica gel, 3% to 8% MeOH/DCM) to deliver tert-butyl(R)-4-(1-(1H-indazol-5-yl)-1H-1,2,3-triazol-4-yl)-1-(6-(trifluoromethyl)pyridin-3-yl)butan-2-ylcarbamate (85 mg, 21%) as a light yellow solid. LCMS (API-ES) m/z: 502.1 (M+H⁺).

(2R)-4-(1-(1H-indazol-5-yl)-1H-1,2,3-triazol-4-yl)-1-(6-(trifluoromethyl)pyridin-3-yl)butan-2-amine bistrifluoroacetate: TFA (1 mL, 13462 μmol) was added to a solution of tert-butyl(R)-4-(1-(1H-indazol-5-yl)-1H-1,2,3-triazol-4-yl)-1-(6-(trifluoromethyl)pyridin-3-yl)butan-2-ylcarbamate (75 mg, 150 μmol) in DCM (1 mL) and the mixture was stirred at room temperature for 2 hours. The mixture was concentrated under reduced pressure, and the resulting yellow oil was purified by reverse phase HPLC (Shimadsu Valiant, Phenomenex Gemini C18 5 μm 100×30 mm, 10% to 70% H₂O/MeCN, 0.1% TFA) to deliver (2R)-4-(1-(1H-indazol-5-yl)-1H-1,2,3-triazol-4-yl)-1-(6-(trifluoromethyl)pyridin-3-yl)butan-2-amine bistrifluoroacetate (86 mg, 91%) as a white solid. LCMS (API-ES) m/z: 402.1 (M+H⁺); ¹H NMR (300 MHz, CD₃OD) δ ppm 2.12 (q, J=7.4 Hz, 2H), 2.93-3.06 (m, 2H), 3.12 (dd, J=14.4, 7.4 Hz, 1H), 3.27 (dd, J=14.4, 6.7 Hz, 1H), 3.74 (quin, J=6.7 Hz, 1H), 7.74 (dt, J=9.1, 0.9 Hz, 1H) 7.79-7.88 (m, 2H), 8.01 (dd, J=8.0, 1.5 Hz, 1H), 8.18 (dd, J=2.0, 0.7 Hz, 1H), 8.19 (d, J=0.7 Hz, 1H), 8.32 (s, 1H), 8.68 (d, J=1.5 Hz, 1H).

Various compounds of the invention with different heterocyclic cores may be prepared as described in the following schemes. It will be understood that these procedures may be used to synthesize a wide variety of compounds. For example, the p-methoxyphenyl group may be replaced with phenyl or with numerous other mono-, di-, or tri-substituted phenyl groups as will be recognized by those skilled in the art. Furthermore, it will be recognized that the p-methoxyphenyl group may be replaced with a wide range of other aryl and heteroaryl groups including, but not limited to, naphthyl groups, pyridyl groups, and the like. Similarly, the isoquinoline group may be replaced with various other groups as will be recognized by those skilled in the art.

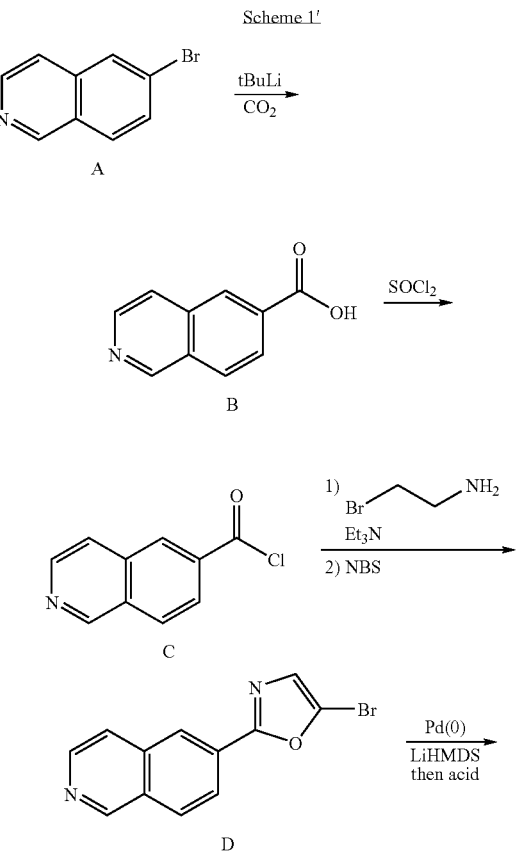

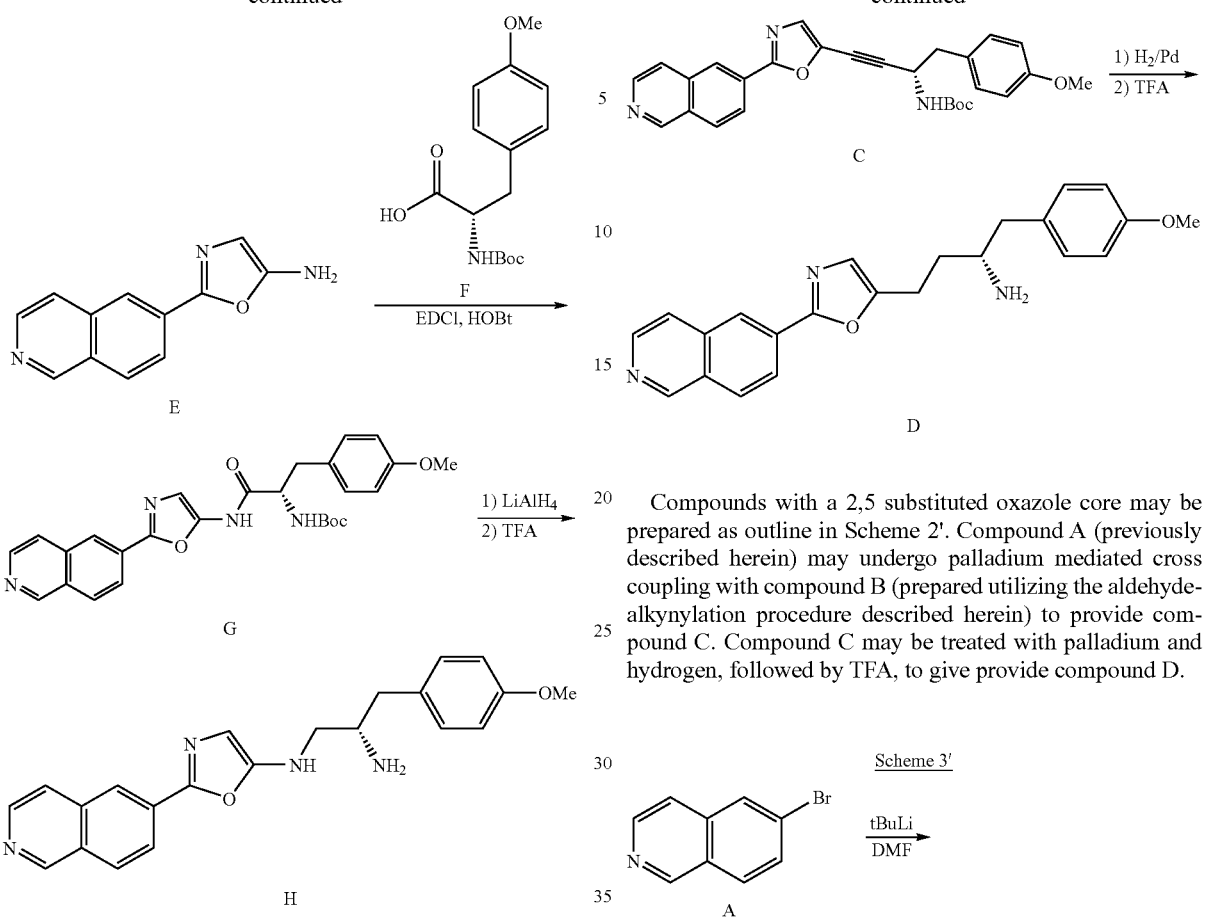
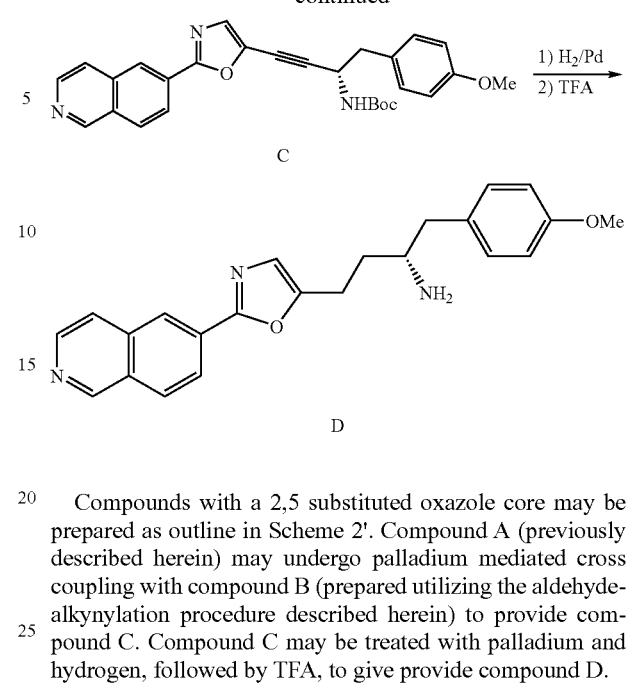
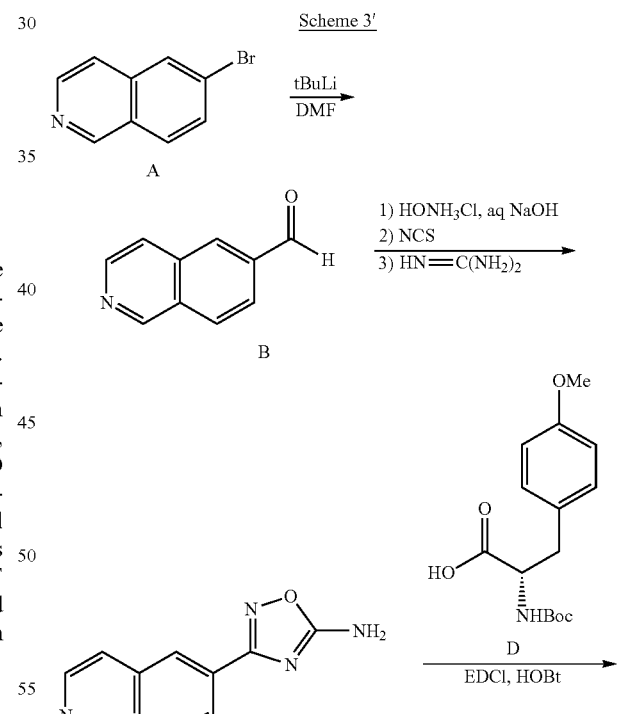

Compounds with a 5-amino 2,5-substituted oxazole core may be prepared as outline in Scheme 1'. Compound A (available from Kalexyn) is lithiated and carboxylated to provide compound B. Compound B is converted to compound C. Compound C is converted to compound D via known procedures ("Synthesis of 2-aryl- and 5-alkyl-2-aryloxazoles from 2-aryl-5-bromooxazoles"; Kashima, Choji; Arao, Hideki, Synthesis, 1989, pages 873-874). Amination of compound D provides compound E via known procedures ("New Ammonia equivalents for the Pd-catalyzed amination of aryl halides"; Buchwald, S. L., et. al; Org. Lett., 2001, pages 3417-3419). Compound E may be coupled with compound F (available from Peptech) to provide compound G. Compound G is reduced with lithium aluminum hydride and treated with TFA to provide compound H.

Compounds with a 2,5 substituted oxazole core may be prepared as outline in Scheme 2'. Compound A (previously described herein) may undergo palladium mediated cross coupling with compound B (prepared utilizing the aldehyde-alkynylation procedure described herein) to provide compound C. Compound C may be treated with palladium and hydrogen, followed by TFA, to give provide compound D.

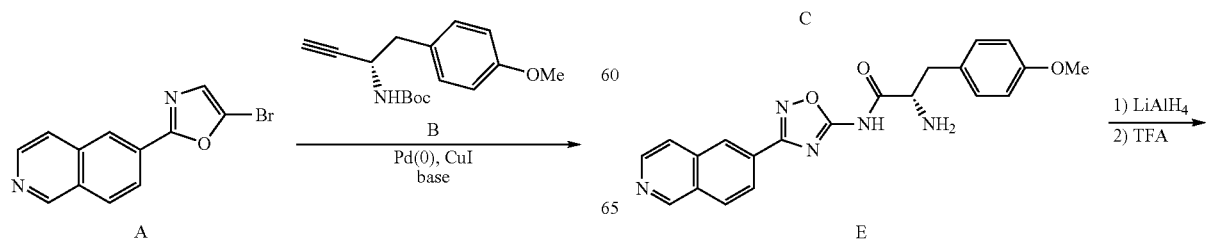

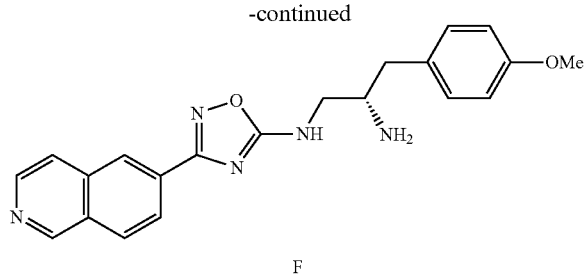

Compounds with a 5-amino-3,5-substituted 1,2,4-oxadiazole core may be prepared as outlined in Scheme 3'. Compound A (previously described herein) may be lithiated and quenched with DMF to provide compound B. Compound B may be converted to compound C utilizing a known method ("Novel 1,2,4-oxadiazoles and 1,2,4-thiadiazoles as dual 5-lipoxygenase and cyclooxygenase inhibitors", Unangst, P. C.; et. al.; J. Med. Chem., 1992, pages 3691-3698). Compound C may be coupled with compound D (previously described herein) to provide compound E. Treatment of compound E with lithium aluminum hydride and TFA may provide compound F.

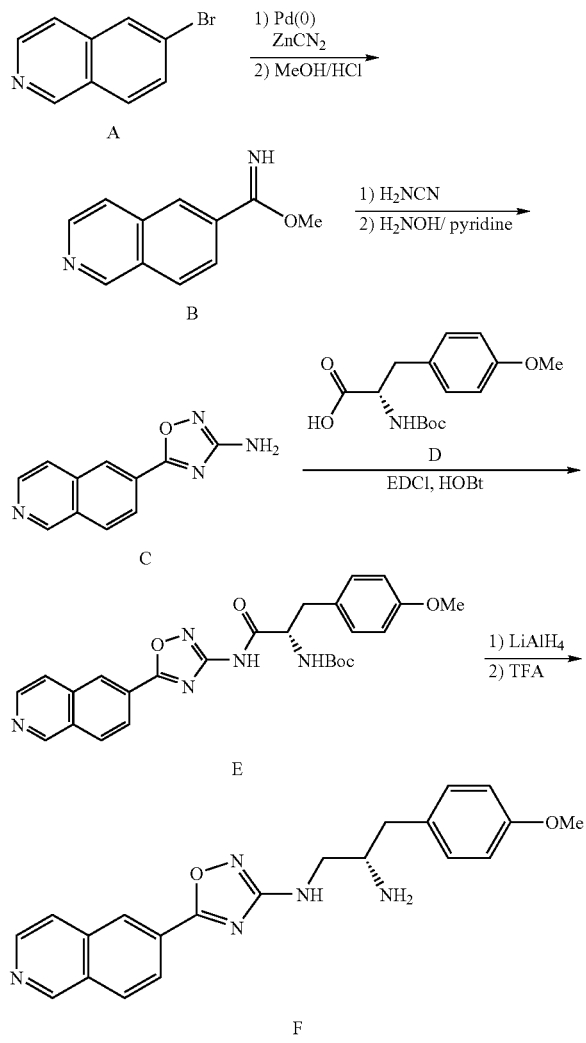

Compounds with a 3-amino-3,5-substituted-1,2,4-oxadiazole core may be prepared as outlined in Scheme 4'. Compound A (previously described herein) may be converted to compound B by palladium mediated coupling with zinc cyanide, followed by treatment with acidic MeOH. Compound B may be converted to compound C using a known procedure ("Novel 1,2,4-oxadiazoles and 1,2,4-thiadiazoles as dual 5-lipoxygenase and cyclooxygenase inhibitors", Unangst, P. C.; et. al.; J. Med. Chem., 1992, pages 3691-3698). Compound C may be coupled with compound D (previously described herein) to provide compound E. Compound E may be treated with lithium aluminum hydride and TFA to provide compound F.

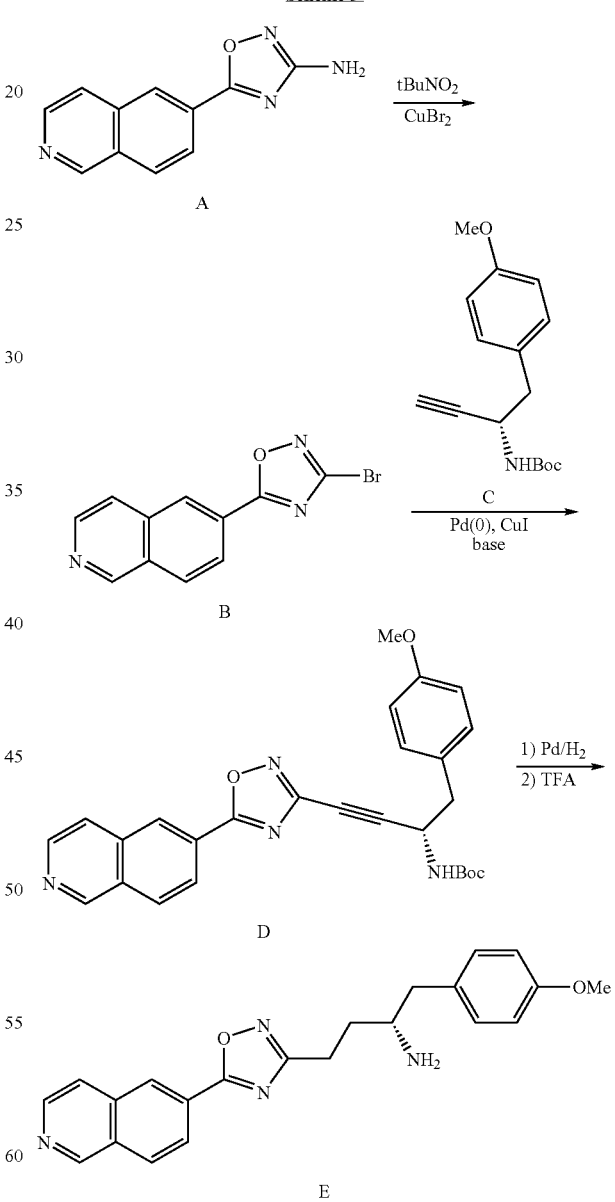

Compounds with a 3,5 substituted 1,2,4-oxadiazole core may be prepared as outlined in Scheme 5'. Compound A (previously described herein) may be converted to compound B. Palladium mediated coupling of compound B with compound C (previously described herein) may provide compound D. Compound D may be treated with palladium and hydrogen, followed by TFA, to provide compound E.

pound F. Treatment of compound F with lithium aluminum hydride, followed by TFA, may provide compound G.

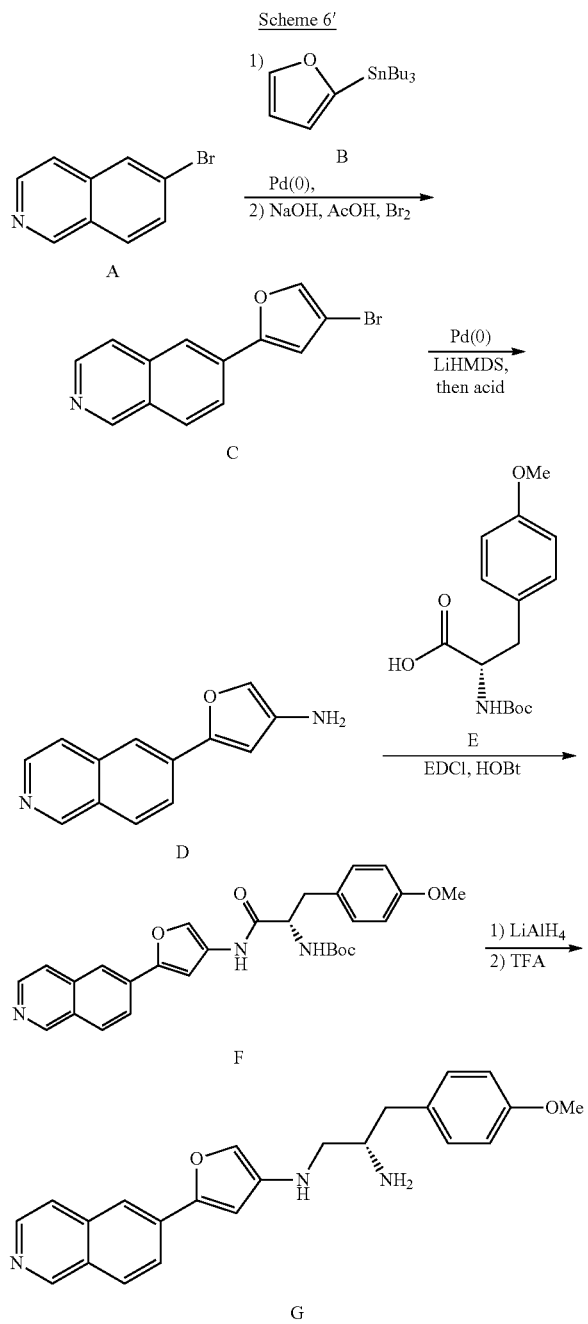

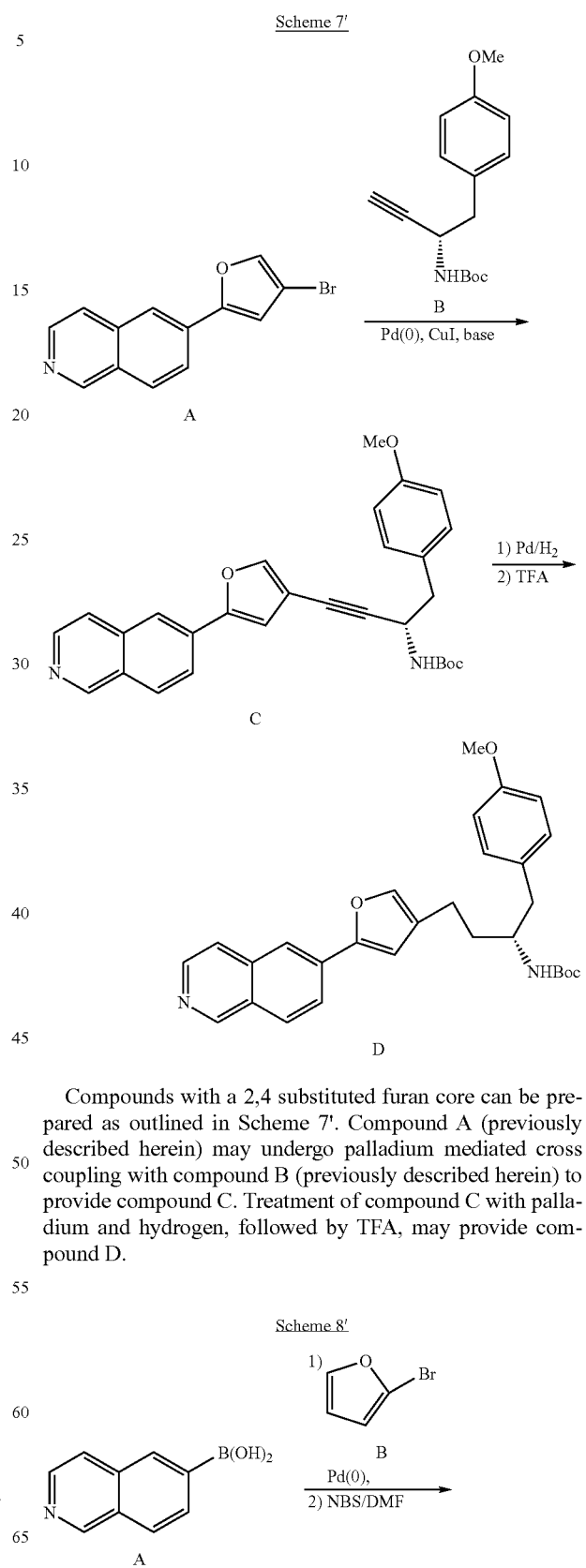

Compounds with a 2,4 substituted furan core can be prepared as outlined in Scheme 7'. Compound A (previously described herein) may undergo palladium mediated cross coupling with compound B (previously described herein) to provide compound C. Treatment of compound C with palladium and hydrogen, followed by TFA, may provide compound D.

Compounds with a 3-amino 3,5 substituted furan core can be prepared as outlined in Scheme 6'. Compound A (previously described herein) may undergo palladium mediated cross coupling with compound B, followed by bromination to form compound C ("General facile synthesis of 2,5-diaryl-heteropentalenes", Vachal, P. T.; et. al. Tetrahedron Lett., 2004, pages 7157-7161). Palladium mediated amination of compound C may provide compound D (procedures previously described herein). Coupling of compound D with compound E (previously described herein) may provide com-

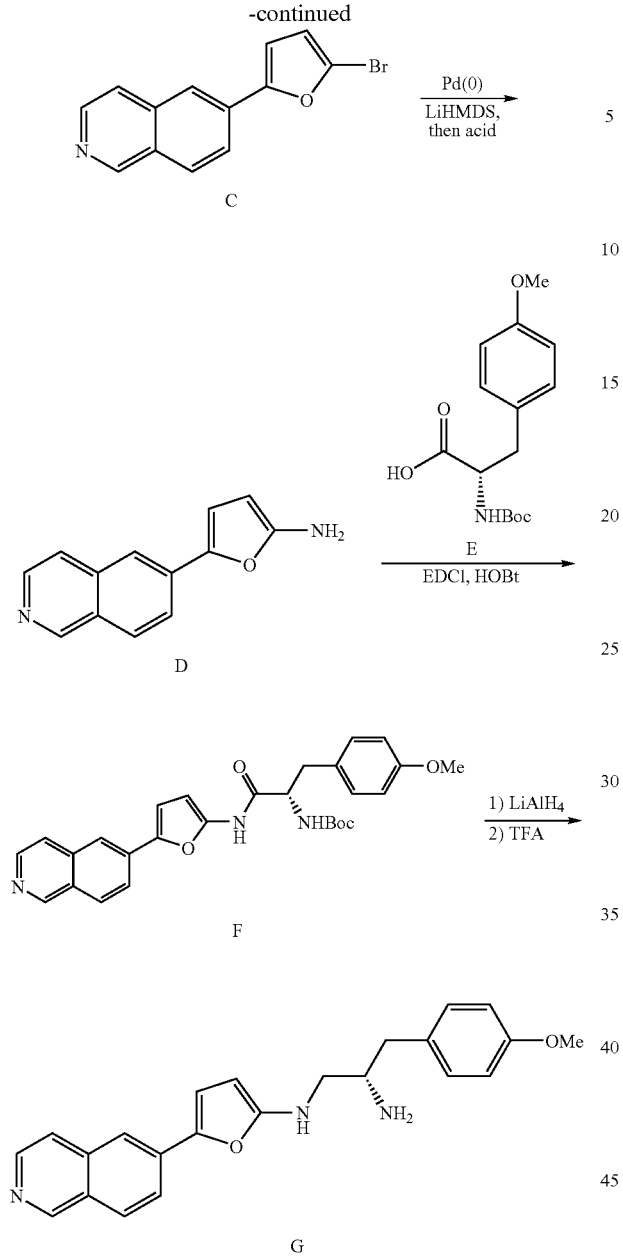

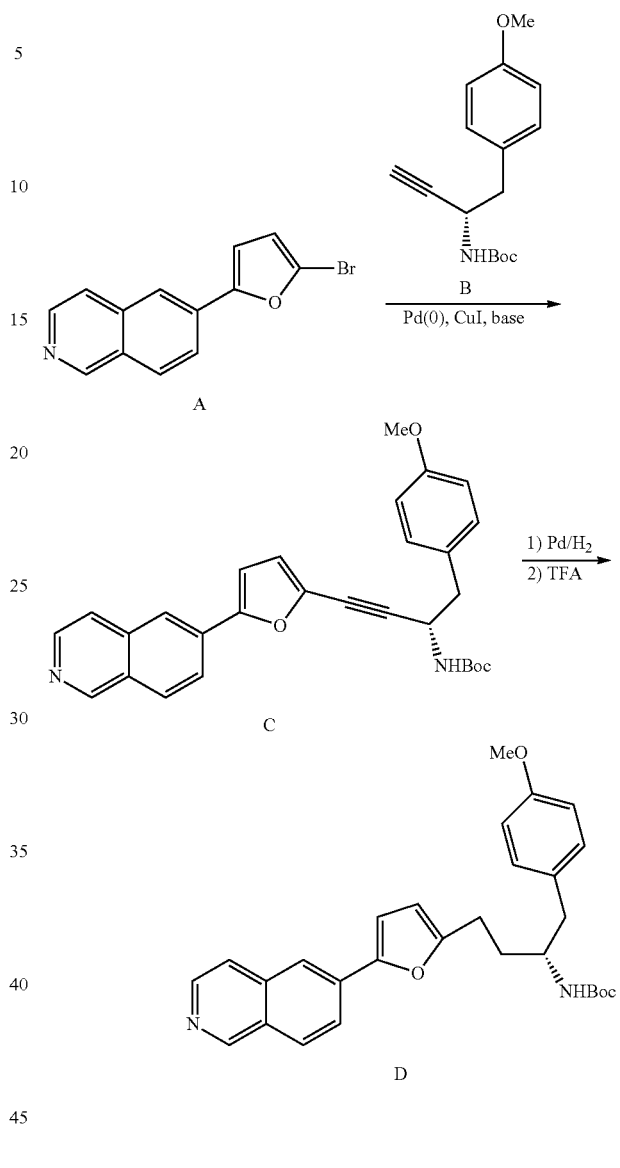

Compounds with a 2-amino 2,5 substituted furan core can be prepared as outlined in Scheme 8'. Compound A (previously described herein) may undergo palladium mediated cross coupling with compound B (available from Maybridge), followed by bromination to provide compound C ("Dicationic DNA-targeted antiprotozoal agents: Naphthalene replacement of benzimidazole"; Chackal-Catoen, S. M.; et. al. Bioorg. Med. Chem. Lett., 2006, pages 7434-7445). Palladium mediated amination of compound C may provide compound D (procedures previously described herein). Coupling of compound D with compound E (previously described herein) may provide compound F. Treatment of compound F with lithium aluminum hydride, followed by TFA, may provide compound G.

Compounds with a 2,5 substituted furan core may be prepared as outlined in Scheme 9'. Compound A (previously described herein) may undergo palladium mediated cross coupling with compound B (previously described herein) to provide compound C. Treatment of compound C with palladium under hydrogen, followed by TFA, may provide compound D.

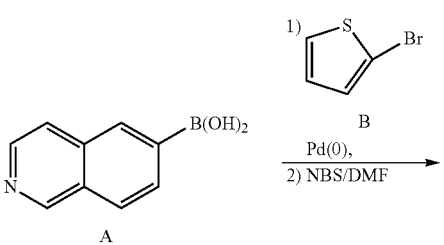

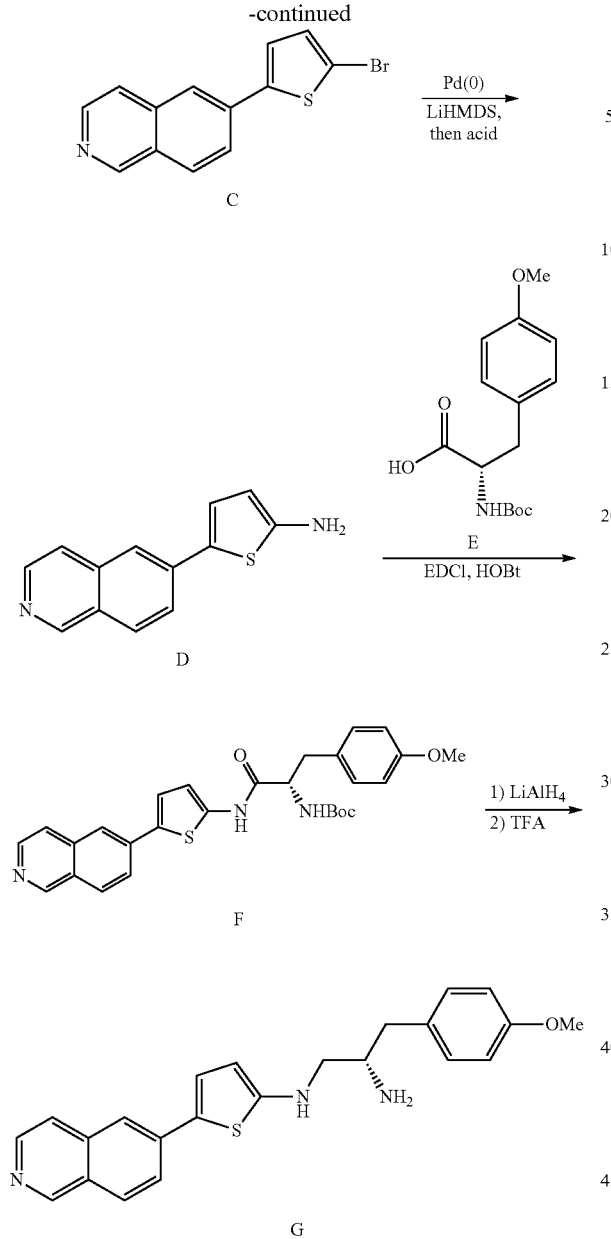

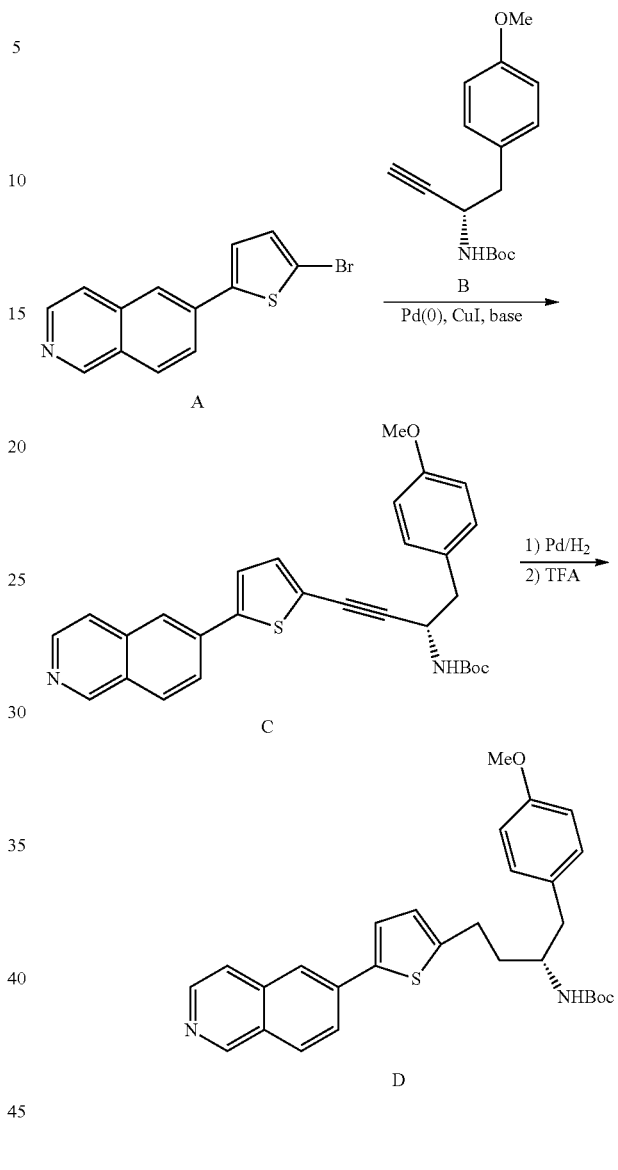

Compounds with a 2-amino 2,5 substituted thiophene core can be prepared as outlined in Scheme 10'. Compound A (previously described herein) may undergo palladium mediated cross coupling with compound B (available from Acros), followed by bromination to form compound C ("Synthesis, Self-Assembly, and Characterization of Supramolecular Polymers from Electroactive Dendron Rodcoil Molecules"; Messmore, B. W.; et. al. J. Am. Chem. Soc., 2004, pages 14452-14458). Palladium mediated amination of compound C may provide compound D (procedures previously described herein). Coupling of compound D with compound E (previously described herein) may provide compound F. Treatment of compound F with lithium aluminum hydride, followed by TFA, may provide compound G.

Compounds with a 2,5 substituted thiophene core may be prepared as outlined in Scheme 11'. Compound A (previously described herein) may undergo palladium mediated cross coupling with compound B (previously described herein) to provide compound C. Treatment of compound C with palladium under hydrogen, followed by TFA, may provide compound D.

Scheme 12'

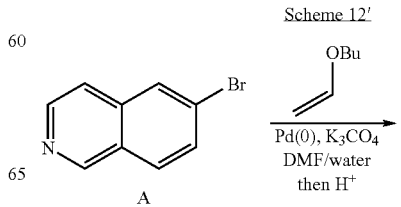

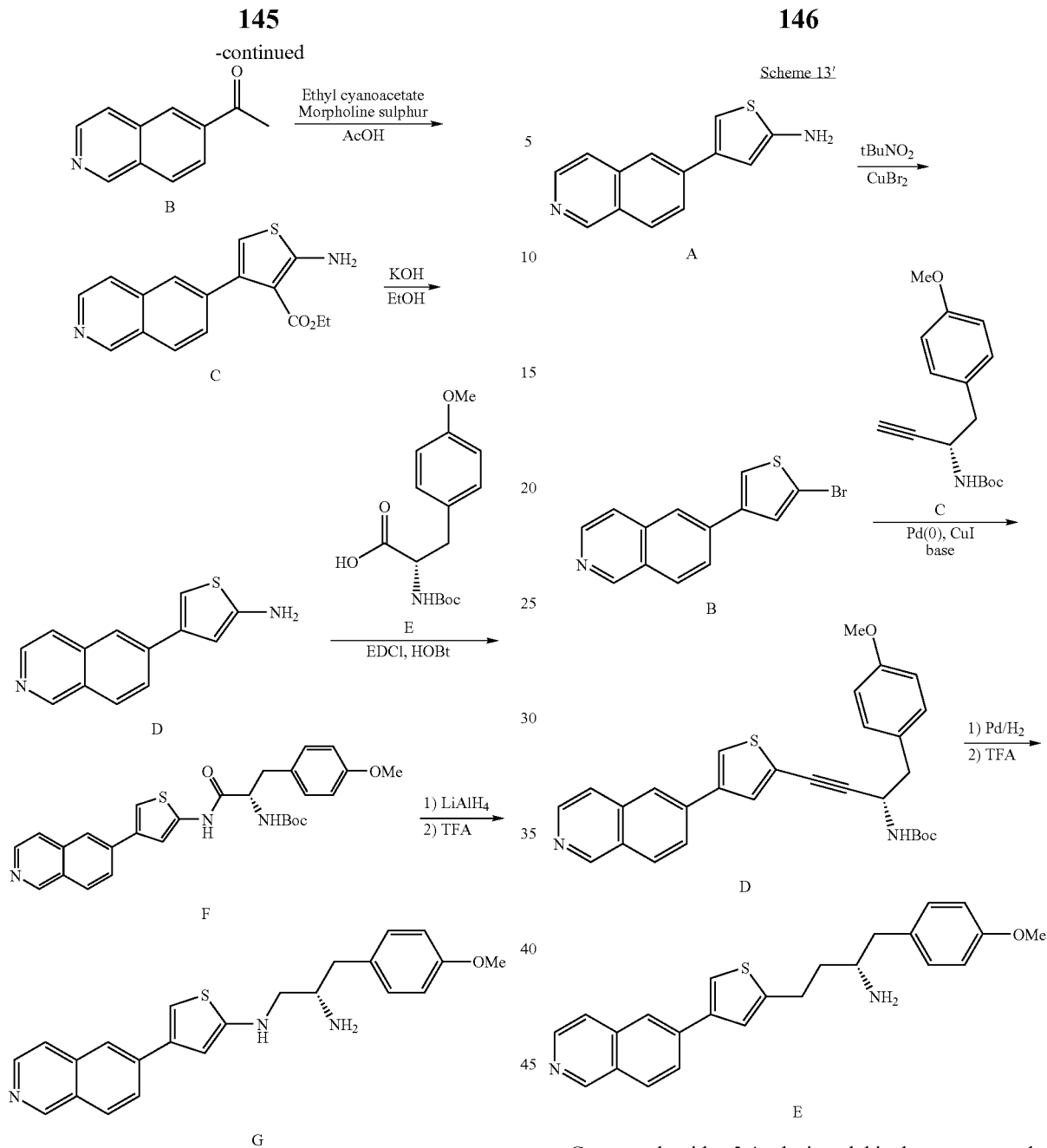

Compounds with a 2-amino 2,4 substituted thiophene core may be prepared as outlined in Scheme 12'. Compound A (previously described herein) may be converted to compound B following a published procedure ("Aqueous DMF-potassium carbonate as a substitute for thallium and silver additives in the palladium-catalyzed conversion of aryl bromides to acetyl arenes", Vallin, K. S. A.; et. al. J. Org. Chem., 2001, pages 4340-4343). Compound B may be converted to compound C following a published procedure (Aryl alkyl ketones in a one-pot Gewald synthesis of 2-aminothiophenes", Tormyshev, V. M.; et. al. Synlett, 2006, pages 2559-2564). Compound C may be converted to compound D following a published procedure ("Reactions of 2-thiophenamines with hydrazine", Gewald, K. Chem. Ber., 1988, pages 573-575). Compound D may be coupled with compound E (previously described herein) to provide compound F. Treatment of compound F with lithium aluminum hydride, followed by TFA, may provide compound G.

Compounds with a 2,4 substituted thiophene core may be prepared as outlined in Scheme 13'. Compound A (previously described herein) may be converted to compound B. Palladium mediated coupling of compound B with compound C (previously described herein) will provide compound D. Compound D will be treated with palladium under hydrogen, followed by TFA, to provide compound E.

Scheme 14'

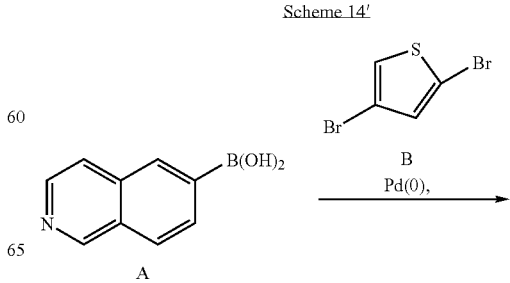

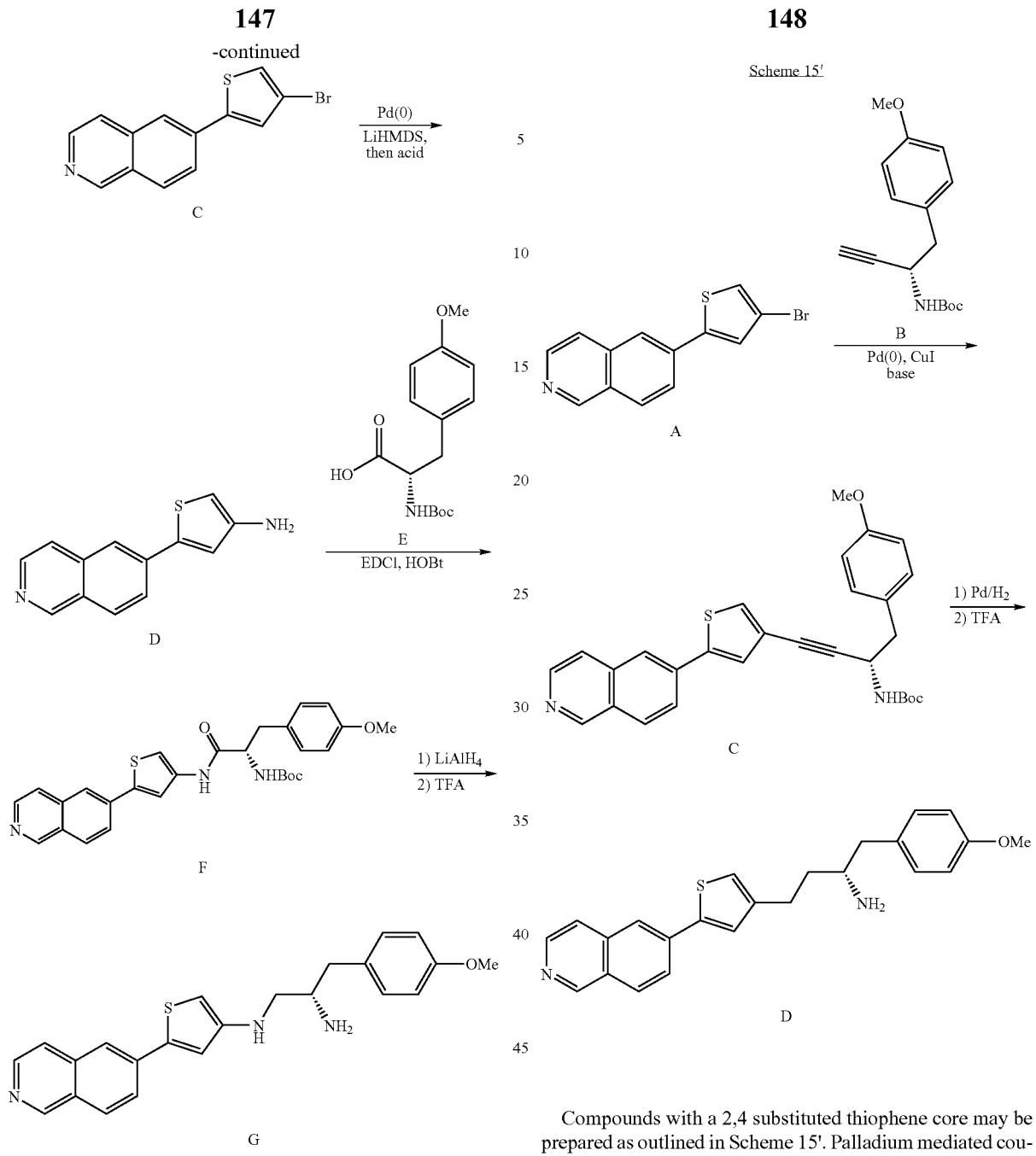

Compounds with a 3-amino 3,5 substituted thiophene core may be prepared as outlined in Scheme 14'. Compound A (previously described herein) may undergo palladium mediated cross coupling with compound B (available from Acros) to provide compound C ("Structure-activity relationship of triaryl propionic acid analogues on the huma EP$_3$ Prostanoid Receptor", Gallant, M. et. al. Bioorg. Med. Chem. Lett., 2003, pages 3813-3816). Palladium mediated amination of compound C may provide compound D (procedures previously described herein). Coupling of compound D with compound E (previously described herein) may provide compound F. Treatment of compound F with lithium aluminum hydride, followed by TFA, may provide compound G.

Compounds with a 2,4 substituted thiophene core may be prepared as outlined in Scheme 15'. Palladium mediated coupling of compound A (previously described herein) with compound B (previously described herein) will provide compound C. Compound C will be treated with palladium under hydrogen, followed by TFA, to provide compound D.

Scheme 16'

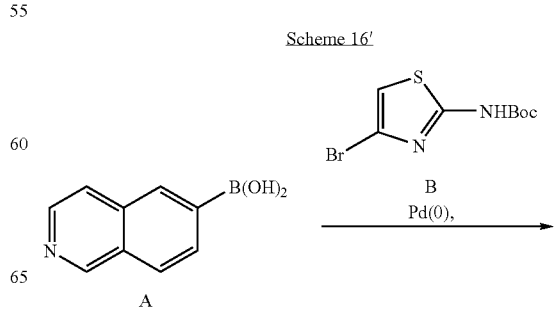

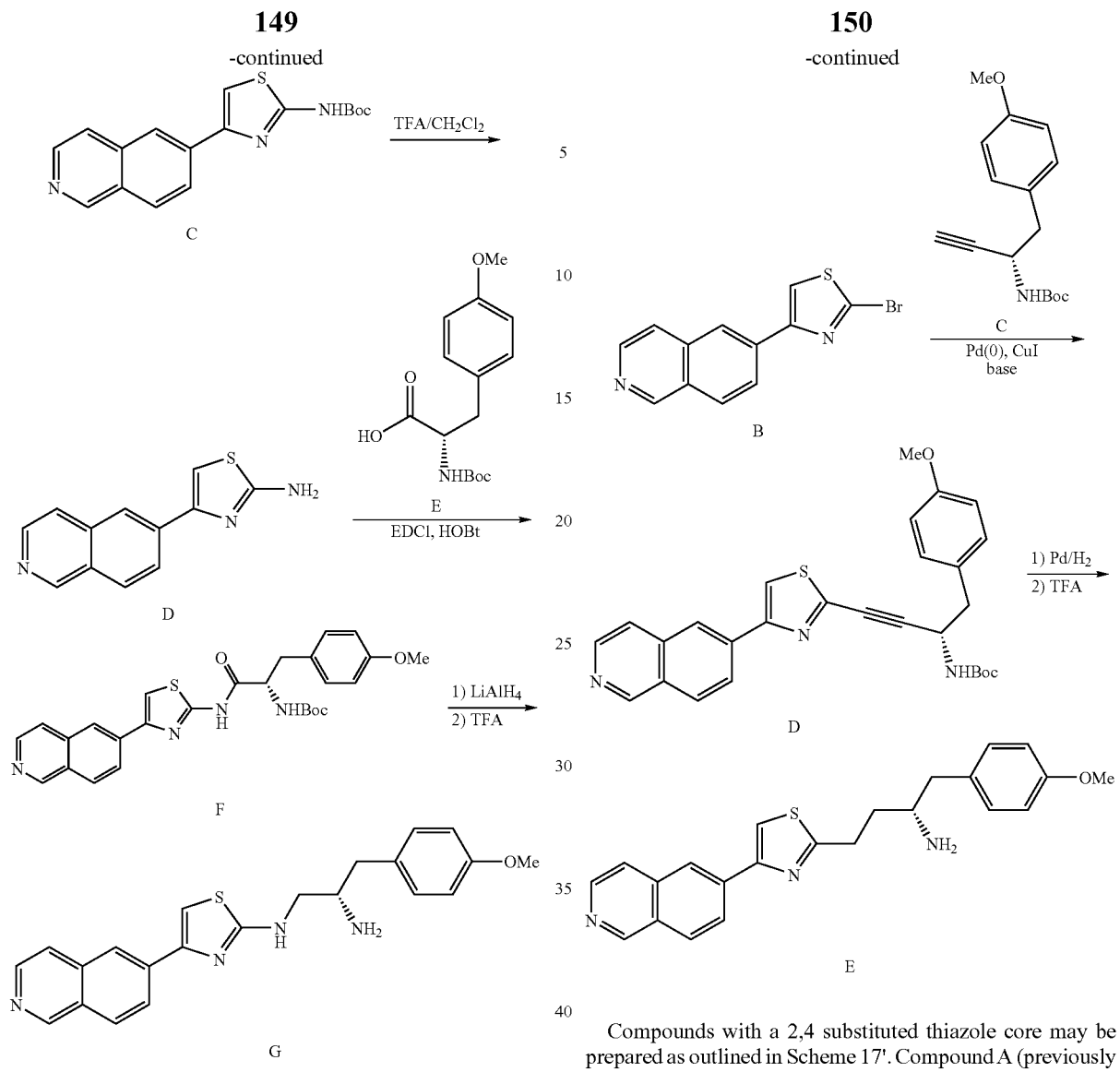

Compounds with 2-amino 2,4 substituted thiazole core may be prepared as outlined in Scheme 16'. Palladium mediated coupling of compound A (previously described herein) with compound B ("Investigations of the halogen dance reaction on N-substituted 2-thiazolamines", Stanetty, P.; et. al., J. Org. Chem., 2005, 567-574) may provide compound C. Treatment of compound C with TFA can provide compound D. Coupling of compound D with compound E (previously described herein) may provide compound F. Treatment of compound F with lithium aluminum hydride, followed by TFA, may provide compound G.

Compounds with a 2,4 substituted thiazole core may be prepared as outlined in Scheme 17'. Compound A (previously described herein) may be converted to compound B. Palladium mediated coupling of compound B with compound C (previously described herein) will provide compound D. Compound D will be treated with palladium under hydrogen, followed by TFA, to provide compound E.

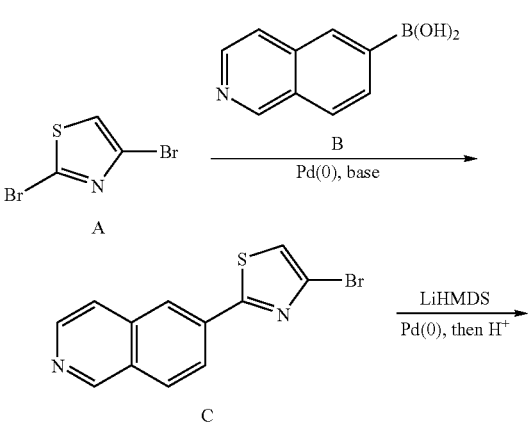

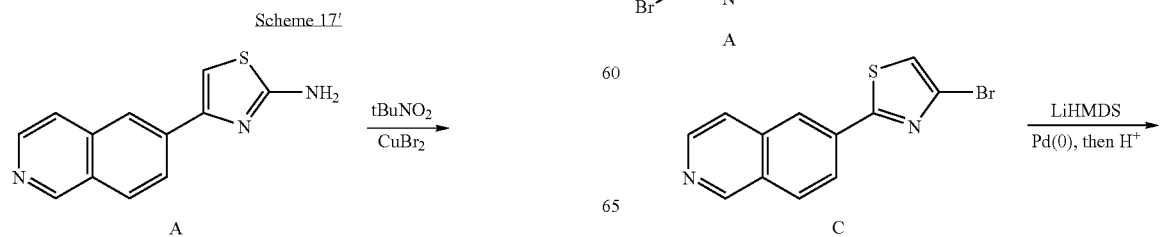

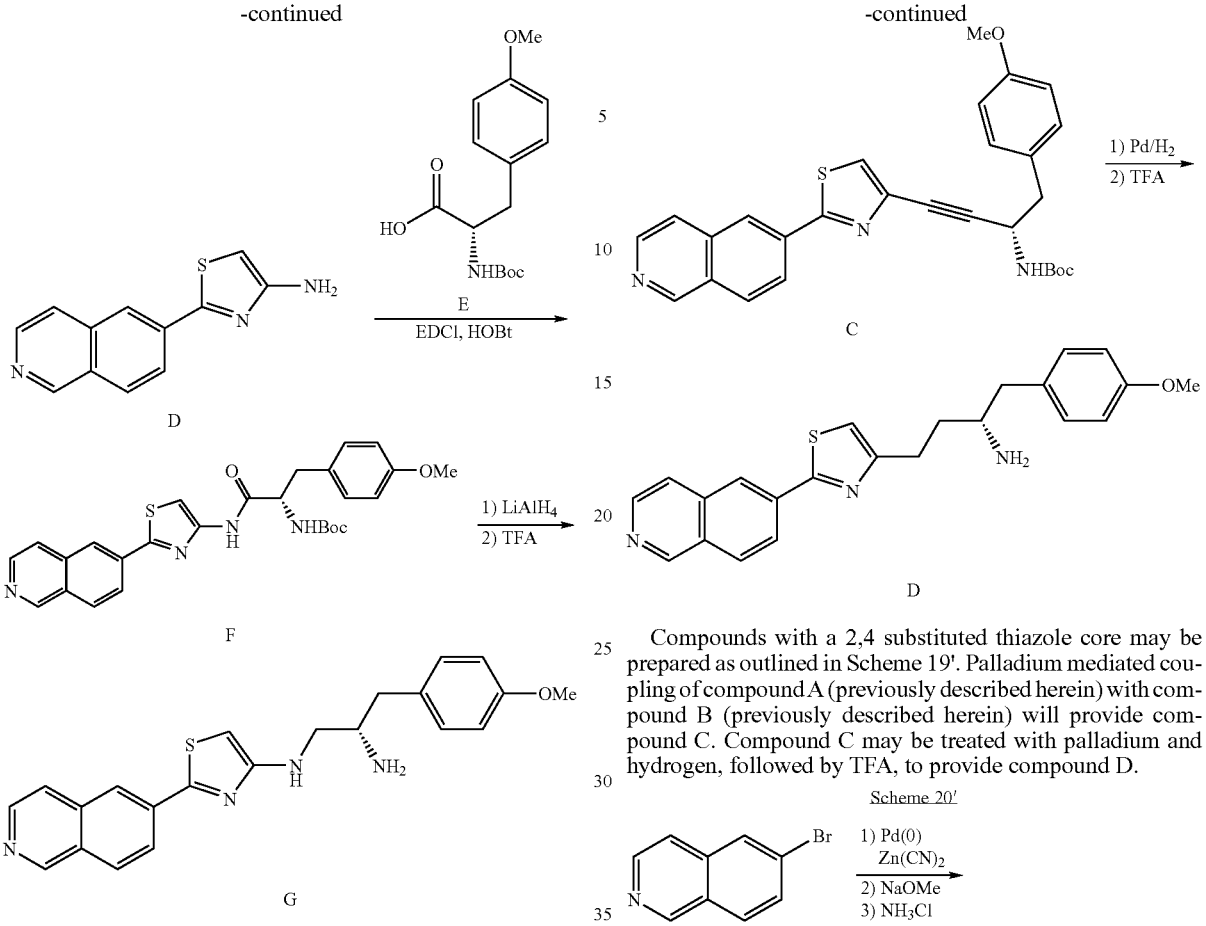

Compounds with a 4-amino 2,4 substituted thiazole core may be prepared as outlined in Scheme 18'. Compound A (available from Matrix) may be coupled with compound B (previously described herein) to provide compound C ("Synthesis of 2'-substituted 2,4'-bithiazoles by regioselective cross-coupling reactions", Bach, T. et. al. J. Org. Chem., 2002, pages 5789-5795. Palladium mediated amination of compound C may provide compound D (procedures previously described herein). Coupling of compound D with compound E (previously described herein) may provide compound F. Treatment of compound F with lithium aluminum hydride, followed by TFA, may provide compound G.

Compounds with a 2,4 substituted thiazole core may be prepared as outlined in Scheme 19'. Palladium mediated coupling of compound A (previously described herein) with compound B (previously described herein) will provide compound C. Compound C may be treated with palladium and hydrogen, followed by TFA, to provide compound D.

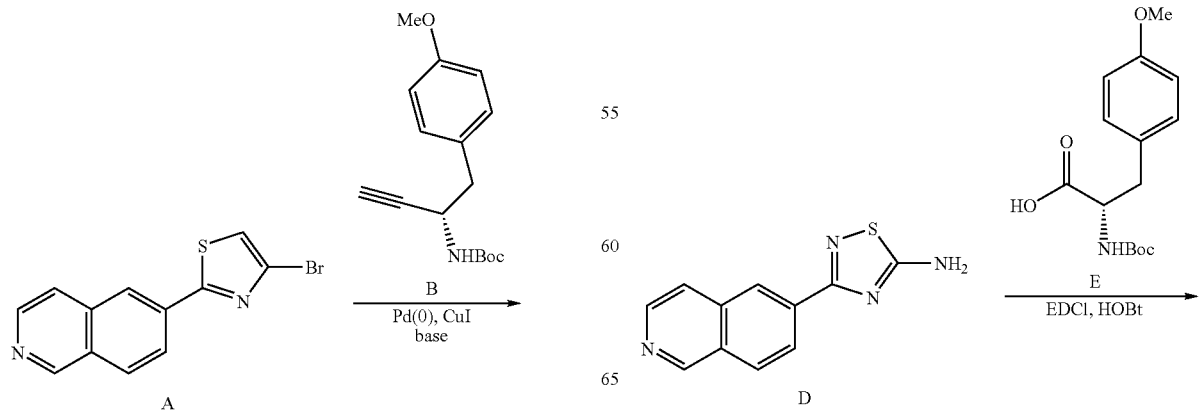

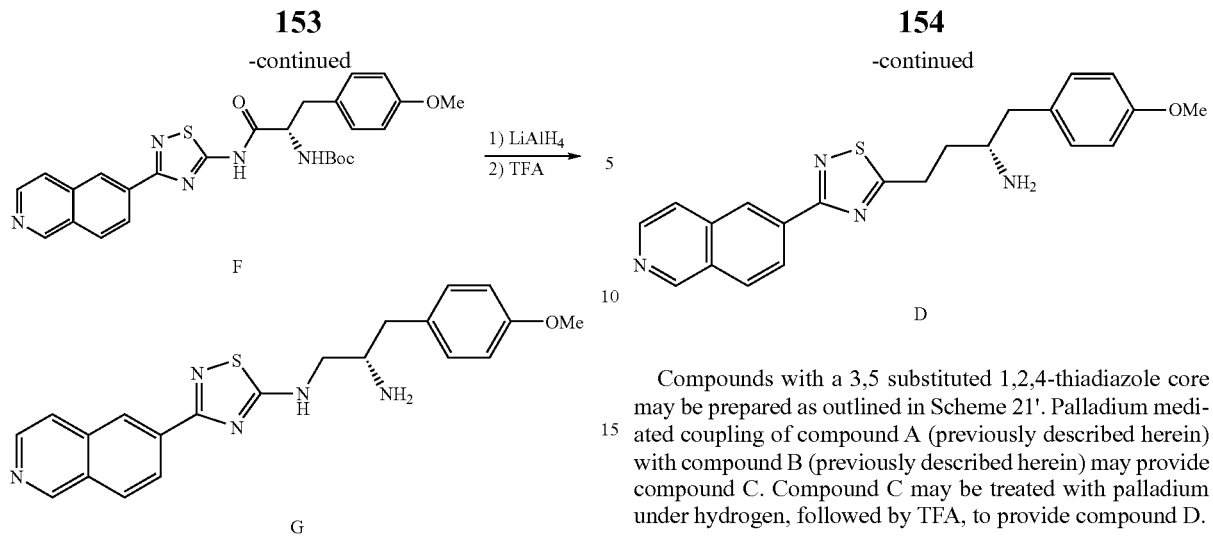

Compounds with a 5-amino-3,5 substituted 1,2,4-thiadiazole core may be prepared as outlined in Scheme 20'. Compound A (previously described herein) may be converted to compound B by palladium mediated cyanation, followed by treatment with sodium methoxide and ammonium chloride ("Structure-activity relationships of thiazole and thiadiazole derivatives as potent and selective human adenosine A₃ receptor antagonists", Jung, K-Y.; et. al., Bioorg. Med. Chem. Lett., 2004, 613-623). Compound B may converted to compound C by treatment with CCl₃SCl (see previous reference). Compound C may be converted to compound D by treatment with ammonia. Coupling of compound D with compound E (previously described herein) may provide compound F. Treatment of compound F with lithium aluminum hydride, followed by TFA, may provide compound G.

Compounds with a 3,5 substituted 1,2,4-thiadiazole core may be prepared as outlined in Scheme 21'. Palladium mediated coupling of compound A (previously described herein) with compound B (previously described herein) may provide compound C. Compound C may be treated with palladium under hydrogen, followed by TFA, to provide compound D.

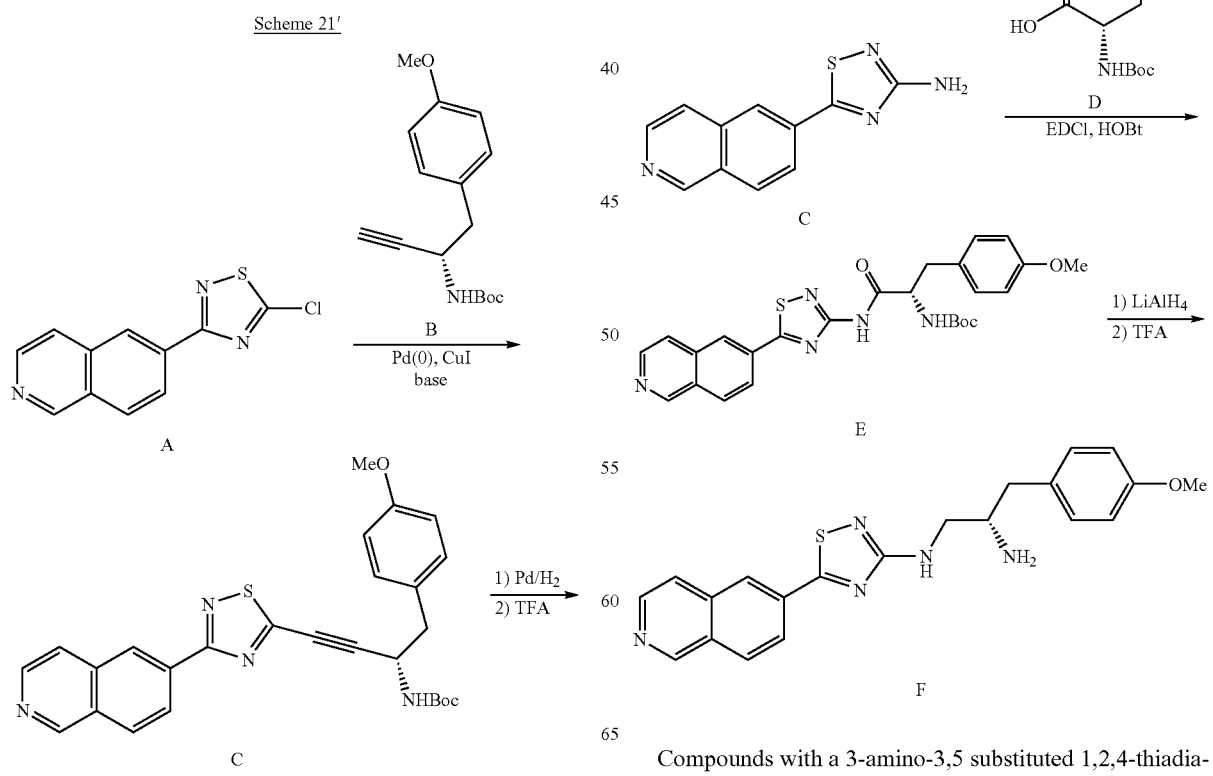

Compounds with a 3-amino-3,5 substituted 1,2,4-thiadiazole core may be prepared as outlined in Scheme X. Compound A (available from Milestone PharTech) may undergo palladium mediated cross coupling with compound B (previously described herein) to provide compound C. Compound C may be coupled with compound D (previously described herein) to provide compound E. Treatment of compound E with lithium aluminum hydride, followed by TFA, may provide compound F.

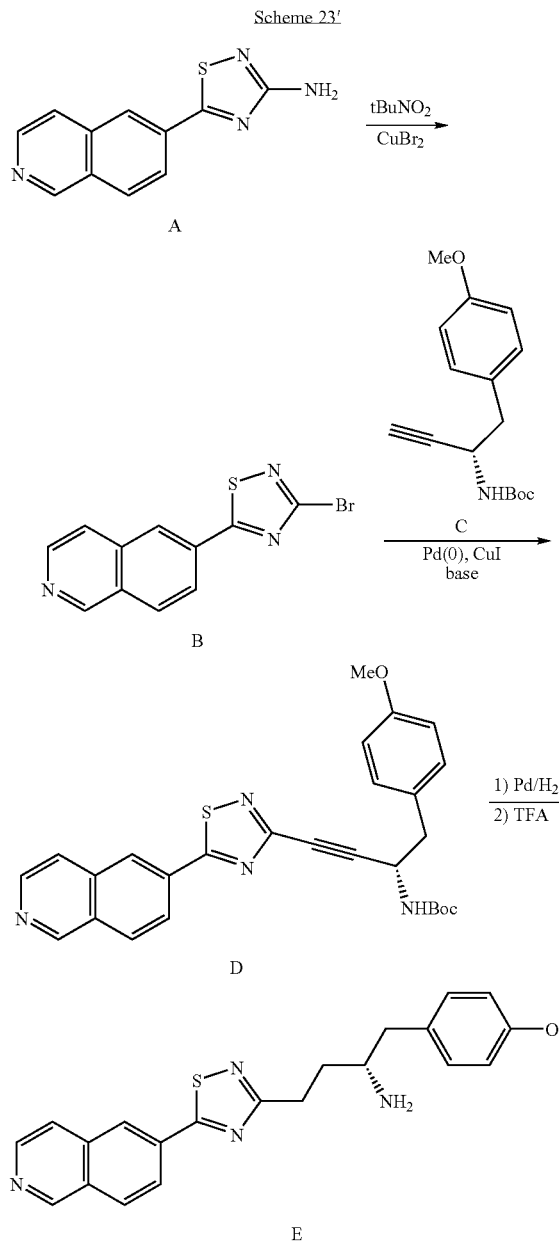

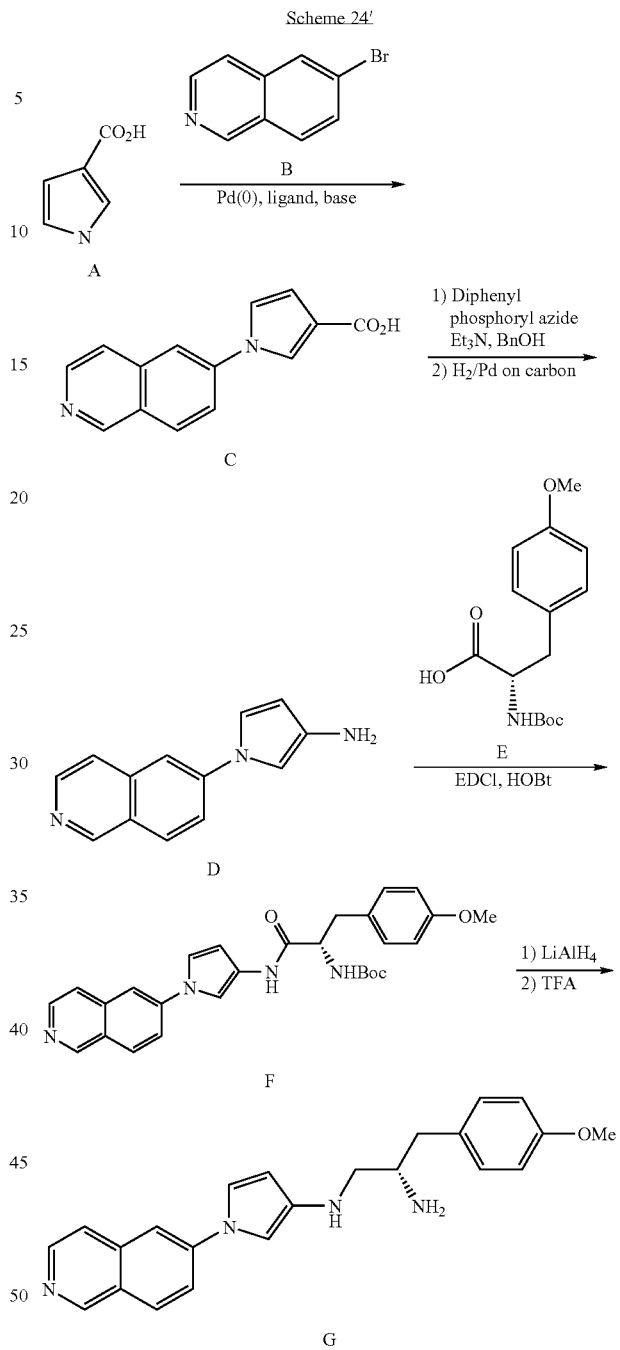

Compounds with a 3,5 substituted 1,2,4-thiadiazole core may be prepared as outlined in Scheme 23'. Compound A (previously described herein) may be converted to compound B. Palladium mediated coupling of compound B with compound C (previously described herein) may provide compound D. Compound D may be treated with palladium under hydrogen, followed by TFA, to provide compound E.

Compounds with a 3-amino 1,3 substituted pyrrole core may be synthesized as outlined in Scheme 24'. Compound A (available from Tyger Pharma) may be coupled with compound B (previously described herein) to provide compound C ("Preparation of N-aryl piperazines and other N-aryl compounds from aryl bromides as scaffolds of bioactive compounds" Pujol, M. D. et al, Tetrahedron, 2006, 9010-9016). Compound C may be converted to compound D by Curtius rearrangement, followed by treatment with palladium and hydrogen ("Synthesis and in vitro antimycobacterial activity of novel 3-(1H-pyrrol-1-yl)-2-oxazolidinone analogues of PNU-100480" Sbardella, G., et. al.; Bio. Org. Med. Chem. Lett., 2004 1537-1541). Compound D may be coupled with compound E (previously described herein) to provide compound F. Treatment of compound F with lithium aluminum hydride, followed by TFA, may provide compound G.

Scheme 25'

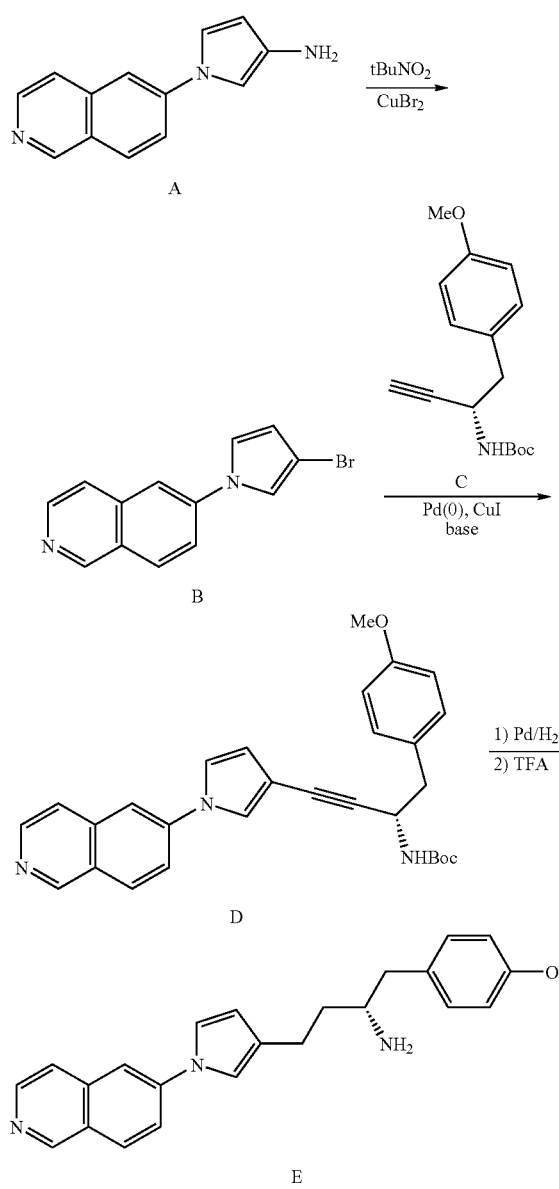

Compounds with a 1,3 substituted pyrrole core may be synthesized as outlined in Scheme 25'. Compound A (previously described herein) may be converted to compound B. Palladium mediated coupling of compound B with compound C (previously described herein) may provide compound D. Compound D may be treated with palladium under hydrogen, followed by TFA, to provide compound E.

Scheme 26'

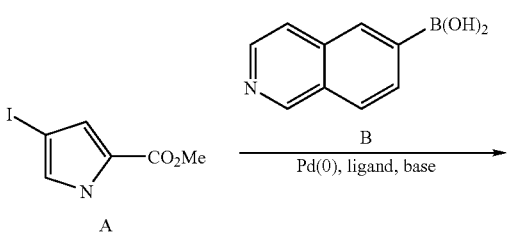

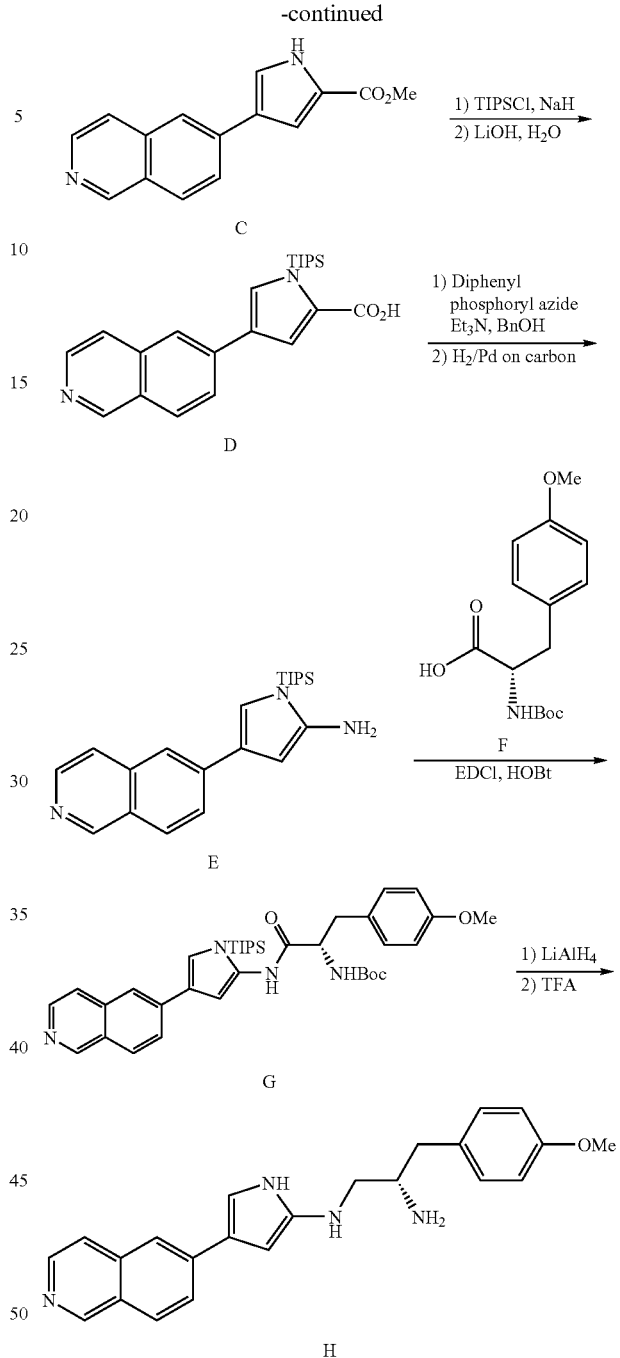

Compounds with a 2-amino 2,4 substituted N(H) pyrrole core may be synthesized as outlined in Scheme 26'. Compound A (available from Asymchem) may undergo palladium mediated coupling with compound B to afford compound C. Compound C may be treated with triisopropylsilyl chloride and sodium hydride, followed by aqueous lithium hydroxide to provide compound D. Compound D may undergo Curtius rearrangement, followed by treatment with palladium and hydrogen to provide compound E. Compound E may be coupled with compound F (previously described herein) to provide compound G. Treatment of compound G with lithium aluminum hydride, followed by TFA, may provide compound H.

Scheme 27'

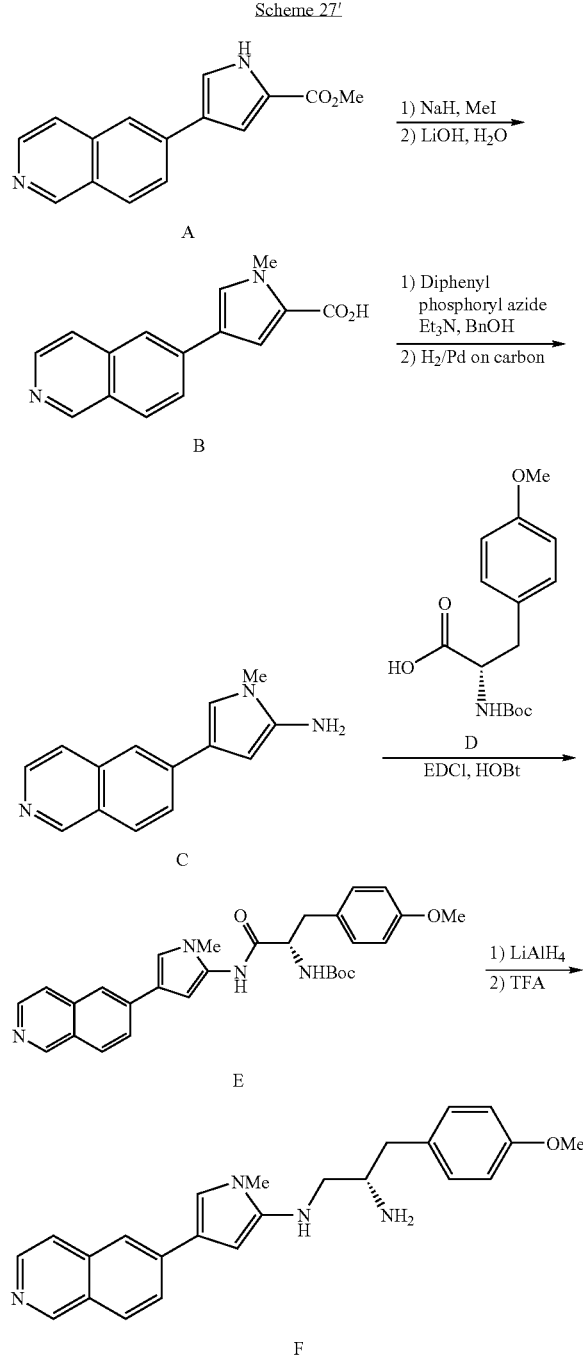

Compounds with a 2 amino 2,4 substituted N(Me)pyrrole core may be synthesized as outlined in Scheme 27'. Compound A (previously described herein) may be treated with sodium hydride and methyl iodide, followed by aqueous lithium hydroxide to provide compound B. Compound B may undergo Curtius rearrangement, followed by treatment with palladium and hydrogen to provide compound C. Compound C may be coupled with compound D (previously described herein) to provide compound E. Treatment of compound E with lithium aluminum hydride, followed by TFA, may provide compound F.

Scheme 28'

Compounds with a 2,4 substituted N(H) pyrrole core may be synthesized as outlined in Scheme 28'. Compound A (previously described herein) may be converted to compound B. Palladium mediated coupling of compound B with compound C (previously described herein) may provide compound D. Compound D will be treated with palladium under hydrogen, followed by TFA, to provide compound E.

Scheme 29'

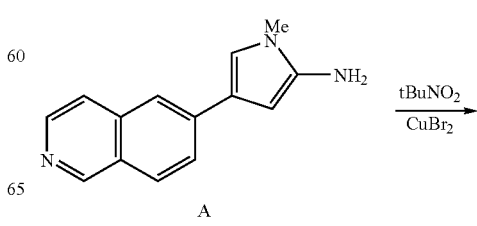

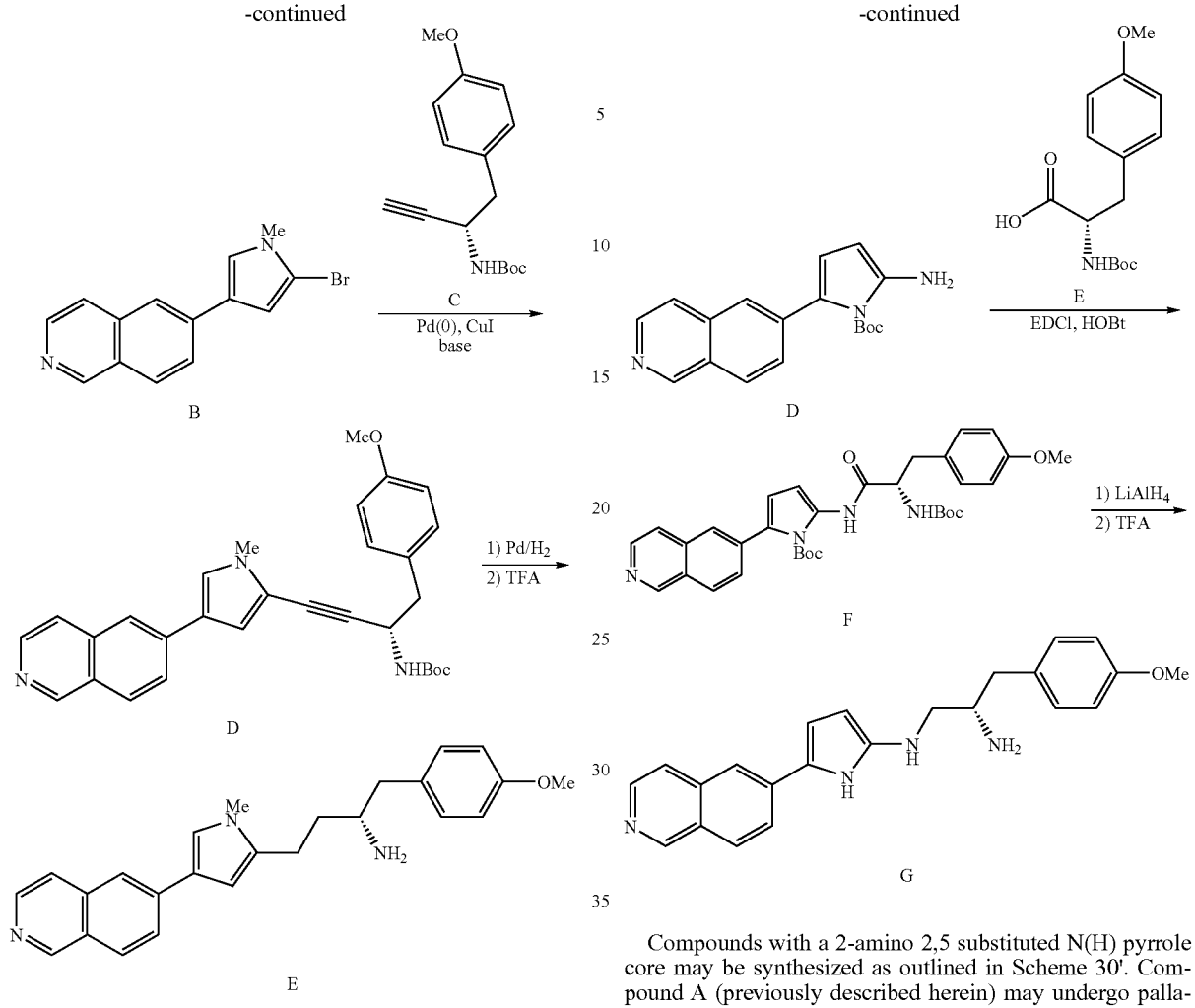

Compounds with a 2,4 substituted N(Me) pyrrole core may be synthesized as outlined in Scheme 29'. Compound A (previously described herein) may be converted to compound B. Palladium mediated coupling of compound B with compound C (previously described herein) may provide compound D. Compound D may be treated with palladium under hydrogen, followed by TFA, to provide compound E.

Compounds with a 2-amino 2,5 substituted N(H) pyrrole core may be synthesized as outlined in Scheme 30'. Compound A (previously described herein) may undergo palladium mediated cross coupling with compound B ("Novel pyrrole-containing progesterone receptor modulators", Collins, M. A., et. al., Biior Med. Chem. Lett., 2004, pages 2185-2189), followed by treatment with N-bromosuccinimide to provide compound C. Compound C may be converted to compound D (procedures previously described herein). Compound D may be coupled with compound E (previously described herein) to provide compound F. Treatment of compound F with lithium aluminum hydride, followed by TFA, may provide compound G.

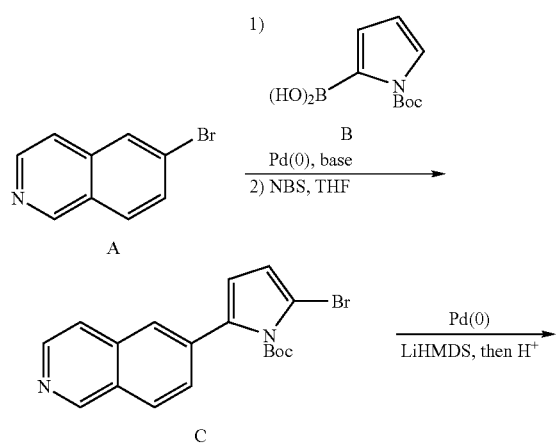

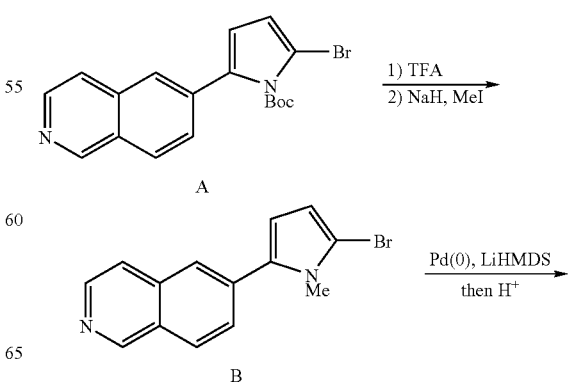

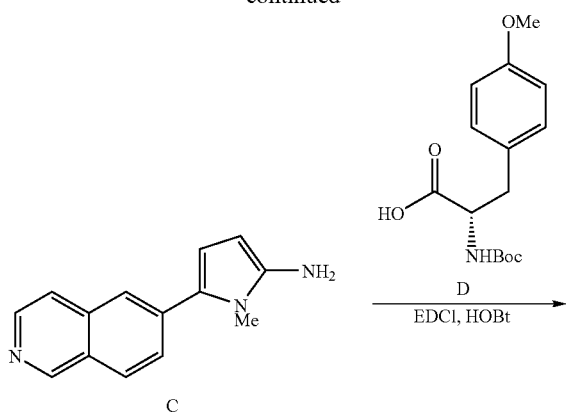

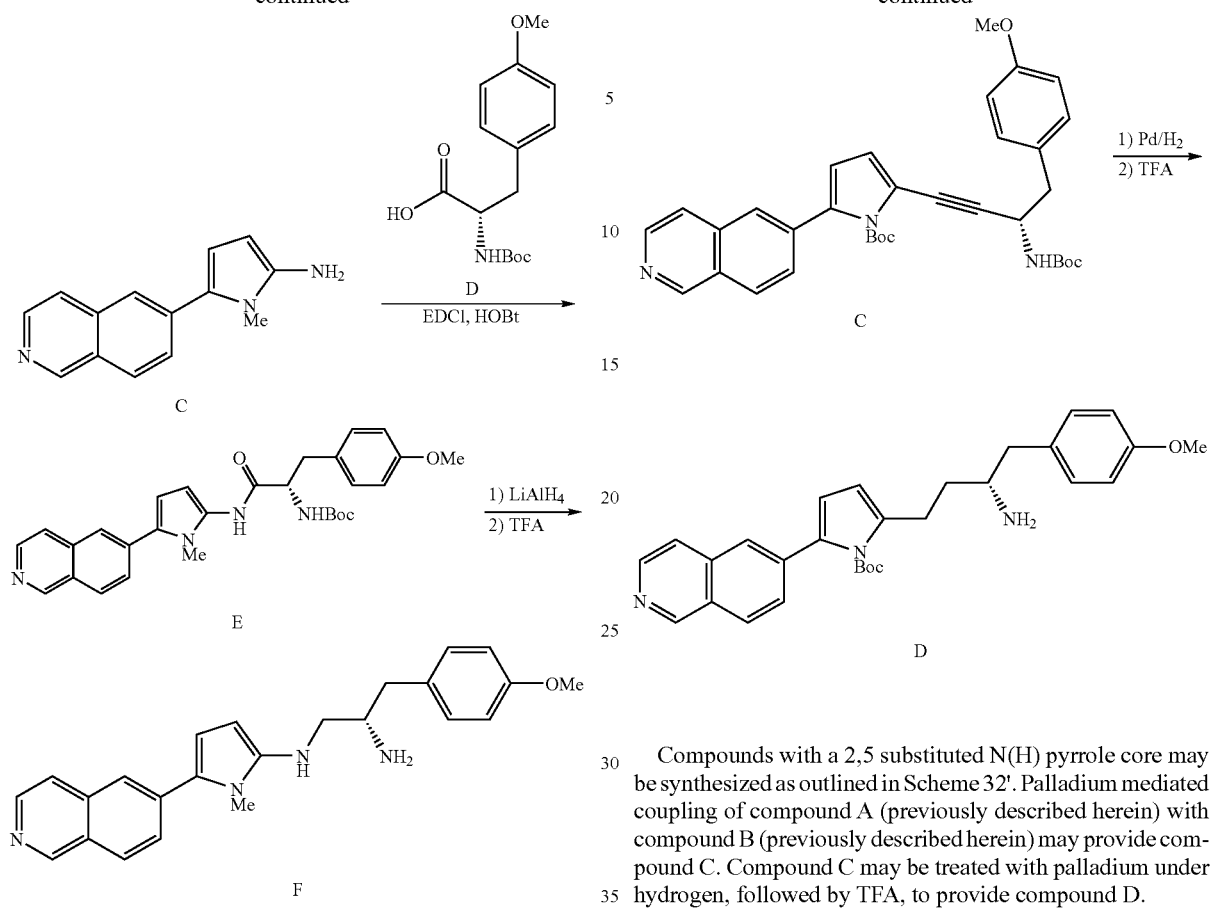

Compounds with a 2-amino 2,5 substituted N(Me) pyrrole core may be synthesized as outlined in Scheme 31'. Compound A (previously described herein) may be treated with trifluoroacetic acid, followed by sodium hydride and methyl iodide to provide compound B. Compound B may be converted to compound C (procedures preciously described herein). Compound C may be coupled with compound D (previously described herein) to provide compound E. Treatment of compound E with lithium aluminum hydride, followed by TFA, may provide compound F.

Compounds with a 2,5 substituted N(H) pyrrole core may be synthesized as outlined in Scheme 32'. Palladium mediated coupling of compound A (previously described herein) with compound B (previously described herein) may provide compound C. Compound C may be treated with palladium under hydrogen, followed by TFA, to provide compound D.

Scheme 33'

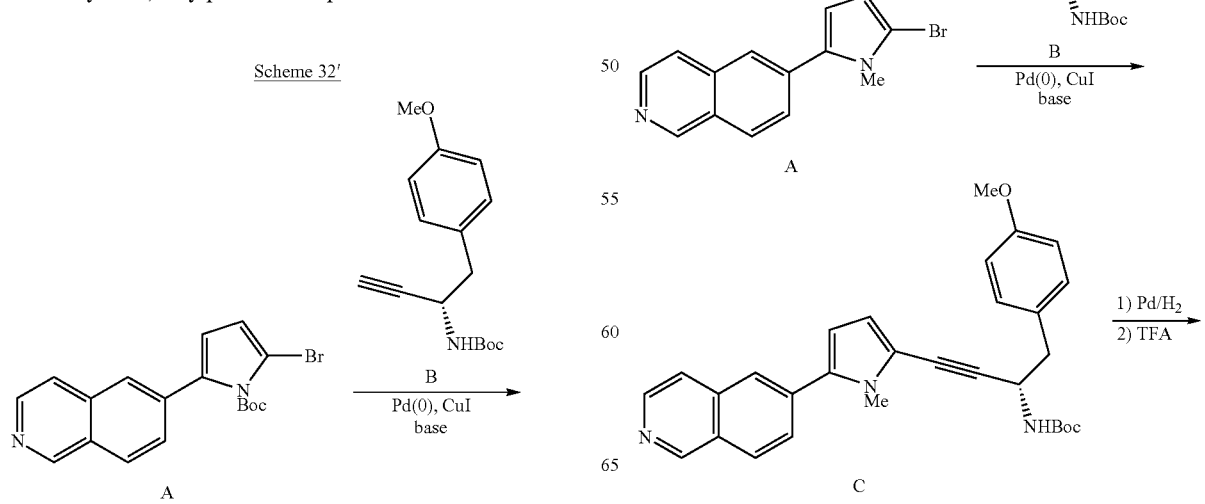

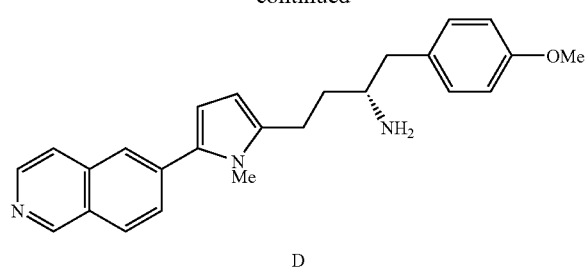

D

Compounds with a 2,5 substituted N(Me) pyrrole core may be synthesized as outlined in Scheme 33'. Palladium mediated coupling of compound A (previously described herein) with compound B (previously described herein) may provide compound C. Compound C may be treated with palladium under hydrogen, followed by TFA, to provide compound D.

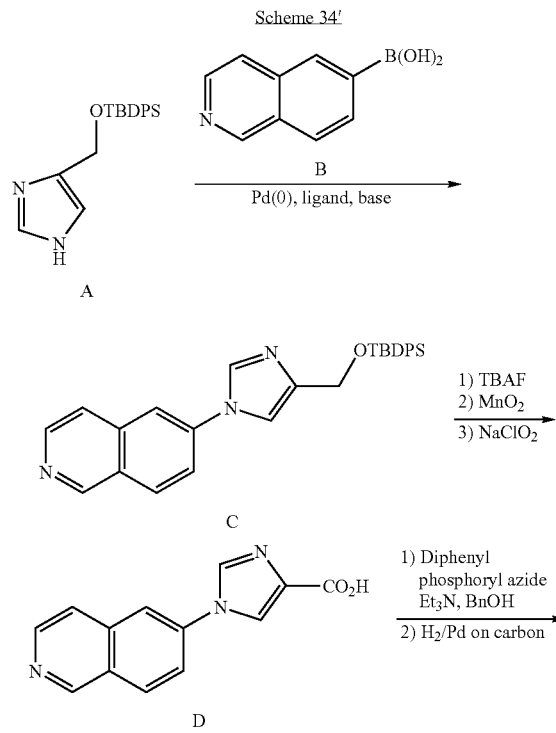

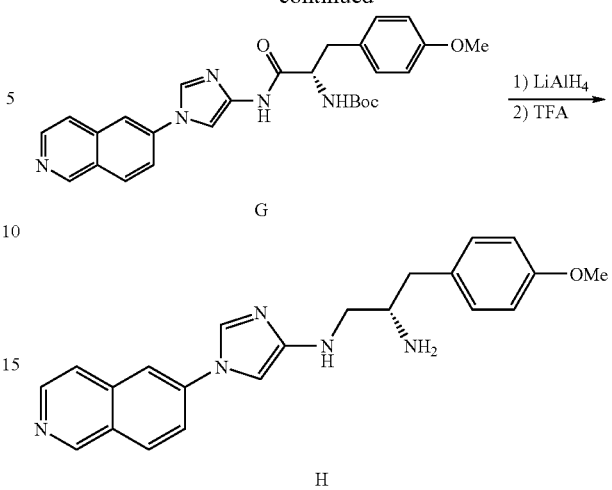

H

Compounds with a 4-amino 1,4-substituted imidazole core may be synthesized as outlined in Scheme 34'. Compound A ("Formation and spectroscopic characterization of the dioxygen adduct of a heme-Cu complex possessing a cross-linked tyrosine-histidine mimic: modeling the active site of cytochrome c oxidase", Liu, J-G, et. al. Chem. Comm., 2004, pages 120-121) may under go palladium mediated cross coupling with compound B (previously described herein) to provide compound C. Compound C may be treated with tetrabutylammonium fluoride, followed by manganese dioxane and sodium chlorite to provide compound D. Compound D may undergo Curtius rearrangement, followed by treatment with palladium and hydrogen to provide compound E. Compound E may be coupled with compound F (previously described herein) to provide compound G. Treatment of compound G with lithium aluminum hydride, followed by TFA, may provide compound H.

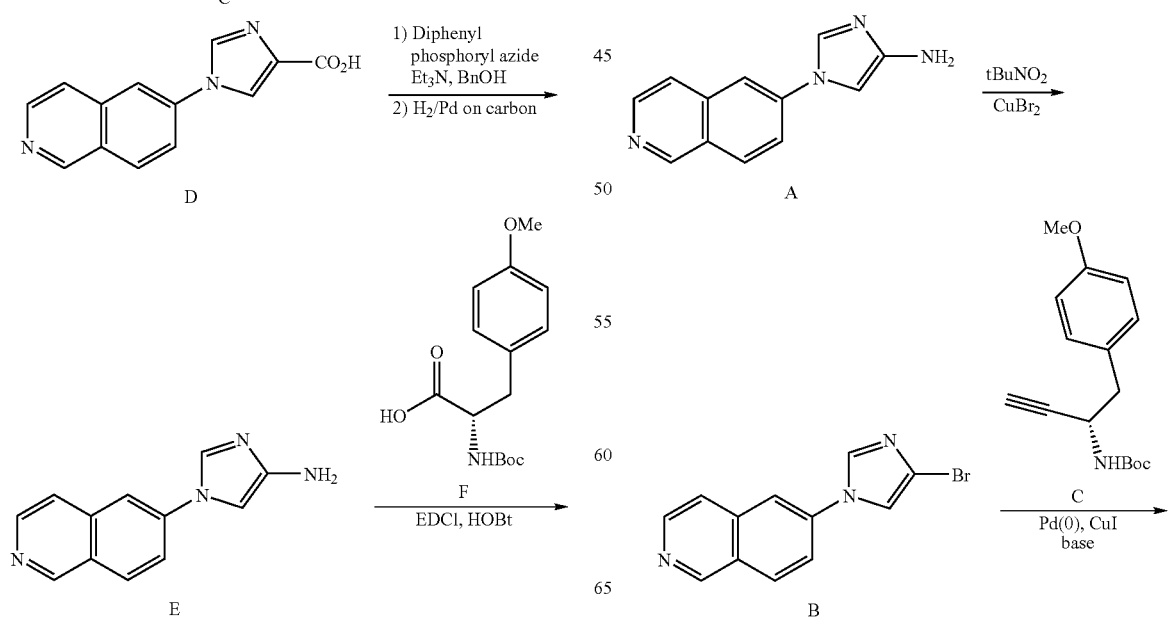

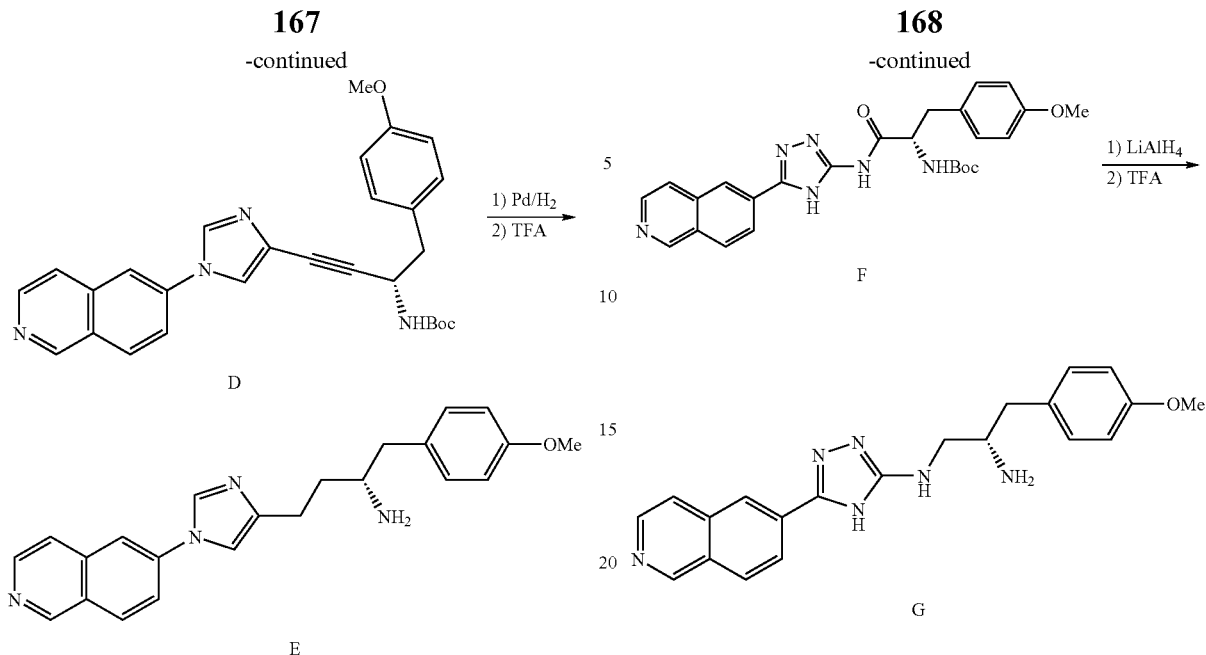

Compounds with a 1,4 substituted imidazole core may be synthesized as outlined in Scheme 35'. Compound A (previously described herein) may be converted to compound B. Palladium mediated coupling of compound B with compound C (previously described herein) will provide compound D. Compound D will be treated with palladium under hydrogen, followed by TFA, to provide compound E.

Compounds with 3-amino 3,5 substituted 1,2,4-triazole core may be synthesized as outlined in Scheme 36'. Compound A (available from TimTec Corporation) may be coupled with compound B (previously described herein) to provide compound C. Compound C may be treated with palladium and hydrogen to provide compound D. Compound D may be coupled with compound E (previously described herein) to provide compound F. Treatment of compound F with lithium aluminum hydride, followed by TFA, may provide compound G.

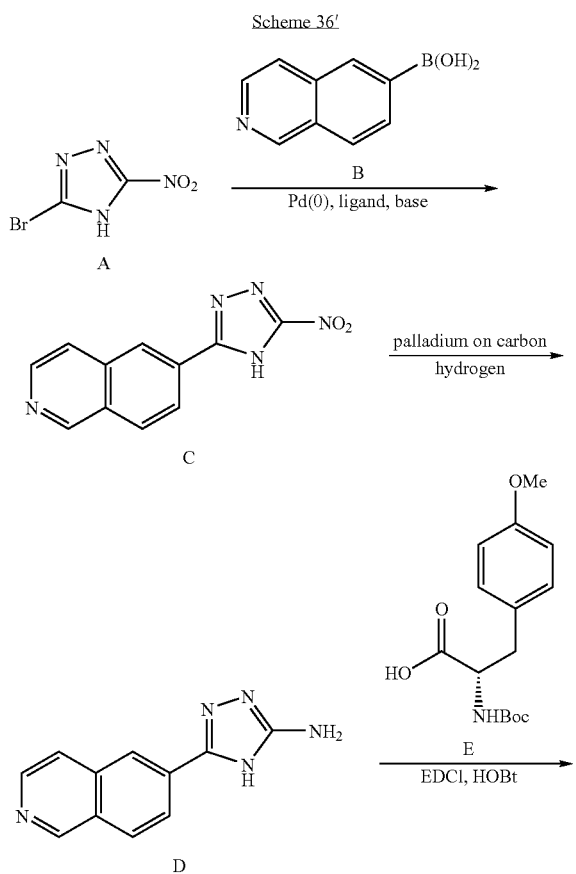

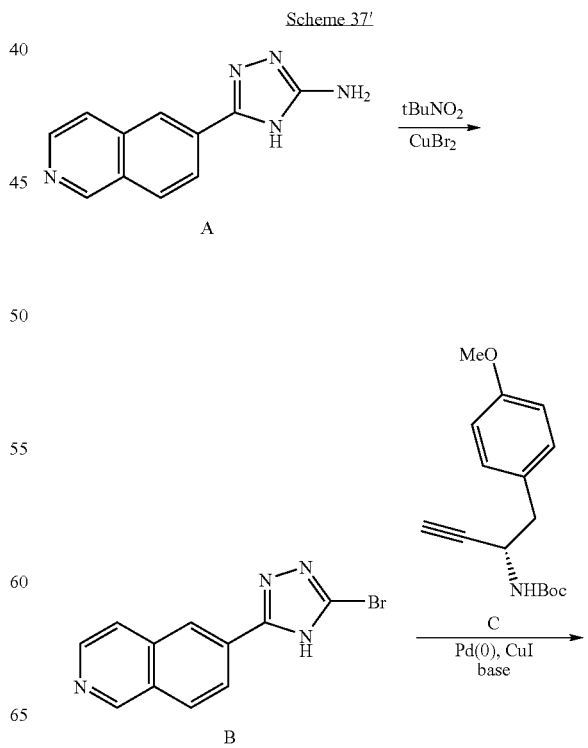

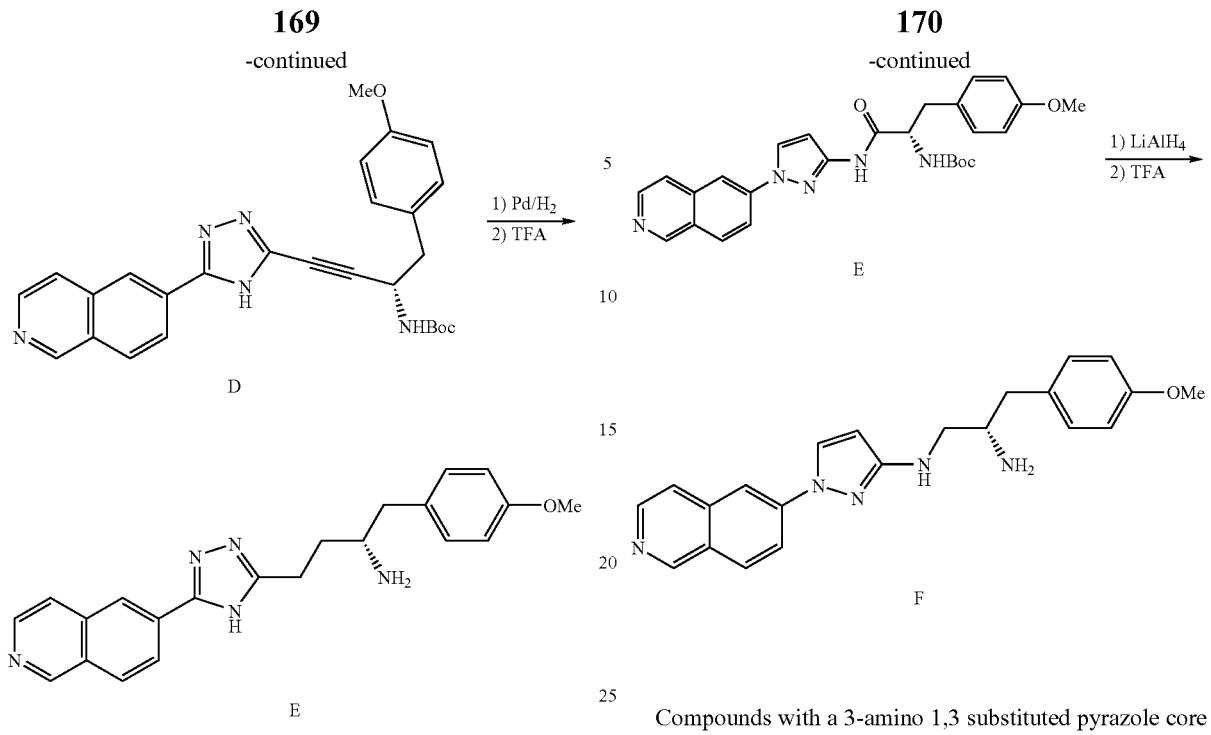

Compounds with a 3,5 substituted 1,2,4 triazole core may be synthesized as outlined in Scheme 37'. Compound A (previously described herein) may be converted to compound B. Palladium mediated coupling of compound B with compound C (previously described herein) will provide compound D. Compound D may be treated with palladium under hydrogen, followed by TFA, to provide compound E.

Compounds with a 3-amino 1,3 substituted pyrazole core may be synthesized as outlined in Scheme 38'. Compound A (available from Aldrich) may under copper mediated coupling with compound B (previously described herein) to provide compound C ("Copper-diamine-catalyzed N-arylation of pyrroles, pyrazoles, indazoles, imidazoles, and triazoles" Buchwald, S. L., Et. al. J. Org. Chem., 2004, pages 5578-5587). Compound C may be coupled with compound D (previously described herein) to provide compound E. Treatment of compound E with lithium aluminum hydride, followed by TFA, may provide compound F.

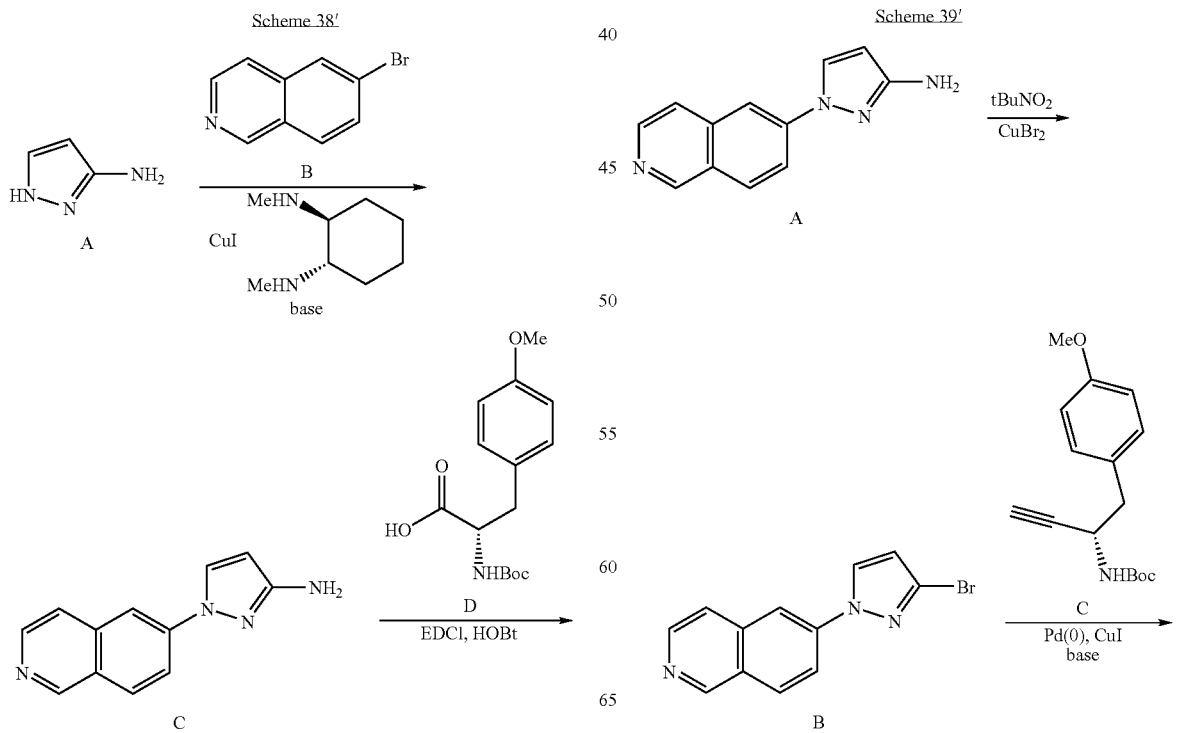

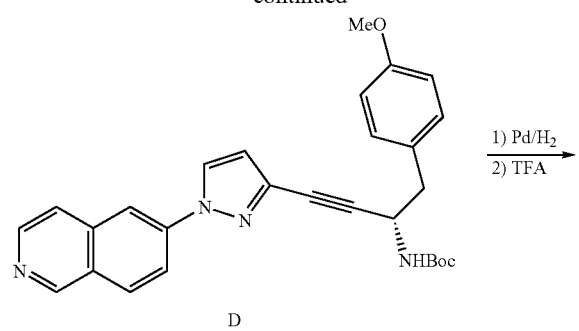

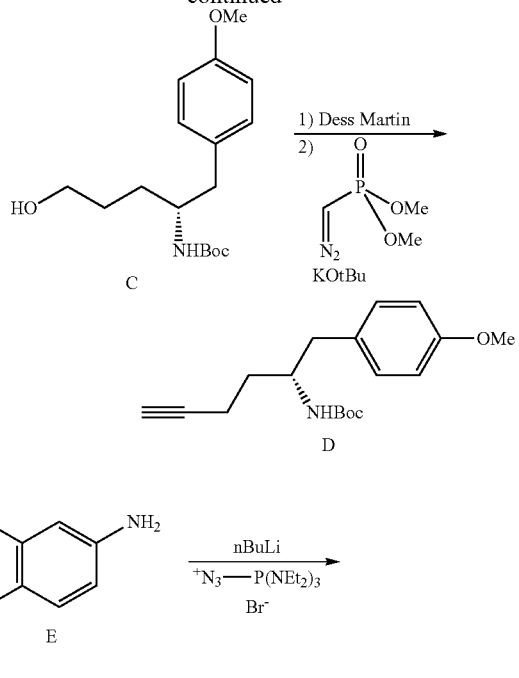

Compounds with a 1,3 substituted pyrazole core may be synthesized as outlined in Scheme 39'. Compound A (previously described herein) may be converted to compound B. Palladium mediated coupling of compound B with compound C (previously described herein) may provide compound D. Compound D may be treated with palladium under hydrogen, followed by TFA, to provide compound E.

Scheme 40'

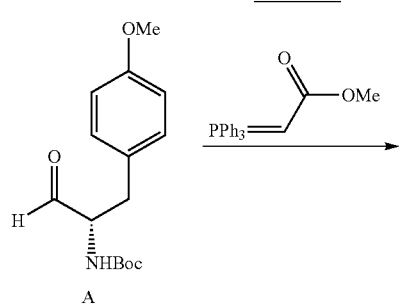

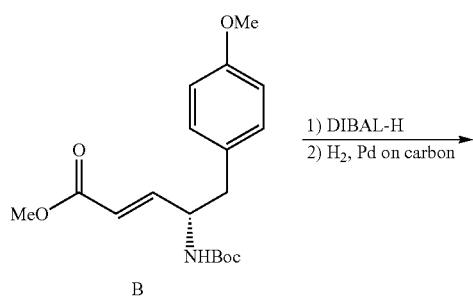

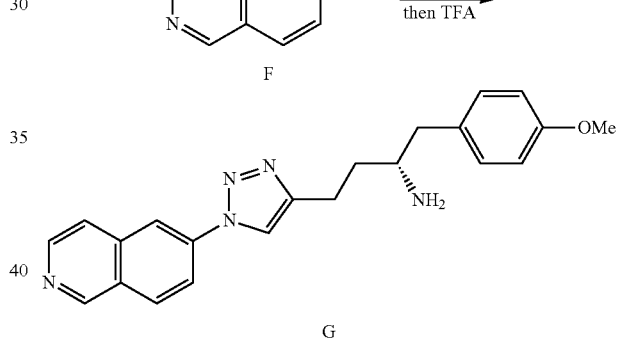

Compounds with a 1,4 substituted 1,2,3-triazole core may be synthesized as outlined in Scheme 40'. Compound A (synthesized from the commercially available amino acid [Peptech] via methodology described herein) may be condensed with methyl (triphenylphosphoranylidene)acetate to provide compound B. Treatment of compound B with diisobutyl aluminum hydride, followed by 1 palladium and hydrogen, may provide compound C. Treatment of compound C with Dess-Martin reagent, followed by dimethyl diazomethylphosphonate and potassium tert-butoxide may provide compound D. Compound E (available from J&W Pharmalab) may be transformed to compound F following know procedures ("Conversions of primary amines to azides by n-butyllithium and azidotris(diethylamino)phosphonium bromide", Klump, S. P. et. al. Tetrahedron Lett., 2002, pages 8421-8423). Compound F may be treated with compound D and copper (I) ("Stabilization of G-quadruplex DNA by highly selective ligands via click chemistry", Moorhouse, A. D.; el. al., J. Am. Chem. Soc., 2006, pages 15972-15973"), followed by TFA to provide compound G.

Scheme 41'

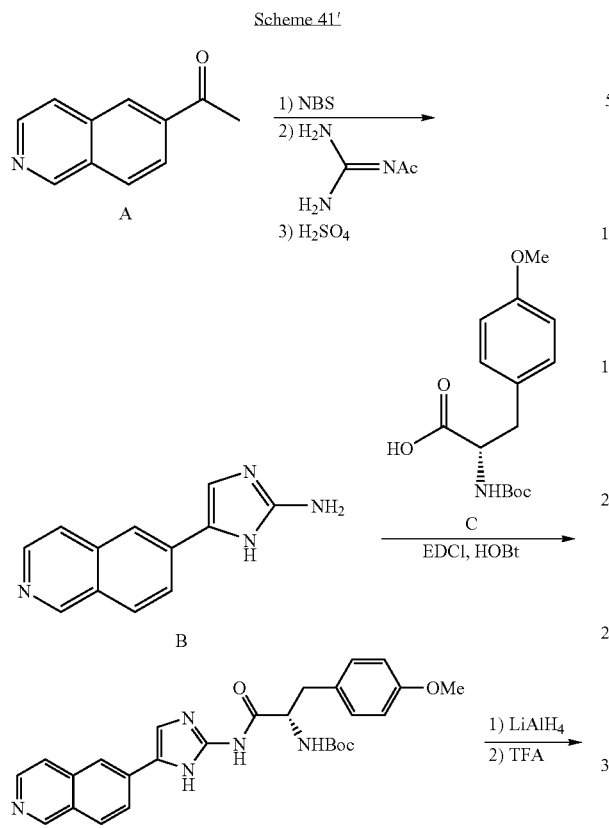

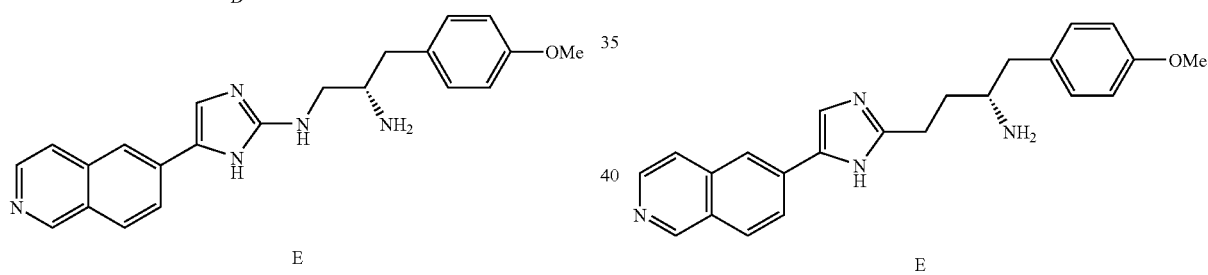

Compounds with a 2-amino 2,5 substituted 1N(H) imidazole core may be synthesized as outlined in Scheme 41'. Compound A (previously described herein) may be converted to compound B by treatment with N-bromosuccinimide, followed by a known procedure ("A simple and practical synthesis of 2-aminoimidazoles" Little, T. L. J. Org. Chem., 1994, pages 7299-7305). Compound B may be coupled with compound C (previously described herein) to provide compound D. Treatment of compound D with lithium aluminum hydride, followed by TFA, may provide compound E.

Compounds with a 2,5 substituted 1N(H) imidazole core may be prepared as outlined in Scheme 42'. Compound A (previously described herein) may be converted to compound B. Palladium mediated coupling of compound B with compound C (previously described herein) may provide compound D. Compound D may be treated with palladium under hydrogen, followed by TFA, to provide compound E.

Scheme 42'

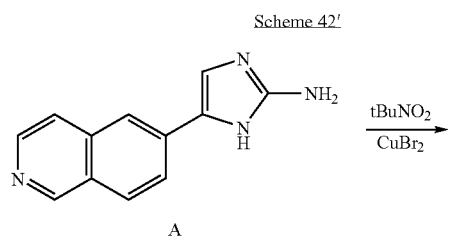

Scheme 43'

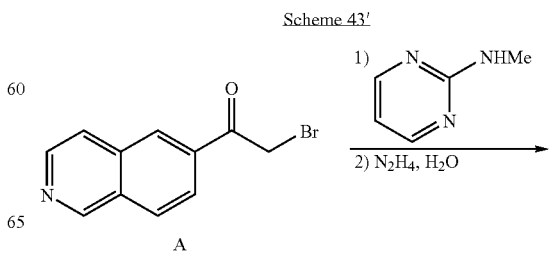

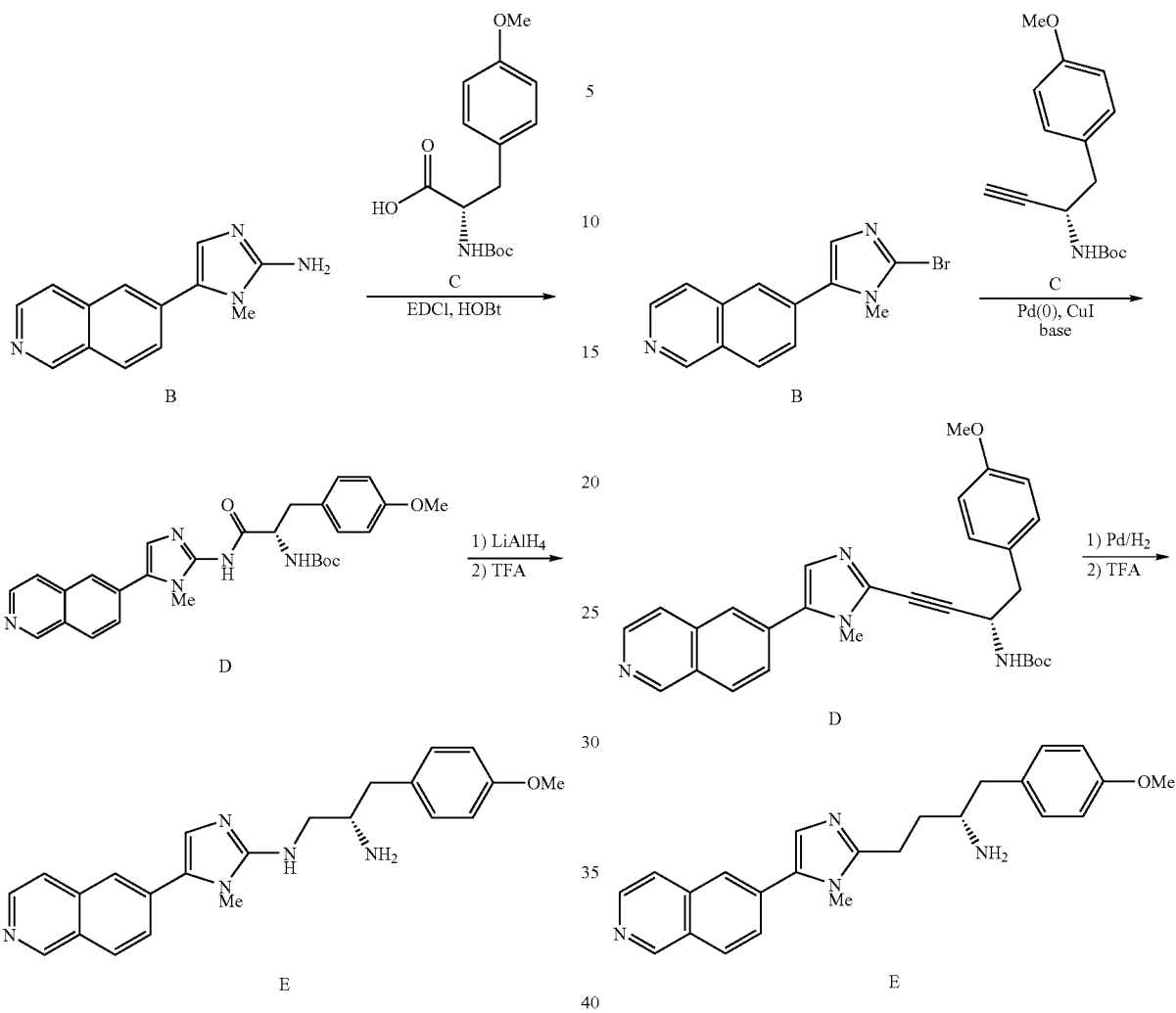

Compounds with a 2-amino-2,5 substituted 1N(Me) imidazole core may be prepared as outlined in Scheme 43'. Compound A (previously described herein) may be treated with N-methylpyrimidin-2-amine, followed by hydrazine to provide compound B ("Efficient One-Pot, Two-Step, Microwave-Assisted Procedure for the Synthesis of Polysubstituted 2-Aminoimidazoles", Ermolat'ev, D. S.; et. al. Org. Lett. 2006, pages 5781-1 5784). Compound B may be coupled with compound C (previously described herein) to provide compound D. Treatment of compound D with lithium aluminum hydride, followed by TFA, may provide compound E.

Compounds with a 2,5 substituted 1 N(Me) imidazole core may be prepared as outlined in Scheme 44'. Compound A (previously described herein) may be converted to compound B. Palladium mediated coupling of compound B with compound C (previously described herein) may provide compound D. Compound D may be treated with palladium under hydrogen, followed by TFA, to provide compound E.

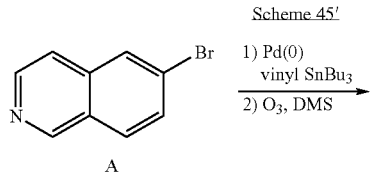

Scheme 44'

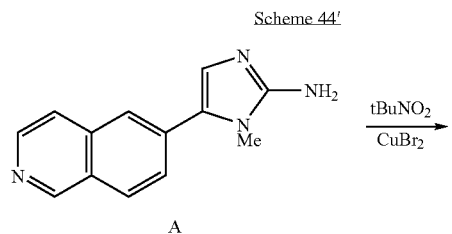

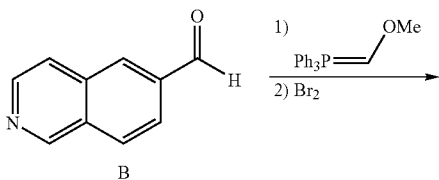

-continued

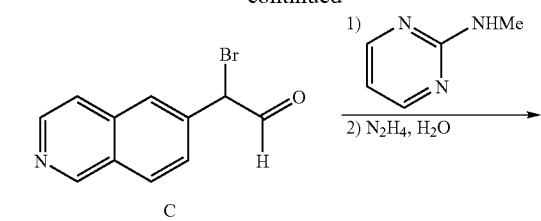

C

Scheme 46'

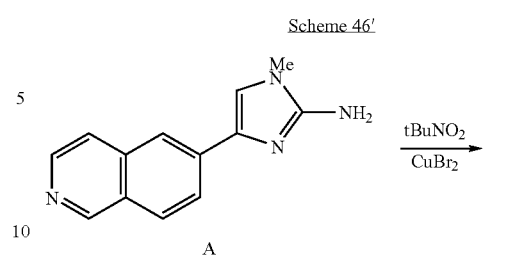

A

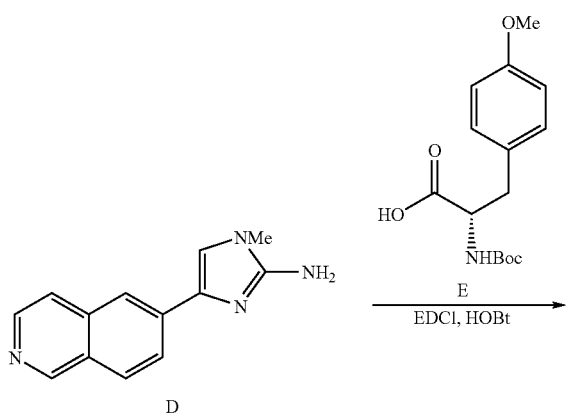

D

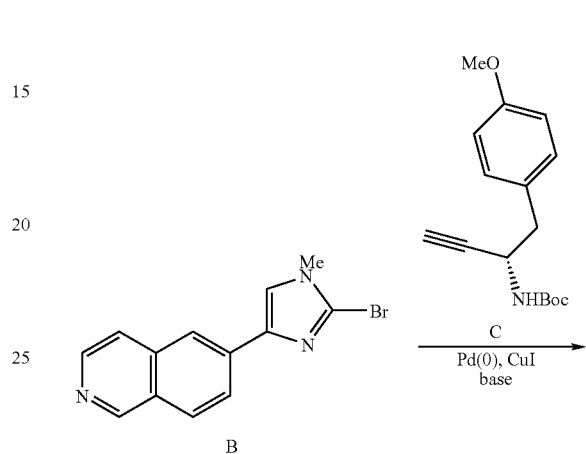

B

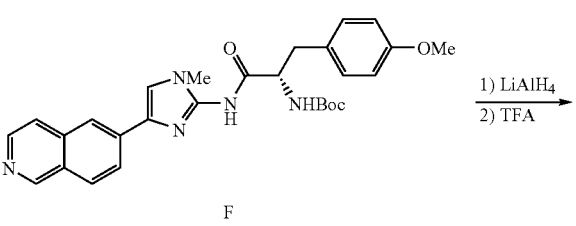

F

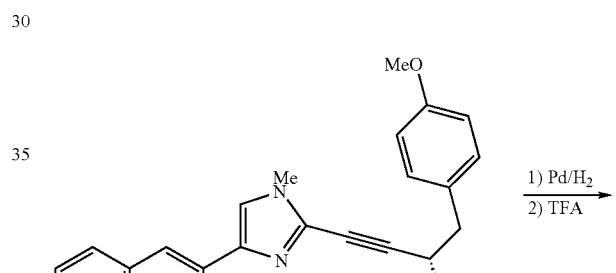

D

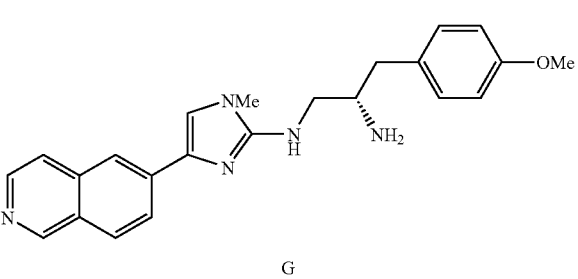

G

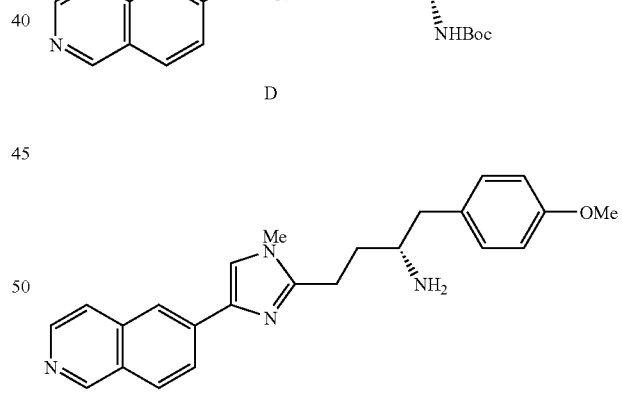

E

Compounds with a 2-amino-2,5 substituted 3-N(Me)imidazole core may be synthesized as outlined in Scheme 45'. Compound A (previously described herein) may undergo palladium mediated cross coupling with vinyl tributyl tin, followed by ozonolysis to provide compound B. Compound B may be elaborated to compound C by treatment with (methoxymethyl)triphenyl phosphonium chloride and base, followed by bromine ("Bromoalkoxystyrenes", Jacobs, T. L., et. al., J. Am. Chem. Soc., 1953, pages 5500-5504). Compound C may be treated with N-methylpyrimidin-2-amine, followed by hydrazine to provide compound D (procedure previously described herein). Compound D may be coupled with compound E (previously described herein) to provide compound F. Treatment of compound F with lithium aluminum hydride, followed by TFA, may provide compound G.

Compounds with a 2,5 substituted 3-N(Me)imidazole core may be synthesized as outlined in Scheme 46'. Compound A (previously described herein) may be converted to compound B. Palladium mediated coupling of compound B with compound C (previously described herein) may provide compound D. Compound D may be treated with palladium and hydrogen, followed by TFA, to provide compound E.

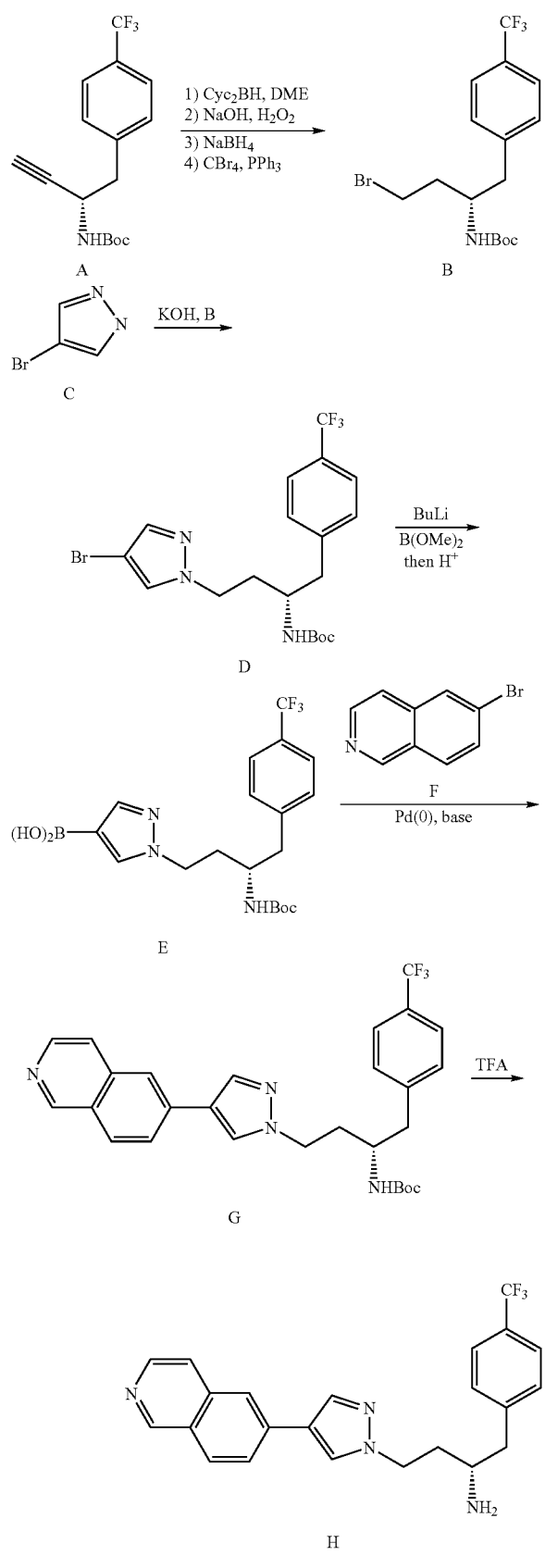

Scheme 47'

Compounds with a 1,4 substituted pyrazole core may be obtained as outlined in Scheme 47'. Compounds A (previously described herein) may undergo hydroboration/oxidation ("Preparation of 3-Substituted (E)-1-Alkenylboronic Esters", Hoffmann, R. W., et. al. Synthesis, 1988, pages 103-106), followed by reduction of the resulting aldehyde and conversion of resulting alcohol to a bromide, to provide compound B. Compound C (available from Aldrich) may be treated with potassium hydroxide and compound B to provide compound D ("Synthesis of pinacol esters of 1-alkyl-1H-pyrazol-5-yl- and 1-alkyl-1H-pyrazol-4-ylboronic acids", Ivachtchenko, A. V.; et. al., J. Heterocyclic. Chem. 2004, pages 931-939). Compound D may then be converted to compound E. Compound E may undergo palladium mediated cross coupling with compound F (previously described herein) to provide compound G. Treatment of compound G with TFA may provide compound H.

2.1 PKB Assay Testing

The kinase assay for evaluating PKB activity comprises active PKB enzymes, a PKB specific substrate, and $P^{33}$-labeled ATP. Two forms of PKBα enzymes were used, the full length PKBα and a kinase domain of PKBα with pleckstrin domain (amino acids 1-117) deleted. Both PKB enzymes were obtained from Upstate cell signaling solutions (Cat.# 14-276 and 14-341). The PKB substrate used is a synthetic peptide (ARKRERTYSFGHHA (SEQ ID NO: 1)) as described in Obata et al., J. Biol. Chem. 275 (46), 36108-36115 (2000). The phosphorylated substrate was captured by a phosphocellulose membrane filter plate (MILLIPORE) and measured by a Wallac Microbeta liquid scintillation counter (Perkin Elmer). Table 1 provides the $IC_{50}$ values obtained for each of the examples with respect to PKBα.

PKB activity in cells was assayed in a PTEN null human breast tumor cell line MDA-MB-468 and U87-MG. The phosphorylation status of PKB substrate PRAS40, FKHRL1, GSK3a/b, and Tuberin were measured by immunoassays utilizing phospho-specific antibodies (Invitrogen, Cell signaling technology).

The effect of PKB inhibition on cell viability was measured in a range of human tumor cell lines including, but not limiting to, MDA-MB-468, MDA-MB-231, U87-MG, LN-229, PC3, DU145. The cells were treated in regular growth media for 72 hours and cell viability was measured by Alamar Blue (Invitrogen).

The effect of PKB inhibition on tumor growth in vivo is assessed in an established U87MG xenograft model. Athymic nude mice bearing U87MG tumors (approximately 200 mm$^3$) in the right flank are treated with the compound orally at the dosage of 15, 30, and 60 mg/kg/day (n=10) for 17 days. Tumor volume and body weight are measured twice per week. Data are expressed as means plus or minus standard errors and plotted as a function of time. Statistical significance of the effect is evaluated by Repeated Measures Analysis of Variance (RMANOVA) followed by Scheffe post hoc testing for multiple comparisons. Tumor stasis and regression are observed.

TABLE 1

| Example | Structure | IC₅₀ |
|---------|-----------|------|
| 1 | | +++ |
| 2 | | ++ |
| 3 | | ++ |
| 4 | | ++ |
| 5 | | ++ |
| 6 | | ++ |

TABLE 1-continued

| Example | Structure[a] | IC$_{50}$[b] |
|---|---|---|
| 7 | 5-phenyl-oxazol-2-yl NH-CH$_2$-(4-methoxyphenyl) | ++ |
| 8 | 5-(pyridin-4-yl)-oxazol-2-yl NH-CH$_2$-(4-methoxyphenyl) | ++ |
| 9 | 5-(3-methyl-1H-indazol-5-yl)-oxazol-2-yl NH-CH$_2$-CH(NH$_2$)-CH$_2$-(4-trifluoromethylphenyl) | +++ |
| 10 | 5-(3-methyl-1H-indazol-5-yl)-oxazol-2-yl NH-CH$_2$-phenyl | ++ |
| 11 | 3-(isoquinolin-6-yl)-isoxazol-5-yl NH-CH$_2$-CH(NH$_2$)-CH$_2$-(4-chlorophenyl) | ++++ |
| 12 | 3-(isoquinolin-6-yl)-isoxazol-5-yl NH-CH$_2$-CH(NH$_2$)-CH$_2$-(4-bromophenyl) | ++++ |
| 13 | 3-(isoquinolin-6-yl)-isoxazol-5-yl NH-CH$_2$-CH(NH$_2$)-CH$_2$-(3-trifluoromethylphenyl) | ++++ |

TABLE 1-continued

| Example | Structure | IC₅₀ |
|---------|-----------|------|
| 14 | isoquinoline-isoxazole-NH-CH₂-CH(NH₂)-CH₂-C₆H₄-CF₃ (4-CF₃) | ++++ |
| 15 | isoquinoline-isoxazole-NH-CH₂-CH(NH₂)-CH₂-C₆H₅ | +++ |
| 16 | isoquinoline-isoxazole-NH-CH₂-CH(NH₂)-CH₂-C₆H₄-Cl (3-Cl) | ++++ |
| 17 | isoquinoline-(4-Me-isoxazole)-NH-CH₂-CH(NH₂)-CH₂-C₆H₅ | ++ |
| 18 | isoquinoline-isoxazole-NH-CH₂-CH(NH₂)-CH₂-C₆H₄-Cl (2-Cl) | +++ |
| 19 | isoquinoline-isoxazole-NH-CH₂-CH(NH₂)-CH₂-(2-naphthyl) | +++ |
| 20 | isoquinoline-(isoxazole regioisomer)-NH-CH₂-CH(NH₂)-CH₂-C₆H₄-CF₃ (4-CF₃) | +++ |

TABLE 1-continued
| Example | Structure[a] | IC$_{50}$[b] |
|---|---|---|
| 21 | 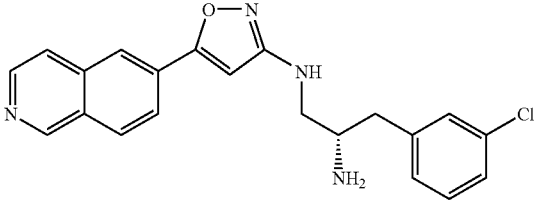 | +++ |
| 22 | 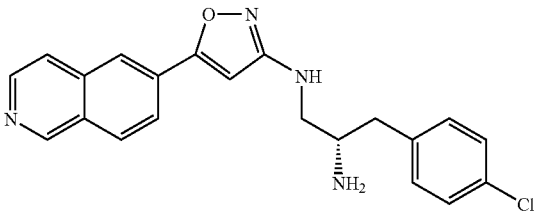 | +++ |
| 23 | 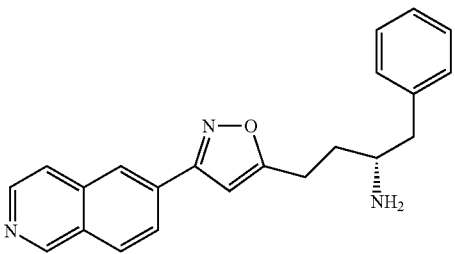 | ++ |
| 24 | 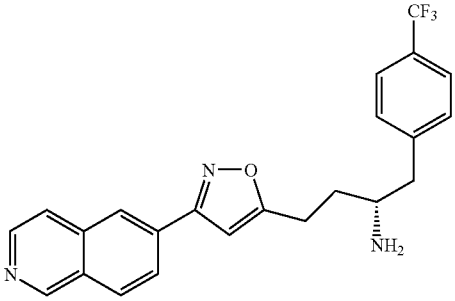 | ++++ |
| 25 | 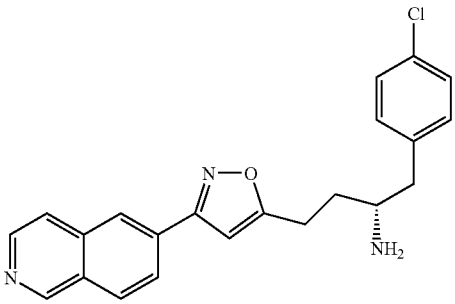 | +++ |
| 26 | 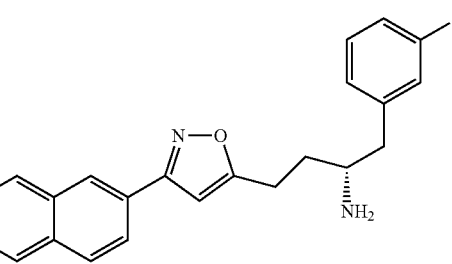 | +++ |

TABLE 1-continued
| Example | Structure[a] | IC$_{50}$[b] |
|---------|--------------|--------------|
| 27 | 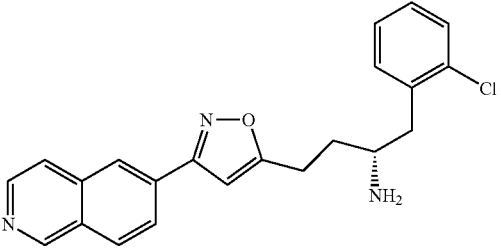 | ++ |
| 28 | 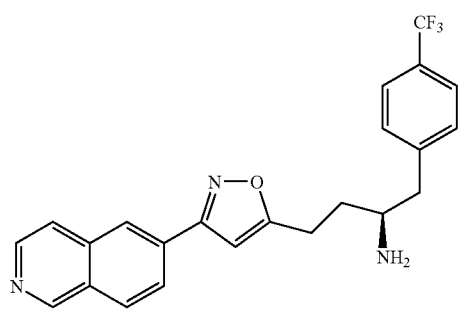 | +++ |
| 29 | 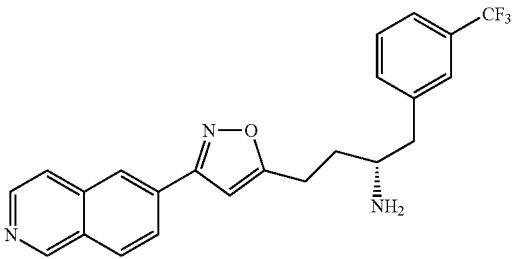 | +++ |
| 30 | 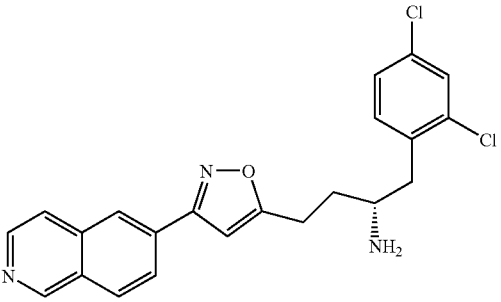 | +++ |
| 31 | 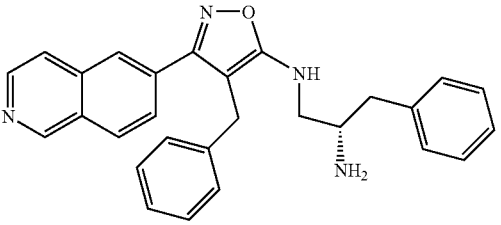 | ++ |

TABLE 1-continued

| Example | Structure | IC$_{50}$$^b$ |
|---|---|---|
| 32 | | +++ |
| 33 | | +++ |
| 34 | | ++ |
| 35 | | ++ |
| 36 | | ++ |
| 37 | | +++ |

TABLE 1-continued
| Example | Structure | IC$_{50}$ |
|---|---|---|
| 38 | 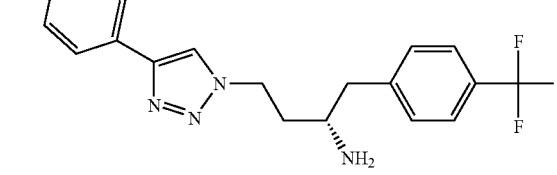 | +++ |
| 39 |  | +++ |
| 40 | 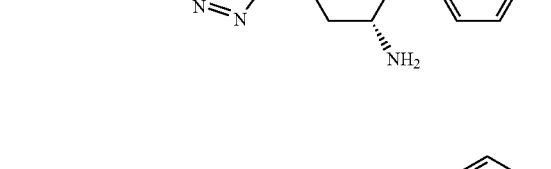 | ++ |
| 41 | 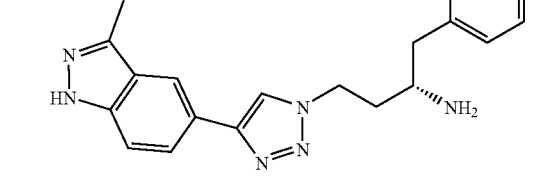 | +++ |
| 42 | 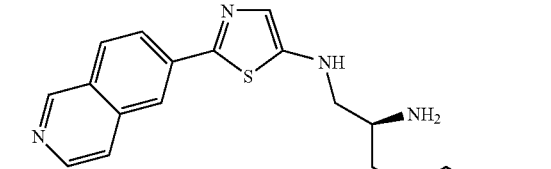 | +++ |

TABLE 1-continued

| Example | Structure[a] | IC$_{50}$[b] |
|---|---|---|
| 43 | | +++ |
| 44 | | ++ |
| 45 | | ++ |
| 46 | | +++ |
| 47 | | +++ |

TABLE 1-continued
| Example | Structure | IC$_{50}$$^b$ |
|---|---|---|
| 48 | 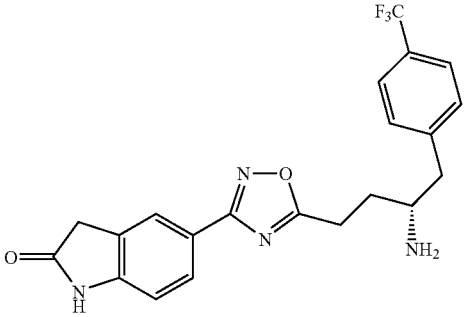 | +++ |
| 49 | 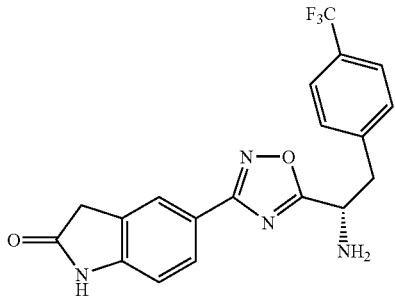 | ++ |
| 50 | 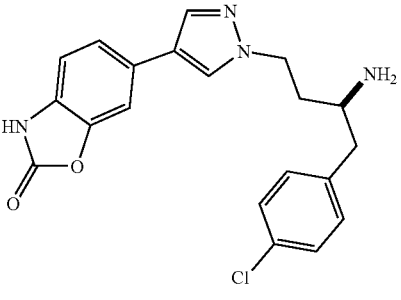 | ++++ |
| 51 | 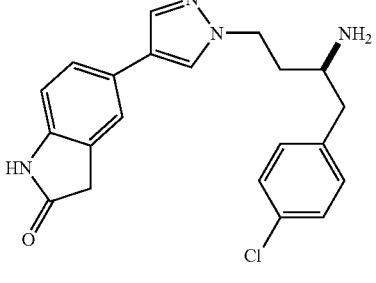 | ++++ |
| 52 | 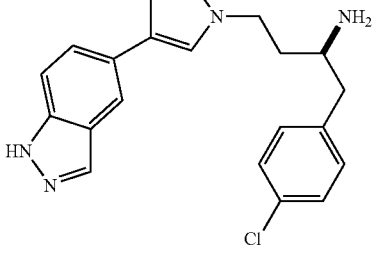 | ++++ |

TABLE 1-continued

| Example | Structure*a* | IC$_{50}$*b* |
|---|---|---|
| 53 | | ++++ |
| 54 | | +++ |
| 55 | | ++++ |
| 56 | | ++++ |
| 57 | | ++++ |

TABLE 1-continued

| Example | Structure[a] | IC$_{50}$[b] |
|---|---|---|
| 58 | | +++ |
| 59 | | +++ |
| 60 | | +++ |
| 61 | | +++ |
| 62 | | +++ |
| 63 | | +++ |
| 64 | | +++ |

TABLE 1-continued

| Example | Structure | IC$_{50}$ |
|---|---|---|
| 65 | 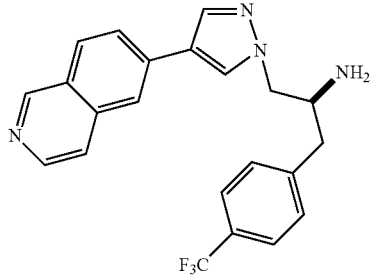 | +++ |
| 66 | 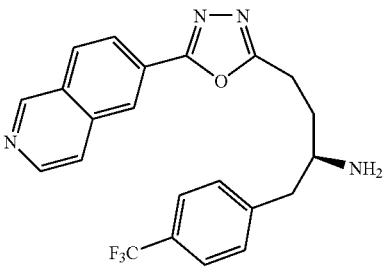 | +++ |
| 67 | 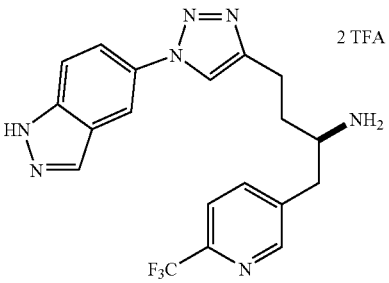 2 TFA | +++ |

[a] When the stereochemistry is not specified at a carbon bonded to four different groups, this indicates a mixture of stereoisomers is present.
[b] IC$_{50}$ Ranges:
+ IC$_{50}$ > 10 μM
++ 1 μM ≤ IC$_{50}$ ≤ 10 μM
+++ 0.05 μM ≤ IC$_{50}$ < 1 μM
++++ IC$_{50}$ < 0.05 μM
[c] IC$_{50}$ value for this compound has not yet been determined.

Each of the compounds in the above table and tautomers, salts, neutral forms, solvates including hydrates, and stereoisomers thereof is preferred both individually and as a member of a group. Each of the groups in these compounds that corresponds to any of the variables in the compounds is also preferred.

The foregoing has demonstrated the pertinent and important features of the present invention. Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

All references cited herein are incorporated herein by reference in their entireties and for all purposes as if specifically set forth herein and to the same extent as if each individual publication or patent or patent application was specifically and individually indicated to be incorporated by reference in its entirety for all purposes.

What is claimed is:

1. A compound of Formula I

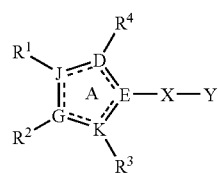

wherein:
Y is selected from

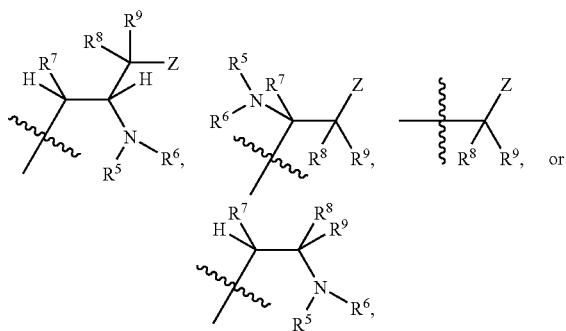

and the wavy line indicates the point of attachment to X, wherein:
D is selected from N, C, O, or S;
E is selected from N or C;
K is selected from N, C, O, or S;
G is selected from N or C;
J is selected from N, C, O, or S;
and further wherein:
at least one of D, E, K, G, and J is other than C;
K is not S when D is N, E is C, G is C, and J is C;
K is not S when D is N, J is N, E is C, and G is C;
0 or 1 of D, K, and J is selected from O or S;
at least two of E, D, K, G, and J are C;
a dashed line indicates that a second bond between the ring atoms is optionally present; and
ring A includes two double bonds;
X is —N($R^{10}$)— or —CR$^{10a}$R$^{10b}$—;
$R^1$ is absent if J is O, or S; or
$R^1$ is selected from —H, $C_1$-$C_6$ alkyl, —($C_1$-$C_6$ alkyl)-O—$R^{11}$, —($C_1$-$C_6$ haloalkyl)-O—$R^{11}$, —($C_2$-$C_6$ alkenyl)-O—$R^{11}$, —($C_1$-$C_6$ alkyl)N($R^{10}$)$_2$, —($C_1$-$C_6$ alkyl)aryl, —CHR$^{12}$—N(H)—$R^{11}$, —CHR$^{12}$—O—$R^{11}$, $C_2$-$C_6$ alkynyl, ($C_2$-$C_6$ alkynyl)-O—$R^{11}$, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl)-N($R^{10}$)S(O)$_2$—$R^{11}$, aryl, heteroaryl, cycloalkyl if J is N; or $R^1$ is absent if J is N and either of the bonds between J and G or J and D is a double bond; or $R^1$ is selected from —H, halo, —OR$^{11}$, $C_1$-$C_6$ alkyl, —($C_1$-$C_6$ alkyl)-O—$R^{11}$, —($C_1$-$C_6$ haloalkyl)-O—$R^{11}$, —($C_2$-$C_6$ alkenyl)-O—$R^{11}$, —($C_1$-$C_6$)alkyl)N($R^{10}$)$_2$, —($C_1$-$C_6$ alkyl)aryl, —C(O)$R^{11}$, —C(O)O—$R^{11}$, —C(O)N ($R^{10}$)$_2$, —CHR$^{12}$—N(H)—$R^{11}$, —CHR$^{12}$—O—$R^{11}$, $C_2$-$C_6$ alkynyl, ($C_2$-$C_6$ alkynyl)-O—$R^{11}$, C≡N, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$)alkynyl)-N($R^{10}$)S(O)$_2$—$R^{11}$, aryl, heteroaryl, cycloalkyl, or heterocyclyl if J is C;
$R^2$ is a carbocyclic ring system or is a heterocyclic ring system;
$R^3$ is absent if K is S or O; or
$R^3$ is selected from —H, $C_1$-$C_6$ alkyl, —($C_1$-$C_6$ alkyl)aryl, or aryl if K is N; or is absent if K is N and either of the bonds between K and E or K and G is a double bond; or
$R^3$ is selected from —H, $C_1$-$C_6$ alkyl, —($C_1$-$C_6$ alkyl)aryl, or aryl if K is C;
$R^4$ is absent if D is S or O; or
$R^4$ is selected from —H, $C_1$-$C_6$ alkyl, —($C_1$-$C_6$ alkyl)aryl, or aryl if D is N; or is absent if D is N and either of the bonds between D and E or D and J is a double bond; or
$R^4$ is selected from —H, $C_1$-$C_6$ alkyl, —($C_1$-$C_6$ alkyl)aryl, or aryl if D is C;
$R^5$ is —H, $C_1$-$C_8$ alkyl, —C(O)(CR$^{13}$R$^{14}$)$_t$N($R^{10}$)$_2$, —C(O)(CR$^{13}$R$^{14}$)$_t$, —C(O)$_2$(CR$^{13}$R$^{14}$)$_t$, —(CR$^{13}$R$^{14}$)$_t$ (aryl), —(CR$^{13}$R$^{14}$)$_t$(heteroaryl), —(CR$^{13}$R$^{14}$)$_t$(cycloalkyl), or —(CR$^{13}$R$^{14}$)$_t$(heterocyclyl);
$R^6$ and $R^{10}$, in each instance, are independently selected from —H, $C_1$-$C_8$ alkyl, —($C_1$-$C_6$ alkyl)aryl, or —C(O) ($C_1$-$C_6$ alkyl);
$R^7$ is —H, —OR$^{11}$, —O—($C_1$-$C_6$ alkyl)-O—$R^{11}$, $C_1$-$C_6$ alkyl, $C_1$-$C_6$ alkenyl, —($C_1$-$C_6$ alkyl)-O—$R^{11}$, or —($C_1$-$C_6$ alkyl)-O—C(O)—$R^{11}$;
$R^8$ is —H, or $C_1$-$C_6$ alkyl;
$R^9$ is —H, —OR$^{11}$, —O—($C_1$-$C_6$ alkyl)-O—$R^{11}$, $C_1$-$C_6$ alkyl, $C_1$-$C_6$ alkenyl, —($C_1$-$C_6$ alkyl)-O—$R^{11}$, or —($C_1$-$C_6$ alkyl)-O—C(O)—$R^{11}$;
$R^{10a}$ and $R^{10b}$ are independently selected from —H, $C_1$-$C_8$ alkyl, —($C_1$-$C_6$ alkyl)aryl, NR$^5$R$^6$, or —C(O)($C_1$-$C_6$ alkyl);
$R^{11}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)-O—($C_1$-$C_6$ alkyl), cycloalkyl, or heterocyclyl;
$R^{12}$, $R^{13}$, and $R^{14}$, in each instance, are independently selected from —H, $C_1$-$C_6$ alkyl, or aryl;
Z is aryl or heteroaryl; and
each t is independently selected from 0, 1, 2, or 3;
and further wherein:
each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo, aryl,
halo,
hydroxyl,
heteroaryl,
$C_1$-$C_6$ hydroxyalkyl, or
—NHS(O)$_2$—($C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_8$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;

or a pharmaceutically acceptable salt, stereoisomer, or mixture thereof.

2. The compound of claim 1, wherein the compound has the formula I'

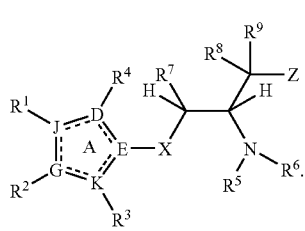

I'

3. The compound of claim 1, wherein X is —N(R$^{10}$)—.

4. The compound of claim 1, wherein X is —CR$^{10a}$R$^{10b}$.

5. The compound of claim 1, wherein two of E, D, K, G, and J are C and the other three of E, D, K, G, and J are not C.

6. The compound of claim 1, wherein three of E, D, K, G, and J are C and the other two of E, D, K, G, and J are not C.

7. The compound of claim 1, wherein four of E, D, K, G, and J are C and the other one of E, D, K, G, and J is not C.

8. The compound of claim 1, wherein the compound has a formula selected from:

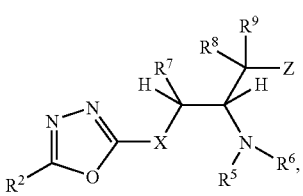

IA

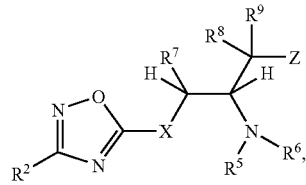

IB

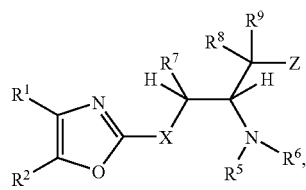

IC

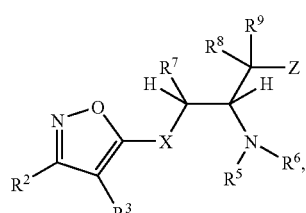

ID

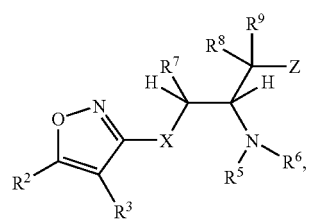

IE

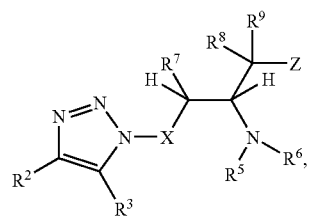

IF

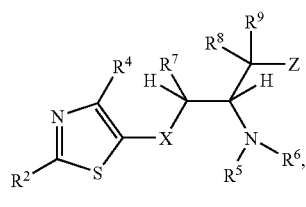

IG

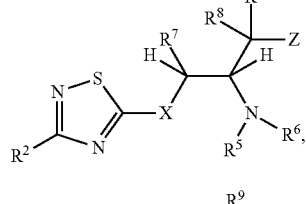

IH

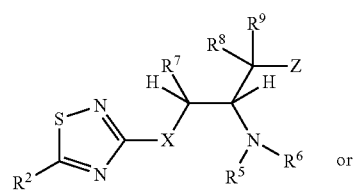

IJ or

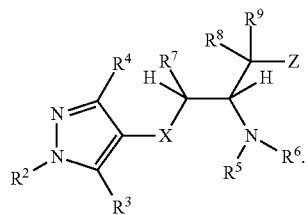

9. The compound of claim 8, wherein the compound has the formula IA.
10. The compound of claim 8, wherein the compound has the formula IB.
11. The compound of claim 8, wherein the compound has the formula IC.
12. The compound of claim 8, wherein the compound has the formula ID.
13. The compound of claim 8, wherein the compound has the formula IE.
14. The compound of claim 8, wherein the compound has the formula IK.
15. The compound of claim 1, wherein the compound has a formula selected from:

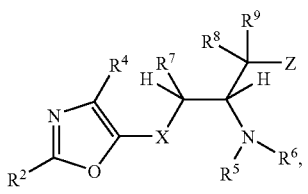
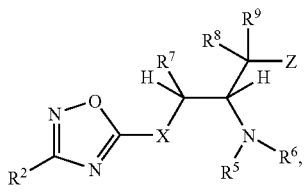
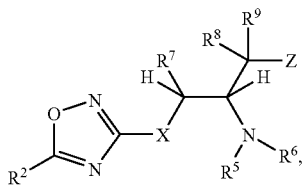
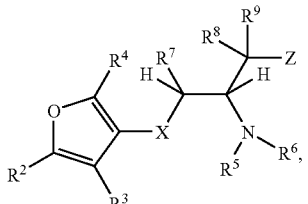
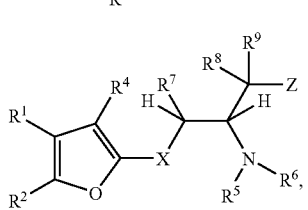
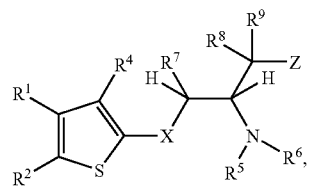
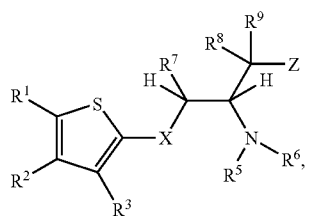
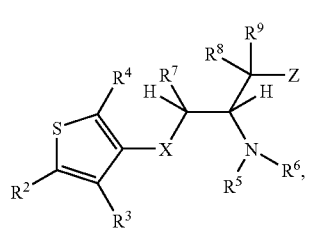
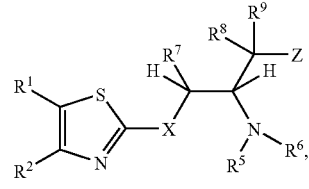
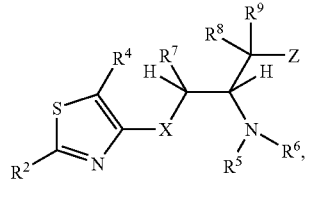
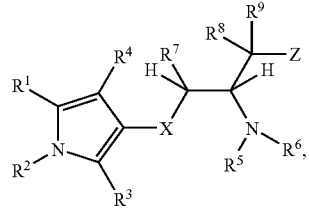
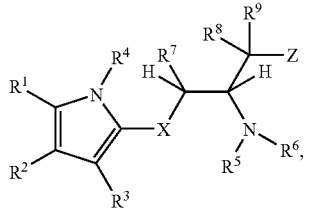

-continued

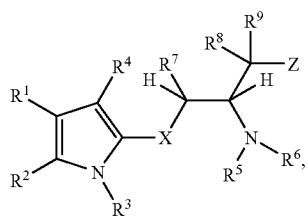
IIN

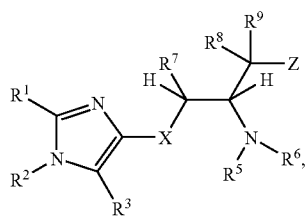
IIO

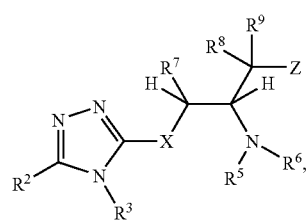
IIP

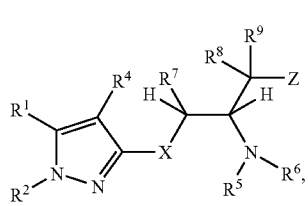
IIQ

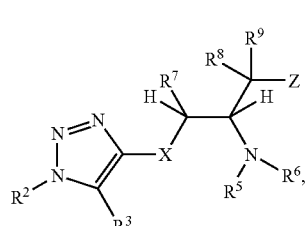
IIR

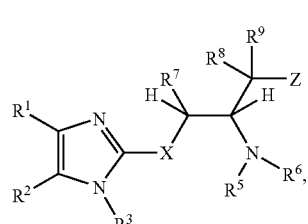
IIS

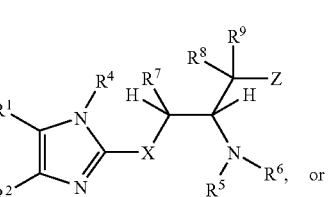
IIT

-continued

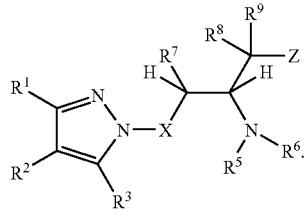
IIU

16. The compound of claim 1, wherein the compound of Formula I has the Formula IIIA

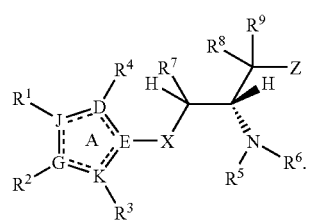
IIIA

17. The compound of claim 1, wherein the compound of Formula I has the Formula IIIB

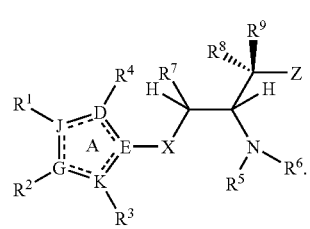
IIIB

18. The compound of claim 1, wherein the compound of Formula I has the Formula IIIC

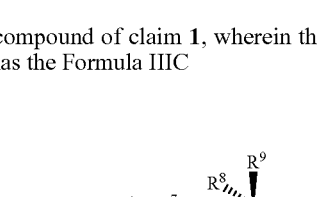
IIIC

19. The compound of claim 1, wherein the compound of Formula I has the Formula IIID

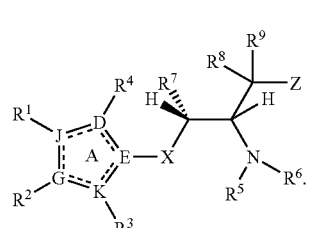
IIID

20. The compound of claim 1, wherein the compound of Formula I has the Formula IIIE

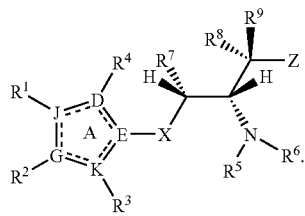

21. The compound of claim 1, wherein $R^1$ is —H.
22. The compound of claim 1, wherein $R^7$ is —H or $C_1$-$C_6$ alkyl.
23. The compound of claim 22, wherein $R^7$ is —H or methyl.
24. The compound of claim 1, wherein $R^8$ is —H.
25. The compound of claim 1, wherein $R^9$ is —H.
26. The compound of claim 1, wherein $R^9$ is —$OR^{11}$, —O—($C_1$-$C_6$ alkyl)-O—$R^{11}$, $C_1$-$C_6$ alkyl, $C_1$-$C_6$ alkenyl, —($C_1$-$C_6$ alkyl)-O—$R^{11}$, or —($C_1$-$C_6$ alkyl)-O—C(O)—$R^{11}$.
27. The compound of claim 1, wherein $R^9$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.
28. The compound of claim 1, wherein Z is selected from optionally substituted phenyl, optionally substituted indolyl, optionally substituted naphthyl, optionally substituted pyridyl, or optionally substituted thiophenyl.
29. The compound of claim 28, wherein Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)-OH, —$C_1$-$C_6$ alkyl, —$OCF_3$, —NH(CO)—O—($C_1$-$C_6$ alkyl)aryl, or —NH(CO)—O—($C_1$-$C_6$ alkyl).
30. The compound of claim 28, wherein Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—$CH_2$-phenyl.
31. The compound of claim 1, wherein $R^{10}$ is H.
32. The compound of claim 1, wherein $R^5$ and $R^6$ are each H.
33. The compound of claim 1, wherein $R^7$ is —H or $C_1$-$C_6$ alkyl, $R^8$ is —H, and $R^9$ is —H, —$OR^{11}$, —O—($C_1$-$C_6$ alkyl)-O—$R^{11}$, $C_1$-$C_6$ alkyl, $C_1$-$C_6$ alkenyl, —($C_1$-$C_6$alkyl)-O—$R^{11}$, or —($C_1$-$C_6$ alkyl)-O—C(O)—$R^{11}$.
34. The compound of claim 33, wherein $R^9$ is —$OR^{11}$, —O—($C_1$-$C_6$ alkyl)-O—$R^{11}$, $C_1$-$C_6$ alkyl, $C_1$-$C_6$ alkenyl, —($C_1$-$C_6$alkyl)-O—$R^{11}$, or —($C_1$-$C_6$ alkyl)-O—C(O)—$R^{11}$.

35. The compound of claim 34, wherein $R^5$, $R^6$, and $R^{10}$ are all H.
36. The compound of claim 1, wherein the carbocyclic ring system or the heterocyclic ring system of $R^2$ comprises at least one aromatic ring.
37. The compound of claim 1, wherein $R^2$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.
38. The compound of claim 1, wherein $R^2$ is selected from one of the following groups which may optionally be substituted and where the wavy line indicates the point of attachment to the ring A:

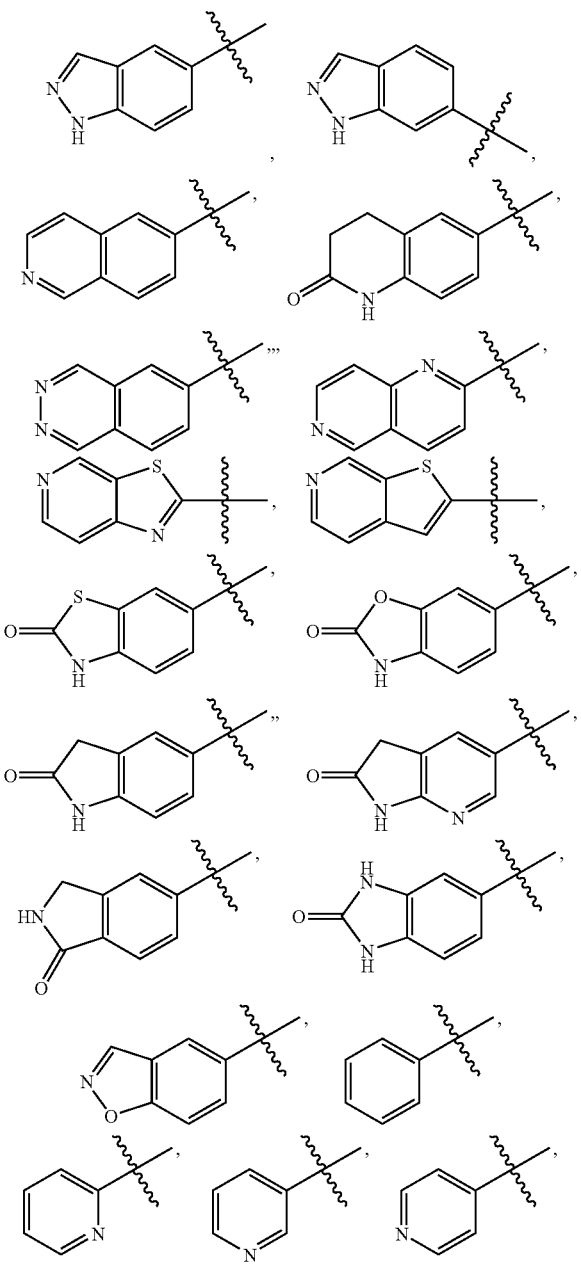

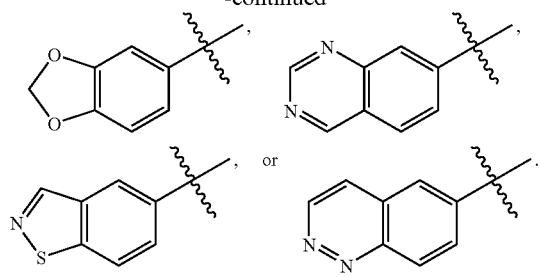
39. The compound of claim 1, wherein $R^2$ is selected from one of the following groups, where the wavy line indicates the point of attachment to the ring A:
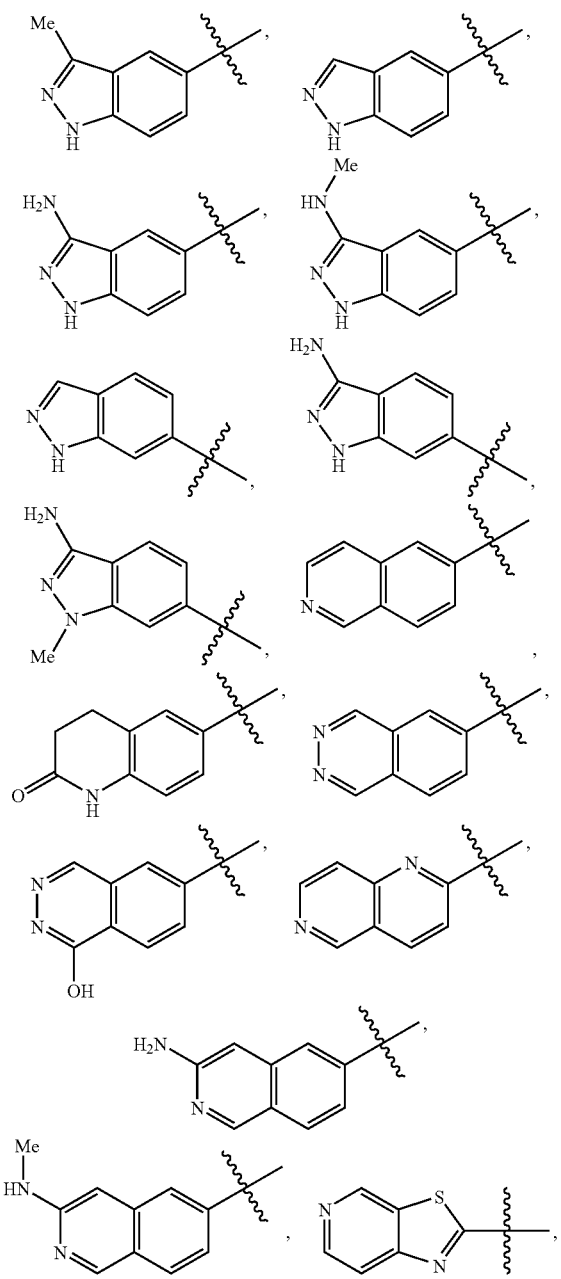
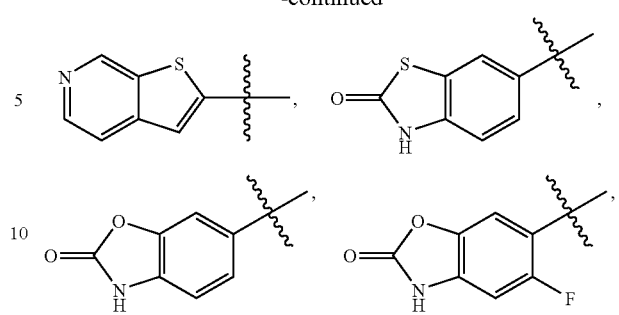
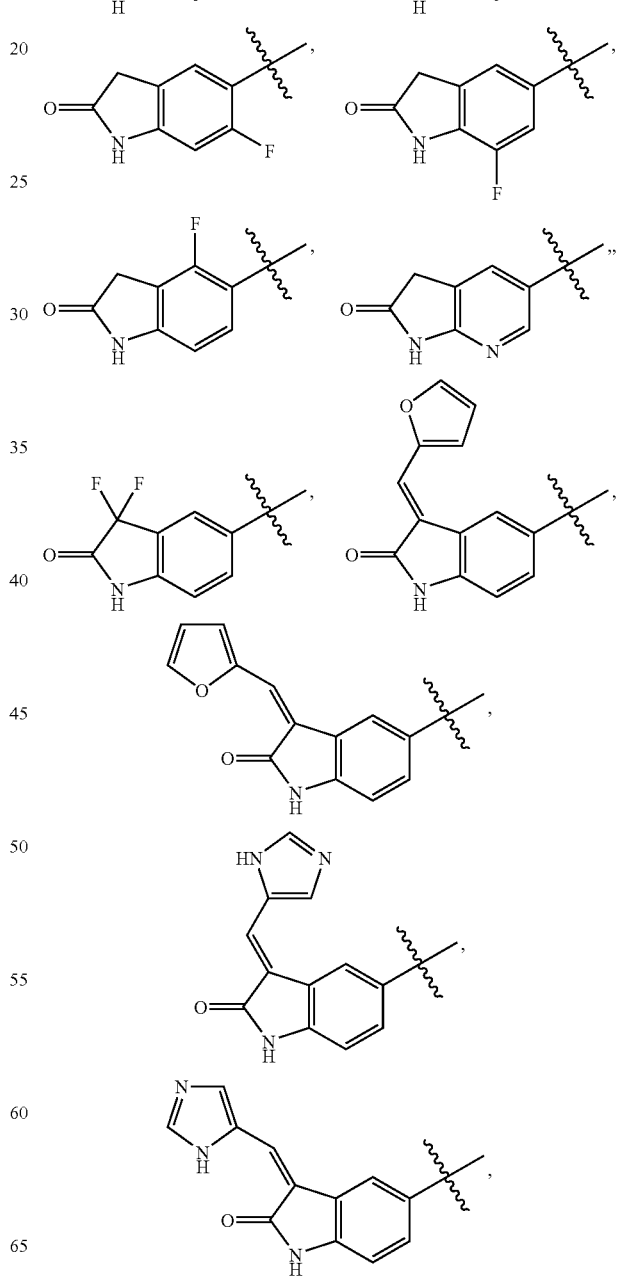

-continued

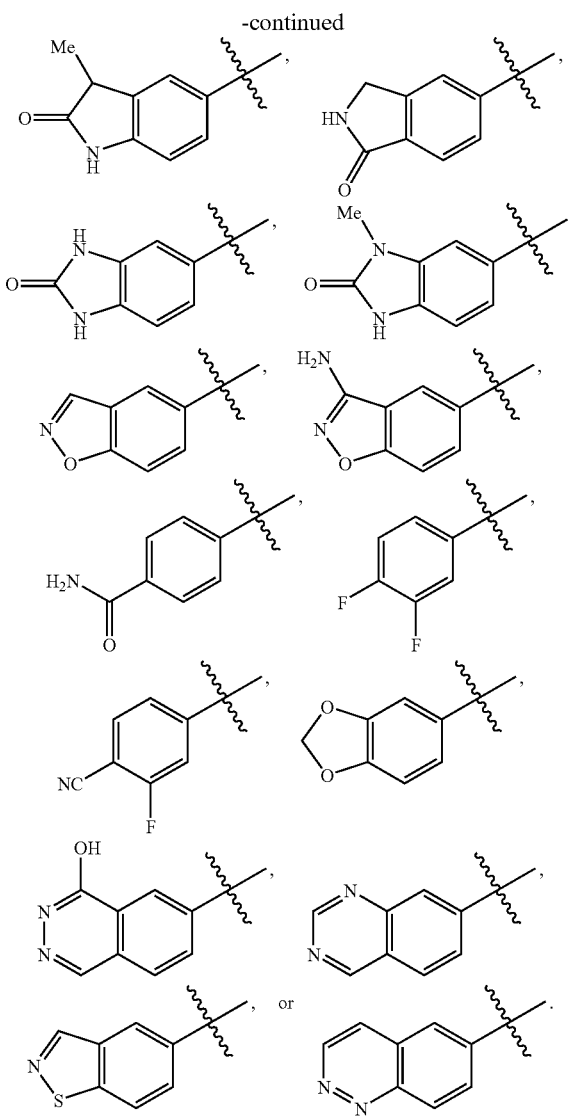

40. The compound of claim 1, wherein $R^1$ is selected from —H, —C≡N, —Br, —Cl, —OH, —CF$_3$, —CH$_3$, —CH$_2$CH$_3$, —CH$_2$CH$_2$OH, —C(H)(CH$_3$)OCH$_3$, —CH$_2$OCH$_2$CF$_3$, —CH$_2$N(H)CH$_3$, —CH$_2$N(CH$_3$)$_2$, —CF$_2$CH$_2$OH, cyclopropyl, furanyl, tetrahydrofuranyl, phenyl, 2,3-difluorophenyl, 3,4-difluorophenyl, 4-fluorophenyl, 3-fluorophenyl, 2-fluorophenyl, pyridyl, oxazolyl, hydroxymethyl, methoxymethyl, ethoxymethyl, —C(O)OMe, —C(O)N(H)CH$_2$CH$_2$OH, —C(O)N(H)CH$_3$, —C(O)NH$_2$, —C(O)N(CH$_3$)$_2$, or a group selected from one of the following groups where the wavy line indicates the point of attachment to the ring A:

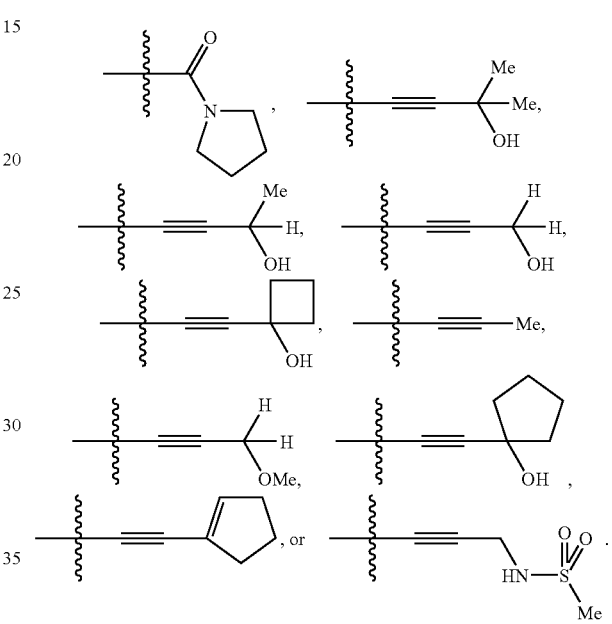

41. A pharmaceutical composition, comprising: a pharmaceutically-acceptable carrier and the compound of claim 1.

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:

<223> OTHER INFORMATION: Synthetic peptide

<400> SEQUENCE: 1

Ala Arg Lys Arg Glu Arg Thr Tyr Ser Phe Gly His His Ala
1               5                   10